United States Patent
Dennis et al.

(10) Patent No.: US 7,608,681 B2
(45) Date of Patent: Oct. 27, 2009

(54) METHODS AND COMPOSITIONS FOR PROLONGING ELIMINATION HALF-TIMES OF BIOACTIVE COMPOUNDS

(75) Inventors: Mark S. Dennis, San Carlos, CA (US); Henry B. Lowman, El Granada, CA (US); Warren L. DeLano, San Carlos, CA (US)

(73) Assignee: Genentech, Inc., So. San Francisco, CA (US)

( * ) Notice: Subject to any disclaimer, the term of this patent is extended or adjusted under 35 U.S.C. 154(b) by 1456 days.

(21) Appl. No.: 10/149,835

(22) PCT Filed: Dec. 22, 2000

(86) PCT No.: PCT/US00/35325

§ 371 (c)(1),
(2), (4) Date: Jun. 14, 2002

(87) PCT Pub. No.: WO01/45746

PCT Pub. Date: Jun. 28, 2001

(65) Prior Publication Data

US 2004/0253247 A1   Dec. 16, 2004

Related U.S. Application Data

(60) Provisional application No. 60/173,048, filed on Dec. 24, 1999.

(51) Int. Cl.
| | |
|---|---|
| A61K 38/00 | (2006.01) |
| A61K 38/12 | (2006.01) |
| C07K 2/00 | (2006.01) |
| C07K 4/00 | (2006.01) |
| C07K 5/00 | (2006.01) |
| C07K 14/00 | (2006.01) |
| C07K 17/00 | (2006.01) |

(52) U.S. Cl. .................. 530/300; 530/317; 530/326; 436/506; 436/507; 436/509

(58) Field of Classification Search ............... 530/300; 436/506
See application file for complete search history.

(56) References Cited

U.S. PATENT DOCUMENTS

| | | | |
|---|---|---|---|
| 3,561,444 A | 2/1971 | Boucher | |
| 3,703,173 A | 11/1972 | Dixon | |
| 3,842,067 A | 10/1974 | Sarantakis | |
| 3,862,925 A | 1/1975 | Sarantakis | |
| 3,972,859 A | 8/1976 | Fujino et al. | |
| 4,105,603 A | 8/1978 | Vale, Jr. et al. | |
| 4,399,216 A | 8/1983 | Axel et al. | |
| 4,624,251 A | 11/1986 | Miller | |
| 4,635,627 A | 1/1987 | Gam | |
| 4,970,198 A | 11/1990 | Lee et al. | |
| 4,975,278 A | 12/1990 | Senter et al. | |
| 5,079,233 A | 1/1992 | Lee et al. | |
| 5,135,736 A | 8/1992 | Anderson | |
| 5,585,089 A | 12/1996 | Queen et al. | |
| 5,606,040 A | 2/1997 | McGahren et al. | |
| 5,679,777 A | 10/1997 | Anderson et al. | |
| 5,693,762 A | 12/1997 | Queen et al. | |
| 5,725,856 A | 3/1998 | Hudziak et al. | |
| 5,739,116 A | 4/1998 | Hamann et al. | |
| 5,767,237 A | 6/1998 | Sakakibara et al. | |
| 5,767,285 A | 6/1998 | Hamann et al. | |
| 5,773,001 A | 6/1998 | Hamann et al. | |
| 5,780,054 A | 7/1998 | Tardi et al. | |
| 5,821,337 A | 10/1998 | Carter et al. | |
| 6,054,297 A | 4/2000 | Carter et al. | |
| 6,124,431 A | 9/2000 | Sakakibara et al. | |
| 6,387,371 B1 | 5/2002 | Hudziak et al. | |

(Continued)

FOREIGN PATENT DOCUMENTS

EP   0486525   6/1994

(Continued)

OTHER PUBLICATIONS

Nef et al. EMBO Journal. vol. 7(3): 595-601; 1988.*
GenBank accession No. P09480; earliest version date 1993; downloaded Sep. 14, 2008.*
Abrahmsen et al., "Analysis of Signals for Secretion in the Staphylococcal Protein A Gene." *EMBO Journal* 4:3901-3906 (1985).
Adams and Schier., "Generating Improved Single-Chain Fv Molecules for Tumor Targeting." *J. Immunol. Methods* 231:249-260 (1999).
Adams., "Improving the Tumor Specificity and Retention of Antibody-Based Molecules." *In Vivo* 12:11-22 (1998).

(Continued)

*Primary Examiner*—Sue Liu
(74) *Attorney, Agent, or Firm*—Elinor Shin; Ginger Dreger; Goodwin Procter LLP

(57) ABSTRACT

Peptide ligands having affinity for IgG or for serum albumin are disclosed. Also disclosed are hybrid molecules comprising a peptide ligand domain and an active domain. The active domain may comprise any molecule having utility as a therapeutic or diagnostic agent. The hybrid molecules of the invention may be prepared using any of a number techniques including production in and purification from recombinant organisms transformed or transfected with an isolated nucleic acid encoding the hybrid molecule, or by chemical synthesis of the hybrid. The hybrid molecules have utility as agents to alter the elimination half-times of active domain molecules. Elimination half-time is altered by generating a hybrid molecule of the present invention wherein the peptide ligand has binding affinity for a plasma protein. In a preferred embodiment, a bioactive molecule having a short elimination half-time is incorporated as or into an active domain of the hybrid molecules of the invention, and the binding affinity of the peptide ligand domain prolongs the elimination half-time of the hybrid as compared to that of the bioactive molecule.

17 Claims, 20 Drawing Sheets

U.S. PATENT DOCUMENTS

| | | |
|---|---|---|
| 6,632,979 B2 | 10/2003 | Erickson et al. |
| 2002/0032315 A1 | 3/2002 | Baca et al. |
| 2003/0069395 A1 | 4/2003 | Sato et al. |
| 2003/0228663 A1 | 12/2003 | Lowman et al. |
| 2004/0001827 A1 | 1/2004 | Dennis |
| 2004/0018194 A1 | 1/2004 | Francisco et al. |
| 2004/0032828 A1 | 2/2004 | Satt |
| 2005/0089932 A1 | 4/2005 | Kolkma et al. |
| 2005/0287153 A1 | 12/2005 | Dennis |
| 2006/0228364 A1 | 10/2006 | Dennis et al. |

FOREIGN PATENT DOCUMENTS

| | | |
|---|---|---|
| EP | 486525 | 6/1994 |
| EP | 602290 | 8/1999 |
| WO | WO 88/07543 | 10/1988 |
| WO | WO 89/06692 | 7/1989 |
| WO | WO 90/01940 | 3/1990 |
| WO | WO 91/01743 | 2/1991 |
| WO | WO 94/18318 | 8/1994 |
| WO | WO 96/40921 | 12/1996 |
| WO | WO 98/22141 | 5/1998 |
| WO | WO 01/45746 | 6/2001 |
| WO | WO 01/79444 | 10/2001 |
| WO | WO 01/79480 | 10/2001 |
| WO | WO 03/031464 A2 | 4/2003 |
| WO | WO 03/043583 A2 | 5/2003 |
| WO | WO 2004/032828 | 4/2004 |

OTHER PUBLICATIONS

Affleck and Embleton., "Monoclonal Antibody Targeting of Methotrexate (MTX) Against MTX-Resistant Tumor Cell Lines." *Br. J. Cancer* 65:838-844 (Jun. 1992).

Aida and Pabst., "Removal of Endotoxin from Protein Solutions by Phase Separation Using Triton X-114." *J. Immunol. Methods* 132:191-195 (1990).

Arap et al., "Cancer Treatment by Targeted Drug Delivery to Tumor Vasculature in a Mouse Model" *Science* 279:377-380 (1998).

Ashkenazi and Chamow., "Immunoadhesins as Research Tools and Therapeutic Agents." *Curr. Op. Immunol.* 9:195-200 (1997).

Batrla et al., "CD40-Expressing Carcinoma Cells Induce Down-Regulation of CD40 Ligand (CD154) and Impair T-Cell Functions." *Cancer Research* 62:2052-2057 (Apr. 2002).

Burger et al., "Pre-Clinical Evaluation of a Methotrexate-Albumin Conjugate (MTX-HSA) in Human Tumor Xenografts In vivo." *Int. J. Cancer.* 92:718-724 (2001).

Carter, "American Chemical Society Symposium Series No. 427" *Protein Purification: From Molecular Mechanisms to Large-Scale Processes.*, Ladisch et al., Eds., Chapter 13, pp. 181-193 (1990).

Clackson and Wells, "In Vitro Selection from Protein and Peptide Libraries." *Trends Biotechnol.* 12:173-184 (1994).

Clark et al., "Long-Acting Growth Hormones Produced by Conjugation with Polyethylene Glycol." *Journal of Biological Chemistry* 271(36) :21969-21977 (Sep. 6, 1996).

Cunningham et al., "Production of an Atrial Natriuretic Peptide Variant that is Specific for Type A Receptor" *EMBO Journal* 13(11) : 2508-2515 (1994).

Cwirla et al., "Peptide Agonist of the Thrombopoietin Receptor as Potent as the Natural Cytokine." *Science* 276(5319) :1696-1699 (1997).

Dennis and Lazarus, "Kunitz Domain Inhibitors of Tissue Factor-Factor VIIa; II. Potent and Specific Inhibitors by Competitive Phage Selection" *Journal of Biological Chemistry* 269(35):22137-22144 (1994).

Dennis et al., "Peptide Exosite Inhibitors of Factor VIIa as Anticoagulants." *Nature* 404:465-470 (Mar. 2000).

Dennis et al., "Selection and Characterization of a New Class of Peptide Exosite Inhibitors of Coagulation Factor VIIIa." *Biochemistry* 40:9513-9521 (2001).

Fendley et al., "Characterization of Murine Monoclonal Antibodies Reactive to Either the Human Epidermal Growth Factor Receptor or HER2/neu Gene Product." *Cancer Research* 50:1550-1558 (Mar. 1990).

Ferrari et al., "Mutations of CD40 Gene Cause an Autosomal Recessive Form of Immunodeficiency with Hyper IgM." *Proc. Natl. Acad. Sci. USA* 98(22) :12614-12619 (Oct. 2001).

Goldberg et al., "The Biodegradation of Albumin Microspheres Used for Regional Chemotherapy in Patients with Colorectal Liver Metastases." *Nucl. Med. Commun.* 12:57-63 (Jan. 1991).

Goodman and Gilman, Eds., "Time Course of Drug Effect: Pharmacokinetic Principles." *The Pharmaceutical Basis of Therapeutics.*, 6th edition, NY:MacMillan Publishing Co., Chapter 1, pp. 21-25 (1980).

Gupta and Hung., "Albumin Microspheres II: Applications in Drug Delivery." *J. Microencapsul.* 6(4) :463-472 (Oct.-Dec. 1989).

Houghten., "General Method for the Rapid Solid-Phase Synthesis of Large Numbers of Peptides: Specificity of Antigen-Antibody Interaction at the Level of Individual Amino Acids." *Proc. Natl. Sci. USA* 82:5131-5135 (Aug. 1985).

Keyt et al., "A Faster-Acting and More Potent Form of Tissue Plasminogen Activator." *Proc. Natl. Acad. Sci. USA* 91:3670-3674 (1994).

Kiessling et al., "Magnetic Resonance Imagine of Nude Mice with Heterotransplanted High-Grade Squamous Cell Carcinomas: Use of a Low-Loaded, Covalently bound Gd-Hsa Conjugate as Contrast Agent with High Tumor Affinity." *Invest. Radiol.* 37:193-198 (Apr. 2002).

Kunkel et al., "Rapid and Efficient Site-specific Mutagenesis Without Phenotypic Selection" *Methods in Enzymology* 154:367-382 (1987).

Kurtzhals et al., "Albumin Binding of Insulins Acylated with Fatty Acids: Characterization of the Lignad-Protein Interaction and Correlation Between Binding Affinity and Timing of the Insulin Effect In Vivo." *Biochemical Journal* 312:725-731 (1995).

Lee et al., "Prolonged Circulating Lives of Single-Chain Fv Proteins Conjugated with Polyethylene Glycol: A Comparison of Conjugation Chemistries and Compounds." *Bioconjugate Chem.* 10(6) :973-981 (1999).

Li et al., "Pharmacokinetics and Biodistribution of Radioimmunoconjugates and Anti-CD19 Antibody and Single-Chain Fv for Treatment of Human B-Cell Malignancy." *Cancer Immunol. Immunother.* 47:121-130 (1998).

Lohrisch and Piccart., "An Overview of HER2." *Semin. Oncol.* (Suppl. 18) 28:3-11 (Dec. 2001).

Lowman and Wells, "Affinity Maturation of Human Growth Hormone by Monovalent Phage Display" *J. Mol. Biol.* 234:564-578 (1993).

Lowman et al., "Molecular Mimics of Insulin-Like Growth Factor 1 (IGF-1) for Inhibiting IGF-1: IGF-Binding Protein Interactions." *Biochemistry* 37(25):8870-8878 (1998).

Lowman et al., "Selecting High-Affinity Binding Proteins by Monovalent Phage Display" *Biochemistry* 30(45) :10832-10838 (1991).

Makrides et al., "Extended In Vivo Half-Life of a Human Soluble Complement Receptor Type 1 Fused to a Serum Albumin-Binding Receptor." *J. Pharmacol. Exptl. Therap.* 277:534-541 (1996).

Merrifield, R.B., "Solid Phase Peptide Synthesis. I. The Synthesis of Tetrapeptide" *J. Am. Chem. Soc.* 84(14) :2149-2154 (Jul. 1963).

Molina et al., "Trastuzumab (Herceptin), a Humanized Anti-HER2 Receptor Monoclonal Antibody, Inhibits Basal and Activated HER2 Ectodomain Cleavage in Breast Cancer Cells." *Cancer Research* 61:4744-4749 (Jun. 2001).

Pasqualini and Ruoslahti, "Organ Targeting In Vivo Using Phage Display Peptide Libraries." *Nature* 380:364-366 (1996).

Pelton et al., "Design and Synthesis of Conformationally Constrained Somatostatin Analogues with High Potency and Specificity for μ Opoid Receptors" *J. Med. Chem.* 29:2370-2375 (1986).

Pietersz et al., "Specific In Vitro Anti-Tumor Activity of Methotrexate-Monoclonal Antibody Conjugates Prepared Using Human Serum Albumin as an Intermediary." *Immunol. Cell. Biol.* 66:43-49 (Feb. 1988).

Pimm, M.V., "Drug-Monoclonal Antibody Conjugates for Cancer Therapy: Potentials and Limitations." *Crit. Rev. Ther. Drug. Carrier Syst.* 5:189-227 (1988).

Presta et al., "Generation of a Humanized, High Affinity Anti-Tissue Factor Antibody for Use as a Novel Antithrombotic Therapeutic." *Thrombosis and Haemostasis.* 85(3) :379-389 (Mar. 2001).

Sands., "Experimental Studies of Radioimmunodetection of Cancer: An Overview." *Cancer Res. (Suppl.)* 50:809s-813s (Feb. 1990).

Sato et al., "Development of Mammalian Serum Albumin Affinity Purification Media by Peptide Phage Display." *Biotechnol. Prog.* 18:182-192 (2002).

Sato et al., "Tumor Targeting and Imaging of Intraperitoneal Tumors by Use of Antisense Oligo-DNA Complexed with Dendrimers and/or Avidin in Mice." *Clin. Cancer Res.* 7:3606-3612 (Nov. 2001).

Sawyer, T.K., "Peptidomimetic Design and Chemical Approaches to Peptide Metabolism." *Peptide Based Drug Design: Controlling Transport and Metabolism.*, Taylor and Amidon, Eds., Washington, DC:ACS, Chapter 17, pp. 387-422 (1995).

Singh et al., "Synergistic Interaction of Growth Factors and Albumin in Regulating Estradiol Synthesis in Breast Cancer Cells." *Mol. Cell Endocrinol.* 85:165-173 (Jun. 1992).

Smith., "Efficacy and Safety of Herceptin in Women with Metastatic Breast Cancer: Results From Pivotal Clinical Studies." *Anticancer Drugs* (Suppl. 4) 12:S3-10 (Dec. 2001).

Stehle et al., "Plasma Protein (Albunmin) Catabolism by the Tumor Itself—Implications for Tumor Metabolism and the Genesis of Cachexia." *Crit. Rev. Oncol. Hematol.* 26:77-100 (Jul. 1997).

Streffer, C., "Glucose Energy-Metabolism and cell Proliferation in Tumors." *Adv. Exp. Med. Biol.* 345:327-333 (1994).

Syed et al., "Potent Antithrombin Activity and Delayed Clearance from the Circulation Characterize Recombinant Hirudin Genetically Fused to Albumin." *Blood.* 89:3243-3252 (May 1997).

Tanaka et al., "Pharmacokinetics of Recombinant Human Granulocyte Colony-Stimulating Factor Conjugated to Polyethylene Glycol in Rats." *Cancer Research* 51:3710-3714 (Jul. 1991).

Timsina and Hewick., "The Use of Enzyme-Linked Immunosorbent Assays to Study the Plasma Disposition of Sheep Polyclonal in Rat Monoclonal Digoxin-Specific Fab Fragments in the Rabbit." *J. Pham. Pharmacol.* 42:572-576 (Jan. 1990).

Wearley, Lorraine L., "Recent Progress in Protein and Peptide Delivery by Noninvasive Routes." *Crit. Rev. Ther. Drug Carrier Systems* 8(4) :331-394 (1991).

Weigand et al., "Mode of Action of Methotrexate-Albumin in a Human T-Cell Leukemia Line and Activity Against an MTX-Resistant Clone." *Anticancer Drug Des.* 16:227-237 (Aug.-Oct. 2001).

Wells and Lowman, "Rapid Evolution of Peptide and Protein Binding Properties in Vitro" *Curr. Opin. Struct. Biol.* 2:597-604 (1992).

Wild and Turner, "Exposure Biomarkers in Chemoprevention Studies of Liver Cancer." *IARC Sci. Publ., Biomarkers in Cancer Chemoprevention.*, Bartsch et al., eds. vol. 154:215-222 (2001).

Wolff and Boker., "Immunohistochemical Demonstration of Immunoglobulins and Albumin in Human Brain Tumors." *Clin. Neuropathol.* 8:72-78 (Mar.-Apr. 1989).

Wrighton et al., "Small Peptides as Potent Mimetics of the Protein Hormone Erythropoietin." *Science* 273:458-463 (1996).

Yanofsky et al., "High Affinity Type I Interleukin 1 Receptor Antagonists Discovered by Screening Recombinant Peptide Libraries." *Proc. Natl. Acad. Sci. USA* 93:7381-7386 (1996).

Yeh et al., "Design of Yeast-Secreted Albumin Derivatives for Human Therapy: Biological and Antiviral Properties of a Serum Albumin-CD4 Genetic Conjugate." *Proc. Natl. Acad. Sci. USA* 89:1904-1908 (Mar. 1992).

Yokota et al., "Rapid Tumor Penetration of a Single-Chain Fv and Comparison with Other Immunoglobulin Forms." *Cancer Research* 52:3402-3408 (Jun. 1992).

Zusman and Ben-Hur., "Serological Markers for Detection of Cancer (Review)." *Int. J. Mol. Med.* 7:547-556 (May 2001).

European Search Report for European Application No. 06017275.6 dated Jan. 26, 2007.

European Search Report for European Application No. 06017276.4 dated Feb. 6, 2007.

Zettlmeissl et al.: "Expression and characterization of human CD4: immunoglobulin fusion proteins" DNA and Cell Biology, vol. 9, No. 3, 1990, pp. 347-353.

Burgess, et al., "Possible dissociation of the heparin-binding and mitogenic activities of heparin-binding (Acidic Fibroblast) growth factor-1 from its receptor-binding activities by site-directed mutagenesis of a single lysine residue", J. Cell Biology, vol. 11, pp. 2129-2138, (1990).

Lazar, et al., Mol. Cell Biol. 8:1247-1252, (1998).

Nygren, et al. (Journal of Molecular Recognition 1988: 1:69-74).

Pratt et al. (Principles of drug action $3^{rd}$ ed., New York: Churchill Livingstone, 1990) p. 231-236 only.

Sato et al. (Biotechnology Prog. 2002, 18, 182-192).

Wen et al. (Proc. Natl. Acad. Sci. U.S.A. 98: 4622-4627, 2001).

* cited by examiner

Species Specificity of Albumin-Binding Phage Peptides

| Library | | Phage Binding | | |
|---|---|---|---|---|
| | Selected on Rabbit SA | Rabbit | Human | Rat |
| BA | G E N W C D S T L M A Y D L C G Q V N M | +++ | - | - |
| BB | M D E L A F Y C G I W E C L M H Q E Q K | +++ | - | - |
| BC | D L C D V D F C W F | +++ | - | - |
| BD | K S C S E L H W L L V E E C L F | +++ | - | - |
| | Selected on Human SA | | | |
| HA | E V R S F C T D W P A E K S C K P L R G | - | +++ | - |
| HB | R A P E S F V C Y W E T I C F E R S E Q | - | ++ | (+) |
| HC | E M C Y F P G I C W M | - | +++ | ++ |
| HE | C E V A L D A C R G G E S G C C R H I C E L I R Q L C | - | (+) | - |
| | Selected on Rat SA | | | |
| RA | R N E D P C V V L L E M G L E C W E G V | - | - | +++ |
| RD | D T C V D L V R L G L E C W G | - | - | +++ |
| RB | Q R Q M V D F C L P Q W G C L W G D G F | ++ | + | +++ |
| RC | D L C L R D W G C L W | - | - | +++ |
| RE | C G C V D V S D W D C W S E C L W S H G A | - | - | +++ |

FIG. 4

|  |  | Human | Binds Rabbit | Rat |
|---|---|---|---|---|
| Sequences Selected on Rabbit Albumin | | | | |
| Library BA | G E N W C D S T L M A Y D L C G Q V N M | | | |
| BA-B44 | G E D W C D S T L L A F D L C G E G A R | - | +++ | - |
| BA-B37 | G E N W C D W V L L A Y D L C G E D N T | - | +++ | - |
| BA-B39 | M E L W C D S T L M A Y D L C G D F N M | - | +++ | - |
| Sequences Selected on Human Albumin | | | | |
| Library HA | E V R S F C T D W P A E K S C K P L R G | | | |
| HA-H74 | E V R S F C T D W P A H Y S C T S L Q G | +++ | - | - |
| HA-H83 | G - R S F C M D W P A H K S C T P L M L | +++ | - | - |
| HA-H73 | G V R T F C Q D W P A H N S C K L L R G | +++ | - | - |
| HA-H76 | Q T R S F C A D W P R H E S C K P L R G | +++ | - | - |
| HA-H84 | R - R T - C - D W P - H N S C K - L R G | +++ | - | - |
| Library HB | R A P E S F V C Y W E T I C F E R S E Q | | | |
| HB-H2 | R A A E S S V C Y W P G I C F D R T E Q | +++ | - | - |
| HB-H8 | M E P S R S V C Y A E G I C F D R G E Q | +++ | - | - |
| HB-H3 | R E P A S L V C Y F E D I C F V R A E A | + | - | - |
| HB-H6 | R G P D - V - C Y W P S I C F E R S M P | + | - | - |
| HB-H4 | L V P E R I V C Y F E S I C Y E R S E L | + | - | - |
| HB-H16 | R M P A S L P C Y W E T I C Y E S S E Q | + | - | - |
| HB-H18 | R T A E S L V C Y W P G I C F A Q S E R | + | - | - |
| HB-H1 | R A P E R W V C Y W E G I C F D R Y E Q | (+) | - | - |
| Library HC | E M C Y F P G I C W M | | | |
| HB-H12 | E I C Y F P G I C W I | ++ | - | - |
| HB-H13 | E L C Y F P G I C W T | ++ | - | - |
| HC-H6 | D I C Y I P G I C W M | ++ | - | - |
| HC-H2 | K L C Y F P G I C W S | ++ | - | - |
| HC-H3 | D L C Y F P G I C W M | ++ | - | - |
| HC-H4 | G M C Y F P G I C W A | ++ | - | - |
| HC-H7 | E M C Y F P G I C W S | ++ | - | - |
| HC-H9 | E M C Y F P G I C W T | ++ | - | - |
| HC-H10 | K T C Y F P G I C W M | ++ | - | - |
| HC-H5 | K V C Y F P G I C W M | ++ | - | - |
| HC-H8 | D V C Y F P G I C W M | ++ | - | - |
| HC-H17 | E I C Y F P G I C W M | ++ | - | - |
| HC-H14 | A L C Y F P G I C W M | ++ | - | - |
| HC-H15 | E L C Y F P G I C W P | ++ | - | - |
| HC-H20 | E L C Y F P G I C W M | ++ | - | - |
| HC-H13 | D M C Y F P G I C W L | ++ | - | - |
| HC-H18 | D M C Y F P G I C F N | ++ | - | - |
| HC-H12 | E T C Y F P G I C W L | ++ | - | - |
| HC-H11 | E V C Y F P G I C W F | ++ | - | - |
| HC-H16 | E V C Y F P G I C W E | ++ | - | - |
| HC-H19 | E V C Y F P G I C W M | ++ | - | - |
| Library HBC | X X E M C Y F P G I C W M X X | | | |
| HBC-H7 | L A E M C Y F P G I C W M S A | +++ | - | - |
| HBC-H4 | G G E I C Y F P G I C R V L P | +++ | - | - |
| HBC-H6 | E H D M C Y F P G I C W I A D | +++ | - | - |
| HBC-H10 | V Q E V C Y F P G I C W M Q E | +++ | - | - |
| HBC-H2 | S R E V C Y Y P G I C W N G A | +++ | - | - |
| HBC-H1 | D S E V C Y F P G I C W S G T | +++ | - | - |
| HBC-H3 | G T E V C Y F P G I C W G G G | +++ | - | - |
| HBC-H8 | S Y A P C Y F P G I C W M G N | +++ | - | - |
| HBC-H17 | H A E I C Y F P G I C W T E R | +++ | - | - |
| HBC-H11 | N D E I C Y F P G V C W K S G | +++ | - | - |
| HBC-H18 | R D T V C Y F P G I C W M A S | +++ | - | - |
| HBC-H19 | V R D M C Y F P G I C W K S E | +++ | - | - |
| HBC-H12 | A S E I C Y F P G I C W M V E | +++ | - | - |
| HBC-H13 | Q T E L C Y F P G I C W N E S | +++ | - | - |
| HBC-H14 | T T E M C Y F P G I C W K T E | +++ | - | - |
| HBC-H15 | K T E I C Y F P G I C W M S G | +++ | - | - |
| HBC-H16 | Q - - - C - F P G - - W V - K | +++ | - | - |
| HB-H10 | I V E M C Y Y P G I C W I S P | +++ | - | - |
| HB-H7 | S G A I C Y V P G I C W T H A | +++ | - | - |
| Sequences Selected on Rat Albumin | | | | |
| Library RB | Q R Q M V D F C L P Q W G C L W G D G F | | | |
| RB-H1 | Q R H P E D I C L P R W G C L W G D D D | ++ | +++ | +++ |
| RB-H6 | N R Q M E D I C L P Q W G C L W G D D F | ++ | +++ | +++ |

FIG. 5A

| | | | | |
|---|---|---|---|---|
| RB-B2 | Q R L M E D I C L P R W G C L W G D R F | ++ | +++ | +++ |
| RB-B5 | Q W H M E D I C L P Q W G C L W G D V L | ++ | +++ | +++ |
| RB-B6 | Q W Q M E N V C L P K W G C L W E E L D | ++ | +++ | +++ |
| RB-B4 | L W A M E D I C L P K W G C L W E D D F | ++ | +++ | +++ |
| RB-B7 | L R L M D N I C L P R W G C L W D D G F | ++ | +++ | +++ |
| RB-B8 | H S Q M E D I C L P R W G C L W G D E L | ++ | +++ | +++ |
| RB-B11 | Q W Q V M D I C L P R W G C L W A D E Y | ++ | +++ | +++ |
| RB-B12 | Q G L I G D I C L P R W G C L W G D S V | ++ | +++ | +++ |
| RB-B16 | H R L V E D I C L P R W G C L W G N D F | ++ | +++ | +++ |
| RB-B9 | Q M H M M D I C L P K W G C L W G D T S | (+) | +++ | +++ |
| RB-B14 | L R I F E D I C L P K W G C L W G E G F | (+) | +++ | +++ |
| RB-B3 | Q S Y M E D I C L P R W G C L S D D A S | (+) | +++ | +++ |
| RB-B10 | Q G D F W D I C L P R W G C L S G E G Y | - | +++ | +++ |
| RB-B1 | R W Q T E D V C L P K W G C L F G D G V | - | +++ | +++ |
| | | | | |
| RB-R8 | Q G L I G D I C L P R W G C L W G D S V | ++ | +++ | +++ |
| RB-R16 | L I F M E D V C L P Q W G C L W E D G V | ++ | +++ | +++ |
| HC-R10 | Q R D M G D I C L P R W G C L W E D G V | ++ | +++ | +++ |
| RB-R4 | Q R H M M D F C L P K W G C L W G D G Y | - | (+) | +++ |
| RB-R7 | Q R P I M D F C L P K W G C L W E D G F | - | (+) | +++ |
| RB-R11 | E R Q M V D F C L P K W G C L W G D G F | - | (+) | +++ |
| RB-R12 | Q G Y M V D F C L P R W G C L W G D A N | - | (+) | +++ |
| RB-R13 | K M G R V D F C L P K W G C L W G D E L | - | (+) | +++ |
| RB-R15 | Q S Q L E D F C L P K W G C L W G D G F | - | (+) | +++ |
| RB-R17 | Q G G M G D F C L P Q W G C L W G E D L | - | (+) | +++ |
| RB-R5 | Q R L M W E I C L P L W G C L W G D G L | - | - | +++ |
| RB-R10 | Q R Q I M D F C L P H W G C L W G D G F | - | - | +++ |
| RB-R2 | G R Q V V D F C L P K W G C L W E E G L | - | - | +++ |
| RB-R3 | Q M Q M S D F C L P Q W G C L W G D G Y | - | - | +++ |
| RB-R9 | K S R M G D F C L P E W G C L W G D E L | - | - | +++ |
| RB-R1 | E R Q M E D F C L P Q W G C L W G D G V | - | - | +++ |
| RB-R14 | Q R Q V V D F C L P Q W G C L W G D G S | - | - | +++ |
| | | | | |
| Library RC | *D L C L R D W G C L W* | | | |
| | | | | |
| RC-R6 | D I C L P E W G C L W | - | - | ++ |
| RC-R8 | D I C L P E W G C L W | - | - | ++ |
| RC-R15 | D I C L P E W G C L W | - | - | ++ |
| RC-R1 | D I C L P V W G C L W | - | - | ++ |
| RC-R2 | D I C L P V W G C L W | - | - | ++ |
| RC-R3 | D I C L P V W G C L W | - | - | ++ |
| RC-R10 | D I C L P V W G C L W | - | - | ++ |
| RC-R12 | D I C L P V W G C L W | - | - | ++ |
| RC-R18 | D I C L P V W G C L W | - | - | ++ |
| RC-R9 | D L C L P E W G C L W | - | - | (+) |
| RC-R4 | D L C L P K W G C L W | - | - | ++ |
| RC-R5 | D L C L P V W G C L W | - | - | (+) |
| RC-R20 | D I C L P A W G C L W | - | - | ++ |
| RC-R17 | D I C L P D W G C L W | - | - | ++ |
| RC-R13 | D I C L P R W G C L W | - | - | ++ |
| RC-R16 | D I C L E R W G C L W | - | - | ++ |
| | | | | |
| Library RBC | *X X D L C L R D W G C L W X X* | | | |
| | | | | |
| RBC-R16 | E W D V C L P H W G C L W D G | - | (+) | +++ |
| RBC-R7 | W D D I C F R D W G C L W G S | - | - | +++ |
| RBC-R1 | M D D I C L H H W G C L W D E | - | - | +++ |
| RBC-R2 | M D D L C L P N W G C L W D | - | - | +++ |
| RBC-R4 | F E D F C L P N W G C L W G S | - | - | +++ |
| RBC-R6 | F E D L C V V R W G C L W G D | - | - | +++ |
| RBC-R5 | W E D L C L P D W G C L W E D | - | - | +++ |
| RBC-R9 | S E D F C L P V W G C L W E D | - | - | +++ |
| RBC-R10 | D F D L C L P D W G C L W D D | - | - | +++ |
| RBC-R8 | N W D L C F P D W G C L W D D | - | - | +++ |
| RBC-R14 | E E D L C L P V W G C L W A | - | - | +++ |
| RBC-R20 | E E D V C L P V W G C L W E G | - | - | +++ |
| RBC-R12 | M F D L C L P K W G C L W G N | - | - | +++ |
| RBC-R13 | E F D L C L P T W G C L W E D | - | - | +++ |
| RBC-R15 | M W D V C F P D W G C L W D V | - | - | +++ |
| RBC-R18 | E W D V C F P A W G C L W D Q | - | - | +++ |
| RBC-R11 | V W D L C L P Q W G C L W D E | - | - | +++ |
| | | | | |
| Library RD | *D T C V D L V R L G L E C W G* | | | |
| | | | | |
| RD-R2 | D T C A D L V R L G L E C W A | - | - | +++ |
| RD-R7 | N T C A D L V R L G L E C W A | - | - | +++ |
| RD-R11 | D T C D D L V Q L G L E C W A | - | - | +++ |
| RD-R5 | D T C E D L V R L G L E C W A | - | - | +++ |
| RD-R6 | D S C G D L L R L G L E C W A | - | - | +++ |
| RD-R1 | D T C S D L V G L G L E C W A | - | - | +++ |

FIG. 5B

| PHAGE | | | | | | | | | | | | | | | | | | | Binds | | |
|---|---|---|---|---|---|---|---|---|---|---|---|---|---|---|---|---|---|---|---|---|---|
| | | | | | | | | | | | | | | | | | | | Human | Rabbit | Rat |
| RB | Q | R | Q | M | V | D | F | C | L | P | Q | W | G | C | L | W | G | D | G | F | + | ++ | +++ |
| RB-H1 | Q | R | H | P | E | D | I | C | L | P | R | W | G | C | L | W | G | D | D | D | ++ | +++ | +++ |
| RB-H6 | N | R | Q | M | E | D | I | C | L | P | Q | W | G | C | L | W | G | D | D | F | ++ | +++ | +++ |
| RB-B12 | Q | G | L | I | G | D | I | C | L | P | R | W | G | C | L | W | G | D | S | V | ++ | +++ | +++ |
| RB-B8 | H | S | Q | M | E | D | I | C | L | P | R | W | G | C | L | W | G | D | E | L | ++ | +++ | +++ |
| RB-B7 | L | R | L | M | D | N | I | C | L | P | R | W | G | C | L | W | D | D | G | F | ++ | +++ | +++ |
| RB-B5 | Q | W | H | M | E | D | I | C | L | P | Q | W | G | C | L | W | G | D | V | L | ++ | +++ | +++ |
| RB-B6 | Q | W | Q | M | E | N | V | C | L | P | K | W | G | C | L | W | E | E | L | D | ++ | +++ | +++ |
| RB-B4 | L | W | A | M | E | D | I | C | L | P | K | W | G | C | L | W | E | D | D | F | ++ | +++ | +++ |
| RB-B11 | Q | W | Q | V | M | D | I | C | L | P | R | W | G | C | L | W | A | D | E | Y | ++ | +++ | +++ |
| RB-B16 | H | R | L | V | E | D | I | C | L | P | R | W | G | C | L | W | G | N | D | F | ++ | +++ | +++ |
| RB-B2 | Q | R | L | M | E | D | I | C | L | P | R | W | G | C | L | W | G | D | R | F | ++ | +++ | +++ |
| RB-R8 | Q | G | L | I | G | D | I | C | L | P | R | W | G | C | L | W | G | D | S | V | ++ | +++ | +++ |
| RB-R16 | L | I | F | M | E | D | V | C | L | P | Q | W | G | C | L | W | E | D | G | V | ++ | +++ | +++ |
| HC-R10 | Q | R | D | M | G | D | I | C | L | P | R | W | G | C | L | W | E | D | G | V | ++ | +++ | +++ |

FIG. 7

Sequences selected on rat albumin

Hard Randomization Library
```
        X X X X X D X C L P X W G C L W X X X X
35      A A Q V G D I C L P R W G C L W S E Y A
33      A G W A A D V C L P R W G C L W E E D V
60      A S V V D D I C L P V W G C L W G E D I
84      A T M E D D I C L P R W G C L W G A E E
10      D E D F E D Y C L P P W G C L W G S S M
34      E G T W D D F C L P R W G C L W L G E R
93      E R W E G D V C L P B W G C L W G E S G
23      G D W M H D I C L P K W G C L W D E K A
71      G I E W G D T C L P K W G C L W R Y E G
36      G Q Q G E D V C L P V W G C L W D T S S
48      G R Y P M D E C L P R W G C L W E D S A
24      G S A G D D L C L P R W G C L W E R G A
9       H A S D W D V C L P G W G C L W E E D D
47      L G V T H D T C L P R W G C L W D E V G
72      L V W E E D F C L P K W G C L W G A E D
11      N V G W N D I C L P R W G C L W A Q E S
83      Q G V E W D V C L P Q W G C L W T R E W
58      R L D A W D H C L P Q W G C L W E E P S
96      S E A P G D Y C L P R W G C L W A Q E K
94      T A M D E D V C L P R W G C L W G S G S
81      T E I G Q D F C L P R W G C L W V P G T
57      T L G W R D F C L P K W G C L W R E S D
12      T L S N Q D I C L P G W G C L W G G I N
46      T S T G G D L C L P R W G C L W D S S E
22      V S E M D D I C L P E W G C L W A D A P
59      V S E W E D I C L P S W G C L W E T Q D
45      V V G D G D F C L P K W G C L W D Q A R
21      V V W D D D V C L P R W G C L W E E Y G
69      W S D S D D V C L P R W G C L W G N V A
95      W V E E G D I C L P R W G C L W E S V E
33      A Q A M G D I C L P R W G C L W E A E J
10      A S D R G D L C L P V W G C L W G P D G
93      A S D P G D V C L P R W G C L W G E S F
71      A S N W E D V C L P T W G C L W G E R N
22      A S T P R D I C L P R W G C L W S E D A
23      D G E E G D L C L P R W G C L W A L E H
24      E G E E V D I C L P Q W G C L W G Y P V
82      E V G D L D L C L P R W G C L W G N D K
81      F R D G E D F C L P Q W G C L W A D T S
46      G D M V N D F C L P R W G C L W G S E N
83      G R M G T D L C L P R W G C L W G E V E
94      H E W E R D I C L P R W G C L W R D G D
35      K K V S G D I C L P I W G C L W D N D Y
96      L E S D D I C L P R W G C L W H E D G
21      M Q A E S D F C L P H W G C L W D E G T
36      M Q G P L D I C L P R W G C L W G G V D
48      Q M P L E D I C L P R W G C L W E G R E
85      R E E W G D L C L P T W G C L W E T K K
47      R V W T E D V C L P R W G C L W S E G N
11      S I R E Y D V C L P K W G C L W E P S A
34      S P T E W D M C L P K W G C L W G D A L
69      S S G L E D I C L P N W G C L W A D G S
9       S V G W G D I C L P V W G C L W G E G G
57      T E E N W D L C L P R W G C L W G D D W
84      T S Q S D D I C L P V W G C L W G E D S
58      T W P G D L C L P R W G C L W E A E S
72      W D H E L D F C L P V W G C L W A E D V
60      W T E S E D I C L P G W G C L W G P E V
59      W V P F E D V C L P R W G C L W S S Y Q
```

Hard Randomization Library
```
        X X X X D X C L P X W G C L W X X X
93      E E D S D I C L P R W G C L W N T S
81      E G Y W D L C L P R W G C L W E L E
10      E L G E D L C L P R W G C L W G S E
24      E T W S D V C L P R W G C L W G A S
83      G D Y V D L C L P G W G C L W E D G
23      G V L D D I C L P R W G C L W G P K
94      H M M D D V C L P G W G C L W A S E
59      I D Y T D L C L P A W G C L W E L E
36      I E H E D L C L P R W G C L W A V D
11      I S E W D L C L P R W G C L W D R S
12      I S W A D V C L P K W G C L W G K D
47      J S W G D L C L P R W G C L W E G S
22      K L W D D I C L P R W G C L W S P L
84      L A W P D V C L P R W G C L W G G M
71      L N E S D I C L P T W G C L W G V D
46      L P E Q D V C L P V W G C L W D A N
35      M A W G D V C L P R W G C L W A G G
48      N E E W D V C L P R W G C L W G G V
60      Q E L Q D F C L P R W G C L W G V G
21      Q R E W D V C L P R W G C L W S D V
9       Q R F W D T C L P R W G C L W G G D
57      R V F T D V C L P R W G C L W D L G
58      S G W D D V C L P V W G C L W G P S
96      S S A S D Y C L P R W G C L W G D L
72      S W Q G D I C L P R W G C L W G V D
69      S Y E T D V C L P Y W G C L W E D A
34      S Y W G D V C L P R W G C L W S E A
45      T L E W D M C L P R W G C L W T E Q
95      V G E F D I C L P R W G C L W D A E
33      V T S W D V C L P R W G C L W E E D
82      W L W E D L C L P K W G C L W E E D
82      A L F E D V C L P V W G C L W G G E
45      A S E W D V C L P T W G C L W M E G
34      A Y S A D I C L P R W G C L W M S E
35      E D W E D I C L P Q W G C L W E G M
83      E D W T D L C L P A W G C L W D T E
```

FIG. 8A

Sequences selected on rabbit albumin

Hard Randomization Library

```
        X X X X X D X C L P X W G C L W X X X X
75      A G L D E D I C L P R W G C L W G K E A
39      A G M M G D I C L P R W G C L W Q G E P
76      A P G D W D F C L P K W G C L W D D D A
74      A Q L E D D I C L P R W G C L W S D G Y
86      A R T M G D I C L P R W G C L W G A S D
63      A W Q D F D V C L P R W G C L W E P E S
26      D T T W G D V C L P R W G C L W S E E A
4       E G E L G D I C L P R W G C L W G H Q A
2       E Q W L H D I C L P K W G C L W D D D D
61      E T Q W P D I C L P R W G C L W E E G E
52      F E L G E D I C L P R W G C L W E E H N
38      G A S L G D I C L P A W G C L W G P E D
88      G E W W E D I C L P R W G C L W G S S S
1       G S L E S D I C L P R W G C L W G L D E
13      G W L E E D I C L P K W G C L W G A D N
64      H E Q W D D I C L P R W G C L W G G S Y
49      Q R V D D D I C L P R W G C L W G E N S
50      S V G W G D I C L P K W G C L W A E S D
40      T L M S N D I C L P R W G C L W D E P K
28      T L V L D D I C L P R W G C L W D M T D
14      T W Q G E D I C L P R W G C L W D T E V
73      V G V F D D I C L P R W G C L W E D P V
25      V P A M G D I C L P R W G C L W E A R N
16      V S L G D D I C L P K W G C L W E P E A
15      V W D R D I C L P R W G C L W D T E N
51      W R W N E D I C L P R W G C L W E E E A
73      A V S W A D I C L P R W G C L W E R A D
37      A W L D E D I C L P K W G C L W N T G V
16      F S L D E D I C L P K W G C L W G A E K
3       G D L G D D I C L P R W G C L W D E Y P
67      G E G W S D I C L P R W G C L W A E D E
38      G L M G E D I C L P R W G C L W K G D I
75      G W H D R D I C L P R W G C L W E Q N D
63      L L G G H D I C L P R W G C L W G G D V
64      M R W S S D I C L P K W G C L W G D E E
13      Q E W A D D I C L P R W G C L W E W E V
49      Q G W W H D I C L P R W G C L W E E G E
51      R E G W P D I C L P R W G C L W S E T G
40      R E L W G D I C L P R W G C L W E H A T
76      R L E L M D I C L P R W G C L W D P Q D
2       S G V L G D I C L P R W G C L W E E A G
14      S L G L T D L C L P R W G C L W E E V Q
27      S S L E Q D I C L P R W G C L W G Q D A
74      S V L S D D I C L P R W G C L W W D F S
15      T S L L D D I C L P R W G C L W Y E E G
50      T S L A D D I C L P R W G C L W S E D G
25      V E M W H D I C L P R W G C L W D S N A
4       W D L A S D I C L P R W G C L W E E E A
```

Hard Randomization Library

Sequences selected on human albumin

Hard Randomization Library

|  | X X X X X | D | X | C | L | P | X | W | G | C | L | W | X X X X |
|---|---|---|---|---|---|---|---|---|---|---|---|---|---|
| 68 | E V R E W | D | R | C | L | P | R | W | G | C | L | W | E N W R |
| 6 | F G Q E W | D | I | C | L | P | R | W | G | C | L | W | G N E Q |
| 17 | I W Q L E | D | I | C | L | P | R | W | G | C | L | W | E D G L |
| 53 | N T P T Y | D | I | C | L | P | R | W | G | C | L | W | G D V P |
| 5 | Q P V W S | D | H | C | L | P | R | W | G | C | L | W | G E D H |
| 18 | S W Y G G | D | I | C | L | P | R | W | G | C | L | W | S E E S |
| 80 | W G M A R | D | W | C | L | P | M | W | G | C | L | W | R G G G |
| 7 | W R L T D | D | I | C | L | P | R | W | G | C | L | W | G D E Q |
| 54 |  |  |  |  |  |  |  |  |  |  |  |  |  |
| 67 | N W A E N | D | I | C | L | P | R | W | G | C | L | W | G D E N |
| 68 | S A R E W | D | I | C | L | P | T | W | G | C | L | W | E K D I |

Hard Randomization Library

|  | X X X X | D | X | C | L | P | X | W | G | C | L | W | X X X |
|---|---|---|---|---|---|---|---|---|---|---|---|---|---|
| 42 | A G E W | D | T | C | L | P | R | W | G | C | L | W | D V E |
| 56 | E I R W | D | F | C | L | P | R | W | G | C | L | W | D E D |
| 8 | E S L G | D | I | C | L | P | R | W | G | C | L | W | G S G |
| 30 | E Y W G | D | I | C | L | P | R | W | G | C | L | W | D W Q |
| 80 | K M W S | D | L | C | L | P | R | W | G | C | L | W | E E E |
| 90 | M G T K | D | I | C | L | P | R | W | G | C | L | W | A E A |
| 7 | M H E W | D | T | C | L | P | R | W | G | C | L | W | E S S |
| 78 | R G L H | D | A | C | L | P | W | W | G | C | L | W | A Q S |
| 19 | R L F G | D | I | C | L | P | R | W | G | C | L | W | Q G E |
| 5 | S G E W | D | I | C | L | P | R | W | G | C | L | W | G E G |
| 6 | S M F F | D | H | C | L | P | M | W | G | C | L | W | A E Q |
| 44 | V G E W | D | I | C | L | P | N | W | G | C | L | W | E R E |
| 32 | W W M A | D | R | C | L | P | L | W | G | C | L | W | R G D |
| 29 | W W V R | D | L | C | L | P | T | W | G | C | L | W | S G K |
| 54 | Y F D G | D | I | C | L | P | R | W | G | C | L | W | G S D |
| 32 | T L F Q | D | I | C | L | P | R | W | G | C | L | W | E E S |
| 68 | W F P K | D | R | C | L | P | V | W | G | C | L | W | E R H |

FIG. 8C

| PEPTIDE | Sequence | RabSA IC$_{50}$ (nM) | Rat SA IC$_{50}$ (nM) | Mouse SA IC$_{50}$ (nM) |
|---|---|---|---|---|
| SA02 | D L C L R D W G C L W -n | | | |
| SA04 | D I C L P R W G C L W -n | 8543 | 787 | 40 |
| SA05 | M E D I C L P R W G C L W E D -n | 804 | 161 | 6 |
| SA06 | Q R L M E D I C L P R W G C L W E D D F -n | 128 | 68 | 8 |
| SA07 | Q G L I G D I C L P R W G C L W G D S V -n | 30 | 35 | 6 |
| SA08 | Ac- Q G L I G D I C L P R W G C L W G D S V K -n | 63 | 68 | 10 |
| SA09 | Ac- E D I C L P R W G C L W E D D -n | 1687 | 258 | 6 |
| SA10 | Ac- R L M E D I C L P R W G C L W E D D -n | 86 | 77 | 4 |
| SA11 | Ac- M E D I C L P R W G C L W E D D -n | 1213 | 232 | 17 |
| SA12 | Ac- M E D I C L P R W G C L W E D -n | 1765 | 205 | 13 |
| SA13 | Ac- R L M E D I C L A R W G C L W E D D -n | 3200 | 2480 | 188 |
| | | | | |
| D3H44-L | Q R L M E D I C L P R W G C L W E D D F -n | 241 | | |
| D3H44-Ls | Q R L M E D I C L P R W G C L W E D D F -n | 75 | | |

FIG. 9

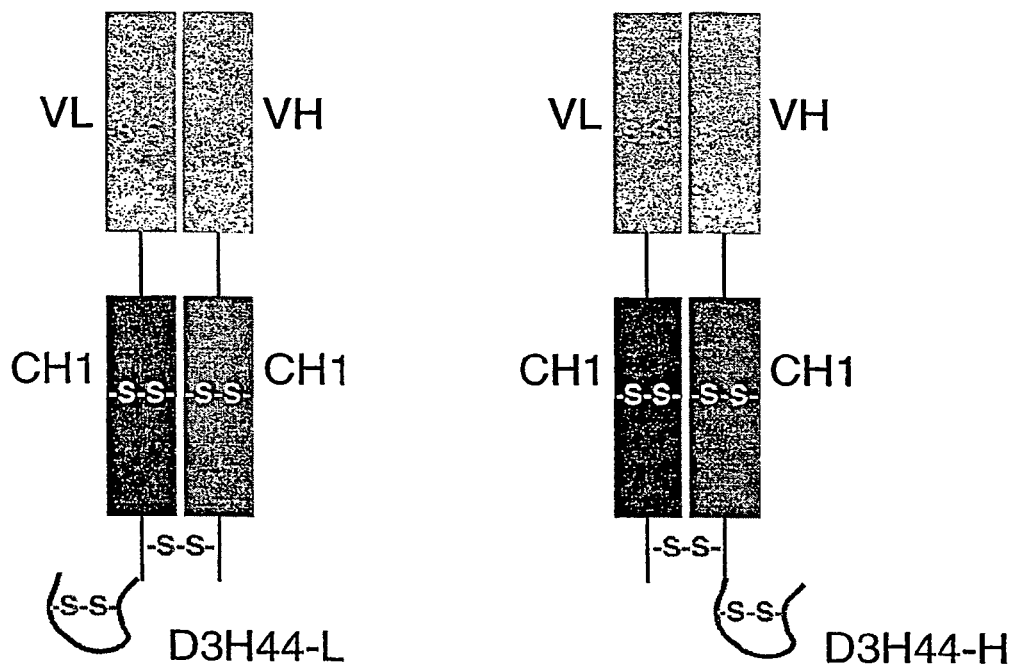
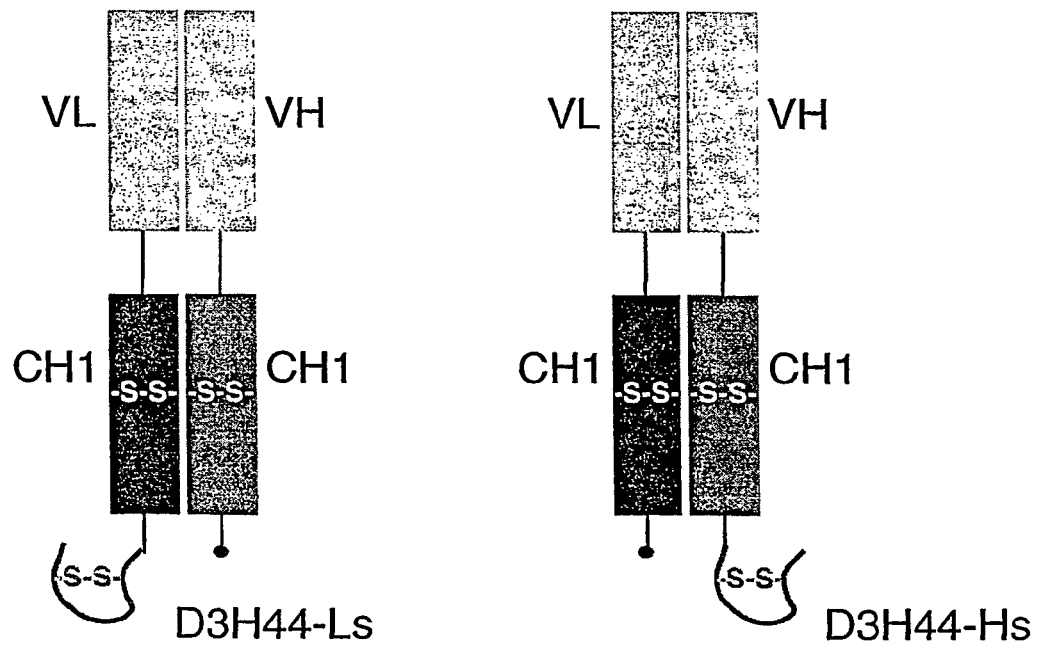
FIG. 11

00-331 Summarized PK Data

| Parameter | Units | D3H44-Fab | | D3H44-L | | D3H44-Ls | |
|---|---|---|---|---|---|---|---|
| | | Average | Stdev | Average | Stdev | Average | Stdev |
| Dose | ug/kg | 396 | | 416 | | 524 | |
| AUC | hr*ug/mL | 5.86 | 1.23 | 349 | 33 | 332 | 82 |
| AUC/Dose(hr*ug/mL)/(mg/kg) | | 14.8 | 3.1 | 840 | 78 | 633 | 157 |
| CL | mL/hr/kg | 69.9 | 16.2 | 1.20 | 0.11 | 1.64 | 0.37 |
| Cmax | ug/mL | 5.00 | 2.30 | 7.55 | 1.23 | 5.98 | 0.11 |
| K10-HL | hr | 0.876 | 0.213 | 32.4 | 3.2 | 38.3 | 8.8 |
| MRT | hr | 3.07 | 0.62 | 95.0 | 13.1 | 110 | 20 |
| V1 | mL/kg | 90.6 | 38.4 | 56.2 | 10.1 | 87.6 | 1.7 | p < 0.05 RC20L vs RC20Ls |
| Vss | mL/kg | 221 | 95 | 113 | 7 | 176 | 11 | p < 0.05 RC20L vs RC20Ls |

99-133 Summarized PK data (historical)

| Parameter | Units | D3H44-20K PEG | | D3H44-40K PEG | | D3H44-Fab | | D3H44-Fab'2 | |
|---|---|---|---|---|---|---|---|---|---|
| | | Average | Stdev | Average | Stdev | Average | Stdev | Average | Stdev |
| AUC | hr*ug/mL | 271 | 33 | 1255 | 383 | 9.8 | 1.6 | 120 | 13 |
| CL | mL/hr/kg | 1.87 | 0.23 | 0.422 | 0.119 | 51.8 | 9.2 | 4.21 | 0.51 |
| K10-HL | hr | 18.0 | 4.2 | 68.9 | 28.5 | 0.760 | 0.123 | 8.84 | 0.73 |
| V1 | ug/mL | 47.4 | 5.4 | 39.2 | 7.4 | 55.9 | 4.7 | 53.5 | 5.3 |
| Vss | mL/kg | 109 | 14 | 78.8 | 13.7 | 127 | 13 | 84.5 | 11.4 |
| Dose | ug/kg | 509 | | 493 | | 500 | | 500 | |
| AUC/Dose(hr*ug/mL)/(mg/kg) | | 532 | 65 | 2546 | 777 | 19.7 | 3.2 | 240 | 26 |

AUC = area under the curve  MRT = mean residence time
CL = clearance  V1 = initial distribution volume  Vss = distribution volume at steady state
K10-HL = half-life from compartment

FIG. 17

SEQUENCE LISTING

<160> NUMBER OF SEQ ID NOS: 492

<210> SEQ ID NO 1
<211> LENGTH: 7
<212> TYPE: PRT
<213> ORGANISM: Artificial Sequence
<220> FEATURE:
<223> OTHER INFORMATION: Synthesized

<400> SEQUENCE: 1

Gly Gly Gly Ser Gly Gly Gly
1               5

<210> SEQ ID NO 2
<211> LENGTH: 20
<212> TYPE: PRT
<213> ORGANISM: Artificial Sequence
<220> FEATURE:
<223> OTHER INFORMATION: Synthesized

<400> SEQUENCE: 2

Glu Thr Gln Arg Cys Thr Trp His Met Gly Glu Leu Val Trp Cys Glu
1               5                   10                  15

Arg Glu His Asn
            20

<210> SEQ ID NO 3
<211> LENGTH: 20
<212> TYPE: PRT
<213> ORGANISM: Artificial Sequence
<220> FEATURE:
<223> OTHER INFORMATION: Synthesized

```
<400> SEQUENCE: 3

Lys Glu Ala Ser Cys Ser Tyr Trp Leu Gly Glu Leu Val Trp Cys Val
1               5                   10                  15

Ala Gly Val Glu
            20

<210> SEQ ID NO 4
<211> LENGTH: 7
<212> TYPE: PRT
<213> ORGANISM: Artificial Sequence
<220> FEATURE:
<223> OTHER INFORMATION: Synthesized

<400> SEQUENCE: 4

Gly Gly Gly Pro Gly Gly Gly
1               5

<210> SEQ ID NO 5
<211> LENGTH: 60
<212> TYPE: DNA
<213> ORGANISM: Artificial Sequence
<220> FEATURE:
<223> OTHER INFORMATION: Synthesized

<400> SEQUENCE: 5
drggwagmar rctgckcttr scacmtgggc gagctggtct ggtgcrvcrv mbkcgaskdw     60

<210> SEQ ID NO 6
<211> LENGTH: 60
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (47)..(47)
<223> OTHER INFORMATION: n is any a or g or c or t/u
<220> FEATURE:
<221> NAME/KEY: misc_feature
<222> LOCATION: (52)..(52)
<223> OTHER INFORMATION: n is any a or g or c or t/u

<400> SEQUENCE: 6
drsvwgsvgr rctgckcctr syrsmtgggc gagctggtct ggtgcrncvv snbsgwskdm     60

<210> SEQ ID NO 7
<211> LENGTH: 60
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (2)..(2)
<223> OTHER INFORMATION: n is any a or g or c or t/u
<220> FEATURE:
<221> NAME/KEY: misc_feature
<222> LOCATION: (4)..(5)
<223> OTHER INFORMATION: n is any a or g or c or t/u
<220> FEATURE:
<221> NAME/KEY: misc_feature
<222> LOCATION: (7)..(8)
<223> OTHER INFORMATION: n is any a or g or c or t/u
<220> FEATURE:
<221> NAME/KEY: misc_feature
<222> LOCATION: (11)..(11)
<223> OTHER INFORMATION: n is any a or g or c or t/u
<220> FEATURE:
<221> NAME/KEY: misc_feature
```

```
<222> LOCATION: (47)..(47)
<223> OTHER INFORMATION: n is any a or g or c or t/u
<220> FEATURE:
<221> NAME/KEY: misc_feature
<222> LOCATION: (49)..(50)
<223> OTHER INFORMATION: n is any a or g or c or t/u
<220> FEATURE:
<221> NAME/KEY: misc_feature
<222> LOCATION: (52)..(53)
<223> OTHER INFORMATION: n is any a or g or c or t/u
<220> FEATURE:
<221> NAME/KEY: misc_feature
<222> LOCATION: (55)..(56)
<223> OTHER INFORMATION: n is any a or g or c or t/u
<220> FEATURE:
<221> NAME/KEY: misc_feature
<222> LOCATION: (58)..(59)
<223> OTHER INFORMATION: n is any a or g or c or t/u

<400> SEQUENCE: 7
dnsnnsnnsv nstgcbvgtd shrsmdsggc gagstckkgw rgtgcrnmnn snnsnnsnnm     60

<210> SEQ ID NO 8
<211> LENGTH: 13
<212> TYPE: PRT
<213> ORGANISM: Artificial Sequence
<220> FEATURE:
<223> OTHER INFORMATION: Synthesized

<400> SEQUENCE: 8

Asp Cys Ala Trp His Leu Gly Glu Leu Val Trp Cys Thr
1               5                   10

<210> SEQ ID NO 9
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(6)
<223> OTHER INFORMATION: Xaa is any amino acid

<400> SEQUENCE: 9

Xaa Xaa Xaa Xaa Xaa Xaa Leu Val Trp
1               5

<210> SEQ ID NO 10
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(4)
<223> OTHER INFORMATION: Xaa is any amino acid

<400> SEQUENCE: 10

Xaa Xaa Xaa Xaa Gly Glu Leu Val Trp
1               5

<210> SEQ ID NO 11
<211> LENGTH: 20
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
```

```
<222> LOCATION: (1)..(4)
<223> OTHER INFORMATION: Xaa is any amino acid
<220> FEATURE:
<221> NAME/KEY: MISC_FEATURE
<222> LOCATION: (6)..(11)
<223> OTHER INFORMATION: Xaa is any amino acid
<220> FEATURE:
<221> NAME/KEY: MISC_FEATURE
<222> LOCATION: (16)..(20)
<223> OTHER INFORMATION: Xaa is any amino acid

<400> SEQUENCE: 11

Xaa Xaa Xaa Xaa Cys Xaa Xaa Xaa Xaa Xaa Xaa Leu Val Trp Cys Xaa
1               5                   10                  15

Xaa Xaa Xaa Xaa
            20

<210> SEQ ID NO 12
<211> LENGTH: 20
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(4)
<223> OTHER INFORMATION: Xaa is any amino acid
<220> FEATURE:
<221> NAME/KEY: MISC_FEATURE
<222> LOCATION: (6)..(9)
<223> OTHER INFORMATION: Xaa is any amino acid
<220> FEATURE:
<221> NAME/KEY: MISC_FEATURE
<222> LOCATION: (16)..(20)
<223> OTHER INFORMATION: Xaa is any amino acid

<400> SEQUENCE: 12

Xaa Xaa Xaa Xaa Cys Xaa Xaa Xaa Xaa Gly Glu Leu Val Trp Cys Xaa
1               5                   10                  15

Xaa Xaa Xaa Xaa
            20

<210> SEQ ID NO 13
<211> LENGTH: 20
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(4)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is Ala, Ser, or Thr
<220> FEATURE:
<221> NAME/KEY: MISC_FEATURE
<222> LOCATION: (7)..(7)
<223> OTHER INFORMATION: Xaa is Trp or Tyr
<220> FEATURE:
<221> NAME/KEY: MISC_FEATURE
<222> LOCATION: (8)..(8)
<223> OTHER INFORMATION: Xaa is His or Trp
<220> FEATURE:
<221> NAME/KEY: MISC_FEATURE
<222> LOCATION: (9)..(9)
<223> OTHER INFORMATION: Xaa is Leu or Met
<220> FEATURE:
<221> NAME/KEY: MISC_FEATURE
<222> LOCATION: (16)..(20)
<223> OTHER INFORMATION: Xaa is any amino acid
```

```
<400> SEQUENCE: 13

Xaa Xaa Xaa Xaa Cys Xaa Xaa Xaa Xaa Gly Glu Leu Val Trp Cys Xaa
1               5                   10                  15

Xaa Xaa Xaa Xaa
            20

<210> SEQ ID NO 14
<211> LENGTH: 20
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is Ser, Arg, or Asp
<220> FEATURE:
<221> NAME/KEY: MISC_FEATURE
<222> LOCATION: (6)..(6)
<223> OTHER INFORMATION: Xaa is Ala, Ser, or Thr
<220> FEATURE:
<221> NAME/KEY: MISC_FEATURE
<222> LOCATION: (7)..(7)
<223> OTHER INFORMATION: Xaa is Trp or Tyr
<220> FEATURE:
<221> NAME/KEY: MISC_FEATURE
<222> LOCATION: (8)..(8)
<223> OTHER INFORMATION: Xaa is His or Trp
<220> FEATURE:
<221> NAME/KEY: MISC_FEATURE
<222> LOCATION: (9)..(9)
<223> OTHER INFORMATION: Xaa is Leu or Met
<220> FEATURE:
<221> NAME/KEY: MISC_FEATURE
<222> LOCATION: (16)..(16)
<223> OTHER INFORMATION: Xaa is Glu, Ser, Thr, or Val
<220> FEATURE:
<221> NAME/KEY: MISC_FEATURE
<222> LOCATION: (17)..(20)
<223> OTHER INFORMATION: Xaa is any amino acid

<400> SEQUENCE: 14

Xaa Xaa Xaa Xaa Cys Xaa Xaa Xaa Xaa Gly Glu Leu Val Trp Cys Xaa
1               5                   10                  15

Xaa Xaa Xaa Xaa
            20

<210> SEQ ID NO 15
<211> LENGTH: 20
<212> TYPE: PRT
<213> ORGANISM: Artificial Sequence
<220> FEATURE:
<223> OTHER INFORMATION: Synthesized

<400> SEQUENCE: 15

Asp Leu Ala Asp Cys Ser Trp His Met Gly Glu Leu Val Trp Cys Ser
1               5                   10                  15

Arg Val Glu Gly
            20

<210> SEQ ID NO 16
<211> LENGTH: 20
<212> TYPE: PRT
<213> ORGANISM: Artificial Sequence
<220> FEATURE:
<223> OTHER INFORMATION: Synthesized
```

```
<400> SEQUENCE: 16

Trp Glu Asp Cys Ala Trp His Leu Gly Glu Leu Val Trp Cys Thr
1               5                   10                  15

Pro Met Glu Phe
            20

<210> SEQ ID NO 17
<211> LENGTH: 20
<212> TYPE: PRT
<213> ORGANISM: Artificial Sequence
<220> FEATURE:
<223> OTHER INFORMATION: Synthesized

<400> SEQUENCE: 17

Lys Glu Ala Ser Cys Ser Tyr Trp Leu Gly Glu Leu Val Trp Cys Asp
1               5                   10                  15

Thr Leu Thr Glu
            20

<210> SEQ ID NO 18
<211> LENGTH: 20
<212> TYPE: PRT
<213> ORGANISM: Artificial Sequence
<220> FEATURE:
<223> OTHER INFORMATION: Synthesized

<400> SEQUENCE: 18

Lys Glu Ala Ser Cys Ser Tyr Trp Leu Gly Glu Leu Val Trp Cys Ser
1               5                   10                  15

Pro Gly Val Glu
            20

<210> SEQ ID NO 19
<211> LENGTH: 20
<212> TYPE: PRT
<213> ORGANISM: Artificial Sequence
<220> FEATURE:
<223> OTHER INFORMATION: Synthesized

<400> SEQUENCE: 19

Lys Glu Ala Ser Cys Ser Tyr Trp Leu Gly Glu Leu Val Trp Cys Ser
1               5                   10                  15

Gly Val Glu Gly
            20

<210> SEQ ID NO 20
<211> LENGTH: 20
<212> TYPE: PRT
<213> ORGANISM: Artificial Sequence
<220> FEATURE:
<223> OTHER INFORMATION: Synthesized

<400> SEQUENCE: 20

Lys Glu Ala Ser Cys Ser Tyr Trp Leu Gly Glu Leu Val Trp Cys Ser
1               5                   10                  15

Ala Gly Val Glu
            20

<210> SEQ ID NO 21
<211> LENGTH: 20
<212> TYPE: PRT
<213> ORGANISM: Artificial Sequence
<220> FEATURE:
```

<223> OTHER INFORMATION: Synthesized

<400> SEQUENCE: 21

Glu Ser Glu Asp Cys Ser Tyr Trp Leu Gly Glu Leu Val Trp Cys Val
1               5                   10                  15

Ala Gly Val Glu
            20

<210> SEQ ID NO 22
<211> LENGTH: 20
<212> TYPE: PRT
<213> ORGANISM: Artificial Sequence
<220> FEATURE:
<223> OTHER INFORMATION: Synthesized

<400> SEQUENCE: 22

Glu Lys Glu Asp Cys Ser Tyr Trp Leu Gly Glu Leu Val Trp Cys Val
1               5                   10                  15

Ala Gly Val Glu
            20

<210> SEQ ID NO 23
<211> LENGTH: 20
<212> TYPE: PRT
<213> ORGANISM: Artificial Sequence
<220> FEATURE:
<223> OTHER INFORMATION: Synthesized

<400> SEQUENCE: 23

Glu Asp Pro Asp Cys Ser Tyr Trp Leu Gly Glu Leu Val Trp Cys Val
1               5                   10                  15

Ala Gly Val Glu
            20

<210> SEQ ID NO 24
<211> LENGTH: 20
<212> TYPE: PRT
<213> ORGANISM: Artificial Sequence
<220> FEATURE:
<223> OTHER INFORMATION: Synthesized

<400> SEQUENCE: 24

Glu Glu Ala Asp Cys Ser Tyr Trp Leu Gly Glu Leu Val Trp Cys Val
1               5                   10                  15

Ala Gly Val Glu
            20

<210> SEQ ID NO 25
<211> LENGTH: 20
<212> TYPE: PRT
<213> ORGANISM: Artificial Sequence
<220> FEATURE:
<223> OTHER INFORMATION: Synthesized

<400> SEQUENCE: 25

Asn Ala Asp Asp Cys Ser Tyr Trp Leu Gly Glu Leu Val Trp Cys Val
1               5                   10                  15

Ala Gly Val Glu
            20

<210> SEQ ID NO 26
<211> LENGTH: 20
<212> TYPE: PRT
<213> ORGANISM: Artificial Sequence

```
<220> FEATURE:
<223> OTHER INFORMATION: Synthesized

<400> SEQUENCE: 26

Ser Glu Thr Thr Cys Ser Tyr Trp Leu Gly Glu Leu Val Trp Cys Val
1               5                   10                  15

Ala Gly Val Glu
            20

<210> SEQ ID NO 27
<211> LENGTH: 19
<212> TYPE: PRT
<213> ORGANISM: Artificial Sequence
<220> FEATURE:
<223> OTHER INFORMATION: Synthesized

<400> SEQUENCE: 27

Ala Trp Lys Thr Cys Gln Trp Leu Gly Glu Leu Val Trp Cys Val Ala
1               5                   10                  15

Gly Val Glu

<210> SEQ ID NO 28
<211> LENGTH: 20
<212> TYPE: PRT
<213> ORGANISM: Artificial Sequence
<220> FEATURE:
<223> OTHER INFORMATION: Synthesized

<400> SEQUENCE: 28

Asp Leu Ala Asp Cys Ser Tyr Trp Leu Gly Glu Leu Val Trp Cys Ser
1               5                   10                  15

Arg Val Glu Gly
            20

<210> SEQ ID NO 29
<211> LENGTH: 20
<212> TYPE: PRT
<213> ORGANISM: Artificial Sequence
<220> FEATURE:
<223> OTHER INFORMATION: Synthesized

<400> SEQUENCE: 29

Lys Glu Ala Asp Cys Ala Trp His Leu Gly Glu Leu Val Trp Cys Val
1               5                   10                  15

Ala Gly Val Glu
            20

<210> SEQ ID NO 30
<211> LENGTH: 20
<212> TYPE: PRT
<213> ORGANISM: Artificial Sequence
<220> FEATURE:
<223> OTHER INFORMATION: Synthesized

<400> SEQUENCE: 30

Lys Glu Ala Glu Cys Ser Tyr His Leu Gly Glu Leu Val Trp Cys Val
1               5                   10                  15

Ala Gly Val Glu
            20

<210> SEQ ID NO 31
<211> LENGTH: 20
<212> TYPE: PRT
<213> ORGANISM: Artificial Sequence
```

```
<220> FEATURE:
<223> OTHER INFORMATION: Synthesized

<400> SEQUENCE: 31

Lys Glu Ala Arg Cys Trp Tyr Trp His Gly Glu Leu Val Trp Cys Ser
1               5                   10                  15

Asp Pro Glu Glu
            20

<210> SEQ ID NO 32
<211> LENGTH: 20
<212> TYPE: PRT
<213> ORGANISM: Artificial Sequence
<220> FEATURE:
<223> OTHER INFORMATION: Synthesized

<400> SEQUENCE: 32

Lys Glu Ala Ser Cys Ser Tyr His Leu Gly Glu Leu Val Trp Cys Val
1               5                   10                  15

Ala Gly Val Glu
            20

<210> SEQ ID NO 33
<211> LENGTH: 20
<212> TYPE: PRT
<213> ORGANISM: Artificial Sequence
<220> FEATURE:
<223> OTHER INFORMATION: Synthesized

<400> SEQUENCE: 33

Lys Glu Ala Ser Cys Ser Trp His Leu Gly Glu Leu Val Trp Cys Val
1               5                   10                  15

Ala Gly Val Glu
            20

<210> SEQ ID NO 34
<211> LENGTH: 20
<212> TYPE: PRT
<213> ORGANISM: Artificial Sequence
<220> FEATURE:
<223> OTHER INFORMATION: Synthesized

<400> SEQUENCE: 34

Lys Glu Ala Ser Cys Ser Tyr Trp Leu Gly Glu Leu Val Trp Cys Thr
1               5                   10                  15

Glu Gly Val Glu
            20

<210> SEQ ID NO 35
<211> LENGTH: 20
<212> TYPE: PRT
<213> ORGANISM: Artificial Sequence
<220> FEATURE:
<223> OTHER INFORMATION: Synthesized

<400> SEQUENCE: 35

Lys Glu Ala Ser Cys Ser Tyr Trp Leu Gly Glu Leu Val Trp Cys Asp
1               5                   10                  15

Asp Gly Val Glu
            20

<210> SEQ ID NO 36
<211> LENGTH: 20
<212> TYPE: PRT
```

```
<213> ORGANISM: Artificial Sequence
<220> FEATURE:
<223> OTHER INFORMATION: Synthesized

<400> SEQUENCE: 36

Lys Glu Ala Ser Cys Ser Tyr Trp Leu Gly Glu Leu Val Trp Cys Ser
1               5                   10                  15

Glu Gly Val Glu
            20

<210> SEQ ID NO 37
<211> LENGTH: 20
<212> TYPE: PRT
<213> ORGANISM: Artificial Sequence
<220> FEATURE:
<223> OTHER INFORMATION: Synthesized

<400> SEQUENCE: 37

Lys Glu Ala Ser Cys Ser Tyr Trp Leu Gly Glu Val Trp Lys Cys Lys
1               5                   10                  15

Ser Gly Val Glu
            20

<210> SEQ ID NO 38
<211> LENGTH: 20
<212> TYPE: PRT
<213> ORGANISM: Artificial Sequence
<220> FEATURE:
<223> OTHER INFORMATION: Synthesized

<400> SEQUENCE: 38

Lys Glu Ala Ser Cys Ser Tyr Trp Leu Gly Glu Leu Val Trp Cys Asp
1               5                   10                  15

Asn Gly Val Glu
            20

<210> SEQ ID NO 39
<211> LENGTH: 20
<212> TYPE: PRT
<213> ORGANISM: Artificial Sequence
<220> FEATURE:
<223> OTHER INFORMATION: Synthesized

<400> SEQUENCE: 39

Lys Glu Ala Ser Cys Ser Tyr Trp Leu Gly Glu Leu Val Trp Cys Asp
1               5                   10                  15

Thr Phe Asp Glu
            20

<210> SEQ ID NO 40
<211> LENGTH: 20
<212> TYPE: PRT
<213> ORGANISM: Artificial Sequence
<220> FEATURE:
<223> OTHER INFORMATION: Synthesized

<400> SEQUENCE: 40

Lys Glu Ala Ser Cys Ser Tyr Trp Leu Gly Glu Leu Val Trp Cys Asp
1               5                   10                  15

Gly Leu Asp Glu
            20

<210> SEQ ID NO 41
<211> LENGTH: 20
```

<212> TYPE: PRT
<213> ORGANISM: Artificial Sequence
<220> FEATURE:
<223> OTHER INFORMATION: Synthesized

<400> SEQUENCE: 41

Lys Glu Ala Ser Cys Ser Tyr Trp Leu Gly Glu Leu Val Trp Cys Val
1               5                   10                  15

Gly Leu Asp Glu
            20

<210> SEQ ID NO 42
<211> LENGTH: 20
<212> TYPE: PRT
<213> ORGANISM: Artificial Sequence
<220> FEATURE:
<223> OTHER INFORMATION: Synthesized

<400> SEQUENCE: 42

Lys Glu Ala Ser Cys Ser Tyr Trp Leu Gly Glu Leu Val Trp Cys Glu
1               5                   10                  15

Asp Thr Leu Glu
            20

<210> SEQ ID NO 43
<211> LENGTH: 20
<212> TYPE: PRT
<213> ORGANISM: Artificial Sequence
<220> FEATURE:
<223> OTHER INFORMATION: Synthesized

<400> SEQUENCE: 43

Lys Glu Ala Ser Cys Ser Tyr Trp Leu Gly Glu Leu Val Trp Cys Glu
1               5                   10                  15

Asp Thr Met Glu
            20

<210> SEQ ID NO 44
<211> LENGTH: 20
<212> TYPE: PRT
<213> ORGANISM: Artificial Sequence
<220> FEATURE:
<223> OTHER INFORMATION: Synthesized

<400> SEQUENCE: 44

Lys Glu Ala Ser Cys Ser Tyr Trp Leu Gly Glu Leu Val Trp Cys Glu
1               5                   10                  15

Asp Met Met Glu
            20

<210> SEQ ID NO 45
<211> LENGTH: 20
<212> TYPE: PRT
<213> ORGANISM: Artificial Sequence
<220> FEATURE:
<223> OTHER INFORMATION: Synthesized

<400> SEQUENCE: 45

Trp Val Glu Asp Cys Ser Trp His Met Gly Glu Leu Val Trp Cys Asp
1               5                   10                  15

Gly Gly Glu Phe
            20

<210> SEQ ID NO 46

```
<211> LENGTH: 20
<212> TYPE: PRT
<213> ORGANISM: Artificial Sequence
<220> FEATURE:
<223> OTHER INFORMATION: Synthesized

<400> SEQUENCE: 46

Lys Glu Ala Ser Cys Ser Tyr Trp Leu Gly Glu Leu Val Trp Cys Asp
1               5                   10                  15

Trp Met Asn Gly
            20

<210> SEQ ID NO 47
<211> LENGTH: 20
<212> TYPE: PRT
<213> ORGANISM: Artificial Sequence
<220> FEATURE:
<223> OTHER INFORMATION: Synthesized

<400> SEQUENCE: 47

Lys Glu Ala Ser Cys Ser Tyr Trp Leu Gly Glu Leu Val Trp Cys Asp
1               5                   10                  15

Asp Thr Pro Val
            20

<210> SEQ ID NO 48
<211> LENGTH: 20
<212> TYPE: PRT
<213> ORGANISM: Artificial Sequence
<220> FEATURE:
<223> OTHER INFORMATION: Synthesized

<400> SEQUENCE: 48

Lys Glu Ala Ser Cys Ser Tyr Trp Leu Gly Glu Leu Val Trp Cys Asp
1               5                   10                  15

Asp Tyr Gly Glu
            20

<210> SEQ ID NO 49
<211> LENGTH: 20
<212> TYPE: PRT
<213> ORGANISM: Artificial Sequence
<220> FEATURE:
<223> OTHER INFORMATION: Synthesized

<400> SEQUENCE: 49

Lys Glu Ala Ser Cys Ser Tyr Trp Leu Gly Glu Leu Val Trp Cys Ser
1               5                   10                  15

Asp Leu Trp Glu
            20

<210> SEQ ID NO 50
<211> LENGTH: 20
<212> TYPE: PRT
<213> ORGANISM: Artificial Sequence
<220> FEATURE:
<223> OTHER INFORMATION: Synthesized

<400> SEQUENCE: 50

Trp Arg Gly Gly Cys Ser Trp His Met Gly Glu Leu Val Trp Cys Glu
1               5                   10                  15

His Asp Met Glu
            20
```

```
<210> SEQ ID NO 51
<211> LENGTH: 20
<212> TYPE: PRT
<213> ORGANISM: Artificial Sequence
<220> FEATURE:
<223> OTHER INFORMATION: Synthesized

<400> SEQUENCE: 51

Ala Val Ser Lys Cys Ser Phe His Met Gly Glu Leu Val Trp Cys Ser
1               5                   10                  15

Asp Val Met Asn
            20

<210> SEQ ID NO 52
<211> LENGTH: 20
<212> TYPE: PRT
<213> ORGANISM: Artificial Sequence
<220> FEATURE:
<223> OTHER INFORMATION: Synthesized

<400> SEQUENCE: 52

Asn Gln Val Ser Cys Ser Tyr Ser Arg Gly Glu Leu Val Trp Cys Ser
1               5                   10                  15

Lys Gln Ser Gln
            20

<210> SEQ ID NO 53
<211> LENGTH: 20
<212> TYPE: PRT
<213> ORGANISM: Artificial Sequence
<220> FEATURE:
<223> OTHER INFORMATION: Synthesized

<400> SEQUENCE: 53

Gly Arg Met Glu Cys Ala Trp His Gln Gly Glu Leu Val Trp Cys Thr
1               5                   10                  15

Pro Thr Leu Glu
            20

<210> SEQ ID NO 54
<211> LENGTH: 20
<212> TYPE: PRT
<213> ORGANISM: Artificial Sequence
<220> FEATURE:
<223> OTHER INFORMATION: Synthesized

<400> SEQUENCE: 54

Gly Thr Met Glu Cys Ser Trp His Gln Gly Glu Leu Val Trp Cys Thr
1               5                   10                  15

Pro Thr Leu Ala
            20

<210> SEQ ID NO 55
<211> LENGTH: 20
<212> TYPE: PRT
<213> ORGANISM: Artificial Sequence
<220> FEATURE:
<223> OTHER INFORMATION: Synthesized

<400> SEQUENCE: 55

Glu Met Arg Asp Cys Ser Trp His Leu Gly Leu Val Trp Cys Ala
1               5                   10                  15

His Met Glu Gly
            20
```

-continued

```
<210> SEQ ID NO 56
<211> LENGTH: 20
<212> TYPE: PRT
<213> ORGANISM: Artificial Sequence
<220> FEATURE:
<223> OTHER INFORMATION: Synthesized

<400> SEQUENCE: 56

Gly Ser Trp Glu Cys Ala Tyr His Leu Gly Glu Leu Val Trp Cys Glu
1               5                   10                  15

Thr Gly Ser Gly
            20

<210> SEQ ID NO 57
<211> LENGTH: 20
<212> TYPE: PRT
<213> ORGANISM: Artificial Sequence
<220> FEATURE:
<223> OTHER INFORMATION: Synthesized

<400> SEQUENCE: 57

Val Ala Glu Pro Cys Ala Tyr His Leu Gly Glu Leu Val Trp Cys Glu
1               5                   10                  15

Val Leu Lys Gly
            20

<210> SEQ ID NO 58
<211> LENGTH: 20
<212> TYPE: PRT
<213> ORGANISM: Artificial Sequence
<220> FEATURE:
<223> OTHER INFORMATION: Synthesized

<400> SEQUENCE: 58

Lys Glu Ala Met Cys Ser Tyr Trp Leu Gly Glu Leu Val Trp Cys Glu
1               5                   10                  15

Ser Asp Met Pro
            20

<210> SEQ ID NO 59
<211> LENGTH: 20
<212> TYPE: PRT
<213> ORGANISM: Artificial Sequence
<220> FEATURE:
<223> OTHER INFORMATION: Synthesized

<400> SEQUENCE: 59

Asp Leu Ala Asp Cys Ser Trp His Leu Gly Glu Leu Val Trp Cys Ser
1               5                   10                  15

Arg Val Glu Gly
            20

<210> SEQ ID NO 60
<211> LENGTH: 20
<212> TYPE: PRT
<213> ORGANISM: Artificial Sequence
<220> FEATURE:
<223> OTHER INFORMATION: Synthesized

<400> SEQUENCE: 60

Asp Leu Ala Asp Cys Ser Trp His Leu Gly Glu Leu Val Trp Cys Val
1               5                   10                  15

Gly Leu Asp Glu
            20
```

```
<210> SEQ ID NO 61
<211> LENGTH: 20
<212> TYPE: PRT
<213> ORGANISM: Artificial Sequence
<220> FEATURE:
<223> OTHER INFORMATION: Synthesized

<400> SEQUENCE: 61

Trp Val Glu Asp Cys Ser Trp His Leu Gly Glu Leu Val Trp Cys Val
1               5                   10                  15

Gly Leu Asp Phe
            20

<210> SEQ ID NO 62
<211> LENGTH: 20
<212> TYPE: PRT
<213> ORGANISM: Artificial Sequence
<220> FEATURE:
<223> OTHER INFORMATION: Synthesized

<400> SEQUENCE: 62

Lys Val Ala Asp Cys Ala Trp His Met Gly Glu Leu Val Trp Cys Thr
1               5                   10                  15

Glu Val Glu Gly
            20

<210> SEQ ID NO 63
<211> LENGTH: 20
<212> TYPE: PRT
<213> ORGANISM: Artificial Sequence
<220> FEATURE:
<223> OTHER INFORMATION: Synthesized

<400> SEQUENCE: 63

Gly Glu Glu Asp Cys Ser Tyr His Leu Gly Leu Val Met Cys Thr
1               5                   10                  15

Glu Leu Asp Asp
            20

<210> SEQ ID NO 64
<211> LENGTH: 20
<212> TYPE: PRT
<213> ORGANISM: Artificial Sequence
<220> FEATURE:
<223> OTHER INFORMATION: Synthesized

<400> SEQUENCE: 64

Gly Val Ala Asp Cys Ala Trp His Leu Gly Glu Leu Val Trp Cys Thr
1               5                   10                  15

Glu Arg Glu Asp
            20

<210> SEQ ID NO 65
<211> LENGTH: 20
<212> TYPE: PRT
<213> ORGANISM: Artificial Sequence
<220> FEATURE:
<223> OTHER INFORMATION: Synthesized

<400> SEQUENCE: 65

Gly Glu Glu Asp Cys Ala Trp His Leu Gly Glu Leu Val Trp Cys Ser
1               5                   10                  15

Gly Gly Asp Phe
```

20

<210> SEQ ID NO 66
<211> LENGTH: 20
<212> TYPE: PRT
<213> ORGANISM: Artificial Sequence
<220> FEATURE:
<223> OTHER INFORMATION: Synthesized

<400> SEQUENCE: 66

Trp Glu Ala Asp Cys Ala Trp His Leu Gly Glu Leu Val Trp Cys Thr
1               5                   10                  15

Lys Val Glu Glu
            20

<210> SEQ ID NO 67
<211> LENGTH: 20
<212> TYPE: PRT
<213> ORGANISM: Artificial Sequence
<220> FEATURE:
<223> OTHER INFORMATION: Synthesized

<400> SEQUENCE: 67

Gly Glu Ala Asp Cys Ser Tyr His Leu Gly Glu Leu Val Trp Cys Asn
1               5                   10                  15

Asp Phe Glu Glu
            20

<210> SEQ ID NO 68
<211> LENGTH: 19
<212> TYPE: PRT
<213> ORGANISM: Artificial Sequence
<220> FEATURE:
<223> OTHER INFORMATION: Synthesized

<400> SEQUENCE: 68

Trp Val Asp Cys Ala Tyr His Leu Gly Glu Leu Val Trp Cys Ser Thr
1               5                   10                  15

Phe Glu Glu

<210> SEQ ID NO 69
<211> LENGTH: 20
<212> TYPE: PRT
<213> ORGANISM: Artificial Sequence
<220> FEATURE:
<223> OTHER INFORMATION: Synthesized

<400> SEQUENCE: 69

Trp Val Glu Asp Cys Ala Trp His Met Gly Glu Leu Val Trp Cys Thr
1               5                   10                  15

Lys Val Asp Glu
            20

<210> SEQ ID NO 70
<211> LENGTH: 20
<212> TYPE: PRT
<213> ORGANISM: Artificial Sequence
<220> FEATURE:
<223> OTHER INFORMATION: Synthesized

<400> SEQUENCE: 70

Arg Glu Ala Asp Cys Ala Trp His Leu Gly Glu Leu Val Trp Cys Ser
1               5                   10                  15

Glu Arg Asp Leu

```
                  20

<210> SEQ ID NO 71
<211> LENGTH: 20
<212> TYPE: PRT
<213> ORGANISM: Artificial Sequence
<220> FEATURE:
<223> OTHER INFORMATION: Synthesized

<400> SEQUENCE: 71

Glu Glu Ala Ser Cys Ala Tyr His Leu Gly Glu Leu Val Trp Cys Asp
1               5                   10                  15

Ala Phe Asp Val
            20

<210> SEQ ID NO 72
<211> LENGTH: 20
<212> TYPE: PRT
<213> ORGANISM: Artificial Sequence
<220> FEATURE:
<223> OTHER INFORMATION: Sythesized

<400> SEQUENCE: 72

Arg Val Ala Ser Cys Ala Trp His Leu Gly Glu Leu Val Trp Cys Asp
1               5                   10                  15

Gly Leu Asp Gly
            20

<210> SEQ ID NO 73
<211> LENGTH: 20
<212> TYPE: PRT
<213> ORGANISM: Artificial Sequence
<220> FEATURE:
<223> OTHER INFORMATION: Synthesized

<400> SEQUENCE: 73

Gly Glu Ala Asp Cys Ala Trp His Leu Gly Glu Leu Val Trp Cys Thr
1               5                   10                  15

Lys Val Glu Glu
            20

<210> SEQ ID NO 74
<211> LENGTH: 20
<212> TYPE: PRT
<213> ORGANISM: Artificial Sequence
<220> FEATURE:
<223> OTHER INFORMATION: Synthesized

<400> SEQUENCE: 74

Gly Glu Ala Ser Cys Ala Tyr His Leu Gly Glu Leu Val Trp Cys Asp
1               5                   10                  15

Glu Gly Glu Gly
            20

<210> SEQ ID NO 75
<211> LENGTH: 20
<212> TYPE: PRT
<213> ORGANISM: Artificial Sequence
<220> FEATURE:
<223> OTHER INFORMATION: Synthesized

<400> SEQUENCE: 75

Arg Val Glu Asp Cys Ala Tyr His Leu Gly Glu Leu Val Trp Cys Thr
1               5                   10                  15
```

```
Glu Gly Asp Glu
        20

<210> SEQ ID NO 76
<211> LENGTH: 20
<212> TYPE: PRT
<213> ORGANISM: Artificial Sequence
<220> FEATURE:
<223> OTHER INFORMATION: Synthesized

<400> SEQUENCE: 76

Glu Glu Pro Asp Cys Ser Trp His Leu Gly Glu Leu Val Met Cys Thr
1               5                   10                  15

Pro Met Glu Val
        20

<210> SEQ ID NO 77
<211> LENGTH: 20
<212> TYPE: PRT
<213> ORGANISM: Artificial Sequence
<220> FEATURE:
<223> OTHER INFORMATION: Synthesized

<400> SEQUENCE: 77

Lys Glu Ala Asp Cys Ala Trp His Met Gly Glu Leu Val Trp Cys Ser
1               5                   10                  15

Glu Met Glu Gly
        20

<210> SEQ ID NO 78
<211> LENGTH: 20
<212> TYPE: PRT
<213> ORGANISM: Artificial Sequence
<220> FEATURE:
<223> OTHER INFORMATION: Synthesized

<400> SEQUENCE: 78

Glu Gln Ala Asp Cys Ala Trp His Leu Gly Glu Leu Val Trp Cys Thr
1               5                   10                  15

Pro Met Val Phe
        20

<210> SEQ ID NO 79
<211> LENGTH: 20
<212> TYPE: PRT
<213> ORGANISM: Artificial Sequence
<220> FEATURE:
<223> OTHER INFORMATION: Synthesized

<400> SEQUENCE: 79

Glu Glu Pro Asp Cys Ser Trp His Leu Gly Glu Leu Val Trp Cys Thr
1               5                   10                  15

Pro Ile Glu Val
        20

<210> SEQ ID NO 80
<211> LENGTH: 20
<212> TYPE: PRT
<213> ORGANISM: Artificial Sequence
<220> FEATURE:
<223> OTHER INFORMATION: Synthesized

<400> SEQUENCE: 80

Gly Glu Pro Asp Cys Ala Trp His Leu Gly Glu Leu Val Trp Cys Thr
1               5                   10                  15
```

```
Pro Met Val Phe
            20

<210> SEQ ID NO 81
<211> LENGTH: 20
<212> TYPE: PRT
<213> ORGANISM: Artificial Sequence
<220> FEATURE:
<223> OTHER INFORMATION: Synthesized

<400> SEQUENCE: 81

Gly Glu Gln Asp Cys Ser Tyr His Met Gly Glu Leu Val Trp Cys Thr
1               5                   10                  15

Thr Val Asp Gly
            20

<210> SEQ ID NO 82
<211> LENGTH: 20
<212> TYPE: PRT
<213> ORGANISM: Artificial Sequence
<220> FEATURE:
<223> OTHER INFORMATION: Synthesized

<400> SEQUENCE: 82

Gly Val Arg Asn Cys Ala Tyr His Leu Gly Glu Leu Val Trp Cys Thr
1               5                   10                  15

Pro Met Glu Phe
            20

<210> SEQ ID NO 83
<211> LENGTH: 20
<212> TYPE: PRT
<213> ORGANISM: Artificial Sequence
<220> FEATURE:
<223> OTHER INFORMATION: Synthesized

<400> SEQUENCE: 83

Arg Val Ala Asp Cys Ala Trp His Met Gly Glu Leu Val Trp Cys Ser
1               5                   10                  15

Glu Leu Glu Val
            20

<210> SEQ ID NO 84
<211> LENGTH: 20
<212> TYPE: PRT
<213> ORGANISM: Artificial Sequence
<220> FEATURE:
<223> OTHER INFORMATION: Synthesized

<400> SEQUENCE: 84

Gly Glu Ala Asp Cys Ala Trp His Leu Gly Glu Leu Val Trp Cys Thr
1               5                   10                  15

Pro Met Asp Leu
            20

<210> SEQ ID NO 85
<211> LENGTH: 20
<212> TYPE: PRT
<213> ORGANISM: Artificial Sequence
<220> FEATURE:
<223> OTHER INFORMATION: Synthesized

<400> SEQUENCE: 85

Gly Glu Gln Asp Cys Ser Trp His Leu Gly Glu Leu Val Trp Cys Thr
```

```
                1               5                  10                  15

Pro Met Glu Val
            20

<210> SEQ ID NO 86
<211> LENGTH: 20
<212> TYPE: PRT
<213> ORGANISM: Artificial Sequence
<220> FEATURE:
<223> OTHER INFORMATION: Synthesized

<400> SEQUENCE: 86

Gly Met Arg Asp Cys Ser Tyr His Leu Gly Glu Leu Val Trp Cys Ser
1               5                   10                  15

Asp Met Glu Leu
            20

<210> SEQ ID NO 87
<211> LENGTH: 20
<212> TYPE: PRT
<213> ORGANISM: Artificial Sequence
<220> FEATURE:
<223> OTHER INFORMATION: Synthesized

<400> SEQUENCE: 87

Glu Val Ala Asp Cys Ser Trp His Leu Gly Leu Val Trp Cys Thr
1               5                   10                  15

Glu Gly Glu Phe
            20

<210> SEQ ID NO 88
<211> LENGTH: 20
<212> TYPE: PRT
<213> ORGANISM: Artificial Sequence
<220> FEATURE:
<223> OTHER INFORMATION: Synthesized

<400> SEQUENCE: 88

Gly Glu Glu Asp Cys Ala Trp His Leu Gly Glu Leu Val Trp Cys Thr
1               5                   10                  15

Asp Val Glu Asp
            20

<210> SEQ ID NO 89
<211> LENGTH: 20
<212> TYPE: PRT
<213> ORGANISM: Artificial Sequence
<220> FEATURE:
<223> OTHER INFORMATION: Synthesized

<400> SEQUENCE: 89

Glu Val Glu Asp Cys Ala Tyr His Leu Gly Glu Leu Val Trp Cys Ser
1               5                   10                  15

Asp Leu Glu Gly
            20

<210> SEQ ID NO 90
<211> LENGTH: 20
<212> TYPE: PRT
<213> ORGANISM: Artificial Sequence
<220> FEATURE:
<223> OTHER INFORMATION: Synthesized

<400> SEQUENCE: 90
```

Trp Glu Glu Asp Cys Ala Trp His Leu Gly Glu Leu Val Trp Cys Ala
1               5                   10                  15

Glu Phe Asp Glu
            20

<210> SEQ ID NO 91
<211> LENGTH: 20
<212> TYPE: PRT
<213> ORGANISM: Artificial Sequence
<220> FEATURE:
<223> OTHER INFORMATION: Synthesized

<400> SEQUENCE: 91

Lys Glu Ala Ser Cys Ala Trp His Leu Gly Glu Leu Val Trp Cys Ser
1               5                   10                  15

Glu Val Glu Glu
            20

<210> SEQ ID NO 92
<211> LENGTH: 20
<212> TYPE: PRT
<213> ORGANISM: Artificial Sequence
<220> FEATURE:
<223> OTHER INFORMATION: Synthesized

<400> SEQUENCE: 92

Ala Glu Ala Asp Cys Ala Trp His Leu Gly Glu Leu Val Trp Cys Thr
1               5                   10                  15

Lys Val Glu Glu
            20

<210> SEQ ID NO 93
<211> LENGTH: 20
<212> TYPE: PRT
<213> ORGANISM: Artificial Sequence
<220> FEATURE:
<223> OTHER INFORMATION: Synthesized

<400> SEQUENCE: 93

Trp Ala Ala Asp Cys Ala Trp His Leu Gly Glu Leu Val Trp Cys Thr
1               5                   10                  15

Lys Val Glu Glu
            20

<210> SEQ ID NO 94
<211> LENGTH: 20
<212> TYPE: PRT
<213> ORGANISM: Artificial Sequence
<220> FEATURE:
<223> OTHER INFORMATION: Synthesized

<400> SEQUENCE: 94

Trp Glu Pro Asp Cys Ala Trp His Leu Gly Glu Leu Val Trp Cys Thr
1               5                   10                  15

Lys Val Glu Glu
            20

<210> SEQ ID NO 95
<211> LENGTH: 20
<212> TYPE: PRT
<213> ORGANISM: Artificial Sequence
<220> FEATURE:
<223> OTHER INFORMATION: Synthesized

<400> SEQUENCE: 95

Trp Glu Ala Ala Cys Ala Trp His Leu Gly Glu Leu Val Trp Cys Thr
1               5                   10                  15

Lys Val Glu Glu
            20

<210> SEQ ID NO 96
<211> LENGTH: 20
<212> TYPE: PRT
<213> ORGANISM: Artificial Sequence
<220> FEATURE:
<223> OTHER INFORMATION: Synthesized

<400> SEQUENCE: 96

Trp Glu Ala Ala Cys Ser Trp His Leu Gly Glu Leu Val Trp Cys Thr
1               5                   10                  15

Lys Val Glu Glu
            20

<210> SEQ ID NO 97
<211> LENGTH: 20
<212> TYPE: PRT
<213> ORGANISM: Artificial Sequence
<220> FEATURE:
<223> OTHER INFORMATION: Synthesized

<400> SEQUENCE: 97

Trp Glu Ala Asp Cys Ala Ala His Leu Gly Glu Leu Val Trp Cys Thr
1               5                   10                  15

Lys Val Glu Glu
            20

<210> SEQ ID NO 98
<211> LENGTH: 20
<212> TYPE: PRT
<213> ORGANISM: Artificial Sequence
<220> FEATURE:
<223> OTHER INFORMATION: Synthesized

<400> SEQUENCE: 98

Trp Glu Ala Asp Cys Ala Trp Ala Leu Gly Glu Leu Val Trp Cys Thr
1               5                   10                  15

Lys Val Glu Glu
            20

<210> SEQ ID NO 99
<211> LENGTH: 20
<212> TYPE: PRT
<213> ORGANISM: Artificial Sequence
<220> FEATURE:
<223> OTHER INFORMATION: Synthesized

<400> SEQUENCE: 99

Trp Glu Ala Asp Cys Ala Trp His Ala Gly Glu Leu Val Trp Cys Thr
1               5                   10                  15

Lys Val Glu Glu
            20

<210> SEQ ID NO 100
<211> LENGTH: 20
<212> TYPE: PRT
<213> ORGANISM: Artificial Sequence
<220> FEATURE:
<223> OTHER INFORMATION: Synthesized

```
<400> SEQUENCE: 100

Trp Glu Ala Asp Cys Ala Trp His Leu Ala Glu Leu Val Trp Cys Thr
1               5                  10                  15

Lys Val Glu Glu
            20

<210> SEQ ID NO 101
<211> LENGTH: 20
<212> TYPE: PRT
<213> ORGANISM: Artificial Sequence
<220> FEATURE:
<223> OTHER INFORMATION: Synthesized

<400> SEQUENCE: 101

Trp Glu Ala Asp Cys Ala Trp His Leu Gly Ala Leu Val Trp Cys Thr
1               5                  10                  15

Lys Val Glu Glu
            20

<210> SEQ ID NO 102
<211> LENGTH: 20
<212> TYPE: PRT
<213> ORGANISM: Artificial Sequence
<220> FEATURE:
<223> OTHER INFORMATION: Synthesized

<400> SEQUENCE: 102

Trp Glu Ala Asp Cys Ala Trp His Leu Gly Glu Ala Val Trp Cys Thr
1               5                  10                  15

Lys Val Glu Glu
            20

<210> SEQ ID NO 103
<211> LENGTH: 20
<212> TYPE: PRT
<213> ORGANISM: Artificial Sequence
<220> FEATURE:
<223> OTHER INFORMATION: Synthesized

<400> SEQUENCE: 103

Trp Glu Ala Asp Cys Ala Trp His Leu Gly Glu Leu Ala Trp Cys Thr
1               5                  10                  15

Lys Val Glu Glu
            20

<210> SEQ ID NO 104
<211> LENGTH: 20
<212> TYPE: PRT
<213> ORGANISM: Artificial Sequence
<220> FEATURE:
<223> OTHER INFORMATION: Synthesized

<400> SEQUENCE: 104

Trp Glu Ala Asp Cys Ala Trp His Leu Gly Glu Leu Val Ala Cys Thr
1               5                  10                  15

Lys Val Glu Glu
            20

<210> SEQ ID NO 105
<211> LENGTH: 20
<212> TYPE: PRT
<213> ORGANISM: Artificial Sequence
<220> FEATURE:
<223> OTHER INFORMATION: Synthesized
```

```
<400> SEQUENCE: 105

Trp Glu Ala Asp Cys Ala Trp His Leu Gly Glu Leu Val Trp Cys Ala
1               5                   10                  15

Lys Val Glu Glu
            20

<210> SEQ ID NO 106
<211> LENGTH: 20
<212> TYPE: PRT
<213> ORGANISM: Artificial Sequence
<220> FEATURE:
<223> OTHER INFORMATION: Synthesized

<400> SEQUENCE: 106

Trp Glu Ala Asp Cys Ala Trp His Leu Gly Glu Leu Val Trp Cys Thr
1               5                   10                  15

Ala Val Glu Glu
            20

<210> SEQ ID NO 107
<211> LENGTH: 20
<212> TYPE: PRT
<213> ORGANISM: Artificial Sequence
<220> FEATURE:
<223> OTHER INFORMATION: Synthesized

<400> SEQUENCE: 107

Trp Glu Ala Asp Cys Ala Trp His Leu Gly Glu Leu Val Trp Cys Thr
1               5                   10                  15

Lys Ala Glu Glu
            20

<210> SEQ ID NO 108
<211> LENGTH: 20
<212> TYPE: PRT
<213> ORGANISM: Artificial Sequence
<220> FEATURE:
<223> OTHER INFORMATION: Synthesized

<400> SEQUENCE: 108

Trp Glu Ala Asp Cys Ala Trp His Leu Gly Glu Leu Val Trp Cys Thr
1               5                   10                  15

Lys Val Ala Glu
            20

<210> SEQ ID NO 109
<211> LENGTH: 16
<212> TYPE: PRT
<213> ORGANISM: Artificial Sequence
<220> FEATURE:
<223> OTHER INFORMATION: Synthesized

<400> SEQUENCE: 109

Asp Cys Ala Trp His Leu Gly Glu Leu Val Trp Cys Thr Gly Gly Gly
1               5                   10                  15

<210> SEQ ID NO 110
<211> LENGTH: 19
<212> TYPE: PRT
<213> ORGANISM: Artificial Sequence
<220> FEATURE:
<223> OTHER INFORMATION: Synthesized

<400> SEQUENCE: 110
```

```
Gly Gly Gly Trp Glu Ala Asp Cys Ala Trp His Leu Gly Glu Leu Val
1               5                   10                  15

Trp Cys Thr

<210> SEQ ID NO 111
<211> LENGTH: 78
<212> TYPE: DNA
<213> ORGANISM: Artificial Sequence
<220> FEATURE:
<223> OTHER INFORMATION: Synthesized

<400> SEQUENCE: 111
acaaacgcgt acgctgactg cgcttggcac ctgggcgagc tggtctggtg caccggagga    60
ggagatatcc agttgacc                                                 78

<210> SEQ ID NO 112
<211> LENGTH: 88
<212> TYPE: DNA
<213> ORGANISM: Artificial Sequence
<220> FEATURE:
<223> OTHER INFORMATION: Synthesized

<400> SEQUENCE: 112
aacaggggag agtgtggagg aggatgggaa gcagactgcg cttggcacct gggcgagctg    60
gtctggtgca cctaagctga tcctctac                                      88

<210> SEQ ID NO 113
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (7)..(9)
<223> OTHER INFORMATION: Xaa is any amino acid

<400> SEQUENCE: 113

Phe Cys Xaa Asp Trp Pro Xaa Xaa Xaa Ser Cys
1               5                   10

<210> SEQ ID NO 114
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (4)..(6)
<223> OTHER INFORMATION: Xaa is any amino acid

<400> SEQUENCE: 114

Val Cys Tyr Xaa Xaa Xaa Ile Cys Phe
1               5

<210> SEQ ID NO 115
<211> LENGTH: 7
<212> TYPE: PRT
<213> ORGANISM: Artificial Sequence
<220> FEATURE:
<223> OTHER INFORMATION: Synthesized
```

```
<220> FEATURE:
<221> NAME/KEY: MISC_FEATURE
<222> LOCATION: (3)..(3)
<223> OTHER INFORMATION: Xaa is selected from the group consisting of
      Ile, Phe, Tyr and Val
<220> FEATURE:
<221> NAME/KEY: MISC_FEATURE
<222> LOCATION: (6)..(6)
<223> OTHER INFORMATION: Xaa is any amino acid

<400> SEQUENCE: 115

Cys Tyr Xaa Pro Gly Xaa Cys
1               5

<210> SEQ ID NO 116
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is any amino acid

<400> SEQUENCE: 116

Asp Xaa Cys Leu Pro Xaa Trp Gly Cys Leu Trp
1               5                   10

<210> SEQ ID NO 117
<211> LENGTH: 12
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (4)..(5)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is any amino acid

<400> SEQUENCE: 117

Trp Cys Asp Xaa Xaa Leu Xaa Ala Xaa Asp Leu Cys
1               5                   10

<210> SEQ ID NO 118
<211> LENGTH: 10
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (4)..(4)
<223> OTHER INFORMATION: Xaa is any amino acid

<400> SEQUENCE: 118

Asp Leu Val Xaa Leu Gly Leu Glu Cys Trp
1               5                   10
```

```
<210> SEQ ID NO 119
<211> LENGTH: 11
<212> TYPE: PRT
<213> ORGANISM: Artificial Sequence
<220> FEATURE:
<223> OTHER INFORMATION: Synthesized

<400> SEQUENCE: 119

Asp Leu Cys Leu Arg Asp Trp Gly Cys Leu Trp
1               5                   10

<210> SEQ ID NO 120
<211> LENGTH: 11
<212> TYPE: PRT
<213> ORGANISM: Artificial Sequence
<220> FEATURE:
<223> OTHER INFORMATION: Synthesized

<400> SEQUENCE: 120

Asp Ile Cys Leu Pro Arg Trp Gly Cys Leu Trp
1               5                   10

<210> SEQ ID NO 121
<211> LENGTH: 15
<212> TYPE: PRT
<213> ORGANISM: Artificial Sequence
<220> FEATURE:
<223> OTHER INFORMATION: Synthesized

<400> SEQUENCE: 121

Met Glu Asp Ile Cys Leu Pro Arg Trp Gly Cys Leu Trp Glu Asp
1               5                   10                  15

<210> SEQ ID NO 122
<211> LENGTH: 20
<212> TYPE: PRT
<213> ORGANISM: Artificial Sequence
<220> FEATURE:
<223> OTHER INFORMATION: Synthesized

<400> SEQUENCE: 122

Gln Arg Leu Met Glu Asp Ile Cys Leu Pro Arg Trp Gly Cys Leu Trp
1               5                   10                  15

Glu Asp Asp Phe
            20

<210> SEQ ID NO 123
<211> LENGTH: 20
<212> TYPE: PRT
<213> ORGANISM: Artificial Sequence
<220> FEATURE:
<223> OTHER INFORMATION: Synthesized

<400> SEQUENCE: 123

Gln Gly Leu Ile Gly Asp Ile Cys Leu Pro Arg Trp Gly Cys Leu Trp
1               5                   10                  15

Gly Asp Ser Val
            20

<210> SEQ ID NO 124
<211> LENGTH: 21
<212> TYPE: PRT
<213> ORGANISM: Artificial Sequence
<220> FEATURE:
<223> OTHER INFORMATION: Synthesized

<400> SEQUENCE: 124
```

```
Gln Gly Leu Ile Gly Asp Ile Cys Leu Pro Arg Trp Gly Cys Leu Trp
1               5                   10                  15

Gly Asp Ser Val Lys
            20

<210> SEQ ID NO 125
<211> LENGTH: 15
<212> TYPE: PRT
<213> ORGANISM: Artificial Sequence
<220> FEATURE:
<223> OTHER INFORMATION: Synthesized

<400> SEQUENCE: 125

Glu Asp Ile Cys Leu Pro Arg Trp Gly Cys Leu Trp Glu Asp Asp
1               5                   10                  15

<210> SEQ ID NO 126
<211> LENGTH: 18
<212> TYPE: PRT
<213> ORGANISM: Artificial Sequence
<220> FEATURE:
<223> OTHER INFORMATION: Synthesized

<400> SEQUENCE: 126

Arg Leu Met Glu Asp Ile Cys Leu Pro Arg Trp Gly Cys Leu Trp Glu
1               5                   10                  15

Asp Asp

<210> SEQ ID NO 127
<211> LENGTH: 16
<212> TYPE: PRT
<213> ORGANISM: Artificial Sequence
<220> FEATURE:
<223> OTHER INFORMATION: Synthesized

<400> SEQUENCE: 127

Met Glu Asp Ile Cys Leu Pro Arg Trp Gly Cys Leu Trp Glu Asp Asp
1               5                   10                  15

<210> SEQ ID NO 128
<211> LENGTH: 18
<212> TYPE: PRT
<213> ORGANISM: Artificial Sequence
<220> FEATURE:
<223> OTHER INFORMATION: Synthesized

<400> SEQUENCE: 128

Arg Leu Met Glu Asp Ile Cys Leu Ala Arg Trp Gly Cys Leu Trp Glu
1               5                   10                  15

Asp Asp

<210> SEQ ID NO 129
<211> LENGTH: 20
<212> TYPE: PRT
<213> ORGANISM: Artificial Sequence
<220> FEATURE:
<223> OTHER INFORMATION: Synthesized

<400> SEQUENCE: 129

Glu Val Arg Ser Phe Cys Thr Asp Trp Pro Ala Glu Lys Ser Cys Lys
1               5                   10                  15

Pro Leu Arg Gly
            20
```

<210> SEQ ID NO 130
<211> LENGTH: 20
<212> TYPE: PRT
<213> ORGANISM: Artificial Sequence
<220> FEATURE:
<223> OTHER INFORMATION: Synthesized

<400> SEQUENCE: 130

Arg Ala Pro Glu Ser Phe Val Cys Tyr Trp Glu Thr Ile Cys Phe Glu
1               5                   10                  15

Arg Ser Glu Gln
            20

<210> SEQ ID NO 131
<211> LENGTH: 11
<212> TYPE: PRT
<213> ORGANISM: Artificial Sequence
<220> FEATURE:
<223> OTHER INFORMATION: Synthesized

<400> SEQUENCE: 131

Glu Met Cys Tyr Phe Pro Gly Ile Cys Trp Met
1               5                   10

<210> SEQ ID NO 132
<211> LENGTH: 5
<212> TYPE: PRT
<213> ORGANISM: Artificial Sequence
<220> FEATURE:
<223> OTHER INFORMATION: Synthesized

<400> SEQUENCE: 132

Gly Glu Leu Val Trp
1               5

<210> SEQ ID NO 133
<211> LENGTH: 10
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (6)..(9)
<223> OTHER INFORMATION: Xaa is any amino acid

<400> SEQUENCE: 133

Cys Xaa Xaa Gly Pro Xaa Xaa Xaa Xaa Cys
1               5                   10

<210> SEQ ID NO 134
<211> LENGTH: 18
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(7)
<223> OTHER INFORMATION: Xaa is any amino acid
<220> FEATURE:
<221> NAME/KEY: MISC_FEATURE
<222> LOCATION: (10)..(18)
<223> OTHER INFORMATION: Xaa is any amino acid

```
<400> SEQUENCE: 134

Xaa Xaa Xaa Xaa Cys Xaa Xaa Gly Pro Xaa Xaa Xaa Xaa Cys Xaa Xaa
1               5                   10                  15

Xaa Xaa

<210> SEQ ID NO 135
<211> LENGTH: 27
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (2)..(7)
<223> OTHER INFORMATION: Xaa is any amino acid
<220> FEATURE:
<221> NAME/KEY: MISC_FEATURE
<222> LOCATION: (9)..(14)
<223> OTHER INFORMATION: Xaa is any amino acid
<220> FEATURE:
<221> NAME/KEY: MISC_FEATURE
<222> LOCATION: (17)..(19)
<223> OTHER INFORMATION: Xaa is any amino acid
<220> FEATURE:
<221> NAME/KEY: MISC_FEATURE
<222> LOCATION: (21)..(26)
<223> OTHER INFORMATION: Xaa is any amino acid

<400> SEQUENCE: 135

Cys Xaa Xaa Xaa Xaa Xaa Xaa Cys Xaa Xaa Xaa Xaa Xaa Xaa Cys Cys
1               5                   10                  15

Xaa Xaa Xaa Cys Xaa Xaa Xaa Xaa Xaa Cys
            20                  25

<210> SEQ ID NO 136
<211> LENGTH: 13
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (3)..(5)
<223> OTHER INFORMATION: Xaa is any amino acid
<220> FEATURE:
<221> NAME/KEY: MISC_FEATURE
<222> LOCATION: (7)..(12)
<223> OTHER INFORMATION: Xaa is any amino acid

<400> SEQUENCE: 136

Cys Cys Xaa Xaa Xaa Cys Xaa Xaa Xaa Xaa Xaa Xaa Cys
1               5                   10

<210> SEQ ID NO 137
<211> LENGTH: 19
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (3)..(7)
<223> OTHER INFORMATION: Xaa is any amino acid
<220> FEATURE:
<221> NAME/KEY: MISC_FEATURE
<222> LOCATION: (9)..(12)
<223> OTHER INFORMATION: Xaa is any amino acid
<220> FEATURE:
<221> NAME/KEY: MISC_FEATURE
<222> LOCATION: (14)..(17)
<223> OTHER INFORMATION: Xaa is any amino acid
```

<400> SEQUENCE: 137

Cys Cys Xaa Xaa Xaa Xaa Xaa Cys Xaa Xaa Xaa Xaa Cys Xaa Xaa Xaa
1               5                   10                  15

Xaa Cys Cys

<210> SEQ ID NO 138
<211> LENGTH: 21
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (4)..(10)
<223> OTHER INFORMATION: Xaa is any amino acid
<220> FEATURE:
<221> NAME/KEY: MISC_FEATURE
<222> LOCATION: (12)..(14)
<223> OTHER INFORMATION: Xaa is any amino acid
<220> FEATURE:
<221> NAME/KEY: MISC_FEATURE
<222> LOCATION: (16)..(21)
<223> OTHER INFORMATION: Xaa is any amino acid

<400> SEQUENCE: 138

Cys Xaa Cys Xaa Xaa Xaa Xaa Xaa Xaa Cys Xaa Xaa Xaa Cys Xaa
1               5                   10                  15

Xaa Xaa Xaa Xaa Xaa
            20

<210> SEQ ID NO 139
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: Xaa is Ala, Ser, or Thr
<220> FEATURE:
<221> NAME/KEY: MISC_FEATURE
<222> LOCATION: (2)..(2)
<223> OTHER INFORMATION: Xaa is Trp or Tyr
<220> FEATURE:
<221> NAME/KEY: MISC_FEATURE
<222> LOCATION: (3)..(3)
<223> OTHER INFORMATION: Xaa is His or Trp
<220> FEATURE:
<221> NAME/KEY: MISC_FEATURE
<222> LOCATION: (4)..(4)
<223> OTHER INFORMATION: Xaa is Leu or Met

<400> SEQUENCE: 139

Xaa Xaa Xaa Xaa Gly Glu Leu Val Trp
1               5

<210> SEQ ID NO 140
<211> LENGTH: 11
<212> TYPE: PRT
<213> ORGANISM: Artificial Sequence
<220> FEATURE:
<223> OTHER INFORMATION: Synthesized

<400> SEQUENCE: 140

```
Glu Met Cys Tyr Phe Pro Gly Ile Cys Trp Met
1               5                  10
```

<210> SEQ ID NO 141
<211> LENGTH: 27
<212> TYPE: PRT
<213> ORGANISM: Artificial Sequence
<220> FEATURE:
<223> OTHER INFORMATION: Synthesized

<400> SEQUENCE: 141

```
Cys Glu Val Ala Leu Asp Ala Cys Arg Gly Gly Glu Ser Gly Cys Cys
1               5                   10                  15

Arg His Ile Cys Glu Leu Ile Arg Gln Leu Cys
            20                  25
```

<210> SEQ ID NO 142
<211> LENGTH: 21
<212> TYPE: PRT
<213> ORGANISM: Artificial Sequence
<220> FEATURE:
<223> OTHER INFORMATION: Synthesized

<400> SEQUENCE: 142

```
Cys Gly Cys Val Asp Val Ser Asp Trp Asp Cys Trp Ser Glu Cys Leu
1               5                   10                  15

Trp Ser His Gly Ala
            20
```

<210> SEQ ID NO 143
<211> LENGTH: 10
<212> TYPE: PRT
<213> ORGANISM: Artificial Sequence
<220> FEATURE:
<223> OTHER INFORMATION: Synthesized

<400> SEQUENCE: 143

```
Asp Leu Cys Asp Val Asp Phe Cys Trp Phe
1               5                   10
```

<210> SEQ ID NO 144
<211> LENGTH: 15
<212> TYPE: PRT
<213> ORGANISM: Artificial Sequence
<220> FEATURE:
<223> OTHER INFORMATION: Synthesized

<400> SEQUENCE: 144

```
Asp Thr Cys Val Asp Leu Val Arg Leu Gly Leu Glu Cys Trp Gly
1               5                   10                  15
```

<210> SEQ ID NO 145
<211> LENGTH: 16
<212> TYPE: PRT
<213> ORGANISM: Artificial Sequence
<220> FEATURE:
<223> OTHER INFORMATION: Synthesized

<400> SEQUENCE: 145

```
Lys Ser Cys Ser Glu Leu His Trp Leu Leu Val Glu Glu Cys Leu Phe
1               5                   10                  15
```

<210> SEQ ID NO 146
<211> LENGTH: 20
<212> TYPE: PRT
<213> ORGANISM: Artificial Sequence -continued

```
<220> FEATURE:
<223> OTHER INFORMATION: Synthesized

<400> SEQUENCE: 146

Met Asp Glu Leu Ala Phe Tyr Cys Gly Ile Trp Glu Cys Leu Met His
1               5                   10                  15

Gln Glu Gln Lys
            20

<210> SEQ ID NO 147
<211> LENGTH: 20
<212> TYPE: PRT
<213> ORGANISM: Artificial Sequence
<220> FEATURE:
<223> OTHER INFORMATION: Synthesized

<400> SEQUENCE: 147

Arg Asn Glu Asp Pro Cys Val Val Leu Leu Glu Met Gly Leu Glu Cys
1               5                   10                  15

Trp Glu Gly Val
            20

<210> SEQ ID NO 148
<211> LENGTH: 20
<212> TYPE: PRT
<213> ORGANISM: Artificial Sequence
<220> FEATURE:
<223> OTHER INFORMATION: Synthesized

<400> SEQUENCE: 148

Glu Val Arg Ser Phe Cys Thr Asp Trp Pro Ala Glu Lys Ser Cys Lys
1               5                   10                  15

Pro Leu Arg Gly
            20

<210> SEQ ID NO 149
<211> LENGTH: 20
<212> TYPE: PRT
<213> ORGANISM: Artificial Sequence
<220> FEATURE:
<223> OTHER INFORMATION: Synthesized

<400> SEQUENCE: 149

Gly Glu Asn Trp Cys Asp Ser Thr Leu Met Ala Tyr Asp Leu Cys Gly
1               5                   10                  15

Gln Val Asn Met
            20

<210> SEQ ID NO 150
<211> LENGTH: 20
<212> TYPE: PRT
<213> ORGANISM: Artificial Sequence
<220> FEATURE:
<223> OTHER INFORMATION: Synthesized

<400> SEQUENCE: 150

Gln Arg Gln Met Val Asp Phe Cys Leu Pro Gln Trp Gly Cys Leu Trp
1               5                   10                  15

Gly Asp Gly Phe
            20

<210> SEQ ID NO 151
<211> LENGTH: 11
<212> TYPE: PRT
```

```
<213> ORGANISM: Artificial Sequence
<220> FEATURE:
<223> OTHER INFORMATION: Synthesized

<400> SEQUENCE: 151

Ala Leu Cys Tyr Phe Pro Gly Ile Cys Trp Met
1               5                   10

<210> SEQ ID NO 152
<211> LENGTH: 15
<212> TYPE: PRT
<213> ORGANISM: Artificial Sequence
<220> FEATURE:
<223> OTHER INFORMATION: Synthesized

<400> SEQUENCE: 152

Ala Ser Glu Ile Cys Tyr Phe Pro Gly Ile Cys Trp Met Val Glu
1               5                   10                  15

<210> SEQ ID NO 153
<211> LENGTH: 11
<212> TYPE: PRT
<213> ORGANISM: Artificial Sequence
<220> FEATURE:
<223> OTHER INFORMATION: Synthesized

<400> SEQUENCE: 153

Asp Ile Cys Tyr Ile Pro Gly Ile Cys Trp Met
1               5                   10

<210> SEQ ID NO 154
<211> LENGTH: 11
<212> TYPE: PRT
<213> ORGANISM: Artificial Sequence
<220> FEATURE:
<223> OTHER INFORMATION: Synthesized

<400> SEQUENCE: 154

Asp Leu Cys Tyr Phe Pro Gly Ile Cys Trp Met
1               5                   10

<210> SEQ ID NO 155
<211> LENGTH: 11
<212> TYPE: PRT
<213> ORGANISM: Artificial Sequence
<220> FEATURE:
<223> OTHER INFORMATION: Synthesized

<400> SEQUENCE: 155

Asp Met Cys Tyr Phe Pro Gly Ile Cys Phe Asn
1               5                   10

<210> SEQ ID NO 156
<211> LENGTH: 11
<212> TYPE: PRT
<213> ORGANISM: Artificial Sequence
<220> FEATURE:
<223> OTHER INFORMATION: Synthesized

<400> SEQUENCE: 156

Asp Met Cys Tyr Phe Pro Gly Ile Cys Trp Leu
1               5                   10

<210> SEQ ID NO 157
<211> LENGTH: 15
<212> TYPE: PRT
<213> ORGANISM: Artificial Sequence
```

```
<220> FEATURE:
<223> OTHER INFORMATION: Synthesized

<400> SEQUENCE: 157

Asp Ser Glu Val Cys Tyr Phe Pro Gly Ile Cys Trp Ser Gly Thr
1               5                   10                  15

<210> SEQ ID NO 158
<211> LENGTH: 11
<212> TYPE: PRT
<213> ORGANISM: Artificial Sequence
<220> FEATURE:
<223> OTHER INFORMATION: Synthesized

<400> SEQUENCE: 158

Asp Val Cys Tyr Phe Pro Gly Ile Cys Trp Met
1               5                   10

<210> SEQ ID NO 159
<211> LENGTH: 15
<212> TYPE: PRT
<213> ORGANISM: Artificial Sequence
<220> FEATURE:
<223> OTHER INFORMATION: Synthesized

<400> SEQUENCE: 159

Glu His Asp Met Cys Tyr Phe Pro Gly Ile Cys Trp Ile Ala Asp
1               5                   10                  15

<210> SEQ ID NO 160
<211> LENGTH: 11
<212> TYPE: PRT
<213> ORGANISM: Artificial Sequence
<220> FEATURE:
<223> OTHER INFORMATION: Synthesized

<400> SEQUENCE: 160

Glu Ile Cys Tyr Phe Pro Gly Ile Cys Trp Ile
1               5                   10

<210> SEQ ID NO 161
<211> LENGTH: 11
<212> TYPE: PRT
<213> ORGANISM: Artificial Sequence
<220> FEATURE:
<223> OTHER INFORMATION: Synthesized

<400> SEQUENCE: 161

Glu Ile Cys Tyr Phe Pro Gly Ile Cys Trp Met
1               5                   10

<210> SEQ ID NO 162
<211> LENGTH: 11
<212> TYPE: PRT
<213> ORGANISM: Artificial Sequence
<220> FEATURE:
<223> OTHER INFORMATION: Synthesized

<400> SEQUENCE: 162

Glu Leu Cys Tyr Phe Pro Gly Ile Cys Trp Met
1               5                   10

<210> SEQ ID NO 163
<211> LENGTH: 11
<212> TYPE: PRT
<213> ORGANISM: Artificial Sequence
<220> FEATURE:
```

```
<223> OTHER INFORMATION: Synthesized

<400> SEQUENCE: 163

Glu Leu Cys Tyr Phe Pro Gly Ile Cys Trp Pro
1               5                   10

<210> SEQ ID NO 164
<211> LENGTH: 11
<212> TYPE: PRT
<213> ORGANISM: Artificial Sequence
<220> FEATURE:
<223> OTHER INFORMATION: Synthesized

<400> SEQUENCE: 164

Glu Leu Cys Tyr Phe Pro Gly Ile Cys Trp Thr
1               5                   10

<210> SEQ ID NO 165
<211> LENGTH: 11
<212> TYPE: PRT
<213> ORGANISM: Artificial Sequence
<220> FEATURE:
<223> OTHER INFORMATION: Synthesized

<400> SEQUENCE: 165

Glu Met Cys Tyr Phe Pro Gly Ile Cys Trp Ser
1               5                   10

<210> SEQ ID NO 166
<211> LENGTH: 11
<212> TYPE: PRT
<213> ORGANISM: Artificial Sequence
<220> FEATURE:
<223> OTHER INFORMATION: Synthesized

<400> SEQUENCE: 166

Glu Met Cys Tyr Phe Pro Gly Ile Cys Trp Thr
1               5                   10

<210> SEQ ID NO 167
<211> LENGTH: 11
<212> TYPE: PRT
<213> ORGANISM: Artificial Sequence
<220> FEATURE:
<223> OTHER INFORMATION: Synthesized

<400> SEQUENCE: 167

Glu Thr Cys Tyr Phe Pro Gly Ile Cys Trp Leu
1               5                   10

<210> SEQ ID NO 168
<211> LENGTH: 11
<212> TYPE: PRT
<213> ORGANISM: Artificial Sequence
<220> FEATURE:
<223> OTHER INFORMATION: Synthesized

<400> SEQUENCE: 168

Glu Val Cys Tyr Phe Pro Gly Ile Cys Trp Glu
1               5                   10

<210> SEQ ID NO 169
<211> LENGTH: 11
<212> TYPE: PRT
<213> ORGANISM: Artificial Sequence
<220> FEATURE:
<223> OTHER INFORMATION: Synthesized
```

```
<400> SEQUENCE: 169

Glu Val Cys Tyr Phe Pro Gly Ile Cys Trp Phe
1               5                   10

<210> SEQ ID NO 170
<211> LENGTH: 11
<212> TYPE: PRT
<213> ORGANISM: Artificial Sequence
<220> FEATURE:
<223> OTHER INFORMATION: Synthesized

<400> SEQUENCE: 170

Glu Val Cys Tyr Phe Pro Gly Ile Cys Trp Met
1               5                   10

<210> SEQ ID NO 171
<211> LENGTH: 20
<212> TYPE: PRT
<213> ORGANISM: Artificial Sequence
<220> FEATURE:
<223> OTHER INFORMATION: Synthesized

<400> SEQUENCE: 171

Glu Val Arg Ser Phe Cys Thr Asp Trp Pro Ala His Tyr Ser Cys Thr
1               5                   10                  15

Ser Leu Gln Gly
            20

<210> SEQ ID NO 172
<211> LENGTH: 20
<212> TYPE: PRT
<213> ORGANISM: Artificial Sequence
<220> FEATURE:
<223> OTHER INFORMATION: Synthesized

<400> SEQUENCE: 172

Gly Glu Asp Trp Cys Asp Ser Thr Leu Leu Ala Phe Asp Leu Cys Gly
1               5                   10                  15

Glu Gly Ala Arg
            20

<210> SEQ ID NO 173
<211> LENGTH: 20
<212> TYPE: PRT
<213> ORGANISM: Artificial Sequence
<220> FEATURE:
<223> OTHER INFORMATION: Synthesized

<400> SEQUENCE: 173

Gly Glu Asn Trp Cys Asp Trp Val Leu Leu Ala Tyr Asp Leu Cys Gly
1               5                   10                  15

Glu Asp Asn Thr
            20

<210> SEQ ID NO 174
<211> LENGTH: 15
<212> TYPE: PRT
<213> ORGANISM: Artificial Sequence
<220> FEATURE:
<223> OTHER INFORMATION: Synthesized

<400> SEQUENCE: 174

Gly Gly Glu Ile Cys Tyr Phe Pro Gly Ile Cys Arg Val Leu Pro
1               5                   10                  15
```

<210> SEQ ID NO 175
<211> LENGTH: 11
<212> TYPE: PRT
<213> ORGANISM: Artificial Sequence
<220> FEATURE:
<223> OTHER INFORMATION: Synthesized

<400> SEQUENCE: 175

Gly Met Cys Tyr Phe Pro Gly Ile Cys Trp Ala
1               5                   10

<210> SEQ ID NO 176
<211> LENGTH: 19
<212> TYPE: PRT
<213> ORGANISM: Artificial Sequence
<220> FEATURE:
<223> OTHER INFORMATION: Synthesized

<400> SEQUENCE: 176

Gly Arg Ser Phe Cys Met Asp Trp Pro Ala His Lys Ser Cys Thr Pro
1               5                   10                  15

Leu Met Leu

<210> SEQ ID NO 177
<211> LENGTH: 15
<212> TYPE: PRT
<213> ORGANISM: Artificial Sequence
<220> FEATURE:
<223> OTHER INFORMATION: Synthesized

<400> SEQUENCE: 177

Gly Thr Glu Val Cys Tyr Phe Pro Gly Ile Cys Trp Gly Gly Gly
1               5                   10                  15

<210> SEQ ID NO 178
<211> LENGTH: 20
<212> TYPE: PRT
<213> ORGANISM: Artificial Sequence
<220> FEATURE:
<223> OTHER INFORMATION: Synthesized

<400> SEQUENCE: 178

Gly Val Arg Thr Phe Cys Gln Asp Trp Pro Ala His Asn Ser Cys Lys
1               5                   10                  15

Leu Leu Arg Gly
            20

<210> SEQ ID NO 179
<211> LENGTH: 15
<212> TYPE: PRT
<213> ORGANISM: Artificial Sequence
<220> FEATURE:
<223> OTHER INFORMATION: Synthesized

<400> SEQUENCE: 179

His Ala Glu Ile Cys Tyr Phe Pro Gly Ile Cys Trp Thr Glu Arg
1               5                   10                  15

<210> SEQ ID NO 180
<211> LENGTH: 15
<212> TYPE: PRT
<213> ORGANISM: Artificial Sequence
<220> FEATURE:
<223> OTHER INFORMATION: Synthesized

```
<400> SEQUENCE: 180

Ile Val Glu Met Cys Tyr Tyr Pro Gly Ile Cys Trp Ile Ser Pro
1               5                   10                  15

<210> SEQ ID NO 181
<211> LENGTH: 11
<212> TYPE: PRT
<213> ORGANISM: Artificial Sequence
<220> FEATURE:
<223> OTHER INFORMATION: Synthesized

<400> SEQUENCE: 181

Lys Leu Cys Tyr Phe Pro Gly Ile Cys Trp Ser
1               5                   10

<210> SEQ ID NO 182
<211> LENGTH: 11
<212> TYPE: PRT
<213> ORGANISM: Artificial Sequence
<220> FEATURE:
<223> OTHER INFORMATION: Synthesized

<400> SEQUENCE: 182

Lys Thr Cys Tyr Phe Pro Gly Ile Cys Trp Met
1               5                   10

<210> SEQ ID NO 183
<211> LENGTH: 15
<212> TYPE: PRT
<213> ORGANISM: Artificial Sequence
<220> FEATURE:
<223> OTHER INFORMATION: Synthesized

<400> SEQUENCE: 183

Lys Thr Glu Ile Cys Tyr Phe Pro Gly Ile Cys Trp Met Ser Gly
1               5                   10                  15

<210> SEQ ID NO 184
<211> LENGTH: 11
<212> TYPE: PRT
<213> ORGANISM: Artificial Sequence
<220> FEATURE:
<223> OTHER INFORMATION: Synthesized

<400> SEQUENCE: 184

Lys Val Cys Tyr Phe Pro Gly Ile Cys Trp Met
1               5                   10

<210> SEQ ID NO 185
<211> LENGTH: 15
<212> TYPE: PRT
<213> ORGANISM: Artificial Sequence
<220> FEATURE:
<223> OTHER INFORMATION: Synthesized

<400> SEQUENCE: 185

Leu Ala Glu Met Cys Tyr Phe Pro Gly Ile Cys Trp Met Ser Ala
1               5                   10                  15

<210> SEQ ID NO 186
<211> LENGTH: 20
<212> TYPE: PRT
<213> ORGANISM: Artificial Sequence
<220> FEATURE:
<223> OTHER INFORMATION: Synthesized

<400> SEQUENCE: 186
```

Leu Val Pro Glu Arg Ile Val Cys Tyr Phe Glu Ser Ile Cys Tyr Glu
1               5                   10                  15

Arg Ser Glu Leu
            20

<210> SEQ ID NO 187
<211> LENGTH: 20
<212> TYPE: PRT
<213> ORGANISM: Artificial Sequence
<220> FEATURE:
<223> OTHER INFORMATION: Synthesized

<400> SEQUENCE: 187

Met Glu Leu Trp Cys Asp Ser Thr Leu Met Ala Tyr Asp Leu Cys Gly
1               5                   10                  15

Asp Phe Asn Met
            20

<210> SEQ ID NO 188
<211> LENGTH: 20
<212> TYPE: PRT
<213> ORGANISM: Artificial Sequence
<220> FEATURE:
<223> OTHER INFORMATION: Synthesized

<400> SEQUENCE: 188

Met Glu Pro Ser Arg Ser Val Cys Tyr Ala Glu Gly Ile Cys Phe Asp
1               5                   10                  15

Arg Gly Glu Gln
            20

<210> SEQ ID NO 189
<211> LENGTH: 15
<212> TYPE: PRT
<213> ORGANISM: Artificial Sequence
<220> FEATURE:
<223> OTHER INFORMATION: Synthesized

<400> SEQUENCE: 189

Asn Asp Glu Ile Cys Tyr Phe Pro Gly Val Cys Trp Lys Ser Gly
1               5                   10                  15

<210> SEQ ID NO 190
<211> LENGTH: 8
<212> TYPE: PRT
<213> ORGANISM: Artificial Sequence
<220> FEATURE:
<223> OTHER INFORMATION: Synthesized

<400> SEQUENCE: 190

Gln Cys Phe Pro Gly Trp Val Lys
1               5

<210> SEQ ID NO 191
<211> LENGTH: 15
<212> TYPE: PRT
<213> ORGANISM: Artificial Sequence
<220> FEATURE:
<223> OTHER INFORMATION: Synthesized

<400> SEQUENCE: 191

Gln Thr Glu Leu Cys Tyr Phe Pro Gly Ile Cys Trp Asn Glu Ser
1               5                   10                  15

<210> SEQ ID NO 192
<211> LENGTH: 20
<212> TYPE: PRT
<213> ORGANISM: Artificial Sequence
<220> FEATURE:
<223> OTHER INFORMATION: Synthesized

<400> SEQUENCE: 192

Gln Thr Arg Ser Phe Cys Ala Asp Trp Pro Arg His Glu Ser Cys Lys
1               5                   10                  15

Pro Leu Arg Gly
            20

<210> SEQ ID NO 193
<211> LENGTH: 20
<212> TYPE: PRT
<213> ORGANISM: Artificial Sequence
<220> FEATURE:
<223> OTHER INFORMATION: Synthesized

<400> SEQUENCE: 193

Arg Ala Ala Glu Ser Ser Val Cys Tyr Trp Pro Gly Ile Cys Phe Asp
1               5                   10                  15

Arg Thr Glu Gln
            20

<210> SEQ ID NO 194
<211> LENGTH: 20
<212> TYPE: PRT
<213> ORGANISM: Artificial Sequence
<220> FEATURE:
<223> OTHER INFORMATION: Synthesized

<400> SEQUENCE: 194

Arg Ala Pro Glu Arg Trp Val Cys Tyr Trp Glu Gly Ile Cys Phe Asp
1               5                   10                  15

Arg Tyr Glu Gln
            20

<210> SEQ ID NO 195
<211> LENGTH: 15
<212> TYPE: PRT
<213> ORGANISM: Artificial Sequence
<220> FEATURE:
<223> OTHER INFORMATION: Synthesized

<400> SEQUENCE: 195

Arg Asp Thr Val Cys Tyr Phe Pro Gly Ile Cys Trp Met Ala Ser
1               5                   10                  15

<210> SEQ ID NO 196
<211> LENGTH: 20
<212> TYPE: PRT
<213> ORGANISM: Artificial Sequence
<220> FEATURE:
<223> OTHER INFORMATION: Synthesized

<400> SEQUENCE: 196

Arg Glu Pro Ala Ser Leu Val Cys Tyr Phe Glu Asp Ile Cys Phe Val
1               5                   10                  15

Arg Ala Glu Ala
            20

<210> SEQ ID NO 197
<211> LENGTH: 18

```
<212> TYPE: PRT
<213> ORGANISM: Artificial Sequence
<220> FEATURE:
<223> OTHER INFORMATION: Synthesized

<400> SEQUENCE: 197

Arg Gly Pro Asp Val Cys Tyr Trp Pro Ser Ile Cys Phe Glu Arg Ser
1               5                   10                  15

Met Pro

<210> SEQ ID NO 198
<211> LENGTH: 20
<212> TYPE: PRT
<213> ORGANISM: Artificial Sequence
<220> FEATURE:
<223> OTHER INFORMATION: Synthesized

<400> SEQUENCE: 198

Arg Met Pro Ala Ser Leu Pro Cys Tyr Trp Glu Thr Ile Cys Tyr Glu
1               5                   10                  15

Ser Ser Glu Gln
            20

<210> SEQ ID NO 199
<211> LENGTH: 15
<212> TYPE: PRT
<213> ORGANISM: Artificial Sequence
<220> FEATURE:
<223> OTHER INFORMATION: Synthesized

<400> SEQUENCE: 199

Arg Arg Thr Cys Asp Trp Pro His Asn Ser Cys Lys Leu Arg Gly
1               5                   10                  15

<210> SEQ ID NO 200
<211> LENGTH: 20
<212> TYPE: PRT
<213> ORGANISM: Artificial Sequence
<220> FEATURE:
<223> OTHER INFORMATION: Synthesized

<400> SEQUENCE: 200

Arg Thr Ala Glu Ser Leu Val Cys Tyr Trp Pro Gly Ile Cys Phe Ala
1               5                   10                  15

Gln Ser Glu Arg
            20

<210> SEQ ID NO 201
<211> LENGTH: 15
<212> TYPE: PRT
<213> ORGANISM: Artificial Sequence
<220> FEATURE:
<223> OTHER INFORMATION: Synthesized

<400> SEQUENCE: 201

Ser Gly Ala Ile Cys Tyr Val Pro Gly Ile Cys Trp Thr His Ala
1               5                   10                  15

<210> SEQ ID NO 202
<211> LENGTH: 15
<212> TYPE: PRT
<213> ORGANISM: Artificial Sequence
<220> FEATURE:
<223> OTHER INFORMATION: Synthesized

<400> SEQUENCE: 202
```

Ser Arg Glu Val Cys Tyr Tyr Pro Gly Ile Cys Trp Asn Gly Ala
1               5                   10                  15

<210> SEQ ID NO 203
<211> LENGTH: 15
<212> TYPE: PRT
<213> ORGANISM: Artificial Sequence
<220> FEATURE:
<223> OTHER INFORMATION: Synthesized

<400> SEQUENCE: 203

Ser Tyr Ala Pro Cys Tyr Phe Pro Gly Ile Cys Trp Met Gly Asn
1               5                   10                  15

<210> SEQ ID NO 204
<211> LENGTH: 15
<212> TYPE: PRT
<213> ORGANISM: Artificial Sequence
<220> FEATURE:
<223> OTHER INFORMATION: Synthesized

<400> SEQUENCE: 204

Thr Thr Glu Met Cys Tyr Phe Pro Gly Ile Cys Trp Lys Thr Glu
1               5                   10                  15

<210> SEQ ID NO 205
<211> LENGTH: 15
<212> TYPE: PRT
<213> ORGANISM: Artificial Sequence
<220> FEATURE:
<223> OTHER INFORMATION: Synthesized

<400> SEQUENCE: 205

Val Gln Glu Val Cys Tyr Phe Pro Gly Ile Cys Trp Met Gln Glu
1               5                   10                  15

<210> SEQ ID NO 206
<211> LENGTH: 15
<212> TYPE: PRT
<213> ORGANISM: Artificial Sequence
<220> FEATURE:
<223> OTHER INFORMATION: Synthesized

<400> SEQUENCE: 206

Val Arg Asp Met Cys Tyr Phe Pro Gly Ile Cys Trp Lys Ser Glu
1               5                   10                  15

<210> SEQ ID NO 207
<211> LENGTH: 20
<212> TYPE: PRT
<213> ORGANISM: Artificial Sequence
<220> FEATURE:
<223> OTHER INFORMATION: Synthesized

<400> SEQUENCE: 207

Asn Arg Gln Met Glu Asp Ile Cys Leu Pro Gln Trp Gly Cys Leu Trp
1               5                   10                  15

Gly Asp Asp Phe
            20

<210> SEQ ID NO 208
<211> LENGTH: 20
<212> TYPE: PRT
<213> ORGANISM: Artificial Sequence
<220> FEATURE:
<223> OTHER INFORMATION: Synthesized

```
<400> SEQUENCE: 208

Gln Arg His Pro Glu Asp Ile Cys Leu Pro Arg Trp Gly Cys Leu Trp
1               5                   10                  15

Gly Asp Asp Asp
            20

<210> SEQ ID NO 209
<211> LENGTH: 15
<212> TYPE: PRT
<213> ORGANISM: Artificial Sequence
<220> FEATURE:
<223> OTHER INFORMATION: Synthesized

<400> SEQUENCE: 209

Asp Phe Asp Leu Cys Leu Pro Asp Trp Gly Cys Leu Trp Asp Asp
1               5                   10                  15

<210> SEQ ID NO 210
<211> LENGTH: 11
<212> TYPE: PRT
<213> ORGANISM: Artificial Sequence
<220> FEATURE:
<223> OTHER INFORMATION: Synthesized

<400> SEQUENCE: 210

Asp Ile Cys Leu Glu Arg Trp Gly Cys Leu Trp
1               5                   10

<210> SEQ ID NO 211
<211> LENGTH: 11
<212> TYPE: PRT
<213> ORGANISM: Artificial Sequence
<220> FEATURE:
<223> OTHER INFORMATION: Synthesized

<400> SEQUENCE: 211

Asp Ile Cys Leu Pro Ala Trp Gly Cys Leu Trp
1               5                   10

<210> SEQ ID NO 212
<211> LENGTH: 11
<212> TYPE: PRT
<213> ORGANISM: Artificial Sequence
<220> FEATURE:
<223> OTHER INFORMATION: Synthesized

<400> SEQUENCE: 212

Asp Ile Cys Leu Pro Asp Trp Gly Cys Leu Trp
1               5                   10

<210> SEQ ID NO 213
<211> LENGTH: 11
<212> TYPE: PRT
<213> ORGANISM: Artificial Sequence
<220> FEATURE:
<223> OTHER INFORMATION: Synthesized

<400> SEQUENCE: 213

Asp Ile Cys Leu Pro Glu Trp Gly Cys Leu Trp
1               5                   10

<210> SEQ ID NO 214
<211> LENGTH: 11
<212> TYPE: PRT
<213> ORGANISM: Artificial Sequence
```

```
<220> FEATURE:
<223> OTHER INFORMATION: Synthesized

<400> SEQUENCE: 214

Asp Ile Cys Leu Pro Val Trp Gly Cys Leu Trp
1               5                   10

<210> SEQ ID NO 215
<211> LENGTH: 11
<212> TYPE: PRT
<213> ORGANISM: Artificial Sequence
<220> FEATURE:
<223> OTHER INFORMATION: Synthesized

<400> SEQUENCE: 215

Asp Leu Cys Leu Pro Glu Trp Gly Cys Leu Trp
1               5                   10

<210> SEQ ID NO 216
<211> LENGTH: 11
<212> TYPE: PRT
<213> ORGANISM: Artificial Sequence
<220> FEATURE:
<223> OTHER INFORMATION: Synthesized

<400> SEQUENCE: 216

Asp Leu Cys Leu Pro Lys Trp Gly Cys Leu Trp
1               5                   10

<210> SEQ ID NO 217
<211> LENGTH: 11
<212> TYPE: PRT
<213> ORGANISM: Artificial Sequence
<220> FEATURE:
<223> OTHER INFORMATION: Synthesized

<400> SEQUENCE: 217

Asp Leu Cys Leu Pro Val Trp Gly Cys Leu Trp
1               5                   10

<210> SEQ ID NO 218
<211> LENGTH: 15
<212> TYPE: PRT
<213> ORGANISM: Artificial Sequence
<220> FEATURE:
<223> OTHER INFORMATION: Synthesized

<400> SEQUENCE: 218

Asp Ser Cys Gly Asp Leu Leu Arg Leu Gly Leu Glu Cys Trp Ala
1               5                   10                  15

<210> SEQ ID NO 219
<211> LENGTH: 15
<212> TYPE: PRT
<213> ORGANISM: Artificial Sequence
<220> FEATURE:
<223> OTHER INFORMATION: Synthesized

<400> SEQUENCE: 219

Asp Thr Cys Ala Asp Leu Val Arg Leu Gly Leu Glu Cys Trp Ala
1               5                   10                  15

<210> SEQ ID NO 220
<211> LENGTH: 15
<212> TYPE: PRT
<213> ORGANISM: Artificial Sequence
<220> FEATURE:
```

<223> OTHER INFORMATION: Synthesized

<400> SEQUENCE: 220

Asp Thr Cys Asp Asp Leu Val Gln Leu Gly Leu Glu Cys Trp Ala
1               5                   10                  15

<210> SEQ ID NO 221
<211> LENGTH: 15
<212> TYPE: PRT
<213> ORGANISM: Artificial Sequence
<220> FEATURE:
<223> OTHER INFORMATION: Synthesized

<400> SEQUENCE: 221

Asp Thr Cys Glu Asp Leu Val Arg Leu Gly Leu Glu Cys Trp Ala
1               5                   10                  15

<210> SEQ ID NO 222
<211> LENGTH: 15
<212> TYPE: PRT
<213> ORGANISM: Artificial Sequence
<220> FEATURE:
<223> OTHER INFORMATION: Synthesized

<400> SEQUENCE: 222

Asp Thr Cys Ser Asp Leu Val Gly Leu Gly Leu Glu Cys Trp Ala
1               5                   10                  15

<210> SEQ ID NO 223
<211> LENGTH: 15
<212> TYPE: PRT
<213> ORGANISM: Artificial Sequence
<220> FEATURE:
<223> OTHER INFORMATION: Synthesized

<400> SEQUENCE: 223

Glu Glu Asp Leu Cys Leu Pro Val Trp Gly Cys Leu Trp Gly Ala
1               5                   10                  15

<210> SEQ ID NO 224
<211> LENGTH: 15
<212> TYPE: PRT
<213> ORGANISM: Artificial Sequence
<220> FEATURE:
<223> OTHER INFORMATION: Synthesized

<400> SEQUENCE: 224

Glu Glu Asp Val Cys Leu Pro Val Trp Gly Cys Leu Trp Glu Gly
1               5                   10                  15

<210> SEQ ID NO 225
<211> LENGTH: 15
<212> TYPE: PRT
<213> ORGANISM: Artificial Sequence
<220> FEATURE:
<223> OTHER INFORMATION: Synthesized

<400> SEQUENCE: 225

Glu Phe Asp Leu Cys Leu Pro Thr Trp Gly Cys Leu Trp Glu Asp
1               5                   10                  15

<210> SEQ ID NO 226
<211> LENGTH: 20
<212> TYPE: PRT
<213> ORGANISM: Artificial Sequence
<220> FEATURE:
<223> OTHER INFORMATION: Synthesized

```
<400> SEQUENCE: 226

Glu Arg Gln Met Glu Asp Phe Cys Leu Pro Gln Trp Gly Cys Leu Trp
1               5                   10                  15

Gly Asp Gly Val
            20

<210> SEQ ID NO 227
<211> LENGTH: 20
<212> TYPE: PRT
<213> ORGANISM: Artificial Sequence
<220> FEATURE:
<223> OTHER INFORMATION: Synthesized

<400> SEQUENCE: 227

Glu Arg Gln Met Val Asp Phe Cys Leu Pro Lys Trp Gly Cys Leu Trp
1               5                   10                  15

Gly Asp Gly Phe
            20

<210> SEQ ID NO 228
<211> LENGTH: 15
<212> TYPE: PRT
<213> ORGANISM: Artificial Sequence
<220> FEATURE:
<223> OTHER INFORMATION: Synthesized

<400> SEQUENCE: 228

Glu Trp Asp Val Cys Phe Pro Ala Trp Gly Cys Leu Trp Asp Gln
1               5                   10                  15

<210> SEQ ID NO 229
<211> LENGTH: 15
<212> TYPE: PRT
<213> ORGANISM: Artificial Sequence
<220> FEATURE:
<223> OTHER INFORMATION: Synthesized

<400> SEQUENCE: 229

Glu Trp Asp Val Cys Leu Pro His Trp Gly Cys Leu Trp Asp Gly
1               5                   10                  15

<210> SEQ ID NO 230
<211> LENGTH: 15
<212> TYPE: PRT
<213> ORGANISM: Artificial Sequence
<220> FEATURE:
<223> OTHER INFORMATION: Synthesized

<400> SEQUENCE: 230

Phe Glu Asp Phe Cys Leu Pro Asn Trp Gly Cys Leu Trp Gly Ser
1               5                   10                  15

<210> SEQ ID NO 231
<211> LENGTH: 15
<212> TYPE: PRT
<213> ORGANISM: Artificial Sequence
<220> FEATURE:
<223> OTHER INFORMATION: Synthesized

<400> SEQUENCE: 231

Phe Glu Asp Leu Cys Val Val Arg Trp Gly Cys Leu Trp Gly Asp
1               5                   10                  15

<210> SEQ ID NO 232
```

```
<211> LENGTH: 20
<212> TYPE: PRT
<213> ORGANISM: Artificial Sequence
<220> FEATURE:
<223> OTHER INFORMATION: Synthesized

<400> SEQUENCE: 232

Gly Arg Gln Val Val Asp Phe Cys Leu Pro Lys Trp Gly Cys Leu Trp
1               5                   10                  15

Glu Glu Gly Leu
            20

<210> SEQ ID NO 233
<211> LENGTH: 20
<212> TYPE: PRT
<213> ORGANISM: Artificial Sequence
<220> FEATURE:
<223> OTHER INFORMATION: Synthesized

<400> SEQUENCE: 233

Lys Met Gly Arg Val Asp Phe Cys Leu Pro Lys Trp Gly Cys Leu Trp
1               5                   10                  15

Gly Asp Glu Leu
            20

<210> SEQ ID NO 234
<211> LENGTH: 20
<212> TYPE: PRT
<213> ORGANISM: Artificial Sequence
<220> FEATURE:
<223> OTHER INFORMATION: Synthesized

<400> SEQUENCE: 234

Lys Ser Arg Met Gly Asp Phe Cys Leu Pro Glu Trp Gly Cys Leu Trp
1               5                   10                  15

Gly Asp Glu Leu
            20

<210> SEQ ID NO 235
<211> LENGTH: 20
<212> TYPE: PRT
<213> ORGANISM: Artificial Sequence
<220> FEATURE:
<223> OTHER INFORMATION: Synthesized

<400> SEQUENCE: 235

Leu Arg Ile Phe Glu Asp Ile Cys Leu Pro Lys Trp Gly Cys Leu Trp
1               5                   10                  15

Gly Glu Gly Phe
            20

<210> SEQ ID NO 236
<211> LENGTH: 15
<212> TYPE: PRT
<213> ORGANISM: Artificial Sequence
<220> FEATURE:
<223> OTHER INFORMATION: Synthesized

<400> SEQUENCE: 236

Met Asp Asp Ile Cys Leu His His Trp Gly Cys Leu Trp Asp Glu
1               5                   10                  15

<210> SEQ ID NO 237
<211> LENGTH: 15
<212> TYPE: PRT
```

```
<213> ORGANISM: Artificial Sequence
<220> FEATURE:
<223> OTHER INFORMATION: Synthesized

<400> SEQUENCE: 237

Met Asp Asp Leu Cys Leu Pro Asn Trp Gly Cys Leu Trp Gly Asp
1               5                   10                  15

<210> SEQ ID NO 238
<211> LENGTH: 15
<212> TYPE: PRT
<213> ORGANISM: Artificial Sequence
<220> FEATURE:
<223> OTHER INFORMATION: Synthesized

<400> SEQUENCE: 238

Met Phe Asp Leu Cys Leu Pro Lys Trp Gly Cys Leu Trp Gly Asn
1               5                   10                  15

<210> SEQ ID NO 239
<211> LENGTH: 15
<212> TYPE: PRT
<213> ORGANISM: Artificial Sequence
<220> FEATURE:
<223> OTHER INFORMATION: Synthesized

<400> SEQUENCE: 239

Met Trp Asp Val Cys Phe Pro Asp Trp Gly Cys Leu Trp Asp Val
1               5                   10                  15

<210> SEQ ID NO 240
<211> LENGTH: 15
<212> TYPE: PRT
<213> ORGANISM: Artificial Sequence
<220> FEATURE:
<223> OTHER INFORMATION: Synthesized

<400> SEQUENCE: 240

Asn Thr Cys Ala Asp Leu Val Arg Leu Gly Leu Glu Cys Trp Ala
1               5                   10                  15

<210> SEQ ID NO 241
<211> LENGTH: 15
<212> TYPE: PRT
<213> ORGANISM: Artificial Sequence
<220> FEATURE:
<223> OTHER INFORMATION: Synthesized

<400> SEQUENCE: 241

Asn Trp Asp Leu Cys Phe Pro Asp Trp Gly Cys Leu Trp Asp Asp
1               5                   10                  15

<210> SEQ ID NO 242
<211> LENGTH: 20
<212> TYPE: PRT
<213> ORGANISM: Artificial Sequence
<220> FEATURE:
<223> OTHER INFORMATION: Synthesized

<400> SEQUENCE: 242

Gln Gly Asp Phe Trp Asp Ile Cys Leu Pro Arg Trp Gly Cys Leu Ser
1               5                   10                  15

Gly Glu Gly Tyr
            20

<210> SEQ ID NO 243
```

```
<211> LENGTH: 20
<212> TYPE: PRT
<213> ORGANISM: Artificial Sequence
<220> FEATURE:
<223> OTHER INFORMATION: Synthesized

<400> SEQUENCE: 243

Gln Gly Gly Met Gly Asp Phe Cys Leu Pro Gln Trp Gly Cys Leu Trp
1               5                   10                  15

Gly Glu Asp Leu
            20

<210> SEQ ID NO 244
<211> LENGTH: 20
<212> TYPE: PRT
<213> ORGANISM: Artificial Sequence
<220> FEATURE:
<223> OTHER INFORMATION: Synthesized

<400> SEQUENCE: 244

Gln Gly Tyr Met Val Asp Phe Cys Leu Pro Arg Trp Gly Cys Leu Trp
1               5                   10                  15

Gly Asp Ala Asn
            20

<210> SEQ ID NO 245
<211> LENGTH: 20
<212> TYPE: PRT
<213> ORGANISM: Artificial Sequence
<220> FEATURE:
<223> OTHER INFORMATION: Synthesized

<400> SEQUENCE: 245

Gln Met His Met Met Asp Ile Cys Leu Pro Lys Trp Gly Cys Leu Trp
1               5                   10                  15

Gly Asp Thr Ser
            20

<210> SEQ ID NO 246
<211> LENGTH: 20
<212> TYPE: PRT
<213> ORGANISM: Artificial Sequence
<220> FEATURE:
<223> OTHER INFORMATION: Synthesized

<400> SEQUENCE: 246

Gln Met Gln Met Ser Asp Phe Cys Leu Pro Gln Trp Gly Cys Leu Trp
1               5                   10                  15

Gly Asp Gly Tyr
            20

<210> SEQ ID NO 247
<211> LENGTH: 20
<212> TYPE: PRT
<213> ORGANISM: Artificial Sequence
<220> FEATURE:
<223> OTHER INFORMATION: Synthesized

<400> SEQUENCE: 247

Gln Arg His Met Met Asp Phe Cys Leu Pro Lys Trp Gly Cys Leu Trp
1               5                   10                  15

Gly Asp Gly Tyr
            20
```

```
<210> SEQ ID NO 248
<211> LENGTH: 20
<212> TYPE: PRT
<213> ORGANISM: Artificial Sequence
<220> FEATURE:
<223> OTHER INFORMATION: Synthesized

<400> SEQUENCE: 248

Gln Arg Leu Met Trp Glu Ile Cys Leu Pro Leu Trp Gly Cys Leu Trp
1               5                   10                  15

Gly Asp Gly Leu
            20

<210> SEQ ID NO 249
<211> LENGTH: 20
<212> TYPE: PRT
<213> ORGANISM: Artificial Sequence
<220> FEATURE:
<223> OTHER INFORMATION: Synthesized

<400> SEQUENCE: 249

Gln Arg Pro Ile Met Asp Phe Cys Leu Pro Lys Trp Gly Cys Leu Trp
1               5                   10                  15

Glu Asp Gly Phe
            20

<210> SEQ ID NO 250
<211> LENGTH: 20
<212> TYPE: PRT
<213> ORGANISM: Artificial Sequence
<220> FEATURE:
<223> OTHER INFORMATION: Synthesized

<400> SEQUENCE: 250

Gln Arg Gln Ile Met Asp Phe Cys Leu Pro His Trp Gly Cys Leu Trp
1               5                   10                  15

Gly Asp Gly Phe
            20

<210> SEQ ID NO 251
<211> LENGTH: 20
<212> TYPE: PRT
<213> ORGANISM: Artificial Sequence
<220> FEATURE:
<223> OTHER INFORMATION: Synthesized

<400> SEQUENCE: 251

Gln Arg Gln Val Val Asp Phe Cys Leu Pro Gln Trp Gly Cys Leu Trp
1               5                   10                  15

Gly Asp Gly Ser
            20

<210> SEQ ID NO 252
<211> LENGTH: 20
<212> TYPE: PRT
<213> ORGANISM: Artificial Sequence
<220> FEATURE:
<223> OTHER INFORMATION: Synthesized

<400> SEQUENCE: 252

Gln Ser Gln Leu Glu Asp Phe Cys Leu Pro Lys Trp Gly Cys Leu Trp
1               5                   10                  15

Gly Asp Gly Phe
            20
```

<210> SEQ ID NO 253
<211> LENGTH: 20
<212> TYPE: PRT
<213> ORGANISM: Artificial Sequence
<220> FEATURE:
<223> OTHER INFORMATION: Synthesized

<400> SEQUENCE: 253

Gln Ser Tyr Met Glu Asp Ile Cys Leu Pro Arg Trp Gly Cys Leu Ser
1               5                   10                  15

Asp Asp Ala Ser
            20

<210> SEQ ID NO 254
<211> LENGTH: 20
<212> TYPE: PRT
<213> ORGANISM: Artificial Sequence
<220> FEATURE:
<223> OTHER INFORMATION: Synthesized

<400> SEQUENCE: 254

Arg Trp Gln Thr Glu Asp Val Cys Leu Pro Lys Trp Gly Cys Leu Phe
1               5                   10                  15

Gly Asp Gly Val
            20

<210> SEQ ID NO 255
<211> LENGTH: 15
<212> TYPE: PRT
<213> ORGANISM: Artificial Sequence
<220> FEATURE:
<223> OTHER INFORMATION: Synthesized

<400> SEQUENCE: 255

Ser Glu Asp Phe Cys Leu Pro Val Trp Gly Cys Leu Trp Glu Asp
1               5                   10                  15

<210> SEQ ID NO 256
<211> LENGTH: 15
<212> TYPE: PRT
<213> ORGANISM: Artificial Sequence
<220> FEATURE:
<223> OTHER INFORMATION: Synthesized

<400> SEQUENCE: 256

Val Trp Asp Leu Cys Leu Pro Gln Trp Gly Cys Leu Trp Asp Glu
1               5                   10                  15

<210> SEQ ID NO 257
<211> LENGTH: 15
<212> TYPE: PRT
<213> ORGANISM: Artificial Sequence
<220> FEATURE:
<223> OTHER INFORMATION: Synthesized

<400> SEQUENCE: 257

Trp Asp Asp Ile Cys Phe Arg Asp Trp Gly Cys Leu Trp Gly Ser
1               5                   10                  15

<210> SEQ ID NO 258
<211> LENGTH: 15
<212> TYPE: PRT
<213> ORGANISM: Artificial Sequence
<220> FEATURE:
<223> OTHER INFORMATION: Synthesized

```
<400> SEQUENCE: 258

Trp Glu Asp Leu Cys Leu Pro Asp Trp Gly Cys Leu Trp Glu Asp
1               5                   10                  15

<210> SEQ ID NO 259
<211> LENGTH: 20
<212> TYPE: PRT
<213> ORGANISM: Artificial Sequence
<220> FEATURE:
<223> OTHER INFORMATION: Synthesized

<400> SEQUENCE: 259

His Arg Leu Val Glu Asp Ile Cys Leu Pro Arg Trp Gly Cys Leu Trp
1               5                   10                  15

Gly Asn Asp Phe
            20

<210> SEQ ID NO 260
<211> LENGTH: 20
<212> TYPE: PRT
<213> ORGANISM: Artificial Sequence
<220> FEATURE:
<223> OTHER INFORMATION: Synthesized

<400> SEQUENCE: 260

His Ser Gln Met Glu Asp Ile Cys Leu Pro Arg Trp Gly Cys Leu Trp
1               5                   10                  15

Gly Asp Glu Leu
            20

<210> SEQ ID NO 261
<211> LENGTH: 20
<212> TYPE: PRT
<213> ORGANISM: Artificial Sequence
<220> FEATURE:
<223> OTHER INFORMATION: Synthesized

<400> SEQUENCE: 261

Leu Ile Phe Met Glu Asp Val Cys Leu Pro Gln Trp Gly Cys Leu Trp
1               5                   10                  15

Glu Asp Gly Val
            20

<210> SEQ ID NO 262
<211> LENGTH: 20
<212> TYPE: PRT
<213> ORGANISM: Artificial Sequence
<220> FEATURE:
<223> OTHER INFORMATION: Synthesized

<400> SEQUENCE: 262

Leu Arg Leu Met Asp Asn Ile Cys Leu Pro Arg Trp Gly Cys Leu Trp
1               5                   10                  15

Asp Asp Gly Phe
            20

<210> SEQ ID NO 263
<211> LENGTH: 20
<212> TYPE: PRT
<213> ORGANISM: Artificial Sequence
<220> FEATURE:
<223> OTHER INFORMATION: Synthesized

<400> SEQUENCE: 263
```

```
Leu Trp Ala Met Glu Asp Ile Cys Leu Pro Lys Trp Gly Cys Leu Trp
1               5                   10                  15

Glu Asp Asp Phe
            20

<210> SEQ ID NO 264
<211> LENGTH: 20
<212> TYPE: PRT
<213> ORGANISM: Artificial Sequence
<220> FEATURE:
<223> OTHER INFORMATION: Synthesized

<400> SEQUENCE: 264

Gln Arg Asp Met Gly Asp Ile Cys Leu Pro Arg Trp Gly Cys Leu Trp
1               5                   10                  15

Glu Asp Gly Val
            20

<210> SEQ ID NO 265
<211> LENGTH: 20
<212> TYPE: PRT
<213> ORGANISM: Artificial Sequence
<220> FEATURE:
<223> OTHER INFORMATION: Synthesized

<400> SEQUENCE: 265

Gln Arg Leu Met Glu Asp Ile Cys Leu Pro Arg Trp Gly Cys Leu Trp
1               5                   10                  15

Gly Asp Arg Phe
            20

<210> SEQ ID NO 266
<211> LENGTH: 20
<212> TYPE: PRT
<213> ORGANISM: Artificial Sequence
<220> FEATURE:
<223> OTHER INFORMATION: Synthesized

<400> SEQUENCE: 266

Gln Trp His Met Glu Asp Ile Cys Leu Pro Gln Trp Gly Cys Leu Trp
1               5                   10                  15

Gly Asp Val Leu
            20

<210> SEQ ID NO 267
<211> LENGTH: 20
<212> TYPE: PRT
<213> ORGANISM: Artificial Sequence
<220> FEATURE:
<223> OTHER INFORMATION: Synthesized

<400> SEQUENCE: 267

Gln Trp Gln Met Glu Asn Val Cys Leu Pro Lys Trp Gly Cys Leu Trp
1               5                   10                  15

Glu Glu Leu Asp
            20

<210> SEQ ID NO 268
<211> LENGTH: 20
<212> TYPE: PRT
<213> ORGANISM: Artificial Sequence
<220> FEATURE:
<223> OTHER INFORMATION: Synthesized

<400> SEQUENCE: 268
```

```
Gln Trp Gln Val Met Asp Ile Cys Leu Pro Arg Trp Gly Cys Leu Trp
1               5                   10                  15

Ala Asp Glu Tyr
            20

<210> SEQ ID NO 269
<211> LENGTH: 11
<212> TYPE: PRT
<213> ORGANISM: Artificial Sequence
<220> FEATURE:
<223> OTHER INFORMATION: Synthesized

<400> SEQUENCE: 269

Asp Ile Cys Leu Pro Arg Trp Gly Cys Leu Trp
1               5                   10

<210> SEQ ID NO 270
<211> LENGTH: 20
<212> TYPE: PRT
<213> ORGANISM: Artificial Sequence
<220> FEATURE:
<223> OTHER INFORMATION: Synthesized

<400> SEQUENCE: 270

Ala Ala Gln Val Gly Asp Ile Cys Leu Pro Arg Trp Gly Cys Leu Trp
1               5                   10                  15

Ser Glu Tyr Ala
            20

<210> SEQ ID NO 271
<211> LENGTH: 20
<212> TYPE: PRT
<213> ORGANISM: Artificial Sequence
<220> FEATURE:
<223> OTHER INFORMATION: Synthesized

<400> SEQUENCE: 271

Ala Gly Trp Ala Ala Asp Val Cys Leu Pro Arg Trp Gly Cys Leu Trp
1               5                   10                  15

Glu Glu Asp Val
            20

<210> SEQ ID NO 272
<211> LENGTH: 18
<212> TYPE: PRT
<213> ORGANISM: Artificial Sequence
<220> FEATURE:
<223> OTHER INFORMATION: Synthesized

<400> SEQUENCE: 272

Ala Leu Phe Glu Asp Val Cys Leu Pro Val Trp Gly Cys Leu Trp Gly
1               5                   10                  15

Gly Glu

<210> SEQ ID NO 273
<211> LENGTH: 20
<212> TYPE: PRT
<213> ORGANISM: Artificial Sequence
<220> FEATURE:
<223> OTHER INFORMATION: Synthesized

<400> SEQUENCE: 273

Ala Gln Ala Met Gly Asp Ile Cys Leu Pro Arg Trp Gly Cys Leu Trp
1               5                   10                  15
```

```
Glu Ala Glu Ile
            20

<210> SEQ ID NO 274
<211> LENGTH: 20
<212> TYPE: PRT
<213> ORGANISM: Artificial Sequence
<220> FEATURE:
<223> OTHER INFORMATION: Synthesized

<400> SEQUENCE: 274

Ala Ser Asp Pro Gly Asp Val Cys Leu Pro Arg Trp Gly Cys Leu Trp
1               5                   10                  15

Gly Glu Ser Phe
            20

<210> SEQ ID NO 275
<211> LENGTH: 20
<212> TYPE: PRT
<213> ORGANISM: Artificial Sequence
<220> FEATURE:
<223> OTHER INFORMATION: Synthesized

<400> SEQUENCE: 275

Ala Ser Asp Arg Gly Asp Leu Cys Leu Pro Tyr Trp Gly Cys Leu Trp
1               5                   10                  15

Gly Pro Asp Gly
            20

<210> SEQ ID NO 276
<211> LENGTH: 18
<212> TYPE: PRT
<213> ORGANISM: Artificial Sequence
<220> FEATURE:
<223> OTHER INFORMATION: Synthesized

<400> SEQUENCE: 276

Ala Ser Glu Trp Asp Val Cys Leu Pro Thr Trp Gly Cys Leu Trp Met
1               5                   10                  15

Glu Gly

<210> SEQ ID NO 277
<211> LENGTH: 20
<212> TYPE: PRT
<213> ORGANISM: Artificial Sequence
<220> FEATURE:
<223> OTHER INFORMATION: Synthesized

<400> SEQUENCE: 277

Ala Ser Asn Trp Glu Asp Val Cys Leu Pro Arg Trp Gly Cys Leu Trp
1               5                   10                  15

Gly Glu Arg Asn
            20

<210> SEQ ID NO 278
<211> LENGTH: 20
<212> TYPE: PRT
<213> ORGANISM: Artificial Sequence
<220> FEATURE:
<223> OTHER INFORMATION: Synthesized

<400> SEQUENCE: 278

Ala Ser Thr Pro Arg Asp Ile Cys Leu Pro Arg Trp Gly Cys Leu Trp
1               5                   10                  15
```

```
Ser Glu Asp Ala
            20

<210> SEQ ID NO 279
<211> LENGTH: 20
<212> TYPE: PRT
<213> ORGANISM: Artificial Sequence
<220> FEATURE:
<223> OTHER INFORMATION: Synthesized

<400> SEQUENCE: 279

Ala Ser Val Val Asp Asp Ile Cys Leu Pro Val Trp Gly Cys Leu Trp
1               5                   10                  15

Gly Glu Asp Ile
            20

<210> SEQ ID NO 280
<211> LENGTH: 20
<212> TYPE: PRT
<213> ORGANISM: Artificial Sequence
<220> FEATURE:
<223> OTHER INFORMATION: Synthesized

<400> SEQUENCE: 280

Ala Thr Met Glu Asp Asp Ile Cys Leu Pro Arg Trp Gly Cys Leu Trp
1               5                   10                  15

Gly Ala Glu Glu
            20

<210> SEQ ID NO 281
<211> LENGTH: 18
<212> TYPE: PRT
<213> ORGANISM: Artificial Sequence
<220> FEATURE:
<223> OTHER INFORMATION: Synthesized

<400> SEQUENCE: 281

Ala Tyr Ser Ala Asp Ile Cys Leu Pro Arg Trp Gly Cys Leu Trp Met
1               5                   10                  15

Ser Glu

<210> SEQ ID NO 282
<211> LENGTH: 20
<212> TYPE: PRT
<213> ORGANISM: Artificial Sequence
<220> FEATURE:
<223> OTHER INFORMATION: Synthesized

<400> SEQUENCE: 282

Asp Glu Asp Phe Glu Asp Tyr Cys Leu Pro Pro Trp Gly Cys Leu Trp
1               5                   10                  15

Gly Ser Ser Met
            20

<210> SEQ ID NO 283
<211> LENGTH: 20
<212> TYPE: PRT
<213> ORGANISM: Artificial Sequence
<220> FEATURE:
<223> OTHER INFORMATION: Synthesized

<400> SEQUENCE: 283

Asp Gly Glu Glu Gly Asp Leu Cys Leu Pro Arg Trp Gly Cys Leu Trp
1               5                   10                  15
```

Ala Leu Glu His
            20

<210> SEQ ID NO 284
<211> LENGTH: 18
<212> TYPE: PRT
<213> ORGANISM: Artificial Sequence
<220> FEATURE:
<223> OTHER INFORMATION: Synthesized

<400> SEQUENCE: 284

Glu Asp Trp Glu Asp Ile Cys Leu Pro Gln Trp Gly Cys Leu Trp Glu
1               5                   10                  15

Gly Met

<210> SEQ ID NO 285
<211> LENGTH: 18
<212> TYPE: PRT
<213> ORGANISM: Artificial Sequence
<220> FEATURE:
<223> OTHER INFORMATION: Synthesized

<400> SEQUENCE: 285

Glu Asp Trp Thr Asp Leu Cys Leu Pro Ala Trp Gly Cys Leu Trp Asp
1               5                   10                  15

Thr Glu

<210> SEQ ID NO 286
<211> LENGTH: 18
<212> TYPE: PRT
<213> ORGANISM: Artificial Sequence
<220> FEATURE:
<223> OTHER INFORMATION: Synthesized

<400> SEQUENCE: 286

Glu Glu Asp Ser Asp Ile Cys Leu Pro Arg Trp Gly Cys Leu Trp Asn
1               5                   10                  15

Thr Ser

<210> SEQ ID NO 287
<211> LENGTH: 20
<212> TYPE: PRT
<213> ORGANISM: Artificial Sequence
<220> FEATURE:
<223> OTHER INFORMATION: Synthesized

<400> SEQUENCE: 287

Glu Gly Glu Glu Val Asp Ile Cys Leu Pro Gln Trp Gly Cys Leu Trp
1               5                   10                  15

Gly Tyr Pro Val
            20

<210> SEQ ID NO 288
<211> LENGTH: 20
<212> TYPE: PRT
<213> ORGANISM: Artificial Sequence
<220> FEATURE:
<223> OTHER INFORMATION: Synthesized

<400> SEQUENCE: 288

Glu Gly Thr Trp Asp Asp Phe Cys Leu Pro Arg Trp Gly Cys Leu Trp
1               5                   10                  15

Leu Gly Glu Arg

<210> SEQ ID NO 289
<211> LENGTH: 18
<212> TYPE: PRT
<213> ORGANISM: Artificial Sequence
<220> FEATURE:
<223> OTHER INFORMATION: Synthesized

<400> SEQUENCE: 289

Glu Gly Tyr Trp Asp Leu Cys Leu Pro Arg Trp Gly Cys Leu Trp Glu
1               5                   10                  15

Leu Glu

<210> SEQ ID NO 290
<211> LENGTH: 18
<212> TYPE: PRT
<213> ORGANISM: Artificial Sequence
<220> FEATURE:
<223> OTHER INFORMATION: Synthesized

<400> SEQUENCE: 290

Glu Leu Gly Glu Asp Leu Cys Leu Pro Arg Trp Gly Cys Leu Trp Gly
1               5                   10                  15

Ser Glu

<210> SEQ ID NO 291
<211> LENGTH: 20
<212> TYPE: PRT
<213> ORGANISM: Artificial Sequence
<220> FEATURE:
<223> OTHER INFORMATION: Synthesized

<400> SEQUENCE: 291

Glu Arg Trp Glu Gly Asp Val Cys Leu Pro Arg Trp Gly Cys Leu Trp
1               5                   10                  15

Gly Glu Ser Gly
            20

<210> SEQ ID NO 292
<211> LENGTH: 18
<212> TYPE: PRT
<213> ORGANISM: Artificial Sequence
<220> FEATURE:
<223> OTHER INFORMATION: Synthesized

<400> SEQUENCE: 292

Glu Thr Trp Ser Asp Val Cys Leu Pro Arg Trp Gly Cys Leu Trp Gly
1               5                   10                  15

Ala Ser

<210> SEQ ID NO 293
<211> LENGTH: 20
<212> TYPE: PRT
<213> ORGANISM: Artificial Sequence
<220> FEATURE:
<223> OTHER INFORMATION: Synthesized

<400> SEQUENCE: 293

Glu Val Gly Asp Leu Asp Leu Cys Leu Pro Arg Trp Gly Cys Leu Trp
1               5                   10                  15

Gly Asn Asp Lys
            20

<210> SEQ ID NO 294
<211> LENGTH: 20
<212> TYPE: PRT
<213> ORGANISM: Artificial Sequence
<220> FEATURE:
<223> OTHER INFORMATION: Synthesized

<400> SEQUENCE: 294

```
Phe Arg Asp Gly Glu Asp Phe Cys Leu Pro Gln Trp Gly Cys Leu Trp
1               5                   10                  15

Ala Asp Thr Ser
            20
```

<210> SEQ ID NO 295
<211> LENGTH: 20
<212> TYPE: PRT
<213> ORGANISM: Artificial Sequence
<220> FEATURE:
<223> OTHER INFORMATION: Synthesized

<400> SEQUENCE: 295

```
Gly Asp Met Val Asn Asp Phe Cys Leu Pro Arg Trp Gly Cys Leu Trp
1               5                   10                  15

Gly Ser Glu Asn
            20
```

<210> SEQ ID NO 296
<211> LENGTH: 20
<212> TYPE: PRT
<213> ORGANISM: Artificial Sequence
<220> FEATURE:
<223> OTHER INFORMATION: Synthesized

<400> SEQUENCE: 296

```
Gly Asp Trp Met His Asp Ile Cys Leu Pro Lys Trp Gly Cys Leu Trp
1               5                   10                  15

Asp Glu Lys Ala
            20
```

<210> SEQ ID NO 297
<211> LENGTH: 18
<212> TYPE: PRT
<213> ORGANISM: Artificial Sequence
<220> FEATURE:
<223> OTHER INFORMATION: Synthesized

<400> SEQUENCE: 297

```
Gly Asp Tyr Val Asp Leu Cys Leu Pro Gly Trp Gly Cys Leu Trp Glu
1               5                   10                  15

Asp Gly
```

<210> SEQ ID NO 298
<211> LENGTH: 20
<212> TYPE: PRT
<213> ORGANISM: Artificial Sequence
<220> FEATURE:
<223> OTHER INFORMATION: Synthesized

<400> SEQUENCE: 298

```
Gly Ile Glu Trp Gly Asp Thr Cys Leu Pro Lys Trp Gly Cys Leu Trp
1               5                   10                  15

Arg Val Glu Gly
            20
```

```
<210> SEQ ID NO 299
<211> LENGTH: 20
<212> TYPE: PRT
<213> ORGANISM: Artificial Sequence
<220> FEATURE:
<223> OTHER INFORMATION: Synthesized

<400> SEQUENCE: 299

Gly Gln Gln Gly Glu Asp Val Cys Leu Pro Val Trp Gly Cys Leu Trp
1               5                   10                  15

Asp Thr Ser Ser
            20

<210> SEQ ID NO 300
<211> LENGTH: 20
<212> TYPE: PRT
<213> ORGANISM: Artificial Sequence
<220> FEATURE:
<223> OTHER INFORMATION: Synthesized

<400> SEQUENCE: 300

Gly Arg Met Gly Thr Asp Leu Cys Leu Pro Arg Trp Gly Cys Leu Trp
1               5                   10                  15

Gly Glu Val Glu
            20

<210> SEQ ID NO 301
<211> LENGTH: 20
<212> TYPE: PRT
<213> ORGANISM: Artificial Sequence
<220> FEATURE:
<223> OTHER INFORMATION: Synthesized

<400> SEQUENCE: 301

Gly Arg Tyr Pro Met Asp Leu Cys Leu Pro Arg Trp Gly Cys Leu Trp
1               5                   10                  15

Glu Asp Ser Ala
            20

<210> SEQ ID NO 302
<211> LENGTH: 20
<212> TYPE: PRT
<213> ORGANISM: Artificial Sequence
<220> FEATURE:
<223> OTHER INFORMATION: Synthesized

<400> SEQUENCE: 302

Gly Ser Ala Gly Asp Asp Leu Cys Leu Pro Arg Trp Gly Cys Leu Trp
1               5                   10                  15

Glu Arg Gly Ala
            20

<210> SEQ ID NO 303
<211> LENGTH: 18
<212> TYPE: PRT
<213> ORGANISM: Artificial Sequence
<220> FEATURE:
<223> OTHER INFORMATION: Synthesized

<400> SEQUENCE: 303

Gly Val Leu Asp Asp Ile Cys Leu Pro Arg Trp Gly Cys Leu Trp Gly
1               5                   10                  15

Pro Lys
```

-continued

<210> SEQ ID NO 304
<211> LENGTH: 20
<212> TYPE: PRT
<213> ORGANISM: Artificial Sequence
<220> FEATURE:
<223> OTHER INFORMATION: Synthesized

<400> SEQUENCE: 304

His Ala Ser Asp Trp Asp Val Cys Leu Pro Gly Trp Gly Cys Leu Trp
1               5                   10                  15

Glu Glu Asp Asp
            20

<210> SEQ ID NO 305
<211> LENGTH: 20
<212> TYPE: PRT
<213> ORGANISM: Artificial Sequence
<220> FEATURE:
<223> OTHER INFORMATION: Synthesized

<400> SEQUENCE: 305

His Glu Trp Glu Arg Asp Ile Cys Leu Pro Arg Trp Gly Cys Leu Trp
1               5                   10                  15

Arg Asp Gly Asp
            20

<210> SEQ ID NO 306
<211> LENGTH: 18
<212> TYPE: PRT
<213> ORGANISM: Artificial Sequence
<220> FEATURE:
<223> OTHER INFORMATION: Synthesized

<400> SEQUENCE: 306

His Met Met Asp Asp Val Cys Leu Pro Gly Trp Gly Cys Leu Trp Ala
1               5                   10                  15

Ser Glu

<210> SEQ ID NO 307
<211> LENGTH: 18
<212> TYPE: PRT
<213> ORGANISM: Artificial Sequence
<220> FEATURE:
<223> OTHER INFORMATION: Synthesized

<400> SEQUENCE: 307

Ile Asp Tyr Thr Asp Leu Cys Leu Pro Ala Trp Gly Cys Leu Trp Glu
1               5                   10                  15

Leu Glu

<210> SEQ ID NO 308
<211> LENGTH: 18
<212> TYPE: PRT
<213> ORGANISM: Artificial Sequence
<220> FEATURE:
<223> OTHER INFORMATION: Synthesized

<400> SEQUENCE: 308

Ile Glu His Glu Asp Leu Cys Leu Pro Arg Trp Gly Cys Leu Trp Ala
1               5                   10                  15

Val Asp

<210> SEQ ID NO 309

```
<211> LENGTH: 18
<212> TYPE: PRT
<213> ORGANISM: Artificial Sequence
<220> FEATURE:
<223> OTHER INFORMATION: Synthesized

<400> SEQUENCE: 309

Ile Ser Glu Trp Asp Leu Cys Leu Pro Arg Trp Gly Cys Leu Trp Asp
1               5                   10                  15

Arg Ser

<210> SEQ ID NO 310
<211> LENGTH: 18
<212> TYPE: PRT
<213> ORGANISM: Artificial Sequence
<220> FEATURE:
<223> OTHER INFORMATION: Synthesized

<400> SEQUENCE: 310

Ile Ser Trp Ala Asp Val Cys Leu Pro Lys Trp Gly Cys Leu Trp Gly
1               5                   10                  15

Lys Asp

<210> SEQ ID NO 311
<211> LENGTH: 18
<212> TYPE: PRT
<213> ORGANISM: Artificial Sequence
<220> FEATURE:
<223> OTHER INFORMATION: Synthesized

<400> SEQUENCE: 311

Ile Ser Trp Gly Asp Leu Cys Leu Pro Arg Trp Gly Cys Leu Trp Glu
1               5                   10                  15

Gly Ser

<210> SEQ ID NO 312
<211> LENGTH: 20
<212> TYPE: PRT
<213> ORGANISM: Artificial Sequence
<220> FEATURE:
<223> OTHER INFORMATION: Synthesized

<400> SEQUENCE: 312

Lys Lys Val Ser Gly Asp Ile Cys Leu Pro Ile Trp Gly Cys Leu Trp
1               5                   10                  15

Asp Asn Asp Tyr
            20

<210> SEQ ID NO 313
<211> LENGTH: 18
<212> TYPE: PRT
<213> ORGANISM: Artificial Sequence
<220> FEATURE:
<223> OTHER INFORMATION: Synthesized

<400> SEQUENCE: 313

Lys Leu Trp Asp Asp Ile Cys Leu Pro Arg Trp Gly Cys Leu Trp Ser
1               5                   10                  15

Pro Leu

<210> SEQ ID NO 314
<211> LENGTH: 18
<212> TYPE: PRT
<213> ORGANISM: Artificial Sequence
```

```
<220> FEATURE:
<223> OTHER INFORMATION: Synthesized

<400> SEQUENCE: 314

Leu Ala Trp Pro Asp Val Cys Leu Pro Arg Trp Gly Cys Leu Trp Gly
1               5                   10                  15

Gly Met

<210> SEQ ID NO 315
<211> LENGTH: 20
<212> TYPE: PRT
<213> ORGANISM: Artificial Sequence
<220> FEATURE:
<223> OTHER INFORMATION: Synthesized

<400> SEQUENCE: 315

Leu Gly Val Thr His Asp Thr Cys Leu Pro Arg Trp Gly Cys Leu Trp
1               5                   10                  15

Asp Glu Val Gly
            20

<210> SEQ ID NO 316
<211> LENGTH: 20
<212> TYPE: PRT
<213> ORGANISM: Artificial Sequence
<220> FEATURE:
<223> OTHER INFORMATION: Synthesized

<400> SEQUENCE: 316

Leu Leu Glu Ser Asp Asp Ile Cys Leu Pro Arg Trp Gly Cys Leu Trp
1               5                   10                  15

His Glu Asp Gly
            20

<210> SEQ ID NO 317
<211> LENGTH: 18
<212> TYPE: PRT
<213> ORGANISM: Artificial Sequence
<220> FEATURE:
<223> OTHER INFORMATION: Synthesized

<400> SEQUENCE: 317

Leu Asn Glu Ser Asp Ile Cys Leu Pro Thr Trp Gly Cys Leu Trp Gly
1               5                   10                  15

Val Asp

<210> SEQ ID NO 318
<211> LENGTH: 18
<212> TYPE: PRT
<213> ORGANISM: Artificial Sequence
<220> FEATURE:
<223> OTHER INFORMATION: Synthesized

<400> SEQUENCE: 318

Leu Pro Glu Gln Asp Val Cys Leu Pro Val Trp Gly Cys Leu Trp Asp
1               5                   10                  15

Ala Asn

<210> SEQ ID NO 319
<211> LENGTH: 20
<212> TYPE: PRT
<213> ORGANISM: Artificial Sequence
<220> FEATURE:
<223> OTHER INFORMATION: Synthesized
```

-continued

<400> SEQUENCE: 319

Leu Val Trp Glu Glu Asp Phe Cys Leu Pro Lys Trp Gly Cys Leu Trp
1               5                   10                  15

Gly Ala Glu Asp
            20

<210> SEQ ID NO 320
<211> LENGTH: 18
<212> TYPE: PRT
<213> ORGANISM: Artificial Sequence
<220> FEATURE:
<223> OTHER INFORMATION: Synthesized

<400> SEQUENCE: 320

Met Ala Trp Gly Asp Val Cys Leu Pro Arg Trp Gly Cys Leu Trp Ala
1               5                   10                  15

Gly Gly

<210> SEQ ID NO 321
<211> LENGTH: 20
<212> TYPE: PRT
<213> ORGANISM: Artificial Sequence
<220> FEATURE:
<223> OTHER INFORMATION: Synthesized

<400> SEQUENCE: 321

Met Gln Ala Glu Ser Asp Phe Cys Leu Pro His Trp Gly Cys Leu Trp
1               5                   10                  15

Asp Glu Gly Thr
            20

<210> SEQ ID NO 322
<211> LENGTH: 20
<212> TYPE: PRT
<213> ORGANISM: Artificial Sequence
<220> FEATURE:
<223> OTHER INFORMATION: Synthesized

<400> SEQUENCE: 322

Met Gln Gly Pro Leu Asp Ile Cys Leu Pro Arg Trp Gly Cys Leu Trp
1               5                   10                  15

Gly Gly Val Asp
            20

<210> SEQ ID NO 323
<211> LENGTH: 18
<212> TYPE: PRT
<213> ORGANISM: Artificial Sequence
<220> FEATURE:
<223> OTHER INFORMATION: Synthesized

<400> SEQUENCE: 323

Asn Glu Glu Trp Asp Val Cys Leu Pro Arg Trp Gly Cys Leu Trp Gly
1               5                   10                  15

Gly Val

<210> SEQ ID NO 324
<211> LENGTH: 20
<212> TYPE: PRT
<213> ORGANISM: Artificial Sequence
<220> FEATURE:
<223> OTHER INFORMATION: Synthesized

<400> SEQUENCE: 324

Asn Val Gly Trp Asn Asp Ile Cys Leu Pro Arg Trp Gly Cys Leu Trp
1               5                   10                  15

Ala Gln Glu Ser
            20

<210> SEQ ID NO 325
<211> LENGTH: 18
<212> TYPE: PRT
<213> ORGANISM: Artificial Sequence
<220> FEATURE:
<223> OTHER INFORMATION: Synthesized

<400> SEQUENCE: 325

Gln Glu Leu Gln Asp Phe Cys Leu Pro Arg Trp Gly Cys Leu Trp Gly
1               5                   10                  15

Val Gly

<210> SEQ ID NO 326
<211> LENGTH: 20
<212> TYPE: PRT
<213> ORGANISM: Artificial Sequence
<220> FEATURE:
<223> OTHER INFORMATION: Synthesized

<400> SEQUENCE: 326

Gln Gly Val Glu Trp Asp Val Cys Leu Pro Gln Trp Gly Cys Leu Trp
1               5                   10                  15

Thr Arg Glu Val
            20

<210> SEQ ID NO 327
<211> LENGTH: 20
<212> TYPE: PRT
<213> ORGANISM: Artificial Sequence
<220> FEATURE:
<223> OTHER INFORMATION: Synthesized

<400> SEQUENCE: 327

Gln Met Pro Leu Glu Asp Ile Cys Leu Pro Arg Trp Gly Cys Leu Trp
1               5                   10                  15

Glu Gly Arg Glu
            20

<210> SEQ ID NO 328
<211> LENGTH: 18
<212> TYPE: PRT
<213> ORGANISM: Artificial Sequence
<220> FEATURE:
<223> OTHER INFORMATION: Synthesized

<400> SEQUENCE: 328

Gln Arg Glu Trp Asp Val Cys Leu Pro Arg Trp Gly Cys Leu Trp Ser
1               5                   10                  15

Asp Val

<210> SEQ ID NO 329
<211> LENGTH: 18
<212> TYPE: PRT
<213> ORGANISM: Artificial Sequence
<220> FEATURE:
<223> OTHER INFORMATION: Synthesized

<400> SEQUENCE: 329

```
Gln Arg Phe Trp Asp Thr Cys Leu Pro Arg Trp Gly Cys Leu Trp Gly
1               5                   10                  15

Gly Asp

<210> SEQ ID NO 330
<211> LENGTH: 20
<212> TYPE: PRT
<213> ORGANISM: Artificial Sequence
<220> FEATURE:
<223> OTHER INFORMATION: Synthesized

<400> SEQUENCE: 330

Arg Glu Glu Trp Gly Asp Leu Cys Leu Pro Thr Trp Gly Cys Leu Trp
1               5                   10                  15

Glu Thr Lys Lys
            20

<210> SEQ ID NO 331
<211> LENGTH: 20
<212> TYPE: PRT
<213> ORGANISM: Artificial Sequence
<220> FEATURE:
<223> OTHER INFORMATION: Synthesized

<400> SEQUENCE: 331

Arg Leu Asp Ala Trp Asp Ile Cys Leu Pro Gln Trp Gly Cys Leu Trp
1               5                   10                  15

Glu Glu Pro Ser
            20

<210> SEQ ID NO 332
<211> LENGTH: 18
<212> TYPE: PRT
<213> ORGANISM: Artificial Sequence
<220> FEATURE:
<223> OTHER INFORMATION: Synthesized

<400> SEQUENCE: 332

Arg Val Phe Thr Asp Val Cys Leu Pro Arg Trp Gly Cys Leu Trp Asp
1               5                   10                  15

Leu Gly

<210> SEQ ID NO 333
<211> LENGTH: 20
<212> TYPE: PRT
<213> ORGANISM: Artificial Sequence
<220> FEATURE:
<223> OTHER INFORMATION: Synthesized

<400> SEQUENCE: 333

Arg Val Trp Thr Glu Asp Val Cys Leu Pro Arg Trp Gly Cys Leu Trp
1               5                   10                  15

Ser Glu Gly Asn
            20

<210> SEQ ID NO 334
<211> LENGTH: 20
<212> TYPE: PRT
<213> ORGANISM: Artificial Sequence
<220> FEATURE:
<223> OTHER INFORMATION: Synthesized

<400> SEQUENCE: 334
```

```
Ser Glu Ala Pro Gly Asp Tyr Cys Leu Pro Arg Trp Gly Cys Leu Trp
1               5                   10                  15

Ala Gln Glu Lys
            20

<210> SEQ ID NO 335
<211> LENGTH: 18
<212> TYPE: PRT
<213> ORGANISM: Artificial Sequence
<220> FEATURE:
<223> OTHER INFORMATION: Synthesized

<400> SEQUENCE: 335

Ser Gly Trp Asp Asp Val Cys Leu Pro Val Trp Gly Cys Leu Trp Gly
1               5                   10                  15

Pro Ser

<210> SEQ ID NO 336
<211> LENGTH: 20
<212> TYPE: PRT
<213> ORGANISM: Artificial Sequence
<220> FEATURE:
<223> OTHER INFORMATION: Synthesized

<400> SEQUENCE: 336

Ser Ile Arg Glu Tyr Asp Val Cys Leu Pro Lys Trp Gly Cys Leu Trp
1               5                   10                  15

Glu Pro Ser Ala
            20

<210> SEQ ID NO 337
<211> LENGTH: 20
<212> TYPE: PRT
<213> ORGANISM: Artificial Sequence
<220> FEATURE:
<223> OTHER INFORMATION: Synthesized

<400> SEQUENCE: 337

Ser Pro Thr Glu Trp Asp Met Cys Leu Pro Lys Trp Gly Cys Leu Trp
1               5                   10                  15

Gly Asp Ala Leu
            20

<210> SEQ ID NO 338
<211> LENGTH: 18
<212> TYPE: PRT
<213> ORGANISM: Artificial Sequence
<220> FEATURE:
<223> OTHER INFORMATION: Synthesized

<400> SEQUENCE: 338

Ser Ser Ala Ser Asp Tyr Cys Leu Pro Arg Trp Gly Cys Leu Trp Gly
1               5                   10                  15

Asp Leu

<210> SEQ ID NO 339
<211> LENGTH: 20
<212> TYPE: PRT
<213> ORGANISM: Artificial Sequence
<220> FEATURE:
<223> OTHER INFORMATION: Synthesized

<400> SEQUENCE: 339

Ser Ser Gly Leu Glu Asp Ile Cys Leu Pro Asn Trp Gly Cys Leu Trp
```

```
1               5                   10                  15
Ala Asp Gly Ser
            20

<210> SEQ ID NO 340
<211> LENGTH: 20
<212> TYPE: PRT
<213> ORGANISM: Artificial Sequence
<220> FEATURE:
<223> OTHER INFORMATION: Synthesized

<400> SEQUENCE: 340

Ser Val Gly Trp Gly Asp Ile Cys Leu Pro Val Trp Gly Cys Leu Trp
1               5                   10                  15

Gly Glu Gly Gly
            20

<210> SEQ ID NO 341
<211> LENGTH: 18
<212> TYPE: PRT
<213> ORGANISM: Artificial Sequence
<220> FEATURE:
<223> OTHER INFORMATION: Synthesized

<400> SEQUENCE: 341

Ser Trp Gln Gly Asp Ile Cys Leu Pro Arg Trp Gly Cys Leu Trp Gly
1               5                   10                  15

Val Asp

<210> SEQ ID NO 342
<211> LENGTH: 18
<212> TYPE: PRT
<213> ORGANISM: Artificial Sequence
<220> FEATURE:
<223> OTHER INFORMATION: Synthesized

<400> SEQUENCE: 342

Ser Tyr Glu Thr Asp Val Cys Leu Pro Tyr Trp Gly Cys Leu Trp Glu
1               5                   10                  15

Asp Ala

<210> SEQ ID NO 343
<211> LENGTH: 18
<212> TYPE: PRT
<213> ORGANISM: Artificial Sequence
<220> FEATURE:
<223> OTHER INFORMATION: Synthesized

<400> SEQUENCE: 343

Ser Tyr Trp Gly Asp Val Cys Leu Pro Arg Trp Gly Cys Leu Trp Ser
1               5                   10                  15

Glu Ala

<210> SEQ ID NO 344
<211> LENGTH: 20
<212> TYPE: PRT
<213> ORGANISM: Artificial Sequence
<220> FEATURE:
<223> OTHER INFORMATION: Synthesized

<400> SEQUENCE: 344

Thr Ala Met Asp Glu Asp Val Cys Leu Pro Arg Trp Gly Cys Leu Trp
1               5                   10                  15
```

Gly Ser Gly Ser
            20

<210> SEQ ID NO 345
<211> LENGTH: 20
<212> TYPE: PRT
<213> ORGANISM: Artificial Sequence
<220> FEATURE:
<223> OTHER INFORMATION: Synthesized

<400> SEQUENCE: 345

Thr Glu Glu Asn Trp Asp Leu Cys Leu Pro Arg Trp Gly Cys Leu Trp
1               5                   10                  15

Gly Asp Asp Trp
            20

<210> SEQ ID NO 346
<211> LENGTH: 20
<212> TYPE: PRT
<213> ORGANISM: Artificial Sequence
<220> FEATURE:
<223> OTHER INFORMATION: Synthesized

<400> SEQUENCE: 346

Thr Glu Ile Gly Gln Asp Phe Cys Leu Pro Arg Trp Gly Cys Leu Trp
1               5                   10                  15

Val Pro Gly Thr
            20

<210> SEQ ID NO 347
<211> LENGTH: 18
<212> TYPE: PRT
<213> ORGANISM: Artificial Sequence
<220> FEATURE:
<223> OTHER INFORMATION: Synthesized

<400> SEQUENCE: 347

Thr Leu Glu Trp Asp Met Cys Leu Pro Arg Trp Gly Cys Leu Trp Thr
1               5                   10                  15

Glu Gln

<210> SEQ ID NO 348
<211> LENGTH: 20
<212> TYPE: PRT
<213> ORGANISM: Artificial Sequence
<220> FEATURE:
<223> OTHER INFORMATION: Synthesized

<400> SEQUENCE: 348

Thr Leu Gly Trp Pro Asp Phe Cys Leu Pro Lys Trp Gly Cys Leu Trp
1               5                   10                  15

Arg Glu Ser Asp
            20

<210> SEQ ID NO 349
<211> LENGTH: 20
<212> TYPE: PRT
<213> ORGANISM: Artificial Sequence
<220> FEATURE:
<223> OTHER INFORMATION: Synthesized

<400> SEQUENCE: 349

Thr Leu Ser Asn Gln Asp Ile Cys Leu Pro Gly Trp Gly Cys Leu Trp
1               5                   10                  15

Gly Gly Ile Asn
            20

<210> SEQ ID NO 350
<211> LENGTH: 20
<212> TYPE: PRT
<213> ORGANISM: Artificial Sequence
<220> FEATURE:
<223> OTHER INFORMATION: Synthesized

<400> SEQUENCE: 350

Thr Ser Gly Ser Asp Asp Ile Cys Leu Pro Val Trp Gly Cys Leu Trp
1               5                   10                  15

Gly Glu Asp Ser
            20

<210> SEQ ID NO 351
<211> LENGTH: 20
<212> TYPE: PRT
<213> ORGANISM: Artificial Sequence
<220> FEATURE:
<223> OTHER INFORMATION: Synthesized

<400> SEQUENCE: 351

Thr Ser Thr Gly Gly Asp Leu Cys Leu Pro Arg Trp Gly Cys Leu Trp
1               5                   10                  15

Asp Ser Ser Glu
            20

<210> SEQ ID NO 352
<211> LENGTH: 19
<212> TYPE: PRT
<213> ORGANISM: Artificial Sequence
<220> FEATURE:
<223> OTHER INFORMATION: Synthesized

<400> SEQUENCE: 352

Thr Trp Pro Gly Asp Leu Cys Leu Pro Arg Trp Gly Cys Leu Trp Glu
1               5                   10                  15

Ala Glu Ser

<210> SEQ ID NO 353
<211> LENGTH: 18
<212> TYPE: PRT
<213> ORGANISM: Artificial Sequence
<220> FEATURE:
<223> OTHER INFORMATION: Synthesized

<400> SEQUENCE: 353

Val Gly Glu Phe Asp Ile Cys Leu Pro Arg Trp Gly Cys Leu Trp Asp
1               5                   10                  15

Ala Glu

<210> SEQ ID NO 354
<211> LENGTH: 20
<212> TYPE: PRT
<213> ORGANISM: Artificial Sequence
<220> FEATURE:
<223> OTHER INFORMATION: Synthesized

<400> SEQUENCE: 354

Val Ser Glu Met Asp Asp Ile Cys Leu Pro Leu Trp Gly Cys Leu Trp
1               5                   10                  15

Ala Asp Ala Pro

20

<210> SEQ ID NO 355
<211> LENGTH: 20
<212> TYPE: PRT
<213> ORGANISM: Artificial Sequence
<220> FEATURE:
<223> OTHER INFORMATION: Synthesized

<400> SEQUENCE: 355

Val Ser Glu Trp Glu Asp Ile Cys Leu Pro Ser Trp Gly Cys Leu Trp
1               5                   10                  15

Glu Thr Gln Asp
            20

<210> SEQ ID NO 356
<211> LENGTH: 18
<212> TYPE: PRT
<213> ORGANISM: Artificial Sequence
<220> FEATURE:
<223> OTHER INFORMATION: Synthesized

<400> SEQUENCE: 356

Val Thr Ser Trp Asp Val Cys Leu Pro Arg Trp Gly Cys Leu Trp Glu
1               5                   10                  15

Glu Asp

<210> SEQ ID NO 357
<211> LENGTH: 20
<212> TYPE: PRT
<213> ORGANISM: Artificial Sequence
<220> FEATURE:
<223> OTHER INFORMATION: Synthesized

<400> SEQUENCE: 357

Val Val Gly Asp Gly Asp Phe Cys Leu Pro Lys Trp Gly Cys Leu Trp
1               5                   10                  15

Asp Gln Ala Arg
            20

<210> SEQ ID NO 358
<211> LENGTH: 20
<212> TYPE: PRT
<213> ORGANISM: Artificial Sequence
<220> FEATURE:
<223> OTHER INFORMATION: Synthesized

<400> SEQUENCE: 358

Val Val Trp Asp Asp Val Cys Leu Pro Arg Trp Gly Cys Leu Trp
1               5                   10                  15

Glu Glu Tyr Gly
            20

<210> SEQ ID NO 359
<211> LENGTH: 20
<212> TYPE: PRT
<213> ORGANISM: Artificial Sequence
<220> FEATURE:
<223> OTHER INFORMATION: Synthesized

<400> SEQUENCE: 359

Trp Asp His Glu Leu Asp Phe Cys Leu Pro Val Trp Gly Cys Leu Trp
1               5                   10                  15

Ala Glu Asp Val

```
                    20

<210> SEQ ID NO 360
<211> LENGTH: 18
<212> TYPE: PRT
<213> ORGANISM: Artificial Sequence
<220> FEATURE:
<223> OTHER INFORMATION: Synthesized

<400> SEQUENCE: 360

Trp Leu Trp Glu Asp Leu Cys Leu Pro Lys Trp Gly Cys Leu Trp Glu
1               5                   10                  15

Glu Asp

<210> SEQ ID NO 361
<211> LENGTH: 20
<212> TYPE: PRT
<213> ORGANISM: Artificial Sequence
<220> FEATURE:
<223> OTHER INFORMATION: Synthesized

<400> SEQUENCE: 361

Trp Ser Asp Ser Asp Val Cys Leu Pro Arg Trp Gly Cys Leu Trp
1               5                   10                  15

Gly Asn Val Ala
            20

<210> SEQ ID NO 362
<211> LENGTH: 20
<212> TYPE: PRT
<213> ORGANISM: Artificial Sequence
<220> FEATURE:
<223> OTHER INFORMATION: Synthesized

<400> SEQUENCE: 362

Trp Thr Glu Ser Glu Asp Ile Cys Leu Pro Gly Trp Gly Cys Leu Trp
1               5                   10                  15

Gly Pro Glu Val
            20

<210> SEQ ID NO 363
<211> LENGTH: 20
<212> TYPE: PRT
<213> ORGANISM: Artificial Sequence
<220> FEATURE:
<223> OTHER INFORMATION: Synthesized

<400> SEQUENCE: 363

Trp Val Glu Glu Gly Asp Ile Cys Leu Pro Arg Trp Gly Cys Leu Trp
1               5                   10                  15

Glu Ser Val Glu
            20

<210> SEQ ID NO 364
<211> LENGTH: 20
<212> TYPE: PRT
<213> ORGANISM: Artificial Sequence
<220> FEATURE:
<223> OTHER INFORMATION: Synthesized

<400> SEQUENCE: 364

Trp Val Pro Phe Glu Asp Val Cys Leu Pro Arg Trp Gly Cys Leu Trp
1               5                   10                  15

Ser Ser Tyr Gln
```

```
<210> SEQ ID NO 365
<211> LENGTH: 18
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(4)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is any amino acid
<220> FEATURE:
<221> NAME/KEY: MISC_FEATURE
<222> LOCATION: (10)..(10)
<223> OTHER INFORMATION: Xaa is any amino acid
<220> FEATURE:
<221> NAME/KEY: MISC_FEATURE
<222> LOCATION: (16)..(18)
<223> OTHER INFORMATION: Xaa is any amino acid

<400> SEQUENCE: 365

Xaa Xaa Xaa Xaa Asp Xaa Cys Leu Pro Xaa Trp Gly Cys Leu Trp Xaa
 1               5                  10                  15

Xaa Xaa

<210> SEQ ID NO 366
<211> LENGTH: 20
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(5)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is any amino acid
<220> FEATURE:
<221> NAME/KEY: MISC_FEATURE
<222> LOCATION: (11)..(11)
<223> OTHER INFORMATION: Xaa is any amino acid
<220> FEATURE:
<221> NAME/KEY: MISC_FEATURE
<222> LOCATION: (17)..(20)
<223> OTHER INFORMATION: Xaa is any amino acid

<400> SEQUENCE: 366

Xaa Xaa Xaa Xaa Xaa Asp Xaa Cys Leu Pro Xaa Trp Gly Cys Leu Trp
 1               5                  10                  15

Xaa Xaa Xaa Xaa
            20

<210> SEQ ID NO 367
<211> LENGTH: 18
<212> TYPE: PRT
<213> ORGANISM: Artificial Sequence
<220> FEATURE:
<223> OTHER INFORMATION: Synthesized

<400> SEQUENCE: 367

Ala Phe Trp Ser Asp Ile Cys Leu Pro Arg Trp Gly Cys Leu Trp Glu
 1               5                  10                  15

Glu Asp
```

```
<210> SEQ ID NO 368
<211> LENGTH: 20
<212> TYPE: PRT
<213> ORGANISM: Artificial Sequence
<220> FEATURE:
<223> OTHER INFORMATION: Synthesized

<400> SEQUENCE: 368

Ala Gly Leu Asp Glu Asp Ile Cys Leu Pro Arg Trp Gly Cys Leu Trp
1               5                   10                  15

Gly Lys Glu Ala
            20

<210> SEQ ID NO 369
<211> LENGTH: 20
<212> TYPE: PRT
<213> ORGANISM: Artificial Sequence
<220> FEATURE:
<223> OTHER INFORMATION: Synthesized

<400> SEQUENCE: 369

Ala Gly Met Met Gly Asp Ile Cys Leu Pro Arg Trp Gly Cys Leu Trp
1               5                   10                  15

Gln Gly Glu Pro
            20

<210> SEQ ID NO 370
<211> LENGTH: 20
<212> TYPE: PRT
<213> ORGANISM: Artificial Sequence
<220> FEATURE:
<223> OTHER INFORMATION: Synthesized

<400> SEQUENCE: 370

Ala Pro Gly Asp Trp Asp Phe Cys Leu Pro Lys Trp Gly Cys Leu Trp
1               5                   10                  15

Asp Asp Asp Ala
            20

<210> SEQ ID NO 371
<211> LENGTH: 20
<212> TYPE: PRT
<213> ORGANISM: Artificial Sequence
<220> FEATURE:
<223> OTHER INFORMATION: Synthesized

<400> SEQUENCE: 371

Ala Gln Leu Phe Asp Asp Ile Cys Leu Pro Arg Trp Gly Cys Leu Trp
1               5                   10                  15

Ser Asp Gly Tyr
            20

<210> SEQ ID NO 372
<211> LENGTH: 20
<212> TYPE: PRT
<213> ORGANISM: Artificial Sequence
<220> FEATURE:
<223> OTHER INFORMATION: Synthesized

<400> SEQUENCE: 372

Ala Arg Thr Met Gly Asp Ile Cys Leu Pro Arg Trp Gly Cys Leu Trp
1               5                   10                  15

Gly Ala Ser Asp
```

-continued

```
              20

<210> SEQ ID NO 373
<211> LENGTH: 20
<212> TYPE: PRT
<213> ORGANISM: Artificial Sequence
<220> FEATURE:
<223> OTHER INFORMATION: Synthesized

<400> SEQUENCE: 373

Ala Val Ser Trp Ala Asp Ile Cys Leu Pro Arg Trp Gly Cys Leu Trp
1               5                   10                  15

Glu Arg Ala Asp
            20

<210> SEQ ID NO 374
<211> LENGTH: 20
<212> TYPE: PRT
<213> ORGANISM: Artificial Sequence
<220> FEATURE:
<223> OTHER INFORMATION: Synthesized

<400> SEQUENCE: 374

Ala Trp Leu Asp Glu Asp Ile Cys Leu Pro Lys Trp Gly Cys Leu Trp
1               5                   10                  15

Asn Thr Gly Val
            20

<210> SEQ ID NO 375
<211> LENGTH: 20
<212> TYPE: PRT
<213> ORGANISM: Artificial Sequence
<220> FEATURE:
<223> OTHER INFORMATION: Synthesized

<400> SEQUENCE: 375

Ala Trp Gln Asp Phe Asp Val Cys Leu Pro Arg Trp Gly Cys Leu Trp
1               5                   10                  15

Glu Pro Glu Ser
            20

<210> SEQ ID NO 376
<211> LENGTH: 20
<212> TYPE: PRT
<213> ORGANISM: Artificial Sequence
<220> FEATURE:
<223> OTHER INFORMATION: Synthesized

<400> SEQUENCE: 376

Asp Thr Thr Trp Gly Asp Ile Cys Leu Pro Arg Trp Gly Cys Leu Trp
1               5                   10                  15

Ser Glu Glu Ala
            20

<210> SEQ ID NO 377
<211> LENGTH: 18
<212> TYPE: PRT
<213> ORGANISM: Artificial Sequence
<220> FEATURE:
<223> OTHER INFORMATION: Synthesized

<400> SEQUENCE: 377

Asp Trp Gly Arg Asp Ile Cys Leu Pro Arg Trp Gly Cys Leu Trp Asp
1               5                   10                  15
```

Glu Glu

<210> SEQ ID NO 378
<211> LENGTH: 18
<212> TYPE: PRT
<213> ORGANISM: Artificial Sequence
<220> FEATURE:
<223> OTHER INFORMATION: Synthesized

<400> SEQUENCE: 378

Glu Ala Trp Gly Asp Ile Cys Leu Pro Arg Trp Gly Cys Leu Trp Glu
1               5                   10                  15

Leu Glu

<210> SEQ ID NO 379
<211> LENGTH: 20
<212> TYPE: PRT
<213> ORGANISM: Artificial Sequence
<220> FEATURE:
<223> OTHER INFORMATION: Synthesized

<400> SEQUENCE: 379

Glu Gly Phe Leu Gly Asp Ile Cys Leu Pro Arg Trp Gly Cys Leu Trp
1               5                   10                  15

Gly His Gln Ala
            20

<210> SEQ ID NO 380
<211> LENGTH: 20
<212> TYPE: PRT
<213> ORGANISM: Artificial Sequence
<220> FEATURE:
<223> OTHER INFORMATION: Synthesized

<400> SEQUENCE: 380

Glu Gln Trp Leu His Asp Ile Cys Leu Pro Lys Trp Gly Cys Leu Trp
1               5                   10                  15

Asp Asp Thr Asp
            20

<210> SEQ ID NO 381
<211> LENGTH: 20
<212> TYPE: PRT
<213> ORGANISM: Artificial Sequence
<220> FEATURE:
<223> OTHER INFORMATION: Synthesized

<400> SEQUENCE: 381

Glu Thr Gly Trp Pro Asp Ile Cys Leu Pro Arg Trp Gly Cys Leu Trp
1               5                   10                  15

Glu Glu Gly Glu
            20

<210> SEQ ID NO 382
<211> LENGTH: 20
<212> TYPE: PRT
<213> ORGANISM: Artificial Sequence
<220> FEATURE:
<223> OTHER INFORMATION: Synthesized

<400> SEQUENCE: 382

Phe Glu Leu Gly Glu Asp Ile Cys Leu Pro Arg Trp Gly Cys Leu Trp
1               5                   10                  15

Glu Glu His Asn

```
            20

<210> SEQ ID NO 383
<211> LENGTH: 18
<212> TYPE: PRT
<213> ORGANISM: Artificial Sequence
<220> FEATURE:
<223> OTHER INFORMATION: Synthesized

<400> SEQUENCE: 383

Phe Ile Thr Gln Asp Ile Cys Leu Pro Arg Trp Gly Cys Leu Trp Gly
1               5                   10                  15

Glu Asn

<210> SEQ ID NO 384
<211> LENGTH: 18
<212> TYPE: PRT
<213> ORGANISM: Artificial Sequence
<220> FEATURE:
<223> OTHER INFORMATION: Synthesized

<400> SEQUENCE: 384

Phe Leu Trp Arg Asp Ile Cys Leu Pro Arg Trp Gly Cys Leu Trp Ser
1               5                   10                  15

Glu Gly

<210> SEQ ID NO 385
<211> LENGTH: 20
<212> TYPE: PRT
<213> ORGANISM: Artificial Sequence
<220> FEATURE:
<223> OTHER INFORMATION: Synthesized

<400> SEQUENCE: 385

Phe Ser Leu Asp Glu Asp Ile Cys Leu Pro Lys Trp Gly Cys Leu Trp
1               5                   10                  15

Gly Ala Glu Lys
            20

<210> SEQ ID NO 386
<211> LENGTH: 18
<212> TYPE: PRT
<213> ORGANISM: Artificial Sequence
<220> FEATURE:
<223> OTHER INFORMATION: Synthesized

<400> SEQUENCE: 386

Phe Val His Glu Asp Ile Cys Leu Pro Arg Trp Gly Cys Leu Trp Gly
1               5                   10                  15

Glu Gly

<210> SEQ ID NO 387
<211> LENGTH: 20
<212> TYPE: PRT
<213> ORGANISM: Artificial Sequence
<220> FEATURE:
<223> OTHER INFORMATION: Synthesized

<400> SEQUENCE: 387

Gly Ala Ser Leu Gly Asp Ile Cys Leu Pro Arg Trp Gly Cys Leu Trp
1               5                   10                  15

Gly Pro Glu Asp
            20
```

```
<210> SEQ ID NO 388
<211> LENGTH: 20
<212> TYPE: PRT
<213> ORGANISM: Artificial Sequence
<220> FEATURE:
<223> OTHER INFORMATION: Synthesized

<400> SEQUENCE: 388

Gly Asp Leu Gly Asp Asp Ile Cys Leu Pro Arg Trp Gly Cys Leu Trp
1               5                   10                  15

Asp Glu Tyr Pro
            20

<210> SEQ ID NO 389
<211> LENGTH: 20
<212> TYPE: PRT
<213> ORGANISM: Artificial Sequence
<220> FEATURE:
<223> OTHER INFORMATION: Synthesized

<400> SEQUENCE: 389

Gly Glu Gly Trp Ser Asp Ile Cys Leu Pro Arg Trp Gly Cys Leu Trp
1               5                   10                  15

Ala Glu Asp Glu
            20

<210> SEQ ID NO 390
<211> LENGTH: 20
<212> TYPE: PRT
<213> ORGANISM: Artificial Sequence
<220> FEATURE:
<223> OTHER INFORMATION: Synthesized

<400> SEQUENCE: 390

Gly Glu Trp Trp Glu Asp Ile Cys Leu Pro Arg Trp Gly Cys Leu Trp
1               5                   10                  15

Gly Ser Ser Ser
            20

<210> SEQ ID NO 391
<211> LENGTH: 18
<212> TYPE: PRT
<213> ORGANISM: Artificial Sequence
<220> FEATURE:
<223> OTHER INFORMATION: Synthesized

<400> SEQUENCE: 391

Gly Leu Gly Asp Asp Ile Cys Leu Pro Arg Trp Gly Cys Leu Trp Gly
1               5                   10                  15

Arg Asp

<210> SEQ ID NO 392
<211> LENGTH: 20
<212> TYPE: PRT
<213> ORGANISM: Artificial Sequence
<220> FEATURE:
<223> OTHER INFORMATION: Synthesized

<400> SEQUENCE: 392

Gly Leu Met Gly Glu Asp Ile Cys Leu Pro Arg Trp Gly Cys Leu Trp
1               5                   10                  15

Lys Gly Asp Ile
            20
```

<210> SEQ ID NO 393
<211> LENGTH: 18
<212> TYPE: PRT
<213> ORGANISM: Artificial Sequence
<220> FEATURE:
<223> OTHER INFORMATION: Synthesized

<400> SEQUENCE: 393

Gly Met Phe Asp Asp Ile Cys Leu Pro Lys Trp Gly Cys Leu Trp Gly
1               5                   10                  15

Leu Gly

<210> SEQ ID NO 394
<211> LENGTH: 18
<212> TYPE: PRT
<213> ORGANISM: Artificial Sequence
<220> FEATURE:
<223> OTHER INFORMATION: Synthesized

<400> SEQUENCE: 394

Gly Pro Gly Trp Asp Ile Cys Leu Pro Arg Trp Gly Cys Leu Trp Gly
1               5                   10                  15

Glu Glu

<210> SEQ ID NO 395
<211> LENGTH: 18
<212> TYPE: PRT
<213> ORGANISM: Artificial Sequence
<220> FEATURE:
<223> OTHER INFORMATION: Synthesized

<400> SEQUENCE: 395

Gly Pro Trp Tyr Asp Ile Cys Leu Pro Arg Trp Gly Cys Leu Trp Asp
1               5                   10                  15

Gly Val

<210> SEQ ID NO 396
<211> LENGTH: 20
<212> TYPE: PRT
<213> ORGANISM: Artificial Sequence
<220> FEATURE:
<223> OTHER INFORMATION: Synthesized

<400> SEQUENCE: 396

Gly Ser Leu Glu Ser Asp Ile Cys Leu Pro Arg Trp Gly Cys Leu Trp
1               5                   10                  15

Gly Ile Asp Glu
            20

<210> SEQ ID NO 397
<211> LENGTH: 18
<212> TYPE: PRT
<213> ORGANISM: Artificial Sequence
<220> FEATURE:
<223> OTHER INFORMATION: Synthesized

<400> SEQUENCE: 397

Gly Trp Asp Asp Asp Ile Cys Leu Pro Arg Trp Gly Cys Leu Trp Gly
1               5                   10                  15

Asp Gly

<210> SEQ ID NO 398
<211> LENGTH: 20

-continued

<212> TYPE: PRT
<213> ORGANISM: Artificial Sequence
<220> FEATURE:
<223> OTHER INFORMATION: Synthesized

<400> SEQUENCE: 398

Gly Trp His Asp Arg Asp Ile Cys Leu Pro Arg Trp Gly Cys Leu Trp
1               5                   10                  15
Glu Gln Asn Asp
            20

<210> SEQ ID NO 399
<211> LENGTH: 20
<212> TYPE: PRT
<213> ORGANISM: Artificial Sequence
<220> FEATURE:
<223> OTHER INFORMATION: Synthesized

<400> SEQUENCE: 399

Gly Trp Leu Glu Glu Asp Ile Cys Leu Pro Lys Trp Gly Cys Leu Trp
1               5                   10                  15
Gly Ala Asp Asn
            20

<210> SEQ ID NO 400
<211> LENGTH: 20
<212> TYPE: PRT
<213> ORGANISM: Artificial Sequence
<220> FEATURE:
<223> OTHER INFORMATION: Synthesized

<400> SEQUENCE: 400

His Glu Gln Trp Asp Asp Ile Cys Leu Pro Arg Trp Gly Cys Leu Trp
1               5                   10                  15
Gly Gly Ser Tyr
            20

<210> SEQ ID NO 401
<211> LENGTH: 18
<212> TYPE: PRT
<213> ORGANISM: Artificial Sequence
<220> FEATURE:
<223> OTHER INFORMATION: Synthesized

<400> SEQUENCE: 401

Leu Glu Tyr Glu Asp Ile Cys Leu Pro Lys Trp Gly Cys Leu Trp Gly
1               5                   10                  15
Gly Glu

<210> SEQ ID NO 402
<211> LENGTH: 18
<212> TYPE: PRT
<213> ORGANISM: Artificial Sequence
<220> FEATURE:
<223> OTHER INFORMATION: Synthesized

<400> SEQUENCE: 402

Leu Ile Leu Ser Asp Ile Cys Leu Pro Arg Trp Gly Cys Leu Trp Asp
1               5                   10                  15
Asp Thr

<210> SEQ ID NO 403
<211> LENGTH: 18
<212> TYPE: PRT

<213> ORGANISM: Artificial Sequence
<220> FEATURE:
<223> OTHER INFORMATION: Synthesized

<400> SEQUENCE: 403

Leu Lys Leu Glu Asp Ile Cys Leu Pro Arg Trp Gly Cys Leu Trp Gly
1               5                   10                  15

Glu Ser

<210> SEQ ID NO 404
<211> LENGTH: 18
<212> TYPE: PRT
<213> ORGANISM: Artificial Sequence
<220> FEATURE:
<223> OTHER INFORMATION: Synthesized

<400> SEQUENCE: 404

Leu Leu Asp Glu Asp Ile Cys Leu Pro Arg Trp Gly Cys Leu Trp Gly
1               5                   10                  15

Val Arg

<210> SEQ ID NO 405
<211> LENGTH: 20
<212> TYPE: PRT
<213> ORGANISM: Artificial Sequence
<220> FEATURE:
<223> OTHER INFORMATION: Synthesized

<400> SEQUENCE: 405

Leu Leu Gly Gly His Asp Ile Cys Leu Pro Arg Trp Gly Cys Leu Trp
1               5                   10                  15

Gly Gly Asp Val
            20

<210> SEQ ID NO 406
<211> LENGTH: 18
<212> TYPE: PRT
<213> ORGANISM: Artificial Sequence
<220> FEATURE:
<223> OTHER INFORMATION: Synthesized

<400> SEQUENCE: 406

Leu Leu Thr Arg Asp Ile Cys Leu Pro Lys Trp Gly Cys Leu Trp Gly
1               5                   10                  15

Ser Asp

<210> SEQ ID NO 407
<211> LENGTH: 18
<212> TYPE: PRT
<213> ORGANISM: Artificial Sequence
<220> FEATURE:
<223> OTHER INFORMATION: Synthesized

<400> SEQUENCE: 407

Leu Met Ser Pro Asp Ile Cys Leu Pro Lys Trp Gly Cys Leu Trp Glu
1               5                   10                  15

Gly Asp

<210> SEQ ID NO 408
<211> LENGTH: 18
<212> TYPE: PRT
<213> ORGANISM: Artificial Sequence
<220> FEATURE:
<223> OTHER INFORMATION: Synthesized -continued

```
<400> SEQUENCE: 408

Leu Arg Trp Ser Asp Ile Cys Leu Pro Arg Trp Gly Cys Leu Trp Glu
1               5                   10                  15

Glu Thr

<210> SEQ ID NO 409
<211> LENGTH: 18
<212> TYPE: PRT
<213> ORGANISM: Artificial Sequence
<220> FEATURE:
<223> OTHER INFORMATION: Synthesized

<400> SEQUENCE: 409

Leu Val Leu Gly Asp Ile Cys Leu Pro Arg Trp Gly Cys Leu Trp Glu
1               5                   10                  15

Ser Asp

<210> SEQ ID NO 410
<211> LENGTH: 18
<212> TYPE: PRT
<213> ORGANISM: Artificial Sequence
<220> FEATURE:
<223> OTHER INFORMATION: Synthesized

<400> SEQUENCE: 410

Leu Tyr Leu Arg Asp Ile Cys Leu Pro Lys Trp Gly Cys Leu Trp Glu
1               5                   10                  15

Ala Asp

<210> SEQ ID NO 411
<211> LENGTH: 18
<212> TYPE: PRT
<213> ORGANISM: Artificial Sequence
<220> FEATURE:
<223> OTHER INFORMATION: Synthesized

<400> SEQUENCE: 411

Met Leu Ser Arg Asp Ile Cys Leu Pro Arg Trp Gly Cys Leu Trp Glu
1               5                   10                  15

Glu Glu

<210> SEQ ID NO 412
<211> LENGTH: 18
<212> TYPE: PRT
<213> ORGANISM: Artificial Sequence
<220> FEATURE:
<223> OTHER INFORMATION: Synthesized

<400> SEQUENCE: 412

Met Pro Trp Thr Asp Ile Cys Leu Pro Arg Trp Gly Cys Leu Trp Ser
1               5                   10                  15

Glu Ser

<210> SEQ ID NO 413
<211> LENGTH: 20
<212> TYPE: PRT
<213> ORGANISM: Artificial Sequence
<220> FEATURE:
<223> OTHER INFORMATION: Synthesized

<400> SEQUENCE: 413

Met Arg Trp Ser Ser Asp Ile Cys Leu Pro Lys Trp Gly Cys Leu Trp
```

```
1               5                   10                  15
Gly Asp Glu Glu
            20

<210> SEQ ID NO 414
<211> LENGTH: 18
<212> TYPE: PRT
<213> ORGANISM: Artificial Sequence
<220> FEATURE:
<223> OTHER INFORMATION: Synthesized

<400> SEQUENCE: 414

Asn Trp Tyr Asp Asp Ile Cys Leu Pro Arg Trp Gly Cys Leu Trp Asp
1               5                   10                  15

Val Glu

<210> SEQ ID NO 415
<211> LENGTH: 17
<212> TYPE: PRT
<213> ORGANISM: Artificial Sequence
<220> FEATURE:
<223> OTHER INFORMATION: Synthesized

<400> SEQUENCE: 415

Gln Asp Trp Glu Asp Ile Cys Leu Pro Arg Trp Gly Cys Leu Trp Gly
1               5                   10                  15

Asp

<210> SEQ ID NO 416
<211> LENGTH: 20
<212> TYPE: PRT
<213> ORGANISM: Artificial Sequence
<220> FEATURE:
<223> OTHER INFORMATION: Synthesized

<400> SEQUENCE: 416

Gln Phe Glu Trp Asp Asp Ile Cys Leu Pro Arg Trp Gly Cys Leu Trp
1               5                   10                  15

Glu Val Glu Val
            20

<210> SEQ ID NO 417
<211> LENGTH: 20
<212> TYPE: PRT
<213> ORGANISM: Artificial Sequence
<220> FEATURE:
<223> OTHER INFORMATION: Synthesized

<400> SEQUENCE: 417

Gln Gly Trp Trp His Asp Ile Cys Leu Pro Arg Trp Gly Cys Leu Trp
1               5                   10                  15

Glu Glu Gly Glu
            20

<210> SEQ ID NO 418
<211> LENGTH: 20
<212> TYPE: PRT
<213> ORGANISM: Artificial Sequence
<220> FEATURE:
<223> OTHER INFORMATION: Synthesized

<400> SEQUENCE: 418

Gln Arg Val Asp Asp Ile Cys Leu Pro Arg Trp Gly Cys Leu Trp
1               5                   10                  15
```

Gly Glu Asn Ser
            20

<210> SEQ ID NO 419
<211> LENGTH: 18
<212> TYPE: PRT
<213> ORGANISM: Artificial Sequence
<220> FEATURE:
<223> OTHER INFORMATION: Synthesized

<400> SEQUENCE: 419

Gln Ser Trp Pro Asp Ile Cys Leu Pro Lys Trp Gly Cys Leu Trp Gly
1               5                   10                  15

Glu Gly

<210> SEQ ID NO 420
<211> LENGTH: 20
<212> TYPE: PRT
<213> ORGANISM: Artificial Sequence
<220> FEATURE:
<223> OTHER INFORMATION: Synthesized

<400> SEQUENCE: 420

Arg Glu Gly Trp Pro Asp Ile Cys Leu Pro Arg Trp Gly Cys Leu Trp
1               5                   10                  15

Ser Glu Thr Gly
            20

<210> SEQ ID NO 421
<211> LENGTH: 20
<212> TYPE: PRT
<213> ORGANISM: Artificial Sequence
<220> FEATURE:
<223> OTHER INFORMATION: Synthesized

<400> SEQUENCE: 421

Arg Glu Leu Trp Gly Asp Ile Cys Leu Pro Arg Trp Gly Cys Leu Trp
1               5                   10                  15

Glu His Ala Thr
            20

<210> SEQ ID NO 422
<211> LENGTH: 20
<212> TYPE: PRT
<213> ORGANISM: Artificial Sequence
<220> FEATURE:
<223> OTHER INFORMATION: Synthesized

<400> SEQUENCE: 422

Arg Leu Glu Leu Met Asp Ile Cys Leu Pro Arg Trp Gly Cys Leu Trp
1               5                   10                  15

Asp Pro Gln Asp
            20

<210> SEQ ID NO 423
<211> LENGTH: 18
<212> TYPE: PRT
<213> ORGANISM: Artificial Sequence
<220> FEATURE:
<223> OTHER INFORMATION: Synthesized

<400> SEQUENCE: 423

Arg Leu Gly Ser Asp Ile Cys Leu Pro Arg Trp Gly Cys Leu Trp Asp
1               5                   10                  15

Tyr Gln

<210> SEQ ID NO 424
<211> LENGTH: 18
<212> TYPE: PRT
<213> ORGANISM: Artificial Sequence
<220> FEATURE:
<223> OTHER INFORMATION: Synthesized

<400> SEQUENCE: 424

Arg Leu Gly Ser Asp Ile Cys Leu Pro Arg Trp Gly Cys Leu Trp Gly
1               5                   10                  15

Ala Gly

<210> SEQ ID NO 425
<211> LENGTH: 20
<212> TYPE: PRT
<213> ORGANISM: Artificial Sequence
<220> FEATURE:
<223> OTHER INFORMATION: Synthesized

<400> SEQUENCE: 425

Ser Gly Val Leu Gly Asp Ile Cys Leu Pro Arg Trp Gly Cys Leu Trp
1               5                   10                  15

Glu Glu Ala Gly
            20

<210> SEQ ID NO 426
<211> LENGTH: 20
<212> TYPE: PRT
<213> ORGANISM: Artificial Sequence
<220> FEATURE:
<223> OTHER INFORMATION: Synthesized

<400> SEQUENCE: 426

Ser Leu Gly Leu Thr Asp Leu Cys Leu Pro Arg Trp Gly Cys Leu Trp
1               5                   10                  15

Glu Glu Glu Gln
            20

<210> SEQ ID NO 427
<211> LENGTH: 18
<212> TYPE: PRT
<213> ORGANISM: Artificial Sequence
<220> FEATURE:
<223> OTHER INFORMATION: Synthesized

<400> SEQUENCE: 427

Ser Pro Trp Met Asp Ile Cys Leu Pro Arg Trp Gly Cys Leu Trp Glu
1               5                   10                  15

Ser Gly

<210> SEQ ID NO 428
<211> LENGTH: 20
<212> TYPE: PRT
<213> ORGANISM: Artificial Sequence
<220> FEATURE:
<223> OTHER INFORMATION: Synthesized

<400> SEQUENCE: 428

Ser Ser Leu Glu Gln Asp Ile Cys Leu Pro Arg Trp Gly Cys Leu Trp
1               5                   10                  15

Gly Gln Asp Ala

```
                    20

<210> SEQ ID NO 429
<211> LENGTH: 18
<212> TYPE: PRT
<213> ORGANISM: Artificial Sequence
<220> FEATURE:
<223> OTHER INFORMATION: Synthesized

<400> SEQUENCE: 429

Ser Thr Phe Thr Asp Ile Cys Leu Pro Arg Trp Gly Cys Leu Trp Glu
1               5                   10                  15

Leu Glu

<210> SEQ ID NO 430
<211> LENGTH: 20
<212> TYPE: PRT
<213> ORGANISM: Artificial Sequence
<220> FEATURE:
<223> OTHER INFORMATION: Synthesized

<400> SEQUENCE: 430

Ser Val Gly Trp Gly Asp Ile Cys Leu Pro Lys Trp Gly Cys Leu Trp
1               5                   10                  15

Ala Glu Ser Asp
            20

<210> SEQ ID NO 431
<211> LENGTH: 20
<212> TYPE: PRT
<213> ORGANISM: Artificial Sequence
<220> FEATURE:
<223> OTHER INFORMATION: Synthesized

<400> SEQUENCE: 431

Ser Val Leu Ser Asp Asp Ile Cys Leu Pro Arg Trp Gly Cys Leu Trp
1               5                   10                  15

Trp Asp Phe Ser
            20

<210> SEQ ID NO 432
<211> LENGTH: 18
<212> TYPE: PRT
<213> ORGANISM: Artificial Sequence
<220> FEATURE:
<223> OTHER INFORMATION: Synthesized

<400> SEQUENCE: 432

Ser Val Leu Ser Asp Ile Cys Leu Pro Arg Trp Gly Cys Leu Trp Glu
1               5                   10                  15

Glu Ser

<210> SEQ ID NO 433
<211> LENGTH: 18
<212> TYPE: PRT
<213> ORGANISM: Artificial Sequence
<220> FEATURE:
<223> OTHER INFORMATION: Synthesized

<400> SEQUENCE: 433

Thr Leu Leu Gln Asp Ile Cys Leu Pro Arg Trp Gly Cys Leu Trp Glu
1               5                   10                  15

Ser Asp
```

```
<210> SEQ ID NO 434
<211> LENGTH: 20
<212> TYPE: PRT
<213> ORGANISM: Artificial Sequence
<220> FEATURE:
<223> OTHER INFORMATION: Synthesized

<400> SEQUENCE: 434

Thr Leu Met Ser Asn Asp Ile Cys Leu Pro Arg Trp Gly Cys Leu Trp
1               5                   10                  15

Asp Glu Pro Lys
            20

<210> SEQ ID NO 435
<211> LENGTH: 20
<212> TYPE: PRT
<213> ORGANISM: Artificial Sequence
<220> FEATURE:
<223> OTHER INFORMATION: Synthesized

<400> SEQUENCE: 435

Thr Leu Val Leu Asp Asp Ile Cys Leu Pro Arg Trp Gly Cys Leu Trp
1               5                   10                  15

Asp Met Thr Asp
            20

<210> SEQ ID NO 436
<211> LENGTH: 20
<212> TYPE: PRT
<213> ORGANISM: Artificial Sequence
<220> FEATURE:
<223> OTHER INFORMATION: Synthesized

<400> SEQUENCE: 436

Thr Ser Leu Ala Asp Asp Ile Cys Leu Pro Arg Trp Gly Cys Leu Trp
1               5                   10                  15

Ser Glu Asp Gly
            20

<210> SEQ ID NO 437
<211> LENGTH: 20
<212> TYPE: PRT
<213> ORGANISM: Artificial Sequence
<220> FEATURE:
<223> OTHER INFORMATION: Synthesized

<400> SEQUENCE: 437

Thr Ser Leu Leu Asp Asp Ile Cys Leu Pro Arg Trp Gly Cys Leu Trp
1               5                   10                  15

Tyr Glu Glu Gly
            20

<210> SEQ ID NO 438
<211> LENGTH: 18
<212> TYPE: PRT
<213> ORGANISM: Artificial Sequence
<220> FEATURE:
<223> OTHER INFORMATION: Synthesized

<400> SEQUENCE: 438

Thr Trp Phe Ser Asp Ile Cys Leu Pro Arg Trp Gly Cys Leu Trp Glu
1               5                   10                  15

Pro Gly
```

```
<210> SEQ ID NO 439
<211> LENGTH: 20
<212> TYPE: PRT
<213> ORGANISM: Artificial Sequence
<220> FEATURE:
<223> OTHER INFORMATION: Synthesized

<400> SEQUENCE: 439

Thr Trp Gln Gly Glu Asp Ile Cys Leu Pro Arg Trp Gly Cys Leu Trp
1               5                   10                  15

Asp Thr Glu Val
            20

<210> SEQ ID NO 440
<211> LENGTH: 20
<212> TYPE: PRT
<213> ORGANISM: Artificial Sequence
<220> FEATURE:
<223> OTHER INFORMATION: Synthesized

<400> SEQUENCE: 440

Val Glu Met Trp His Asp Ile Cys Leu Pro Arg Trp Gly Cys Leu Trp
1               5                   10                  15

Asp Ser Asn Ala
            20

<210> SEQ ID NO 441
<211> LENGTH: 20
<212> TYPE: PRT
<213> ORGANISM: Artificial Sequence
<220> FEATURE:
<223> OTHER INFORMATION: Synthesized

<400> SEQUENCE: 441

Val Gly Val Phe Asp Asp Ile Cys Leu Pro Arg Trp Gly Cys Leu Trp
1               5                   10                  15

Glu Gln Pro Val
            20

<210> SEQ ID NO 442
<211> LENGTH: 18
<212> TYPE: PRT
<213> ORGANISM: Artificial Sequence
<220> FEATURE:
<223> OTHER INFORMATION: Synthesized

<400> SEQUENCE: 442

Val His Gln Ala Asp Ile Cys Leu Pro Arg Trp Gly Cys Leu Trp Gly
1               5                   10                  15

Asp Thr

<210> SEQ ID NO 443
<211> LENGTH: 18
<212> TYPE: PRT
<213> ORGANISM: Artificial Sequence
<220> FEATURE:
<223> OTHER INFORMATION: Synthesized

<400> SEQUENCE: 443

Val Leu Leu Gly Asp Ile Cys Leu Pro Leu Trp Gly Cys Leu Trp Gly
1               5                   10                  15

Glu Asp
```

```
<210> SEQ ID NO 444
<211> LENGTH: 18
<212> TYPE: PRT
<213> ORGANISM: Artificial Sequence
<220> FEATURE:
<223> OTHER INFORMATION: Synthesized

<400> SEQUENCE: 444

Val Asn Trp Gly Asp Ile Cys Leu Pro Arg Trp Gly Cys Leu Trp Gly
1               5                   10                  15

Glu Ser

<210> SEQ ID NO 445
<211> LENGTH: 20
<212> TYPE: PRT
<213> ORGANISM: Artificial Sequence
<220> FEATURE:
<223> OTHER INFORMATION: Synthesized

<400> SEQUENCE: 445

Val Pro Ala Met Gly Asp Ile Cys Leu Pro Arg Trp Gly Cys Leu Trp
1               5                   10                  15

Glu Ala Arg Asn
            20

<210> SEQ ID NO 446
<211> LENGTH: 18
<212> TYPE: PRT
<213> ORGANISM: Artificial Sequence
<220> FEATURE:
<223> OTHER INFORMATION: Synthesized

<400> SEQUENCE: 446

Val Arg Leu Met Asp Ile Cys Leu Pro Arg Trp Gly Cys Leu Trp Gly
1               5                   10                  15

Glu Glu

<210> SEQ ID NO 447
<211> LENGTH: 18
<212> TYPE: PRT
<213> ORGANISM: Artificial Sequence
<220> FEATURE:
<223> OTHER INFORMATION: Synthesized

<400> SEQUENCE: 447

Val Arg Trp Glu Asp Ile Cys Leu Pro Arg Trp Gly Cys Leu Trp Gly
1               5                   10                  15

Glu Glu

<210> SEQ ID NO 448
<211> LENGTH: 20
<212> TYPE: PRT
<213> ORGANISM: Artificial Sequence
<220> FEATURE:
<223> OTHER INFORMATION: Synthesized

<400> SEQUENCE: 448

Val Ser Leu Gly Asp Asp Ile Cys Leu Pro Lys Trp Gly Cys Leu Trp
1               5                   10                  15

Glu Pro Glu Ala
            20

<210> SEQ ID NO 449
<211> LENGTH: 18
```

```
<212> TYPE: PRT
<213> ORGANISM: Artificial Sequence
<220> FEATURE:
<223> OTHER INFORMATION: Synthesized

<400> SEQUENCE: 449

Val Val Trp Ser Asp Ile Cys Leu Pro Arg Trp Gly Cys Leu Trp Asp
1               5                   10                  15

Lys Glu

<210> SEQ ID NO 450
<211> LENGTH: 20
<212> TYPE: PRT
<213> ORGANISM: Artificial Sequence
<220> FEATURE:
<223> OTHER INFORMATION: Synthesized

<400> SEQUENCE: 450

Val Trp Ile Asp Arg Asp Ile Cys Leu Pro Arg Trp Gly Cys Leu Trp
1               5                   10                  15

Asp Thr Glu Asn
            20

<210> SEQ ID NO 451
<211> LENGTH: 18
<212> TYPE: PRT
<213> ORGANISM: Artificial Sequence
<220> FEATURE:
<223> OTHER INFORMATION: Synthesized

<400> SEQUENCE: 451

Val Trp Tyr Lys Asp Ile Cys Leu Pro Arg Trp Gly Cys Leu Trp Glu
1               5                   10                  15

Ala Glu

<210> SEQ ID NO 452
<211> LENGTH: 20
<212> TYPE: PRT
<213> ORGANISM: Artificial Sequence
<220> FEATURE:
<223> OTHER INFORMATION: Synthesized

<400> SEQUENCE: 452

Trp Asp Leu Ala Ser Asp Ile Cys Leu Pro Arg Trp Gly Cys Leu Trp
1               5                   10                  15

Glu Glu Glu Ala
            20

<210> SEQ ID NO 453
<211> LENGTH: 18
<212> TYPE: PRT
<213> ORGANISM: Artificial Sequence
<220> FEATURE:
<223> OTHER INFORMATION: Synthesized

<400> SEQUENCE: 453

Trp Asp Val Ala Asp Ile Cys Leu Pro Arg Trp Gly Cys Leu Trp Ala
1               5                   10                  15

Glu Asp

<210> SEQ ID NO 454
<211> LENGTH: 18
<212> TYPE: PRT
<213> ORGANISM: Artificial Sequence
```

-continued

<220> FEATURE:
<223> OTHER INFORMATION: Synthesized

<400> SEQUENCE: 454

Trp Asp Tyr Gly Asp Ile Cys Leu Pro Arg Trp Gly Cys Leu Trp Glu
1               5                   10                  15

Glu Gly

<210> SEQ ID NO 455
<211> LENGTH: 18
<212> TYPE: PRT
<213> ORGANISM: Artificial Sequence
<220> FEATURE:
<223> OTHER INFORMATION: Synthesized

<400> SEQUENCE: 455

Trp Glu Val Gln Asp Ile Cys Leu Pro Arg Trp Gly Cys Leu Trp Gly
1               5                   10                  15

Asp Asp

<210> SEQ ID NO 456
<211> LENGTH: 18
<212> TYPE: PRT
<213> ORGANISM: Artificial Sequence
<220> FEATURE:
<223> OTHER INFORMATION: Synthesized

<400> SEQUENCE: 456

Trp His Met Gly Asp Ile Cys Leu Pro Arg Trp Gly Cys Leu Trp Ser
1               5                   10                  15

Glu Val

<210> SEQ ID NO 457
<211> LENGTH: 18
<212> TYPE: PRT
<213> ORGANISM: Artificial Sequence
<220> FEATURE:
<223> OTHER INFORMATION: Synthesized

<400> SEQUENCE: 457

Trp Lys Asp Phe Asp Ile Cys Leu Pro Arg Trp Gly Cys Leu Trp Asp
1               5                   10                  15

Asp His

<210> SEQ ID NO 458
<211> LENGTH: 18
<212> TYPE: PRT
<213> ORGANISM: Artificial Sequence
<220> FEATURE:
<223> OTHER INFORMATION: Synthesized

<400> SEQUENCE: 458

Trp Leu Ser Asp Asp Ile Cys Leu Pro Arg Trp Gly Cys Leu Trp Asp
1               5                   10                  15

Asp Leu

<210> SEQ ID NO 459
<211> LENGTH: 18
<212> TYPE: PRT
<213> ORGANISM: Artificial Sequence
<220> FEATURE:
<223> OTHER INFORMATION: Synthesized

<400> SEQUENCE: 459

Trp Leu Ser Glu Asp Ile Cys Leu Pro Gln Trp Gly Cys Leu Trp Glu
1               5                   10                  15

Glu Ser

<210> SEQ ID NO 460
<211> LENGTH: 18
<212> TYPE: PRT
<213> ORGANISM: Artificial Sequence
<220> FEATURE:
<223> OTHER INFORMATION: Synthesized

<400> SEQUENCE: 460

Trp Leu Ser Glu Asp Ile Cys Leu Pro Arg Trp Gly Cys Leu Trp Ala
1               5                   10                  15

Ala Asp

<210> SEQ ID NO 461
<211> LENGTH: 20
<212> TYPE: PRT
<213> ORGANISM: Artificial Sequence
<220> FEATURE:
<223> OTHER INFORMATION: Synthesized

<400> SEQUENCE: 461

Trp Arg Trp Asn Glu Asp Ile Cys Leu Pro Arg Trp Gly Cys Leu Trp
1               5                   10                  15

Glu Glu Glu Ala
            20

<210> SEQ ID NO 462
<211> LENGTH: 18
<212> TYPE: PRT
<213> ORGANISM: Artificial Sequence
<220> FEATURE:
<223> OTHER INFORMATION: Synthesized

<400> SEQUENCE: 462

Tyr Ile Trp Arg Asp Ile Cys Leu Pro Arg Trp Gly Cys Leu Trp Glu
1               5                   10                  15

Gly Glu

<210> SEQ ID NO 463
<211> LENGTH: 18
<212> TYPE: PRT
<213> ORGANISM: Artificial Sequence
<220> FEATURE:
<223> OTHER INFORMATION: Synthesized

<400> SEQUENCE: 463

Tyr Arg Asp Tyr Asp Ile Cys Leu Pro Arg Trp Gly Cys Leu Trp Asp
1               5                   10                  15

Glu Arg

<210> SEQ ID NO 464
<211> LENGTH: 18
<212> TYPE: PRT
<213> ORGANISM: Artificial Sequence
<220> FEATURE:
<223> OTHER INFORMATION: Synthesized

<400> SEQUENCE: 464

Ala Gly Glu Trp Asp Ile Cys Leu Pro Arg Trp Gly Cys Leu Trp Asp
1               5                   10                  15

Val Glu

<210> SEQ ID NO 465
<211> LENGTH: 18
<212> TYPE: PRT
<213> ORGANISM: Artificial Sequence
<220> FEATURE:
<223> OTHER INFORMATION: Synthesized

<400> SEQUENCE: 465

Glu Ile Arg Trp Asp Phe Cys Leu Pro Arg Trp Gly Cys Leu Trp Asp
1               5                   10                  15

Glu Asp

<210> SEQ ID NO 466
<211> LENGTH: 18
<212> TYPE: PRT
<213> ORGANISM: Artificial Sequence
<220> FEATURE:
<223> OTHER INFORMATION: Synthesized

<400> SEQUENCE: 466

Glu Ser Leu Gly Asp Ile Cys Leu Pro Arg Trp Gly Cys Leu Trp Gly
1               5                   10                  15

Ser Gly

<210> SEQ ID NO 467
<211> LENGTH: 20
<212> TYPE: PRT
<213> ORGANISM: Artificial Sequence
<220> FEATURE:
<223> OTHER INFORMATION: Synthesized

<400> SEQUENCE: 467

Glu Val Arg Glu Trp Asp Ile Cys Leu Pro Arg Trp Gly Cys Leu Trp
1               5                   10                  15

Glu Asn Trp Arg
            20

<210> SEQ ID NO 468
<211> LENGTH: 18
<212> TYPE: PRT
<213> ORGANISM: Artificial Sequence
<220> FEATURE:
<223> OTHER INFORMATION: Synthesized

<400> SEQUENCE: 468

Glu Tyr Trp Gly Asp Ile Cys Leu Pro Arg Trp Gly Cys Leu Trp Asp
1               5                   10                  15

Trp Gln

<210> SEQ ID NO 469
<211> LENGTH: 20
<212> TYPE: PRT
<213> ORGANISM: Artificial Sequence
<220> FEATURE:
<223> OTHER INFORMATION: Synthesized

<400> SEQUENCE: 469

Phe Gly Gln Glu Trp Asp Ile Cys Leu Pro Arg Trp Gly Cys Leu Trp
1               5                   10                  15

Gly Asn Glu Gln
            20

-continued

```
<210> SEQ ID NO 470
<211> LENGTH: 20
<212> TYPE: PRT
<213> ORGANISM: Artificial Sequence
<220> FEATURE:
<223> OTHER INFORMATION: Synthesized

<400> SEQUENCE: 470

Ile Trp Gln Leu Glu Asp Ile Cys Leu Pro Arg Trp Gly Cys Leu Trp
1               5                   10                  15

Glu Asp Gly Leu
            20

<210> SEQ ID NO 471
<211> LENGTH: 18
<212> TYPE: PRT
<213> ORGANISM: Artificial Sequence
<220> FEATURE:
<223> OTHER INFORMATION: Synthesized

<400> SEQUENCE: 471

Lys Met Trp Ser Asp Ile Cys Leu Pro Arg Trp Gly Cys Leu Trp Glu
1               5                   10                  15

Glu Glu

<210> SEQ ID NO 472
<211> LENGTH: 18
<212> TYPE: PRT
<213> ORGANISM: Artificial Sequence
<220> FEATURE:
<223> OTHER INFORMATION: Synthesized

<400> SEQUENCE: 472

Met Gly Thr Lys Asp Ile Cys Leu Pro Arg Trp Gly Cys Leu Trp Ala
1               5                   10                  15

Glu Ala

<210> SEQ ID NO 473
<211> LENGTH: 18
<212> TYPE: PRT
<213> ORGANISM: Artificial Sequence
<220> FEATURE:
<223> OTHER INFORMATION: Synthesized

<400> SEQUENCE: 473

Met His Glu Trp Asp Ile Cys Leu Pro Arg Trp Gly Cys Leu Trp Glu
1               5                   10                  15

Ser Ser

<210> SEQ ID NO 474
<211> LENGTH: 20
<212> TYPE: PRT
<213> ORGANISM: Artificial Sequence
<220> FEATURE:
<223> OTHER INFORMATION: Synthesized

<400> SEQUENCE: 474

Asn Thr Pro Thr Tyr Asp Ile Cys Leu Pro Arg Trp Gly Cys Leu Trp
1               5                   10                  15

Gly Asp Val Pro
            20
```

```
<210> SEQ ID NO 475
<211> LENGTH: 20
<212> TYPE: PRT
<213> ORGANISM: Artificial Sequence
<220> FEATURE:
<223> OTHER INFORMATION: Synthesized

<400> SEQUENCE: 475

Asn Trp Ala Glu Asn Asp Ile Cys Leu Pro Arg Trp Gly Cys Leu Trp
1               5                   10                  15

Gly Asp Glu Asn
            20

<210> SEQ ID NO 476
<211> LENGTH: 20
<212> TYPE: PRT
<213> ORGANISM: Artificial Sequence
<220> FEATURE:
<223> OTHER INFORMATION: Synthesized

<400> SEQUENCE: 476

Gln Pro Val Trp Ser Asp Ile Cys Leu Pro Arg Trp Gly Cys Leu Trp
1               5                   10                  15

Gly Glu Asp His
            20

<210> SEQ ID NO 477
<211> LENGTH: 18
<212> TYPE: PRT
<213> ORGANISM: Artificial Sequence
<220> FEATURE:
<223> OTHER INFORMATION: Synthesized

<400> SEQUENCE: 477

Arg Gly Leu His Asp Ala Cys Leu Pro Trp Trp Gly Cys Leu Trp Ala
1               5                   10                  15

Gly Ser

<210> SEQ ID NO 478
<211> LENGTH: 18
<212> TYPE: PRT
<213> ORGANISM: Artificial Sequence
<220> FEATURE:
<223> OTHER INFORMATION: Synthesized

<400> SEQUENCE: 478

Arg Leu Phe Gly Asp Ile Cys Leu Pro Arg Trp Gly Cys Leu Trp Gln
1               5                   10                  15

Gly Glu

<210> SEQ ID NO 479
<211> LENGTH: 20
<212> TYPE: PRT
<213> ORGANISM: Artificial Sequence
<220> FEATURE:
<223> OTHER INFORMATION: Synthesized

<400> SEQUENCE: 479

Ser Ala Arg Glu Trp Asp Ile Cys Leu Pro Thr Trp Gly Cys Leu Trp
1               5                   10                  15

Glu Lys Asp Ile
            20

<210> SEQ ID NO 480
```

<211> LENGTH: 18
<212> TYPE: PRT
<213> ORGANISM: Artificial Sequence
<220> FEATURE:
<223> OTHER INFORMATION: Synthesized

<400> SEQUENCE: 480

Ser Gly Glu Trp Asp Ile Cys Leu Pro Arg Trp Gly Cys Leu Trp Gly
1               5                   10                  15

Glu Gly

<210> SEQ ID NO 481
<211> LENGTH: 18
<212> TYPE: PRT
<213> ORGANISM: Artificial Sequence
<220> FEATURE:
<223> OTHER INFORMATION: Synthesized

<400> SEQUENCE: 481

Ser Met Phe Phe Asp His Cys Leu Pro Met Trp Gly Cys Leu Trp Ala
1               5                   10                  15

Glu Gln

<210> SEQ ID NO 482
<211> LENGTH: 19
<212> TYPE: PRT
<213> ORGANISM: Artificial Sequence
<220> FEATURE:
<223> OTHER INFORMATION: Synthesized

<400> SEQUENCE: 482

Ser Trp Tyr Gly Gly Asp Ile Cys Leu Pro Trp Gly Cys Leu Trp Ser
1               5                   10                  15

Glu Glu Ser

<210> SEQ ID NO 483
<211> LENGTH: 18
<212> TYPE: PRT
<213> ORGANISM: Artificial Sequence
<220> FEATURE:
<223> OTHER INFORMATION: Synthesized

<400> SEQUENCE: 483

Thr Leu Phe Gln Asp Ile Cys Leu Pro Arg Trp Gly Cys Leu Trp Glu
1               5                   10                  15

Glu Ser

<210> SEQ ID NO 484
<211> LENGTH: 18
<212> TYPE: PRT
<213> ORGANISM: Artificial Sequence
<220> FEATURE:
<223> OTHER INFORMATION: Synthesized

<400> SEQUENCE: 484

Val Gly Glu Trp Asp Ile Cys Leu Pro Asn Trp Gly Cys Leu Trp Glu
1               5                   10                  15

Arg Glu

<210> SEQ ID NO 485
<211> LENGTH: 18
<212> TYPE: PRT
<213> ORGANISM: Artificial Sequence
<220> FEATURE:

```
<223> OTHER INFORMATION: Synthesized

<400> SEQUENCE: 485

Trp Phe Pro Lys Asp Arg Cys Leu Pro Val Trp Gly Cys Leu Trp Glu
1               5                   10                  15

Arg His

<210> SEQ ID NO 486
<211> LENGTH: 20
<212> TYPE: PRT
<213> ORGANISM: Artificial Sequence
<220> FEATURE:
<223> OTHER INFORMATION: Synthesized

<400> SEQUENCE: 486

Trp Gly Met Ala Arg Asp Trp Cys Leu Pro Met Trp Gly Cys Leu Trp
1               5                   10                  15

Arg Gly Gly Gly
            20

<210> SEQ ID NO 487
<211> LENGTH: 20
<212> TYPE: PRT
<213> ORGANISM: Artificial Sequence
<220> FEATURE:
<223> OTHER INFORMATION: Synthesized

<400> SEQUENCE: 487

Trp His Leu Thr Asp Asp Ile Cys Leu Pro Arg Trp Gly Cys Leu Trp
1               5                   10                  15

Gly Asp Glu Gln
            20

<210> SEQ ID NO 488
<211> LENGTH: 18
<212> TYPE: PRT
<213> ORGANISM: Artificial Sequence
<220> FEATURE:
<223> OTHER INFORMATION: Synthesized

<400> SEQUENCE: 488

Trp Trp Met Ala Asp Arg Cys Leu Pro Leu Trp Gly Cys Leu Trp Arg
1               5                   10                  15

Gly Asp

<210> SEQ ID NO 489
<211> LENGTH: 18
<212> TYPE: PRT
<213> ORGANISM: Artificial Sequence
<220> FEATURE:
<223> OTHER INFORMATION: Synthesized

<400> SEQUENCE: 489

Trp Trp Val Arg Asp Leu Cys Leu Pro Thr Trp Gly Cys Leu Trp Ser
1               5                   10                  15

Gly Lys

<210> SEQ ID NO 490
<211> LENGTH: 18
<212> TYPE: PRT
<213> ORGANISM: Artificial Sequence
<220> FEATURE:
<223> OTHER INFORMATION: Synthesized
```

```
-continued

<400> SEQUENCE: 490

Tyr Phe Asp Gly Asp Ile Cys Leu Pro Arg Trp Gly Cys Leu Trp Gly
1               5                   10                  15

Ser Asp

<210> SEQ ID NO 491
<211> LENGTH: 15
<212> TYPE: PRT
<213> ORGANISM: Artificial Sequence
<220> FEATURE:
<223> OTHER INFORMATION: Synthesized

<400> SEQUENCE: 491

Glu Asp Ile Cys Leu Pro Arg Trp Gly Cys Leu Trp Glu Asp Asp
1               5                   10                  15

<210> SEQ ID NO 492
<211> LENGTH: 19
<212> TYPE: PRT
<213> ORGANISM: Artificial Sequence
<220> FEATURE:
<223> OTHER INFORMATION: synthesized

<400> SEQUENCE: 492

Ser Trp Tyr Gly Gly Asp Ile Cys Leu Pro Trp Gly Cys Leu Trp Ser
1               5                   10                  15

Glu Glu Ser
```

METHODS AND COMPOSITIONS FOR PROLONGING ELIMINATION HALF-TIMES OF BIOACTIVE COMPOUNDS

This application is the National Stage of International Application No. PCT/US00/35325, filed Dec. 22, 2000, which claims benefit of U.S. Provisional Application No. 60/173,048, filed Dec. 24, 1999.

FIELD OF THE INVENTION

This invention relates to novel compounds termed peptide ligands which bind a predetermined molecule such as a plasma protein. In particular aspects, the invention relates to compositions comprising a hybrid molecule comprising a peptide ligand domain and an active domain such as a biologically active molecule. The active domain may comprise a molecule useful for diagnostic or therapeutic purposes. In preferred embodiments, the hybrid compositions comprising the peptide ligand domain and active domain have improved pharmacokinetic or pharmacological properties. The invention further provides for the research, diagnostic and therapeutic use of the peptide ligand and includes compositions such as pharmaceutical compositions comprising the peptide ligand molecules.

DESCRIPTION OF RELATED DISCLOSURES

Phage-display provides a means for generating constrained and unconstrained peptide libraries (Devlin et al., (1990) *Science* 249:404-406; Cwirla et al., (1990) *Proc. Natl. Acad. Sci. USA* 87:6378-6382; Lowman (1997) *Ann. Rev. Biophys. Biomol. Struct.* 26:401-424). These libraries can be used to identify and select peptide ligands that can bind a predetermined target molecule (Lowman (1997), supra); Clackson and Wells (1994) *Trends Biotechnol.* 12:173-184; Devlin et al., (1990) supra). The technique has been used to identify peptide motifs that home to a cellular target (Arap et al., (1998) *Science* 279:377-380); bind the human type I interleukin 1 (IL-1) receptor blocking the binding of IL-α (Yanofsky et al., (1996) *Proc. Natl. Acad. Sci. USA* 93:7381-7386); bind to and activate the receptor for the cytokine erythropoietin (EPO) (Wrighton et al., (1996) *Science* 273:458-463); bind the human thrombopoietin receptor and compete with the binding of the natural ligand thrombopoietin (TPO) (Cwirla et al., (1996) *Science* 276:1696-1699), or to generate affinity improved or matured peptide ligands from native protein binding ligands (Lowman et al., (1991) *Biochemistry* 30:10832-10838).

Using structurally constrained peptide libraries generated by monovalent phage display, 14 amino acid peptides that specifically bind to insulin-like growth factor 1 binding proteins (IGFBPs) have been isolated (Lowman et al. (1998), Biochemistry 37:8870-8878). The peptides contain a helix structure and bind IGFBPs in vitro liberating insulin like growth factor-a (IGF-1) activity (Lowman et al., (1998) supra). Utilizing in vivo phage selection peptides capable of mediating selective localization to various organs such as brain and kidney (Pasqualini and Ruoslohti (1996) *Nature* 380:364-366) as well as peptides that home to particular tumor types bearing $\alpha_v\beta_3$ or $\alpha V\beta_5$ integrins have been identified (Arap et al. (1998), *Science* 279:377-380). U.S. Pat. No. 5,627,263 describes peptides that are recognized by and selectively bind the $\alpha_5\beta_1$ integrin. Examples of affinity or specificity improved proteins include human growth hormone, zinc fingers, protease inhibitors, atrial natriuretic factor, and antibodies (Wells, J. and Lowman H. (1992), *Curr. Opin. Struct. Biol.* 2:597-604; Clackson, T. and Wells, J. (1994), *Trends Biotechnol.* 12:173-184; Lowman et al., (1991) *Biochemistry* 30(10):832-838; Lowman and Wells J. (1993), *J. Mol. Biol.* 234:564-578; Dennis M. and Lazarus R. (1994), *J. Biol. Chem.* 269(22):137-144).

It has been suggested that the pharmakodynamics of insulin are altered if bound to serum albumin. Acylation of insulin with saturated fatty acids containing 10-16 carbon atoms produces insulin with affinity for albumin (Kurtzhals, P. et al. (1995) *Biochem. J.* 312:725-731). Differences in albumin binding affinity among acylated insulins were correlated with the timing of the blood-glucose lowering effects of the various molecules after subcutaneous injection into rabbits. Tighter binding to albumin was correlated with a delay in blood glucose lowering, possibly due to acylated insulin binding albumin in the subcutaneous tissue, resulting in a lower absorption rate of the acylated insulins when compared with non-acylated insulin.

A serum albumin-CD4 conjugate in which the V1 and V2 domains of CD4 were fused with human serum albumin (HSA) has been described (Yeh, P. et al. (1992), *Proc. Natl. Acad. Sci. USA* 89:1904-1908). The conjugate's elimination half-time was 140-fold that of a soluble CD4 (sCD4) in a rabbit experimental model.

Extended in vivo half-times of human soluble complement receptor type 1 (sCR1) fused to the albumin binding domains from Streptococcal protein G have been reported (Makrides, S. et al. (1996) *J. Pharmacol. Exptl. Ther.* 277:532-541). The constructs contained albumin binding domains of protein G having approximately 80 amino acids (fragment BA), and approximately 155 amino acids (fragment BABA).

The pharmacokinetics of a labeled IgG binding domain derived from the Z domain of protein A having approximately 60 amino acids and of a serum albumin binding domain derived from Streptococcal protein G (B-domain) having approximately 200 amino acids have been described (EP 0 486,525).

SUMMARY OF THE INVENTION

The present invention provides novel compounds that bind to plasma proteins. The compounds of the present invention (referred to as peptide ligands) are, for example, peptides or peptide derivatives such as peptide mimetics and peptide analogs. According to preferred aspects of the invention, the compounds are non-naturally occurring amino acid sequences that bind plasma proteins such as serum albumin or a portion of an immunoglobulin, as for example, IgG-Fc. Preferably the peptide ligand is a non-naturally occurring amino acid sequence of between about 10 and 20 amino acid residues.

Such compounds preferably bind a desired plasma protein with an affinity characterized by a dissociation constant, $K_d$, that is less than about 100 µM, preferably less than about 100 nM, and preferably do not substantially bind other plasma proteins. Specific examples of such compounds include linear or cyclic, especially cyclic peptides, preferably between about 10 and 20 amino acid residues in length, and combinations thereof, optionally modified at the N-terminus or C-terminus or both, as well as their salts and derivatives, functional analogues thereof and extended peptide chains carrying amino acids or polypeptides at the termini of the sequences.

Preferred peptide ligands bind IgG-Fc and include linear and cyclic peptides, preferably cyclic peptide compounds comprising the following core formula:

$Xaa_i$-Cys-$Xaa_j$-Cys-$Xaa_k$, wherein $Xaa_i$ is absent or is a peptide of between 1 and 4 amino acids, preferably 4 amino acids; $X_j$ is preferably 9 amino acids having a preferred sequence Xaa-Xaa-Xaa-Xaa-Xaa-Xaa-Leu-Val-Trp (SEQ ID NO: 9); or Xaa-Xaa-Xaa-Xaa-Gly-Glu-Leu-Val-Trp (SEQ ID NO: 10); or $Xaa_1$-$Xaa_2$-$Xaa_3$-$Xaa_4$-Gly-Glu-Leu-Val-Trp (SEQ ID NO: 139), wherein $Xaa_1$ preferably is Ala, Ser, or Thr; $Xaa_2$ preferably is Trp or Tyr; $Xaa_3$ preferably is His, or Trp; $Xaa_4$ preferably is Leu or Met, and $Xaa_k$ is absent or between 1 and 5 amino acids, preferably 5 amino acids, so long as the cyclic peptide or analog thereof retains the qualitative biological activity of IgG-Fc binding.

Preferred among this group of compounds are compounds that bind IgG-Fc comprising the sequence:

Xaa-Xaa-Xaa-Xaa-Cys-Xaa-Xaa-Xaa-Xaa-Xaa-Xaa-Leu-Val-Trp-Cys-Xaa-Xaa-Xaa-Xaa-Xaa (SEQ ID NO: 11);

Xaa-Xaa-Xaa-Xaa-Cys-Xaa-Xaa-Xaa-Xaa-Gly-Glu-Leu-Val-Trp-Cys-Xaa-Xaa-Xaa-Xaa-Xaa (SEQ ID NO: 12);

$Xaa_1$-$Xaa_2$-$Xaa_3$-$Xaa_4$-Cys-$Xaa_5$-$Xaa_6$-$Xaa_7$-$Xaa_8$-Gly-Glu-Leu-Val-Trp-Cys-$Xaa_9$-$Xaa_{10}$-$Xaa_{11}$-$Xaa_{12}$-$Xaa_{13}$ (SEQ ID NO: 13), wherein $Xaa_5$ is Ala, Ser, or Thr; $Xaa_6$ is Trp or Tyr; $Xaa_7$ is His or Trp; and $Xaa_8$ is Leu or Met; and $Xaa_1$-$Xaa_2$-$Xaa_3$-$Xaa_4$-Cys-$Xaa_5$-$Xaa_6$-$Xaa_7$-$Xaa_8$-Gly-Glu-Leu-Val-Trp-Cys-$Xaa_9$-$Xaa_{10}$-$Xaa_{11}$-$Xaa_{12}$-$Xaa_{13}$ (SEQ ID NO: 14) wherein $Xaa_4$ is Ser, Arg, or Asp; $Xaa_5$ is. Ala, Ser, or Thr; $Xaa_6$ is Trp or Tyr; $Xaa_7$ is His or Trp; $Xaa_8$ is Leu or Met; and $Xaa_9$ is Glu, Ser, Thr or Val.

Preferred peptide ligands that bind serum albumin include linear and cyclic peptides, preferably cyclic peptide compounds comprising the following formulae:

Xaa-Xaa-Cys-Xaa-Xaa-Xaa-Xaa-Xaa-Cys-Xaa-Xaa Phe-Cys-Xaa-Asp-Trp-Pro-Xaa-Xaa-Xaa-Ser-Cys (SEQ ID NO: 113)

Val-Cys-Tyr-Xaa-Xaa-Xaa-Ile-Cys-Phe (SEQ ID NO: 114)

Cys-Try-$Xaa_1$-Pro-Gly-Xaa-Cys (SEQ ID NO: 115) and Asp-Xaa-Cys-Leu-Pro-Xaa-Trp-Gly-Cys-Leu-Trp (SEQ ID NO: 116)

wherein the general formulae further comprises the sequence $(Xaa)_x$ at the N terminus and $(Xaa)_z$ at the C-terminus.

Preferred are peptide compounds of the general formulae wherein Xaa is an amino acid and x and z are a whole number greater or equal to 0 (zero), generally less than 100, preferably less than 10 and more preferably 0, 1, 2, 3, 4 or 5 and more preferably 4 or 5 and $Xaa_1$ is selected from the group consisting of Ile, Phe, Tyr and Val.

In particular aspects the invention is directed to combinations of a peptide ligand with a bioactive compound to form a hybrid molecule that comprises a peptide ligand domain and an active domain. The bioactive compounds of the invention include any compound useful as a therapeutic or diagnostic agent. Non-limiting examples of bioactive compounds include polypeptides such as enzymes, hormones, cytokines, antibodies or antibody fragments, as well as organic compounds such as analgesics, antipyretics, antiinflammatory agents, antibiotics, antiviral agents, anti-fungal drugs, cardiovascular drugs, drugs that affect renal function and electrolyte metabolism, drugs that act on the central nervous system and chemotherapeutic drugs, to name but a few.

In preferred embodiments, the hybrid molecules comprising a peptide ligand domain and an active domain have improved pharmacokinetic or pharmacodynamic properties as compared to the same bioactive molecule comprising the active domain but lacking the peptide ligand domain. The improved pharmacokinetic or pharmacodynamic properties of the hybrids thereby provide for low-dose pharmaceutical formulations and novel pharmaceutical compositions. In certain aspects, the invention provides for methods of using the novel compositions including the therapeutic or diagnostic use of the hybrid molecules.

In particular aspects, the invention is directed to combinations of peptide ligands with bioactive compounds that have relatively short elimination half-times. The combinations are prepared with various objectives in mind, including improving the therapeutic or diagnostic efficacy of the bioactive compound in aspects of the invention involving in vivo use of the bioactive compound, by for example, increasing the elimination half-time of the bioactive compound. Fusing or linking (i.e., "conjugating") the peptide ligand directed against a plasma protein such as serum albumin, an immunoglobulin, an apolipoprotein or transferrin to a bioactive compound provides compositions with increased elimination half-times. Such combinations or fusions are conveniently made in recombinant host cells, or by the use of bifunctional crosslinking agents.

Other aspects of the invention include methods and compositions to purify antibodies using peptide ligands having binding affinity for immunoglobulins, such as, for example, the IgG-Fc peptide ligands disclosed herein.

The present invention further extends to therapeutic and diagnostic applications for the compositions described herein. Therefore, the invention includes pharmaceutical compositions comprising a pharmaceutically acceptable excipient and the hybrid molecules of the invention.

BRIEF DESCRIPTION OF THE DRAWINGS

FIG. 4. The peptide sequences (SEQ ID NOs: 119, 130 and 140-150) displayed by phage clones selected for binding to rabbit, human or rat albumin are shown in FIG. 4. Also indicated is the ability of individual phage clones to bind the 3 species of immobilized albumin.

FIGS. 5A and 5B. Sequences identified following soft randomization (SEQ ID NOs: 120, 130, 140 and 148-269) are shown in FIG. 5 along with their species specificity as determined by phage ELISA.

FIG. 7. Clones that bind to multiple species of albumin (multi-species binders) are listed in FIG. 7 (SEQ ID NOs: 123, 150, 207, 208 and 259-268).

FIGS. 8A, 8B and 8C. Sequences from libraries selected against rat, rabbit and human albumin are shown in FIGS. 8A, 8B, and 8C, respectively (SEQ ID NOs: 270-490 and 492).

FIG. 9. Peptides corresponding to identified phage sequences (SEQ ID NOs: 119, 121-124, 126-128, 269 and 491) were synthesized and their affinity for rat, rabbit or mouse albumin measured using the SA08b binding assay.

FIG. 11. The SA06 sequence was added to the carboxy terminus of either the light chain (D3H44-L) or heavy chain (D3H44-Ls) of the Fab. In addition, identical constructs were made with the intra-chain disulfide replaced by alanines (D3H44-Ls and D3H44-Hs, respectively) as depicted in FIG. 11.

FIG. 17. Fusion of the albumin binding peptide to D3H44 results in a protein having improved pharmacokinetic parameters.

DETAILED DESCRIPTION OF THE PREFERRED EMBODIMENTS

I. Definitions

Figure 1:
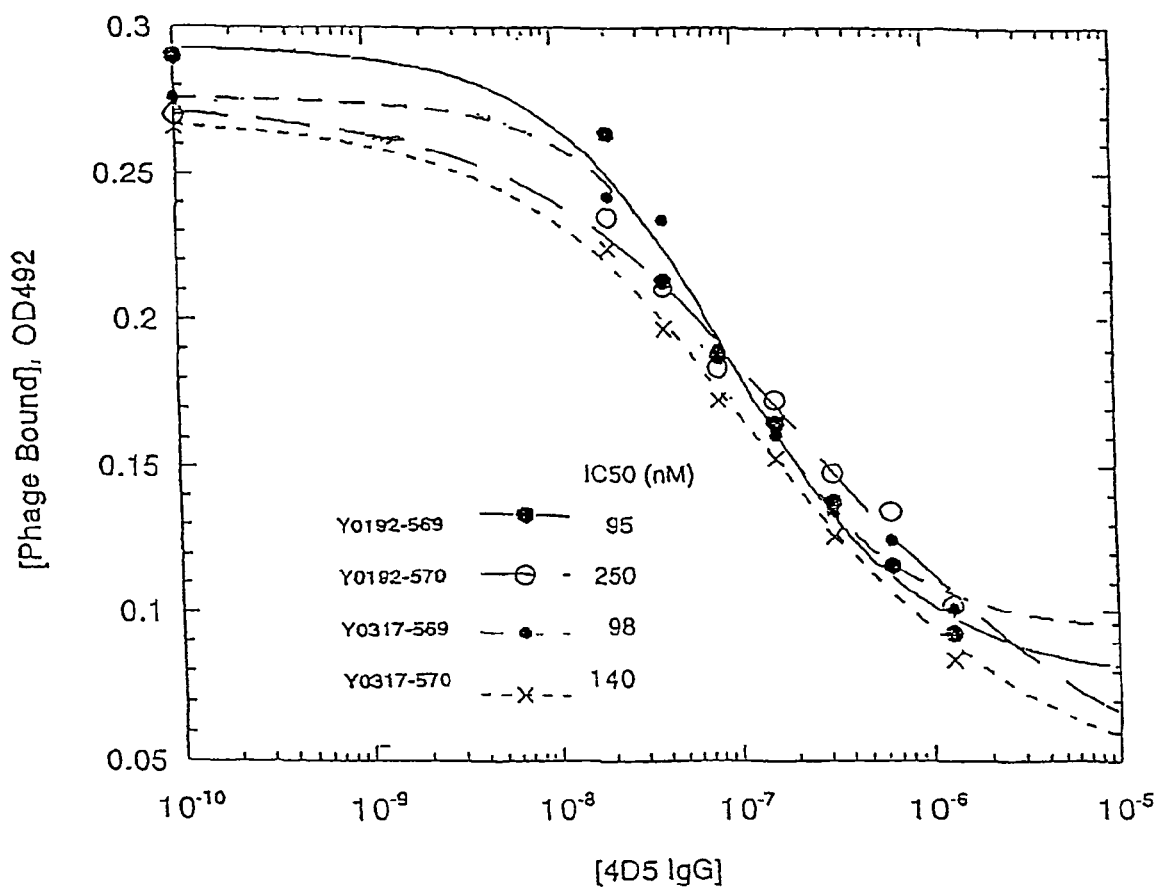
FIG. 1. Phage competitive ELISA assay showing IgG binding of peptide-ligand tagged anti-VEGF Fab-phagemid particles. Four different constructs are shown: pY0192-569 (large filled circles), pY0192-570 (large open circles), PY0317-569 (small filled circles), and pY0317-570 ("x"'s).

The term "peptide ligand" within the context of the present invention is meant to refer to non-naturally occurring amino acid sequences that function to bind a particular target molecule. Peptide ligands within the context of the present invention are generally constrained (that is, having some element of structure as, for example, the presence of amino acids which initiate a β turn or β pleated sheet, or for example, cyclized by the presence of disulfide-bonded Cys residues) or unconstrained (linear) amino acid sequences of less than about 50 amino acid residues, and preferably less than about 40 amino acids residues. Of the peptide ligands less than about 40 amino acid residues, preferred are the peptide ligands of between about 10 and about 30 amino acid residues and especially the peptide ligands of about 20 amino acid residues. However, upon reading the instant disclosure, the skilled artisan will recognize that it is not the length of a particular peptide ligand but its ability to bind a particular target molecule that distinguishes the peptide ligand of the present invention. Therefore peptide ligands of 3, 4, 5, 6, 7, 8, 9, 10, 11, 12, 13, 14, 15, 16, 17, 18, 19, 20, 21, 22, 23, 24 and 25 amino acid residues, for example, are equally likely to be peptide ligands within the context of the present invention.

A peptide ligand of the present invention will bind a target molecule with sufficient affinity and specificity if the peptide ligand "homes" to, "binds" or "targets" a target molecule such as a specific cell type bearing the target molecule in vitro and preferably in vivo (see, for example, the use of the term "homes to," "homing," and "targets" in Pasqualini and Ruoslahti (1996) *Nature*, 380:364-366 and Arap et al., (1998) *Science*, 279:377-380). In general, the peptide ligand will bind a target molecule with an affinity characterized by a dissociation constant, $K_d$, of less than about 1 µM, preferably less than about 100 nM and more preferably less than about 10 nM. However, peptide ligands having an affinity for a target molecule of less than about 1 nM and preferably between about 1 pM and 1 nM are equally likely to be peptide ligands within the context of the present invention. In general a peptide ligand that binds a particular target molecule as described above can be isolated and identified by any of a number of art-standard techniques as described herein.

Peptides ligands are amino acid sequences as described above which may contain naturally as well as non-naturally occurring amino acid residues. Therefore, so-called "peptide mimetics" and "peptide analogs" which may include non-amino acid chemical structures that mimic the structure of a particular amino acid or peptide may be peptide ligands within the context of the invention. Such mimetics or analogs are characterized generally as exhibiting similar physical characteristics such as size, charge or hydrophobicity present in the appropriate spacial orientation as found in their peptide counterparts. A specific example of a peptide mimetic compound is a compound in which the amide bond between one or more of the amino acids is replaced by, for example, a carbon-carbon bond or other bond as is well known in the art (see, for example Sawyer, in *Peptide Based Drug Design* pp. 378-422 (ACS, Washington D.C. 1995)).

Therefore, the term "amino acid" within the scope of the present invention is used in its broadest sense and is meant to include naturally occurring L α-amino acids or residues. The commonly used one and three letter abbreviations for naturally occurring amino acids are used herein (Lehninger, A. L., *Biochemistry*, 2d ed., pp. 71-92, (1975), Worth Publishers, New York). The correspondence between the standard single letter codes and the standard three letter codes is well known to the skilled artisan, and is reproduced here: A=Ala; C=Cys; D=Asp; E=Glu; F=Phe; G=Gly; H=His; I=Ile; K=Lys; L=Leu; M=Met; N=Asn; P=Pro; Q=Gln; R=Arg; S=Ser; T=Thr, V=Val; W=Trp; Y=Tyr. The term includes D-amino acids as well as chemically modified amino acids such as amino acid analogs, naturally occurring amino acids that are not usually incorporated into proteins such as norleucine, and chemically synthesized compounds having properties known in the art to be characteristic of an amino acid. For example, analogs or mimetics of phenylalanine or proline, which allow the same conformational restriction of the peptide compounds as natural Phe or Pro are included within the definition of amino acid. Such analogs and mimetics are referred to herein as "functional equivalents" of an amino acid. Other examples of amino acids are listed by Roberts and Vellaccio *The Peptides: Analysis, Synthesis, Biology*, Gross and Meiehofer, eds., Vol. 5 p. 341, Academic Press, Inc., N.Y. 1983, which is incorporated herein by reference.

Peptide ligands synthesized by, for example, standard solid phase synthesis techniques, are not limited to amino acids encoded by genes. Commonly encountered amino acids which are not encoded by the genetic code, include, for example, those described in International Publication No. WO 90/01940 such as, for example, 2-amino adipic acid (Aad) for Glu and Asp; 2-aminopimelic acid (Apm) for Glu and Asp; 2-aminobutyric (Abu) acid for Met, Leu, and other aliphatic amino acids; 2-aminoheptanoic acid (Ahe) for Met, Leu and other aliphatic amino acids; 2-aminoisobutyric acid (Aib) for Gly; cyclohexylalanine (Cha) for Val, and Leu and Ile; homoarginine (Har) for Arg and Lys; 2,3-diaminopropionic acid (Dpr) for Lys, Arg and His; N-ethylglycine (EtGly) for Gly, Pro, and Ala; N-ethylglycine (EtGly) for Gly, Pro, and Ala; N-ethylasparigine (EtAsn) for Asn, and Gln; Hydroxyllysine (Hyl) for Lys; allohydroxyllysine (AHyl) for Lys; 3-(and 4)-hydoxyproline (3Hyp, 4Hyp) for Pro, Ser, and Thr; allo-isoleucine (AIle) for Ile, Leu, and Val; p-amidinophenylalanine for Ala; N-methylglycine (MeGly, sarcosine) for Gly, Pro, and Ala; N-methylisoleucine (MeIle) for Ile; Norvaline (Nva) for Met and other aliphatic amino acids; Norleucine (Nle) for Met and other aliphatic amino acids; Ornithine (Orn) for Lys, Arg and His; Citrulline (Cit) and methionine sulfoxide (MSO) for Thr, Asn and Gln; N-methylphenylalanine (MePhe), trimethylphenylalanine, halo (F, Cl, Br, and I) phenylalanine, trifluorylphenylalanine, for Phe.

Peptide ligands within the context of the present invention may be "engineered", i.e., they are non-native or non-naturally occurring peptide ligands. By "non-native" or "non-naturally occurring" is meant that the amino acid sequence of the particular peptide ligand is not found in nature. That is to say, amino acid sequences of non-native or non-naturally occurring peptide ligands do not correspond to an amino acid sequence of a naturally occurring protein or polypeptide. Peptide ligands of this variety may be produced or selected using a variety of techniques well known to the skilled artisan. For example, constrained or unconstrained peptide libraries may be randomly generated and displayed on phage utilizing art standard techniques, for example, Lowman et al., (1998) Biochemistry 37:8870-8878.

Peptide ligands, when used within the context of the present invention, may be "conjugated" to a therapeutic or diagnostic substance. The term "conjugated" is used in its broadest sense to encompass all methods of attachment or joining that are known in the art. For example, in a typical embodiment, the therapeutic or diagnostic substance is a protein (referred to herein as a "protein therapeutic"), and the peptide ligand will be an amino acid extension of the C- or N-terminus of the protein therapeutic. In addition, a short amino acid linker sequence may lie between the protein therapeutic and the peptide ligand. In this scenario, the peptide ligand, optional linker and protein therapeutic will be coded for by a nucleic acid comprising a sequence encoding protein therapeutic operably linked to (in the sense that the DNA sequences are contiguous and in reading frame) an optional linker sequence encoding a short polypeptide as described below, and a sequence encoding the peptide ligand. In this typical scenario, the peptide ligand is considered to be "conjugated" to the protein therapeutic optionally via a linker sequence. In a related embodiment, the peptide ligand amino acid sequence may interrupt or replace a section of the protein therapeutic amino acid sequence, provided, of course, that the insertion of the peptide ligand amino acid sequence does not interfere with the function of the protein therapeutic. In this embodiment, the "conjugate" may be coded for by a nucleic acid comprising a sequence encoding protein therapeutic interrupted by and operably linked to a sequence encoding the peptide ligand. In a further typical embodiment, the peptide will be linked, e.g. by chemical conjugation to the protein therapeutic or other therapeutic optionally via a linker sequence. Typically, according to this embodiment, the peptide ligand will be linked to the protein therapeutic via a side chain of an amino acid somewhere in the middle of the protein therapeutic that doesn't interfere with the therapeutic's activity. Here again, the peptide is considered to be "conjugated" to the therapeutic.

As used within the context of the present invention the term "target molecule" includes, proteins, peptides, glycoproteins, glycopeptides, glycolipids, polysaccharides, oligosaccharides, nucleic acids, and the like. Target molecules include, for example, extracellular molecules such as various serum factors including but not limited to plasma proteins such as serum albumin, immunoglobulins, apolipoproteins or transferrin, or proteins found on the surface of erythrocytes or lymphocytes, provided, of course, that binding of the peptide ligand to the cell surface protein does not substantially interfere with the normal function of the cell.

"Antibodies" and "immunoglobulins" are usually heterotetrameric glycoproteins of about 150,000 Daltons, composed of two identical light (L) chains and two identical heavy (H) chains.

Papain digestion of antibodies produces two identical antigen-binding fragments, called "Fab" fragments or regions, each with a single antigen-binding site, and a residual "Fc" fragment or region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof.

Pepsin treatment yields an $F(ab')_2$ fragment that has two antigen-combining sites and is still capable of cross-linking antigen. The Fab' fragment contains the constant domain of the light chain and the first constant domain (CH1) of the heavy chain.

"Treatment" refers to both therapeutic treatment and prophylactic or preventative measures. Those in need of treatment include those already with the disorder as well as those in which the disorder is to be prevented.

"Mammal" for purposes of treatment refers to any animal classified as a mammal, including humans, domestic and farm animals, and zoo, sports, or pet animals, such as dogs, horses, cats, cows, etc. Preferably, the mammal is human.

A "disorder" is any condition that would benefit from treatment with the compositions comprising the peptide ligands of the invention. This includes chronic and acute disorders or diseases including those pathological conditions which predispose the mammal to the disorder in question.

"Elimination half-time" is used in its ordinary sense, as is described in *Goodman and Gillman's The Pharmaceutical Basis of Therapeutics* 21-25 (Alfred Goodman Gilman, Louis S. Goodman, and Alfred Gilman, eds., 6th ed. 1980). Briefly, the term is meant to encompass a quantitative measure of the time course of drug elimination. The elimination of most drugs is exponential (i.e., follows first-order kinetics), since drug concentrations usually do not approach those required for saturation of the elimination process. The rate of an exponential process may be expressed by its rate constant, k, which expresses the fractional change per unit of time, or by its half-time, $t_{1/2}$, the time required for 50% completion of the process. The units of these two constants are $time^{-1}$ and time, respectively. A first-order rate constant and the half-time of the reaction are simply related ($k \times t_{1/2} = 0.693$) and may be interchanged accordingly. Since first-order elimination kinetics dictates that a constant fraction of drug is lost per unit time, a plot of the log of drug concentration versus time is linear at all times following the initial distribution phase (i.e. after drug absorption and distribution are complete). The half-time for drug elimination can be accurately determined from such a graph.

"Transfection" refers to the taking up of an expression vector by a host cell whether or not any coding sequences are in fact expressed. Numerous methods of transfection are known to the ordinarily skilled artisan, for example, $CaPO_4$ precipitation and electroporation. Successful transfection is generally recognized when any indication of the operation of this vector occurs within the host cell.

"Transformation" means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., *Molecular Cloning* (2nd ed.), Cold Spring Harbor Laboratory, NY (1989), is generally used for prokaryotes or other cells that contain substantial cell-wall barriers. Infection with *Agrobacterium tumefaciens* is used for transformation of certain plant cells, as described by Shaw et al., (1983) *Gene*, 23:315 and WO 89/05859 published 29 Jun. 1989. For mammalian cells without such cell walls, the calcium phosphate precipitation method described in sections 16.30-16.37 of Sambrook et al., supra, is preferred. General aspects of mammalian cell host system transformations have been described by Axel in U.S. Pat. No. 4,399,216 issued 16 Aug. 1983. Transformations into yeast are typically carried out according to the method of Van Solingen et al., (1977) *J. Bact.*, 130:946 and Hsiao et al., (1979) *Proc. Natl. Acad. Sci.* (USA), 76:3829. However, other methods for introducing DNA into cells such as by nuclear injection, electroporation, or by protoplast fusion may also be used.

As used herein, the term "pulmonary administration" refers to administration of a formulation of the invention through the lungs by inhalation. As used herein, the term "inhalation" refers to intake of air to the alveoli. In specific examples, intake can occur by self-administration of a formulation of the invention while inhaling, or by administration via a respirator, e.g., to an patient on a respirator. The term "inhalation" used with respect to a formulation of the invention is synonymous with "pulmonary administration."

As used herein, the term "parenteral" refers to introduction of a compound of the invention into the body by other than the intestines, and in particular, intravenous (i.v.), intraarterial (i.a.), intraperitoneal (i.p.), intramuscular (i.m.), intraventricular, and subcutaneous (s.c.) routes.

As used herein, the term "aerosol" refers to suspension in the air. In particular, aerosol refers to the particlization of a formulation of the invention and its suspension in the air. According to the present invention, an aerosol formulation is a formulation comprising a compound of the present invention that is suitable for aerosolization, i.e., particlization and suspension in the air, for inhalation or pulmonary administration.

II. MODES FOR CARRYING OUT THE INVENTION

A. Peptide Ligands

Peptide ligands within the context of the present invention bind a target, preferably a serum protein such as serum albumin or an immunoglobulin, and can be identified in a direct binding assay, or by their ability to compete for target binding with a known ligand for the target. Preferred peptide ligands that bind serum albumin include linear and cyclic peptides, preferably cyclic peptide compounds comprising the following formulae or are peptides that compete for binding serum albumin of a particular mammalian species with peptides of the following formulae:

Xaa-Xaa-Cys-Xaa-Xaa-Xaa-Xaa-Xaa-Cys-Xaa-Xaa Phe-Cys-Xaa-Asp-Trp-Pro-Xaa-Xaa-Xaa-Ser-Cys (SEQ ID NO: 113) Val-Cys-Tyr-Xaa-Xaa-Xaa-Ile-Cys-Phe (SEQ ID NO: 114)

Cys-Tyr-Xaa$_1$-Pro-Gly-Xaa-Cys (SEQ ID NO: 115) and Asp-Xaa-Cys-Leu-Pro-Xaa-Trp-Gly-Cys-Leu-Trp (SEQ ID NO: 116)

wherein the general formulae further comprises the sequence (Xaa)$_x$ at the N-terminus and the sequence (Xaa)$_z$ at the C-terminus.

Preferred are peptide compounds of the foregoing general formulae wherein Xaa is an amino acid and x and z are a whole number greater or equal to 0 (zero), generally less than 100, preferably less than 10 and more preferably 0, 1, 2, 3, 4 or 5 and more preferably 4 or 5 and wherein Xaa$_1$ is selected from the group consisting of Ile, Phe, Tyr and Val.

Further preferred peptide ligands that bind a serum albumin are identified as described herein in the context of the following general formulae Trp-Cys-Asp -Xaa-Xaa-Leu-Xaa-Ala-Xaa-Asp-Leu-Cys (SEQ ID NO: 117) and Asp-Leu-Val-Xaa-Leu-Gly-Leu-Glu-Cys-Trp (SEQ ID NO: 118), wherein the general formulae further comprises the sequence (Xaa)$_x$ at the N-terminus and the sequence (Xaa)$_z$ at the C-terminus and wherein Xaa is an amino acid and x and z are a whole number greater or equal to zero, generally less than 100, preferably less than 10 and more preferably 0, 1, 2, 3, 4 or 5 and more preferably 4 or 5.

According to this aspect of the invention reference is made to the Figures and especially FIGS. 5A and 5B, 8A, 8B and 8C and FIG. 9 for exemplary peptides and appropriate amino acids for selecting peptides ligands that bind a mammalian serum albumin. In a preferred aspect, reference is made to FIG. 9 for selecting peptide ligands that bind across several species of serum albumin.

Preferred compounds according to this aspect of the invention include:

Asp-Leu-Cys-Leu-Arg-Asp-Trp-Gly-Cys-Leu-Trp (SEQ ID NO: 119)

Asp-Ile-Cys-Leu-Pro-Arg-Trp-Gly-Cys-Leu-Trp (SEQ ID NO: 120)

Met-Glu-Asp-Ile-Cys-Leu-Pro-Arg-Trp-Gly-Cys-Leu-Trp-Glu-Asp (SEQ ID NO: 121) Gln-Arg-Leu-Met-Glu-Asp-Ile-Cys-Leu-Pro-Arg-Trp-Gly-Cys-Leu-Trp-Glu-Asp-Asp-Phe (SEQ ID NO: 122)

Gln-Gly-Leu-Ile-Gly-Asp-Ile-Cys-Leu-Pro-Arg-Trp-Gly-Cys-Leu-Trp-Gly-Asp-Ser-Val (SEQ ID NO: 123)

Gln-Gly-Leu-Ile-Gly-Asp-Ile-Cys-Leu-Pro-Arg-Trp-Gly-Cys-Leu-Trp-Gly-Asp-Ser-Val-Lys (SEQ ID NO: 124)

Glu-Asp-Ile-Cys-Leu-Pro-Arg-Trp-Gly-Cys-Leu-Trp-Glu-Asp-Asp (SEQ ID NO: 125) Arg-Leu-Met-Glu-Asp-Ile-Cys-Leu-Pro-Arg-Trp-Gly-Cys-Leu-Trp-Glu-Asp-Asp (SEQ ID NO: 126)

Met-Glu-Asp-Ile-Cys-Leu-Pro-Arg-Trp-Gly-Cys-Leu-Trp-Glu-Asp-Asp (SEQ ID NO: 127)

Met-Glu-Asp-Ile-Cys-Leu-Pro-Arg-Trp-Gly-Cys-Leu-Trp-Glu-Asp (SEQ ID NO: 121) Arg-Leu-Met-Glu-Asp-Ile-Cys-Leu-Ala-Arg-Trp-Gly-Cys-Leu-Trp-Glu-Asp-Asp (SEQ ID NO: 128) Glu-Val-Arg-Ser-Phe-Cys-Thr-Asp-Trp-Pro-Ala-Glu-Lys-Ser-Cys-Lys-Pro-Leu-Arg-Gly (SEQ ID NO: 129)

Arg-Ala-Pro-Glu-Ser-Phe-Val-Cys-Tyr-Trp-Glu-Thr-Ile-Cys-Phe-Glu-Arg-Ser-Glu-Gln (SEQ ID NO: 130)

Glu-Met-Cys-Tyr-Phe-Pro-Gly-Ile-Cys-Trp-Met (SEQ ID NO: 131)

In a preferred embodiment, peptide ligands of the present invention bind IgG-Fc and can be identified by their ability to compete for binding of IgG-Fc in an in vitro assay with a peptide ligand having the general formula:

Xaa$_i$-Cys-Xaa$_j$-Cys-Xaa$_k$, wherein Xaa$_i$ is absent or is a peptide of between 1 and 4 amino acids, preferably 4 amino acids; X$_j$ is preferably 9 amino acids having a preferred sequence Xaa-Xaa-Xaa-Xaa-Xaa-Xaa-Leu-Val-Trp (SEQ ID NO: 9); or Xaa -Xaa-Xaa-Xaa-Gly-Glu-Leu-Val-Trp (SEQ ID NO: 10); or Xaa$_1$-Xaa$_2$-Xaa$_3$-Xaa$_4$-Gly -Glu-Leu-Val-Trp (SEQ ID NO: 139), wherein Xaa$_1$ is Ala, Ser, or Thr; Xaa$_2$ is Trp or Tyr; Xaa$_3$ is His, or Trp; Xaa$_4$ is Leu or Met, and Xaa$_k$ is absent or between 1 and 5 amino acids, preferably 5 amino acids, so long as the cyclic peptide or analog thereof retains the qualitative biological activity of binding IgG-Fc described above.

Preferred among this group of compounds are compounds comprising the sequence:

Xaa-Xaa-Xaa-Xaa-Cys-Xaa-Xaa-Xaa-Xaa-Xaa-Xaa-Leu-Val-Trp-Cys Xaa-Xaa-Xaa-Xaa-Xaa (SEQ ID NO: 11);

Xaa-Xaa-Xaa-Xaa-Cys-Xaa-Xaa-Xaa-Xaa-Gly-Glu-Leu-Val-Trp-Cys-Xaa-Xaa-Xaa-Xaa- Xaa (SEQ ID NO: 12);

Xaa$_1$Xaa$_2$-Xaa$_3$-Xaa$_4$-Cys-Xaa$_5$-Xaa$_6$-Xaa$_7$-Xaa$_8$-Gly-Glu-Leu-Val-Trp-Cys-Xaa$_9$-Xaa$_{10}$-Xaa$_{11}$-Xaa$_{12}$-Xaa$_{13}$ (SEQ ID NO: 13), wherein Xaa$_5$ is Ala, Ser, or Thr; Xaa$_6$ is Trp or Tyr; Xaa$_7$ is His, or Trp; and Xaa$_8$ is Leu or Met; and Xaa$_1$-Xaa$_2$-Xaa$_3$-Xaa$_4$-Cys-Xaa$_5$-Xaa$_6$-Xaa$_7$-Xaa$_8$-Gly-Glu-Leu-Val-Trp-Cys-Xaa$_9$-Xaa$_{10}$-Xaa$_{11}$-Xaa$_{12}$-Xaa$_{13}$ (SEQ ID NO: 14) wherein Xaa$_4$ is Ser, Arg, or Asp; Xaa$_5$ is Ala, Ser, or Thr; Xaa$_6$ is Trp, Tyr; Xaa$_7$ is His, or Trp; Xaa$_8$ is Leu or Met; and Xaa$_9$ is Glu, Ser, Thr or Val. In particular embodiments, the IgG-Fc binding peptide ligands of the present invention will compete with any of the peptide ligands represented in SEQ ID NO: 2- SEQ ID NO: 3, SEQ ID NO: 8; and SEQ ID NO: 11-SEQ ID NO: 111 described herein and preferably will compete with SEQ ID NO: 8 for binding IgG-Fc.

In another preferred embodiment, peptide ligands of the present invention bind human serum albumin and can be identified by their ability to compete for binding of human serum albumin in an in vitro assay with peptide ligands having the general formulae shown below:

Asp-Xaa-Cys-Leu-Pro-Xaa-Trp-Gly-Cys-Leu-Trp (SEQ ID NO: 116) Phe-Cys-Xaa-Asp-Trp-Pro-Xaa-Xaa-Xaa-Ser-Cys (SEQ ID NO: 113)

Val-Cys-Tyr-Xaa-Xaa-Xaa-Ile-Cys-Phe (SEQ ID NO: 114) or Cys-Tyr-Xaa$_1$-Pro-Gly-Xaa-Cys (SEQ ID NO: 115)

wherein the general formulae further comprises the sequence (Xaa)$_x$ at the N-terminus and the sequence (Xaa)$_z$ at the C-terminus.

In particular embodiments, the human serum albumin binding peptide ligands of the present invention will compete with any of the peptide ligands represented in SEQ ID NO: 120-131 described herein above and preferably will compete with SEQ ID NO: 122 for binding human serum albumin.

As will be appreciated from the foregoing, the term "compete" and "ability to compete" are relative terms. Thus the terms, when used to describe the peptide ligands of the present invention, refer to peptide ligands that produce a 50% inhibition of binding of, for example SEQ ID NO: 8 or SEQ ID NO: 122, when present at 50 µM, preferably when present at 1 µM, more preferably 100 nM, and preferably when present at 1 nM or less in a standard competition assay as described herein. Such peptide ligands generally will bind IgG-Fc with an affinity of less than 1 µM, preferably less than about 100 nM and more preferably less than about 10 nM as determined by a standard competition assay such as the one described in the Example sections. However, peptide ligands having an affinity for a serum protein such as serum albumin or IgG-Fc of less than about 1 nM and preferably between about 1 pM and 1 nM are equally likely to be peptide ligands within the context of the present invention.

For in vitro assay systems to determine whether a peptide or other compound has the "ability" to compete with a peptide ligand for binding to an IgG-Fc (or other plasma protein such as, e.g., serum albumin) as noted herein, the skilled artisan can employ any of a number of standard competition assays. Competitive binding assays rely on the ability of a labeled standard to compete with the test sample analyte for binding with a limited amount of ligand. The amount of analyte in the test sample is inversely proportional to the amount of standard that becomes bound to the ligand.

Thus, the skilled artisan may determine whether a peptide or other compound has the ability to compete with a peptide ligand for binding to an IgG-Fc (or other target such as a plasma protein) employing procedures which include but are not limited to competitive assay systems using techniques such as radioimmunoassays (RIA), enzyme immunoassays (EIA), preferably the enzyme linked immunosorbent assay (ELISA), "sandwich" immunoassays, immunoradiometric assays, fluorescent immunoassays, and immunoelectrophoresis assays, to name but a few.

For these purposes the selected peptide ligand will be labeled with a detectable moiety (the detectably labeled peptide ligand hereafter called the "tracer") and used in a competition assay with a candidate compound for binding IgG-Fc domain or other target. Numerous detectable labels are available which can be preferably grouped into the following categories:

(a) Radioisotopes, such as $^{35}$S, $^{14}$C, $^{125}$I, $^3$H, and $^{131}$I. The peptide compound can be labeled with the radioisotope using the techniques described in Coligen et al., eds., *Current Protocols in Immunology*, Volumes 1 and 2 (1991), Wiley-Interscience, New York, N.Y., for example and radioactivity can be measured using scintillation counting.

(b) Fluorescent labels such as rare earth chelates (europium chelates) or fluorescein and its derivatives, rhodamine and its derivatives, dansyl, lissamine, phycoerythrin and Texas Red are available. The fluorescent labels can be conjugated to the peptide compounds using the techniques disclosed in *Current Protocols in Immunology*, supra, for example. Fluorescence can be quantified using a fluorimeter.

(c) Various enzyme-substrate labels are available and U.S. Pat. No. 4,275,149 provides a review of some of these. The enzyme preferably catalyzes a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRP), alkaline phosphatase, θ-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like.

Examples of enzyme-substrate combinations include, for example:

(i) Horseradish peroxidase (HRP) with hydrogen peroxidase as a substrate, wherein the hydrogen peroxidase oxidizes a dye precursor (e.g. ABTS, orthophenylene diamine (OPD) or 3,3',5,5'-tetramethyl benzidine hydrochloride (TMB));

(ii) alkaline phosphatase (AP) with para-nitrophenyl phosphate as chromogenic substrate; and (iii) β-D-galactosidase (β-D-Gal) with a chromogenic substrate (e.g. p-nitrophenyl-β-D-galactosidase) or fluorogenic substrate 4-methylumbelliferyl-β-D-galactosidase.

According to a particular assay, the tracer is incubated with immobilized target in the presence of varying concentrations of unlabeled candidate compound. Increasing concentrations of successful candidate compound effectively compete with binding of the tracer to immobilized target. The concentration of unlabeled candidate compound at which 50% of the maximally-bound tracer is displaced is referred to as the "$IC_{50}$" and reflects the IgG binding affinity of the candidate compound. Therefore a candidate compound with an $IC_{50}$ of 1 mM displays a substantially weaker interaction with the target than a candidate compound with an $IC_{50}$ of 1 µM.

In some phage display ELISA assays, binding affinity of a mutated ("mut") sequence was directly compared of a control ("con") peptide using methods described in B. C. Cunningham, D. G. Lowe, B. Li, B. D. Bennett, and J. A. Wells, *EMBO J.* 13:2508 (1994) and characterized by the parameter $EC_{50}$. Assays were performed under conditions where $EC_{50}(con)/EC_{50}(mut)$ will approximate $K_d(con)/K_d(mut)$.

Accordingly, the invention provides compounds "having the ability to compete" for target molecules such as IgG or human serum albumin binding in an in vitro assay as described. Preferably the compound has an $IC_{50}$ for the target such as IgG or human serum albumin of less than 1 µM. Preferred among these compound are compounds having an $IC_{50}$ of less than about 100 nM and preferably less than about 10 nM or less than about 1 nM. In further preferred embodiments according to this aspect of the invention the compounds display an $IC_{50}$ for the target molecule such as IgG or human serum albumin of less than about 100 pM and more preferably less than about 10 pM.

A preferred in vitro assay for the determination of a candidate compound's ability to compete with a peptide ligand described herein is as follows and is described more fully in the Examples. In preferred embodiments the candidate compound is a peptide. The ability of a candidate compound to compete with a labeled peptide ligand tracer for binding to IgG or human serum albumin is monitored using an ELISA. Dilutions of a candidate compound in buffer are added to microtiter plates coated with IgG or human serum albumin (as described in the Example Sections) along with tracer for 1 hr. The microtiter plate is washed with wash buffer and the amount of tracer bound to IgG or human serum albumin measured.

B. Peptide Ligand Combinations

According to the present invention, the peptide ligand is optionally linked to a bioactive compound to form a hybrid molecule that comprises a peptide ligand domain and an active domain. The bioactive compounds of the invention include any compound useful as a therapeutic or diagnostic agent. Non-limiting examples of bioactive compounds include polypeptides such as enzymes, hormones, cytokines, antibodies or antibody fragments, as well as organic compounds such as analgesics, antipyretics, antiinflammatory agents, antibiotics, antiviral agents, anti-fungal drugs, cardiovascular drugs, drugs that affect renal function and electrolyte metabolism, drugs that act on the central nervous system, chemotherapeutic drugs, etc. According to the present invention the peptide ligand domain is joined to an active domain, optionally via a flexible linker domain.

The hybrid molecules of the present invention are constructed by combining a peptide ligand domain with a suitable active domain. Depending on the type of linkage and its method of production, the peptide ligand domain may be joined via its N- or C-terminus to the N- or C-terminus of the active domain. For example, when preparing the hybrid molecules of the present invention via recombinant techniques, nucleic acid encoding a peptide ligand will be operably linked to nucleic acid encoding the active domain sequence, optionally via a linker domain. Typically the construct encodes a fusion protein wherein the C-terminus of the peptide ligand is joined to the N-terminus of the active domain. However, especially when synthetic techniques are employed, fusions where, for example, the N-terminus of the peptide ligand is joined to the N- or C-terminus of the active domain also are possible. In some instances, the peptide ligand domain may be inserted within the active domain molecule rather than being joined to the active domain at its N- or C-terminus. This configuration may be used to practice the invention so long as the functions of the peptide ligand domain and the active domain are preserved. For example, a peptide ligand may be inserted into a non-binding light chain CDR of an immunoglobulin without interfering with the ability of the immunoglobulin to bind to its target. Regions of active domain molecules that can accommodate peptide ligand domain insertions may be identified empirically (i.e. by selecting an insertion site, randomly, and assaying the resulting conjugate for the function of the active domain), or by sequence comparisons amongst a family of related active domain molecules (e.g., for active domains that are proteins) to locate regions of low sequence homology. Low sequence homology regions are more likely to tolerate insertions of peptide ligands domains than are regions that are well-conserved. For active domain molecules whose three-dimensional structures are known (e.g. from X-ray crystallographic or NMR studies), the three-dimensional structure may provide guidance as to peptide ligand insertion sites. For example, loops or regions with high mobility (i.e., large temperature or "B" factors) are more likely to accommodate peptide ligand domain insertions than are highly ordered regions of the structure, or regions involved in ligand binding or catalysis.

C. Linker Domains

According to the present invention, the peptide ligand domain is optionally linked to the active domain via a linker. The linker component of the hybrid molecule of the invention does not necessarily participate in but may contribute to the function of the hybrid molecule. Therefore, according to the present invention, the linker domain, is any group of molecules that provides a spatial bridge between the active domain and the peptide ligand domain.

The linker domain can be of variable length and makeup, however, according to the present invention, it is the length of the linker domain and not its structure that is important. The linker domain preferably allows for the peptide ligand domain of the hybrid molecule to bind, substantially free of steric and/or conformational restrictions to the target molecule. Therefore, the length of the linker domain is dependent upon the character of the two "functional" domains of the hybrid molecule, i.e., the peptide ligand domain and the active domain.

One skilled in the art will recognize that various combinations of atoms provide for variable length molecules based upon known distances between various bonds (Morrison, and Boyd, *Organic Chemistry,* 3rd Ed, Allyn and Bacon, Inc., Boston, Mass. (1977)). For example, the linker domain may be a polypeptide of variable length. The amino acid composition of the polypeptide determines the character and length of the linker. In a preferred embodiment, the linker molecule comprises a flexible, hydrophilic polypeptide chain. Exem-

D. Recombinant Synthesis

The present invention encompasses a composition of matter comprising an isolated nucleic acid, preferably DNA, encoding a peptide ligand or a hybrid molecule comprising a peptide ligand domain and a polypeptide active domain as described herein. DNAs encoding the peptides of the invention can be prepared by a variety of methods known in the art. These methods include, but are not limited to, chemical synthesis by any of the methods described in Engels et al. (1989), *Agnew. Chem. Int. Ed. Engl.* 28:716-734, the entire disclosure of which is incorporated herein by reference, such as the triester, phosphite, phosphoramidite and H-phosphonate methods. In one embodiment, codons preferred by the expression host cell are used in the design of the encoding DNA. Alternatively, DNA encoding the peptides of the invention can be altered to encode one or more variants by using recombinant DNA techniques, such as site specific mutagenesis (Kunkel et al. (1991), *Methods Enzymol.*, 204:125-139; Carter et al. (1986), *Nucl. Acids Res.* 13:4331; Zoller et al. (1982), *Nucl. Acids Res.* 10:6487), cassette mutagenesis (Wells et al. (1985), *Gene* 34:315), restriction selection mutagenesis (Carter, *Directed Mutagenesis: A Practical Approach* (M. J. McPherson, ed.) IRL Press, Oxford, 1991), and the like.

According to preferred aspects described above, the nucleic acid encodes a peptide ligand capable of binding a target molecule. Target molecules include, for example, extracellular molecules such as various serum factors including but not limited to plasma proteins such as serum albumin, immunoglobulins, apolipoproteins or transferrin, or proteins found on the surface of erythrocytes or lymphocytes, provided, of course, that binding of the peptide ligand to the cell surface protein does not substantially interfere with the normal function of the cell.

According to another preferred aspect of the invention, the nucleic acid encodes a hybrid molecule comprising a peptide ligand domain sequence and an active domain. In this aspect of the invention, the active domain may comprise any polypeptide compound useful as a therapeutic or diagnostic agent, e.g., enzymes, hormones, cytokines, antibodies or antibody fragments. The nucleic acid molecule according to this aspect of the present invention encodes a hybrid molecule and the nucleic acid encoding the peptide ligand domain sequence is operably linked to (in the sense that the DNA sequences are contiguous and in reading frame) the nucleic acid encoding the biologically active agent. Optionally these DNA sequences may be linked through a nucleic acid sequence encoding a linker domain amino acid sequence.

According to this aspect, the invention further comprises an expression control sequence operably linked to the DNA molecule encoding a peptide of the invention, an expression vector, such as a plasmid, comprising the DNA molecule, wherein the control sequence is recognized by a host cell transformed with the vector, and a host cell transformed with the vector. In general, plasmid vectors contain replication and control sequences which are derived from species compatible with the host cell. The vector ordinarily carries a replication site, as well as sequences which encode proteins that are capable of providing phenotypic selection in transformed cells.

For expression in prokaryotic hosts, suitable vectors include pBR322 (ATCC No. 37,017), phGH107 (ATCC No. 40,011), pBO475, pS0132, pRIT5, any vector in the pRIT20 or pRIT30 series (Nilsson and Abrahmsen (1990), *Meth. Enzymol.* 185:144-161), pRIT2T, pKK233-2, pDR540 and pPL-lambda. Prokaryotic host cells containing the expression vectors of the present invention include *E. coli* K12 strain 294 (ATCC NO. 31,446), *E. coli* strain JM101 (Messing et al. (1981), *Nucl. Acid Res.* 9:309), *E. coli* strain B, *E. coli* strain 1776 (ATCC No. 31537), *E. coli* c600, *E. coli* W3110 (F-, gamma-, prototrophic, ATCC No. 27,325), *E. coli* strain 27C7 (W3110, tonA, phoA E15, (argF-lac)169, ptr3, degP41, ompT, kan$^r$) (U.S. Pat. No. 5,288,931, ATCC No. 55,244), *Bacillus subtilis, Salmonella typhimurium, Serratia marcesans*, and *Pseudomonas* species.

In addition to prokaryotes, eukaryotic organisms, such as yeasts, or cells derived from multicellular organisms can be used as host cells. For expression in yeast host cells, such as common baker's yeast or *Saccharomyces cerevisiae*, suitable vectors include episomally-replicating vectors based on the 2-micron plasmid, integration vectors, and yeast artificial chromosome (YAC) vectors. For expression in insect host cells, such as Sf9 cells, suitable vectors include baculoviral vectors. For expression in plant host cells, particularly dicotyledonous plant hosts, such as tobacco, suitable expression vectors include vectors derived from the Ti plasmid of *Agrobacterium tumefaciens*.

Examples of useful mammalian host cells include monkey kidney CV1 line transformed by SV40 (COS-7, ATCC CRL 1651); human embryonic kidney line (293 or 293 cells subcloned for growth in suspension culture, Graham et al. (1977), *J. Gen Virol* 36:59); baby hamster kidney cells (BHK, ATCC CCL 10); Chinese hamster ovary cells/-DHFR (CHO, Urlaub and Chasin (1980), *Proc. Natl. Acad. Sci. USA* 77:4216); mouse sertoli cells (TM4, Mather (1980), *Biol. Reprod.* 23:243-251); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al. (1982), *Annals N.Y. Acad. Sci.* 383:44-68); MRC 5 cells; FS4 cells; and a human hepatoma cell line (Hep G2). For expression in mammalian host cells, useful vectors include vectors derived from SV40, vectors derived from cytomegalovirus such as the pRK vectors, including pRK5 and pRK7 (Suva et al. (1987), *Science* 237:893-896; EP 307,247 (Mar. 15, 1989), EP 278,776 (Aug. 17, 1988)) vectors derived from vaccinia viruses or other pox viruses, and retroviral vectors such as vectors derived from Moloney's murine leukemia virus (MoMLV).

Optionally, the DNA encoding the peptide of interest is operably linked to a secretory leader sequence resulting in secretion of the expression product by the host cell into the culture medium. Examples of secretory leader sequences include STII, ecotin, lamB, herpes GD, lpp, alkaline phosphatase, invertase, and alpha factor. Also suitable for use herein is the 36 amino acid leader sequence of protein A (Abrahmsen et al. (1985), *EMBO J.* 4:3901).

Host cells are transfected and preferably transformed with the above-described expression or cloning vectors of this invention and cultured in conventional nutrient media modified as appropriate for inducing promoters, selecting transformants, or amplifying the genes encoding the desired sequences.

Prokaryotic host cells used to produce the present peptides can be cultured as described generally in Sambrook et al., supra.

The mammalian host cells used to produce peptides of the invention can be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM, Sigma) are suitable for culturing the host cells. In addition, any of the media described in Ham and Wallace (1979), *Meth. in Enz.* 58:44, Barnes and Sato (1980), *Anal. Biochem.* 102:255, U.S. Pat. Nos. 4,767,704; 4,657,866; 4,927,762; or 4,560,655; WO 90/03430; WO 87/00195; U.S. Pat. No. Re. 30,985; or U.S. Pat. No. 5,122,469, the disclosures of all of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The host cells referred to in this disclosure encompass cells in in vitro culture as well as cells that are within a host animal.

E. Chemical Synthesis

Another method of producing the compounds of the invention involves chemical synthesis. This can be accomplished by using methodologies well known in the art (see Kelley, R. F. & Winkler, M. E. in *Genetic Engineering Principles and Methods*, Setlow, J. K., ed., Plenum Press, N.Y., Vol. 12, pp 1-19 (1990); Stewart, J. M. Young, J. D., *Solid Phase Peptide Synthesis*, Pierce Chemical Co., Rockford, Ill. (1984); see also U.S. Pat. Nos. 4,105,603; 3,972,859; 3,842,067; and 3,862,925).

Peptide ligands of the invention can be prepared conveniently using solid-phase peptide synthesis. Merrifield (1964), *J. Am. Chem. Soc.* 85:2149; Houghten (1985), *Proc. Natl. Acad. Sci. USA* 82:5132. Solid-phase peptide synthesis also can be used to prepare the hybrid molecule compositions of the invention if the active domain is or comprises a polypeptide.

Figure 2:
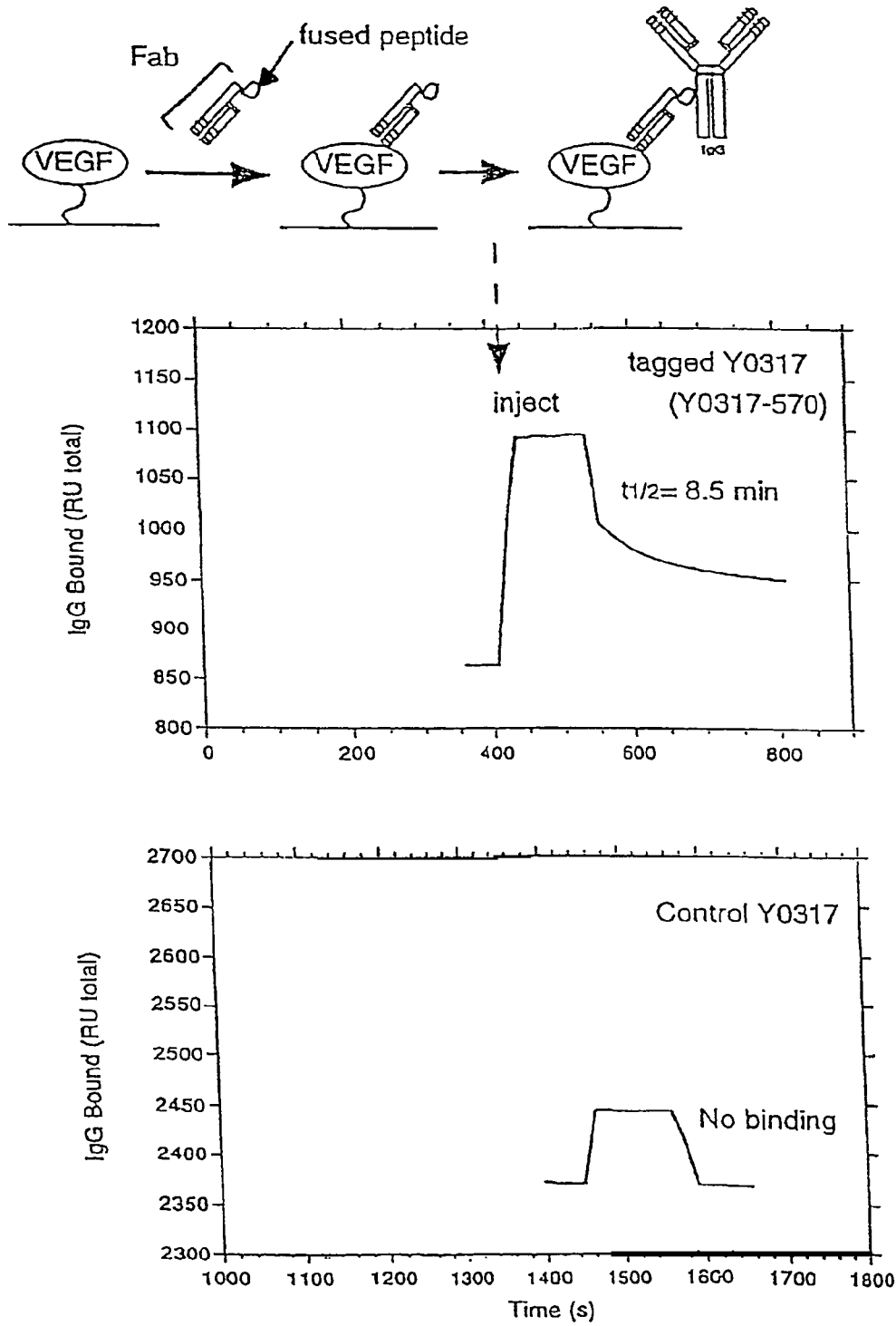
FIG. 2. BIAcore™ analysis of IgG binding to peptide-ligand tagged anti-VEGF Fab Y0317-570 (tagged; top panel) Y0317 Fab (control; bottom panel). A cartoon illustration at top shows a model for the binding events observed in the tagged Fab experiment.

Solid-phase synthesis begins at the carboxy terminus of the nascent peptide by coupling a protected amino acid to an inert solid support. The inert solid support can be any macromolecule capable of serving as an anchor for the C-terminus of the initial amino acid. Typically, the macromolecular support is a cross-linked polymeric resin (e.g., a polyamide or polystyrene resin) as shown in FIGS. 1-1 and 1-2, on pages 2 and 4 of Stewart and Young, supra. In one embodiment, the C-terminal amino acid is coupled to a polystyrene resin to form a benzyl ester. A macromolecular support is selected such that the peptide anchor link is stable under the conditions used to deprotect the α-amino group of the blocked amino acids in peptide synthesis. If a base-labile α-protecting group is used, then it is desirable to use an acid-labile link between the peptide and the solid support. For example, an acid-labile ether resin is effective for base-labile Fmoc-amino acid peptide synthesis as described on page 16 of Stewart and Young, supra. Alternatively, a peptide anchor link and α-protecting group that are differentially labile to acidolysis can be used. For example, an aminomethyl resin such as the phenylacetamidomethyl (Pam) resin works well in conjunction with Boc-amino acid peptide synthesis as described on pages 11-12 of Stewart and Young, supra.

After the initial amino acid is coupled to an inert solid support, the α-amino protecting group of the initial amino acid is removed with, for example, trifluoroacetic acid (TFA) in methylene chloride and neutralized in, for example, triethylamine (TEA). Following deprotection of the initial amino acid's amino group, the next α-amino and side chain protected amino acid in the synthesis is added. The remaining α-amino and, if necessary, side chain protected amino acids are then coupled sequentially in the desired order by condensation to obtain an intermediate compound connected to the solid support. Alternatively, some amino acids may be coupled to one another to form a fragment of the desired peptide followed by addition of the peptide fragment to the growing solid phase peptide chain.

The condensation reaction between two amino acids, or an amino acid and a peptide, or a peptide and a peptide can be carried out according to the usual condensation methods such as the axide method, mixed acid anhydride method, DCC(N, N'-dicyclohexylcarbodiimide) or DIC (N,N'-diisopropylcarbodiimide) methods, active ester method, p-nitrophenyl ester method, BOP (benzotriazole-1-yl-oxy-tris [dimethylamino] phosphonium hexafluorophosphate) method, N-hydroxysuccinic acid imido ester method, etc., and Woodward reagent K method.

It is common in the chemical synthesis of peptides to protect any reactive side chain groups of the amino acids with suitable protecting groups. Ultimately, these protecting groups are removed after the desired polypeptide chain has been sequentially assembled. Also common is the protection of the α-amino group on an amino acid or peptide fragment while the C-terminal carboxy group of the amino acid or peptide fragment reacts with the free N-terminal amino group of the growing solid phase polypeptide chain, followed by the selective removal of the α-amino group to permit the addition of the next amino acid or peptide fragment to the solid phase polypeptide chain. Accordingly, it is common in polypeptide synthesis that an intermediate compound is produced which contains each of the amino acid residues located in the desired sequence in the peptide chain wherein individual residues still carry side-chain protecting groups. These protecting groups can be removed substantially at the same time to produce the desired polypeptide product following removal from the solid phase.

α- and ε-amino side chains can be protected with benzyloxycarbonyl (abbreviated Z), isonicotinyloxycarbonyl (iNOC), o-chlorobenzyloxycarbonyl [Z(2Cl)], p-nitrobenzyloxycarbonyl [$ZNO_2$)], p-methoxybenzyloxycarbonyl [Z(OMe)], t-butoxycarbonyl (Boc), t-amyloxycarbonyl (Aoc), isobornyloxycarbonyl adamantyloxycarbonyl, 2-(4-biphenyl)-2-propyloxycarbonyl (Bpoc), 9-fluorenylmethoxycarbonyl (Fmoc), methylsulfonyethoxycarbonyl (Msc), trifluoroacetyl phthalyl, formyl 2-nitrophenylsulphenyl (NPS), diphenylphosphinothioyl (Ppt), and dimethylphosphinothioyl (Mpt) groups, and the like.

Protective groups for the carboxy functional group are exemplified by benzyl ester (OBzl), cyclohexyl ester (Chx), 4-nitrobenzyl ester (ONb), t-butyl ester (Obut), 4-pyridylmethyl ester (OPic), and the like. It is often desirable that specific amino acids such as arginine, cysteine, and serine possessing a functional group other than amino and carboxyl groups are protected by a suitable protective group. For example, the guanidino group of arginine may be protected with nitro, p-toluenesulfonyl, benzyloxycarbonyl, adamantyloxycarbonyl, p-methoxybenzesulfonyl, 4-methoxy-2,6- dimethylbenzenesulfonyl (Nds), 1,3,5-trimethylphenysulfonyl (Mts), and the like. The thiol group of cysteine can be protected with p-methoxybenzyl, trityl, and the like.

Many of the blocked amino acids described above can be obtained from commercial sources such as Novabiochem (San Diego, Calif.), Bachem CA (Torrence, Calif.) or Peninsula Labs (Belmont, Calif.).

Stewart and Young, supra, provides detailed information regarding procedures for preparing peptides. Protection of α-amino groups is described on pages 14-18, and side chain blockage is described on pages 18-28. A table of protecting groups for amine, hydroxyl and sulfhydryl functions is provided on pages 149-151.

After the desired amino acid sequence has been completed, the peptide can be cleaved away from the solid support, recovered and purified. The peptide is removed from the solid support by a reagent capable of disrupting the peptide-solid phase link, and optionally deprotects blocked side chain functional groups on the peptide. In one embodiment, the peptide is cleaved away from the solid phase by acidolysis with liquid hydrofluoric acid BF), which also removes any remaining side chain protective groups. Preferably, in order to avoid alkylation of residues in the peptide (for example, alkylation of methionine, cysteine, and tyrosine residues), the acidolysis reaction mixture contains thio-cresol and cresol scavengers. Following HF cleavage, the resin is washed with ether, and the free peptide is extracted from the solid phase with sequential washes of acetic acid solutions. The combined washes are lyophilized, and the peptide is purified.

F. Chemical Conjugation of Hybrids

In certain embodiments of the present invention, the hybrid molecules may comprise active domains that are organic compounds having diagnostic or therapeutic utility, or alternatively, fusions between a peptide ligand domain and a polypeptide active domain in configurations that cannot be encoded in a single nucleic acid. Examples of the latter embodiment include fusions between the amino terminus of a peptide ligand and the amino terminus of the active domain, or fusions between the carboxy-terminus of a peptide ligand and the carboxy-terminus of the active domain.

Chemical conjugation may be employed to prepare these embodiments of the hybrid molecule, using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene, 2,6-diisocyanate), and bis-active fluorine compounds (such as 1,5-difluoro-2,4-dinitrobenzene).

G. Disulfide-Linked Peptides

As described above, some embodiments of the invention include cyclized peptide ligands. Peptide ligands may be cyclized by formation of a disulfide bond between cysteine residues. Such peptides can be made by chemical synthesis as described above and then cyclized by any convenient method used in the formation of disulfide linkages. For example, peptides can be recovered from solid phase synthesis with sulfhydryls in reduced form, dissolved in a dilute solution wherein the intramolecular cysteine concentration exceeds the intermolecular cysteine concentration in order to optimize intramolecular disulfide bond formation, such as a peptide concentration of 25 mM to 1 μM, and preferably 500 μM to 1 μM, and more preferably 25 μM to 1 μM, and then oxidized by exposing the free sulfhydryl groups to a mild oxidizing agent that is sufficient to generate intramolecular disulfide bonds, e.g., molecular oxygen with or without catalysts such as metal cations, potassium ferricyanide, sodium tetrathionate, etc. Alternatively, the peptides can be cyclized as described in Pelton et al. (1986), *J. Med. Chem.* 29:2370-2375.

Cyclization can be achieved by the formation, for example, of a disulfide bond or a lactam bond between a first Cys and a second Cys. Residues capable of forming a disulfide bond include, for example, Cys, Pen, Mpr, and Mpp and its 2-amino group-containing equivalents. Residues capable of forming a lactam bridge include, for example, Asp Glu, Lys, Orn, αβ-diaminobutyric acid, diaminoacetic acid, aminobenzoic acid and mercaptobenzoic acid. The compounds herein can be cyclized for example via a lactam bond which can utilize the side chain group of a non-adjacent residue to form a covalent attachment to the N-terminus amino group of Cys or other amino acid. Alternative bridge structures also can be used to cyclize the compounds of the invention, including for example, peptides and peptidomimetics, which can cyclize via S—S, CH2—S, CH2—O—CH2, lactam ester or other linkages.

H. Pharmaceutical Compositions

Pharmaceutical compositions which comprise the hybrid molecules of the invention may be administered in any suitable manner, including parental, topical, oral, or local (such as aerosol or transdermal) or any combination thereof.

Other suitable compositions of the present invention comprise any of the above-noted compositions with a pharmaceutically acceptable carrier, the nature of the carrier differing with the mode of administration, for example, in oral administration, usually using a solid carrier and in i.v. administration, a liquid salt solution carrier.

The compositions of the present invention include pharmaceutically acceptable components that are compatible with the subject and the protein of the invention. These generally include suspensions, solutions and elixirs, and most especially biological buffers, such as phosphate buffered saline, saline, Dulbecco's Media, and the like. Aerosols may also be used, or carriers such as starches, sugars, microcrystalline cellulose, diluents, granulating agents, lubricants, binders, disintegrating agents, and the like (in the case of oral solid preparations, such as powders, capsules, and tablets).

As used herein, the term "pharmaceutically acceptable" generally means approved by a regulatory agency of the Federal or a state government or listed in the U.S. Pharmacopeia or other generally recognized pharmacopeia for use in animals, and more particularly in humans.

The formulation of choice can be accomplished using a variety of the aforementioned buffers, or even excipients including, for example, pharmaceutical grades of mannitol, lactose, starch, magnesium stearate, sodium saccharin cellulose, magnesium carbonate, and the like. "PEGylation" of the compositions may be achieved using techniques known to the art (see for example International Patent Publication No. WO92/16555, U.S. Pat. No. 5,122,614 to Enzon, and International Patent Publication No. WO92/00748).

A preferred route of administration of the present invention is in the aerosol or inhaled form. The compounds of the present invention, combined with a dispersing agent, or dispersant, can be administered in an aerosol formulation as a dry powder or in a solution or suspension with a diluent.

As used herein, the term "dispersant" refers to a agent that assists aerosolization of the compound or absorption of the protein in lung tissue, or both. Preferably the dispersant is pharmaceutically acceptable. Suitable dispersing agents are well known in the art, and include but are not limited to surfactants and the like. For example, surfactants that are generally used in the art to reduce surface induced aggregation of a compound, especially a peptide compound, caused by atomization of the solution forming the liquid aerosol, may be used. Nonlimiting examples of such surfactants are surfactants such as polyoxyethylene fatty acid esters and alcohols, and polyoxyethylene sorbitan fatty acid esters. Amounts of surfactants used will vary, being generally within the range of from about 0.001% to about 4% by weight of the formulation. In a specific aspect, the surfactant is polyoxyethylene sorbitan monooleate or sorbitan trioleate. Suitable surfactants are well known in the art, and can be selected on the basis of desired properties, depending on the specific formulation, concentration of the compound, diluent (in a liquid formulation) or form of powder (in a dry powder formulation), etc.

Moreover, depending on the choice of the peptide ligand, the desired therapeutic effect, the quality of the lung tissue (e.g., diseased or healthy lungs), and numerous other factors, the liquid or dry formulations can comprise additional components, as discussed further below.

The liquid aerosol formulations generally contain the peptide ligand/active domain hybrid and a dispersing agent in a physiologically acceptable diluent. The dry powder aerosol formulations of the present invention consist of a finely divided solid form of the peptide ligand/active domain hybrid and a dispersing agent. With either the liquid or dry powder aerosol formulation, the formulation must be aerosolized. That is, it must be broken down into liquid or solid particles in order to ensure that the aerosolized dose actually reaches the alveoli. In general the mass median dynamic diameter will be 5 micrometers or less in order to ensure that the drug particles reach the lung alveoli (Wearley, L. L. (1991), *Crit. Rev. in Ther. Drug Carrier Systems* 8:333). The term "aerosol particle" is used herein to describe the liquid or solid particle suitable for pulmonary administration, i.e., that will reach the alveoli. Other considerations such as construction of the delivery device, additional components in the formulation and particle characteristics are important. These aspects of pulmonary administration of a drug are well known in the art, and manipulation of formulations, aerosolization means and construction of a delivery device require at most routine experimentation by one of ordinary skill in the art.

With regard to construction of the delivery device, any form of aerosolization known in the art, including but not limited to nebulization, atomization or pump aerosolization of a liquid formulation, and aerosolization of a dry powder formulation, can be used in the practice of the invention. A delivery device that is uniquely designed for administration of solid formulations is envisioned. Often, the aerosolization of a liquid or a dry powder formulation will require a propellant. The propellant may be any propellant generally used in the art. Specific nonlimiting examples of such useful propellants are a chloroflourocarbon, a hydrofluorocarbon, a hydochlorofluorocarbon, or a hydrocarbon, including triflouromethane, dichlorodiflouromethane, dichlorotetrafuoroethanol, and 1,1,1,2-tetrafluoroethane, or combinations thereof.

In a preferred aspect of the invention, the device for aerosolization is a metered dose inhaler. A metered dose inhaler provides a specific dosage when administered, rather than a variable dose depending on administration. Such a metered dose inhaler can be used with either a liquid or a dry powder aerosol formulation. Metered dose inhalers are well known in the art.

Once the peptide ligand/active domain hybrid reaches the lung, a number of formulation-dependent factors affect the drug absorption. It will be appreciated that in treating a disease or disorder that requires circulatory levels of the compound, such factors as aerosol particle size, aerosol particle shape, the presence or absence of infection, lung disease or emboli may affect the absorption of the compounds. For each of the formulations described herein, certain lubricators, absorption enhancers, protein stabilizers or suspending agents may be appropriate. The choice of these additional agents will vary depending on the goal. It will be appreciated that in instances where local delivery of the compounds is desired or sought, such variables as absorption enhancement will be less critical.

I. Liquid Aerosol Formulations

The liquid aerosol formulations of the present invention will typically be used with a nebulizer. The nebulizer can be either compressed air driven or ultrasonic. Any nebulizer known in the art can be used in conjunction with the present invention such as but not limited to: Ultravent, Mallinckrodt, Inc. (St. Louis, Mo.); the Acorn II nebulizer (Marquest Medical Products, Englewood Colo.). Other nebulizers useful in conjunction with the present invention are described in U.S. Pat. No. 4,624,251 issued Nov. 25, 1986; U.S. Pat. No. 3,703,173 issued Nov. 21, 1972; U.S. Pat. No. 3,561,444 issued Feb. 9, 1971 and U.S. Pat. No. 4,635,627 issued Jan. 13, 1971.

The formulation may include a carrier. The carrier is a macromolecule which is soluble in the circulatory system and which is physiologically acceptable where physiological acceptance means that those of skill in the art would accept injection of said carrier into a patient as part of a therapeutic regime. The carrier preferably is relatively stable in the circulatory system with an acceptable elimination half-time. Such macromolecules include but are not limited to soya lecithin, oleic acid and sorbetan trioleate, with sorbitan trioleate preferred.

The formulations of the present embodiment may also include other agents useful for protein stabilization or for the regulation of osmotic pressure. Examples of the agents include but are not limited to salts, such as sodium chloride, or potassium chloride, and carbohydrates, such as glucose, galactose or mannose, and the like.

J. Aerosol Dry Powder Formulations

It is also contemplated that the present pharmaceutical formulation will be used as a dry powder inhaler formulation comprising a finely divided powder form of the peptide ligand and a dispersant. The form of the compound will generally be a lyophilized powder. Lyophilized forms of peptide ligand/active domain hybrid compounds can be obtained through standard techniques.

In another embodiment, the dry powder formulation will comprise a finely divided dry powder containing one or more compounds of the present invention, a dispersing agent and also a bulking agent. Bulking agents useful in conjunction with the present formulation include such agents as lactose, sorbitol, sucrose, or mannitol, in amounts that facilitate the dispersal of the powder from the device.

K. Research, Manufacturing, and Diagnostic Compositions

In a preferred embodiment, the peptide ligands or the hybrid molecules of the invention are non-covalently adsorbed or covalently bound to a macromolecule, such as a solid support. It will be appreciated that the invention encompasses macromolecules complexed with the peptide ligands or hybrid molecules. In a preferred embodiment, the peptide ligands of the invention are directed against an immunoglobulin, such as, e.g., the IgG-Fc peptide ligands disclosed infra. Such peptide ligands may be used as affinity purification agents. In this process, the peptide ligands are immobilized on a solid phase support such as a Sephadex resin or filter paper, using methods well known in the art. The immobilized peptide ligand is contacted with a sample containing the immunoglobulin protein (or fragment thereof) to be purified, and thereafter the support is washed with a suitable solvent that will remove substantially all the material in the sample except the immunoglobulin protein, which is bound to the immobilized peptide ligand. Finally, the support is washed with another suitable solvent, such as glycine buffer, pH 5.0, that will release the immunoglobulin protein from the peptide ligand.

In general, the solid support is an inert matrix, such as a polymeric gel, comprising a three-dimensional structure, lattice or network of a material. Almost any macromolecule, synthetic or natural, can form a gel in a suitable liquid when suitably cross-linked with a bifunctional reagent. Preferably, the macromolecule selected is convenient for use in affinity chromatography. Most chromatographic matrices used for affinity chromatography are xerogels. Such gels shrink on drying to a compact solid comprising only the gel matrix. When the dried xerogel is resuspended in the liquid, the gel matrix imbibes liquid, swells and returns to the gel state. Xerogels suitable for use herein include polymeric gels, such as cellulose, cross-linked dextrans (e.g. Sepharose), agarose, cross-linked agarose, polyacrylamide gels, and polyacrylamide-agarose gels.

Alternatively, aerogels can be used for affinity chromatography. These gels do not shrink on drying but merely allow penetration of the surrounding air. When the dry gel is exposed to liquid, the latter displaces the air in the gel. Aerogels suitable for use herein include porous glass and ceramic gels.

Also encompassed herein are the peptide ligands or hybrid molecules of the invention coupled to derivatized gels wherein the derivative moieties facilitate the coupling of the hybrid molecules to the gel matrix and avoid steric hindrance of the peptide ligand-target molecule interaction in affinity chromatography. Alternatively, spacer arms can be interposed between the gel matrix and the hybrid molecules for similar benefits.

A variation on the above contemplates the use of gene fusions and the use of the peptide ligands as purification reagents. According to this aspect of the invention the gene encoding a peptide ligand is associated, in a vector, with a gene encoding another protein or a fragment of another protein. This results in the peptide ligand being produced by the host cell as a fusion with another protein or peptide. The "other" protein or peptide is often a protein or peptide which can be secreted by the cell, making it possible to isolate and purify the other protein from the culture medium and eliminating the necessity of destroying the host cells which arises when the other protein remains inside the cell. Alternatively, the fusion protein can be expressed intracellularly. It is useful to use fusion proteins that are highly expressed.

The use of gene fusions is analogous to the use of Protein A fusions which are often used because the binding of protein A, or more specifically the Z domain of protein A binds to IgG and provides an "affinity handle" for the purification of the fused protein. According to a preferred aspect of the invention, peptide ligands which bind serum albumin are use as "affinity handles" for the purification of fused proteins on a solid serum albumin support. For example, a DNA sequence encoding the desired peptide ligand can be fused by site directed mutagenesis to the gene for protein. After expression and secretion, the fusion protein can be purified on a matrix of serum albumin to which the peptide ligand will bind. After purification the peptide ligand can be enzymatically or chemically cleaved to yield free protein or left intact to aid in increasing the elimination half life of the fused protein. Fusion proteins can be cleaved using chemicals, such as cyanogen bromide, which cleaves at a methionine, or hydroxylamine, which cleaves between an Asn and Gly residue. Using standard recombinant DNA methodology, the nucleotide base pairs encoding these amino acids may be inserted just prior to the 5' end of the gene encoding the desired peptide. Alternatively, one can employ proteolytic cleavage of fusion protein. Carter, in Protein Purification: From Molecular Mechanisms to Large-Scale Processes, Ladisch et al., eds. (American Chemical Society Symposium Series No. 427, 1990), Ch 13, pages 181-193.

The following examples are offered by way of illustration and not by way of limitation. The disclosures of all citations in the specification are expressly incorporated herein by reference.

EXAMPLE 1

IgG-Fc Peptide Ligands

An in vitro selection designed to identify peptide ligands which bind the IgG-Fc surface without the constraint that the peptides function in vivo was performed. The selection was accomplished using a combination of polyvalent and monovalent phage display which has recently been applied to generate peptides that bind a variety of cellular hormones and receptors. N. C. Wrighton, et al. (1996), *Science* 273:458, O. Livnah, et al. (1996), *Science* 273:464. A single disulfide-constrained peptide library was constructed that consisted of $4 \times 10^9$ different peptides of the form $Xaa_i$-Cys-$Xaa_j$-Cys-$Xaa_k$ wherein Xaa is a random amino acid from an NNS codon, i+j+k=18, and j=4 through 10. This library was expressed on the surface of M13 bacteriophage as an N-terminal fusion to the gene VIII protein with a short linker consisting of glycine and serine residues. H. B. Lowman et al. (1998), *Biochemistry* 37: 8870-8878. More particularly, the library construct contained an STII secretion signal peptide, the peptide library of twenty amino acid length, i.e., $Xaa_i$-Cys-$Xaa_j$-Cys-$Xaa_k$ wherein Xaa is a random amino acid from an NNS codon, i+j+k=18, and j=4 through 10, a Gly-Gly-Gly-Ser-Gly-Gly-Gly linker (SEQ ID NO: 1), and the M13 gene VIII starting at the first residue of the mature protein.

In principle, peptides could be selected that bind to potentially any region of the IgG-Fc due to the unbiased nature of this library. However, after several rounds of selection, the library became dominated by a single peptide, Fc-I (Glu-Thr-Gln-Arg-Cys-Thr-Trp-His-Met-Gly-Glu-Leu-Val-Trp-Cys-Glu-Arg-Glu-His-Asn) (SEQ ID NO: 2). Selections were performed as described in H. B. Lowman, et al., supra, with the following modifications: microtiter wells were coated using 5 μg/ml IgG-Fc; Casein Blocker Buffer (Pierce) was used in place of 0.1% BSA to better prevent non-specific binding; elution of phage was effected with either 75 mM DTT or 0.2 mM glycine pH 2.0 with equivalent results. IgG- Fc was obtained by papain cleavage of CD4-IgG$_1$ immunoadhesin protein, Capon et al. (1989), *Nature*, 337: 525. Cleaved material was purified over Protein A Sepharose followed by Superdex-75 (Pharmacia) and then quantified by absorbance at 280 nm.

Repetition of the selection experiment again gave Fc-I and also a related peptide, Fc-II (Lys-Glu-Ala-Ser-Cys-Ser-Tyr-Trp-Leu-Gly-Glu-Leu-Val-Trp-Cys-Val-Ala-Gly-Val-Glu) (SEQ ID NO: 3). The Fc-II peptide shared the cysteine spacing and the internal Gly-Glu-Leu-Val-Trp (SEQ ID NO: 132) sequence seen in Fc-I. Apparently, these two peptides bound IgG-Fc with an affinity high enough to be selected over any of the other IgG-Fc binding peptides present in the starting pool. Both peptides were synthesized on solid phase using standard 9-fluorenylmethoxycarbonyl protocols and purified by reversed-phase HPLC. Masses were confirmed by electrospray mass spectrometry, and purified peptides were quantified by UV absorbance at 280 nm.

Competition ELISAs were performed in a manner similar to the method described in H. B. Lowman, et al., supra. Briefly, Protein A Z-domain was immobilized on microtiter wells at a concentration of 5 μg/ml, blocked, and washed as described. A matrix of mixtures of biotinylated-IgG-Fc at concentrations from 312 nM to 0.3 nM and peptide at concentrations from 215 μM to 0.8 nM was prepared. These mixtures were incubated with immobilized Protein A Z-domain for 1 hour. Plates were then washed and developed as described using avidin/HRP conjugate. Inhibition curves were then computed for each concentration of biotin-IgG-Fc, and then the curve of half-maximal inhibition, "IC$_{50}$", was extrapolated to zero biotin-IgG-Fc concentration in order to obtain a K$_i$. The Fc-I and Fc-II peptides both were found to compete with Protein A (Z-domain) (B. Nilsson et al. (1987), *Protein Eng.* 1:107) for binding to IgG-Fc with inhibition constants (K$_i$) of about 5 μM. The results imply that these peptides bind to an overlapping site on IgG-Fc that coincides with the Protein A binding site.

The DNA sequence of the Fc-II peptide was moved to a monovalent phage display format by cassette mutagenesis to give a construct with the STII signal sequence, the Fc-II peptide Lys-Glu-Ala-Ser-Cys-Ser-Tyr-Trp-Leu-Gly-Glu-Leu-Val-Trp-Cys-Val-Ala-Gly-Val-Glu (SEQ ID NO: 3), a Gly-Gly-Gly-Pro-Gly-Gly-Gly linker (SEQ ID NO: 4), and the M13 gene III protein starting at residue 253. The Fc-II sequence was affinity-matured by monovalent phage display. Five residue blocks were randomly mutated in six separate libraries to exhaustively cover the non-cysteine positions in the peptide sequence and then screened against IgG-Fc.

A series of second generation monovalent phage display libraries were constructed based on the Fc-II sequence Lys-Glu-Ala-Ser-Cys-Ser-Tyr-Trp-Leu-Gly-Glu-Leu-Val-Trp-Cys-Val-Ala-Gly-Val-Glu (SEQ ID NO: 3) in which five sequential residues were randomized using NNS codons in each library starting at positions 1, 4, 7, 10, 12, and 16, excluding the two cysteines. Each library had a diversity of approximately 1×10$^8$. These libraries were independently screened for binding to IgG-Fc for six rounds and then sequenced. Preferred residues from this selection were then recombined using three additional libraries that spanned the entire peptide sequence. The three additional libraries were constructed using the degeneracy of the genetic code to recombine the preferred amino acids at each position into one peptide. The DNA sequences for these libraries contained the following mixtures of bases (IUPAC codes): DRG GWA GMA RRC TGC KCT TRS CAC MTG GGC GAG CTG GTC TGG TGC RVC RVM BKC GAS KDW (SEQ ID NO: 5), DRS VWG SVG RRC TGC KCC TRS YRS MTG GGC GAG CTG GTC TGG TGC RNC VVS NBS GWS KDM (SEQ ID NO: 6), and DNS NNS NNS VNS TGC BVG TDS HRS MDS GGC GAG STC KKG WRG TGC RNM NNS NNS NNS NNM (SEQ ID NO: 7). These libraries also were sorted against IgG-Fc for six rounds and then sequenced.

After screening against IgG-Fc, the consensus patterns from these libraries suggested a highly conserved 13-residue core sequence (Asp-Cys-Ala-Trp-His-Leu-Gly-Glu-Leu-Val-Trp-Cys-Thr) (SEQ ID NO: 8). The corresponding peptide (Fc-III) was synthesized and found to inhibit binding of Protein A (Z-domain) to Fc with an IC$_{50}$ of 100 nM. Thus, although Fc-III is seven residues shorter than Fc-II, it binds 50-times more tightly. Despite its smaller size, the binding affinity of Fc-III to Fc was only ten-fold weaker than that of the domains from Protein A and Protein G, which are each about four times larger and bind with K$_d$S around 10 nM. S. R. Fahnestock, et al. in *Bacterial Immunoglobulin-Binding Proteins* (Academic Press, Inc. 1990) Vol. 1, chap. 11. R. Karlsson, L. Jendeberg, B. Nilsson, J. Nilsson, P. Nygren (1995), *J. Immuno. Methods* 183:43.

Table 1 lists the amino acid sequences and IgG-Fc binding affinities of exemplary IgG-Fc peptide ligands that were identified using the procedures described above.

TABLE I

IgG-Fc Peptide Ligand Sequences and Affinities

| Sequence | Sequence ID NO | Binding Affinity |
|---|---|---|
| Peptides | | |
| *All peptides have an N-terminal amine and a C-terminal amide | | |
| KEASCSYWLGELVWCVAGVE | SEQ ID NO: 3 | 5000 nM (K$_i$) |
| ETQRCTWHMGELVWCEREHN | SEQ ID NO: 2 | 5000 nM (K$_i$) |
| DLADCSWHMGELVWCSRVEG | SEQ ID NO: 15 | 50 nM (K$_d$) |
| WEADCAWHLGELVWCTPMEF | SEQ ID NO: 16 | 30 nM (IC$_{50}$) |
| DCAWHLGELVWCT | SEQ ID NO: 8 | 100 nM (IC$_{50}$) |
| Phage Clones (M13/gIII Display) | | All phage affinities are EC$_{50S}$ |

TABLE I-continued

IgG-Fc Peptide Ligand Sequences and Affinities

| Sequence | Sequence ID NO | Binding Affinity |
|---|---|---|

N/A = Not individually assayed. Since they were selected for binding, $EC_{50}$ likely to be <1 uM or better.
All of the peptides listed bind IgG-Fc.

Focused Libraries

| Sequence | Sequence ID NO | Binding Affinity |
|---|---|---|
| KEASCSYWLGELVWCDTLTE | SEQ ID NO: 17 | N/A |
| KEASCSYWLGELVWCSPGVE | SEQ ID NO: 18 | 734 nM |
| KEASCSYWLGELVWCSGVEG | SEQ ID NO: 19 | N/A |
| KEASCSYWLGELVWCSAGVE | SEQ ID NO: 20 | N/A |
| ESEDCSYWLGELVWCVAGVE | SEQ ID NO: 21 | N/A |
| EKEDCSYWLGELVWCVAGVE | SEQ ID NO: 22 | N/A |
| EDPDCSYWLGELVWCVAGVE | SEQ ID NO: 23 | N/A |
| EEADCSYWLGELVWCVAGVE | SEQ ID NO: 24 | N/A |
| NADDCSYWLGELVWCVAGVE | SEQ ID NO: 25 | N/A |
| SETTCSYWLGELVWCVAGVE | SEQ ID NO: 26 | N/A |
| AWKTCQWLGELVWCVAGVE | SEQ ID NO: 27 | N/A |
| DLADCSYWLGELVWCSRVEG | SEQ ID NO: 28 | 776 nM |
| KEADCAWHLGELVWCVAGVE | SEQ ID NO: 29 | 138 nM |
| KEAECSYHLGELVWCVAGVE | SEQ ID NO: 30 | N/A |
| KEARCWYWHGELVWCSDPEE | SEQ ID NO: 31 | 809 nM |
| KEASCSYHLGELVWCVAGVE | SEQ ID NO: 32 | 416 nM |
| KEASCSWHLGELVWCVAGVE | SEQ ID NO: 33 | 225 nM |
| KEASCSYWLGELVWCTEGVE | SEQ ID NO: 34 | 818 nM |
| KEASCSYWLGELVWCDDGVE | SEQ ID NO: 35 | N/A |
| KEASCSYWLGELVWCSEGVE | SEQ ID NO: 36 | N/A |
| KEASCSYWLGELVWCSPGVE | SEQ ID NO: 18 | N/A |
| KEASCSYWLGEVWKCKSGVE | SEQ ID NO: 37 | N/A |
| KEASCSYWLGELVWCDNGVE | SEQ ID NO: 38 | N/A |
| KEASCSYWLGELVWCDTFDE | SEQ ID NO: 39 | 301 nM |
| KEASCSYWLGELVWCDGLDE | SEQ ID NO: 40 | 326 nM |
| KEASCSYWLGELVWCVGLDE | SEQ ID NO: 41 | 278 nM |
| KEASCSYWLGELVWCEDTLE | SEQ ID NO: 42 | N/A |
| KEASCSYWLGELVWCEDTME | SEQ ID NO: 43 | N/A |
| KEASCSYWLGELVWCEDMME | SEQ ID NO: 44 | N/A |
| WVEDCSWHMGELVWCDGGEF | SEQ ID NO: 45 | 139 nM |
| KEASCSYWLGELVWCDWMNG | SEQ ID NO: 46 | N/A |
| KEASCSYWLGELVWCDDTPV | SEQ ID NO: 47 | N/A |
| KEASCSYWLGELVWCDDYGE | SEQ ID NO: 48 | N/A |

TABLE I-continued

IgG-Fc Peptide Ligand Sequences and Affinities

| Sequence | Sequence ID NO | Binding Affinity |
|---|---|---|
| KEASCSYWLGELVWCSDLWE | SEQ ID NO: 49 | N/A |
| WRGGCSWHMGELVWCEHDME | SEQ ID NO: 50 | N/A |
| AVSKCSFHMGELVWCSDVMN | SEQ ID NO: 51 | N/A |
| NQVSCSYSRGELVWCSKQSQ | SEQ ID NO: 52 | N/A |
| GRMECAWHQGELVWCTPTLE | SEQ ID NO: 53 | N/A |
| GTMECSWHQGELVWCTPTLA | SEQ ID NO: 54 | N/A |
| EMRDCSWHLGELVWCAHMEG | SEQ ID NO: 55 | N/A |
| GSWECAYHLGELVWCETGSG | SEQ ID NO: 56 | N/A |
| VAEPCAYHLGELVWCEVLKG | SEQ ID NO: 57 | N/A |
| KEAMCSYWLGELVWCESDMP | SEQ ID NO: 58 | N/A |
| Designed Clones | | |
| DLADCSWHLGELVWCSRVEG | SEQ ID NO: 59 | 9 nM |
| DLADCSWHLGELVWCVGLDE | SEQ ID NO: 60 | 28 nM |
| WVEDCSWHLGELVWCVGLDF | SEQ ID NO: 61 | 31 nM |
| Secondary Optimization | | |
| KVADCAWHMGELVWCTEVEG | SEQ ID NO: 62 | 23 nM |
| GEEDCSYHLGELVMCTELDD | SEQ ID NO: 63 | 69 nM |
| GVADCAWHLGELVWCTERED | SEQ ID NO: 64 | N/A |
| GEEDCAWHLGELVWCSGGDF | SEQ ID NO: 65 | 100 nM |
| WEADCAWHLGELVWCTKVEE | SEQ ID NO: 66 | 7 nM |
| GEADCSYHLGELVWCNDFEE | SEQ ID NO: 67 | 156 nM |
| WVDCAYHLGELVWCSTFEE | SEQ ID NO: 68 | 9 nM |
| WVEDCAWHMGELVWCTKVDE | SEQ ID NO: 69 | 70 nM |
| READCAWHLGELVWCSERDL | SEQ ID NO: 70 | 47 nM |
| EEASCAYHLGELVWCDAFDV | SEQ ID NO: 71 | 77 nM |
| RVASCAWHLGELVWCDGLDG | SEQ ID NO: 72 | N/A |
| GEADCAWHLGELVWCTKVEE | SEQ ID NO: 73 | 38 nM |
| GEASCAYHLGELVWCDEGEG | SEQ ID NO: 74 | 386 nM |
| RVEDCAYHLGELVWCTEGDE | SEQ ID NO: 75 | 63 nM |
| EEPDCSWHLGELVMCTPMEV | SEQ ID NO: 76 | 14 nM |
| KEADCAWHMGELVWCSEMEG | SEQ ID NO: 77 | 66 nM |
| EQADCAWHLGELVWCTPMVF | SEQ ID NO: 78 | 8 nM |
| EEPDCSWHLGELVWCTPIEV | SEQ ID NO: 79 | 15 nM |
| GEPDCAWHLGELVWCTPMVF | SEQ ID NO: 80 | 7 nM |
| GEQDCSYHMGELVWCTTVDG | SEQ ID NO: 81 | 210 nM |
| GVRNCAYHLGELVWCTPMEF | SEQ ID NO: 82 | 10 nM |
| RVADCAWHMGELVWCSELEV | SEQ ID NO: 83 | 44 nM |

TABLE I-continued

IgG-Fc Peptide Ligand Sequences and Affinities

| Sequence | Sequence ID NO | Binding Affinity |
|---|---|---|
| GEADCAWHLGELVWCTPMDL | SEQ ID NO: 84 | N/A |
| GEQDCSWHLGELVWCTPMEV | SEQ ID NO: 85 | N/A |
| GMRDCSYHLGELVWCSDMEL | SEQ ID NO: 86 | N/A |
| EVADCSWHLGELVWCTEGEF | SEQ ID NO: 87 | 54 nM |
| GEEDCAWHLGELVWCTDVED | SEQ ID NO: 88 | 52 nM |
| EVEDCAYHLGELVWCSDLEG | SEQ ID NO: 89 | 82 nM |
| WEEDCAWHLGELVWCAEFDE | SEQ ID NO: 90 | 44 nM |
| KEASCAWHLGELVWCSEVEE | SEQ ID NO: 91 | 130 nM |
| ALA Scan on Phage | | |
| AEADCAWHLGELVWCTKVEE | SEQ ID NO: 92 | 20 nM |
| WAADCAWHLGELVWCTKVEE | SEQ ID NO: 93 | 34 nM |
| WEPDCAWHLGELVWCTKVEE | SEQ ID NO: 94 | 36 nM |
| WEAACAWHLGELVWCTKVEE | SEQ ID NO: 95 | 55 nM |
| WEAACSWHLGELVWCTKVEE | SEQ ID NO: 96 | 10 nM |
| WEADCAAHLGELVWCTKVEE | SEQ ID NO: 97 | 798 nM |
| WEADCAWALGELVWCTKVEE | SEQ ID NO: 98 | 139 nM |
| WEADCAWHAGELVWCTKVEE | SEQ ID NO: 99 | 56 nM |
| WEADCAWHLAELVWCTKVEE | SEQ ID NO: 100 | 12 nM |
| WEADCAWHLGALVWCTKVEE | SEQ ID NO: 101 | 11 nM |
| WEADCAWHLGEAVWCTKVEE | SEQ ID NO: 102 | 1890 nM |
| WEADCAWHLGELAWCTKVEE | SEQ ID NO: 103 | 4670 nM |
| WEADCAWHLGELVACTKVEE | SEQ ID NO: 104 | 3380 nM |
| WEADCAWHLGELVWCAKVEE | SEQ ID NO: 105 | 101 nM |
| WEADCAWHLGELVWCTAVEE | SEQ ID NO: 106 | 10 nM |
| WEADCAWHLGELVWCTKAEE | SEQ ID NO: 107 | 8 nM |
| WEADCAWHLGELVWCTKVAE | SEQ ID NO: 108 | 4 nM |

EXAMPLE 2

Construction of Anti-VEGF Fabs Tagged with IgG-Fc Peptide Ligands

IgG-Fc peptide ligands may be combined with a bioactive compound to form a hybrid molecule that comprises a peptide ligand domain and an active domain. In this Example, IgG-Fc peptide ligands are combined with a Fab fragment that recognizes human VEGF. A neutralizing antibody to human VEGF has been previously identified from murine hybridoma, humanized, and optimized by phage display. See Muller et al. (1998), *Structure* 6:1153-1167; Chen et al. (1999), *J. Mol. Biol.* 293:865-881; and International Patent Publication No. WO 98/45331. Two humanized Fab forms of this antibody were chosen to test whether binding affinity to an irrelevant IgG could be added to the Fabs without disrupting their antigen-binding affinity. An IgG-Fc peptide ligand, DCAWHLGELVWCT (SEQ ID NO: 8), identified and optimized by the peptide-phage display method described in Example 1 was used, along with a short peptide linker (Gly-Gly-Gly) to provide flexibility between the peptide and the Fab. The light chain of the Fab was chosen for fusions because in the case of this antibody, the light chain is known to have little contribution to antigen binding (Muller et al., 1998, supra). In principle the peptide ligand domain could function to introduce IgG-binding whether introduced at the N-terminus, C-terminus, or inserted within the original Fab sequence. Described here are N-terminal fusions DCAWHLGELVWCTGGG-(light chain) (SEQ ID NO: 109) as well as C-terminal fusions (light chain)-GGGWEAD-CAWHLGELVWCT (SEQ ID NO: 110).

An oligodeoxynucleotide, HL-569, was designed and synthesized for mutation of anti-VEGF plasmids to create fusions of the IgG-Fc peptide ligand at the N-terminus of the antibody light chain. The sequence of HL-569 (with added peptide sequence underlined) is: 5-ACA AAC GCG TAC GCT GAC TGC GCT TGG CAC CTG GGC GAG CTG GTC TGG TGC ACC GGA GGA GGA GAT ATC CAG TTG ACC-3' (SEQ ID NO: 111). The GAC codon follows the STII secretion-signal sequence at the N-terminus of the light chain, and the GAT codon corresponds to the first residue of the mature (wild-type) light chain.

Another oligodeoxynucleotide, HL-570, was designed and synthesized for construction of peptide ligand fusions to the C-terminus of the antibody light chain. The sequence of HL-570 (with added peptide sequence underlined) is: 5'-AAC AGG GGA GAG TGT GGA GGA GGA TGG GAA GCA GAC TGC GCT TGG CAC CTG GGC GAG CTG GTC TGG TGC ACC TAA GCT GAT CCT CTA C-3' (SEQ ID NO: 112). The TGT codon preceding the underscored GGA codon corresponds to residue Cys-214 of the light chain, and the TAA "stop codon" marks the end of the translated peptide sequence. Phagemids pY0192 and pY0317 (described Muller et al., 1998, supra; Chen et al., 1999; and International Patent Publication No. WO 98/45331, encoding low-affinity and high-affinity forms of a humanized anti-VEGF antibody, respectively, were mutated with each of the two IgG-peptide oligos to yield constructs pY0192-569, pY0192-570, pY0317-569, and pY0317-570.

EXAMPLE 3

Phage-ELISA Analysis of Hybrid Molecules Comprising Peptide-Ligand Tagged Anti-VEGF Fabs A phage-ELISA competitive binding assay (Lowman (1998), *Methods Mol. Biol.* 87:249-264) was used to compare the apparent binding affinities of anti-VEGF antibody variants tagged with an IgG-Fc peptide ligand at their N-terminus or C-terminus and displayed monovalently on bacteriophage M13 particles as fusions to the C-terminal domain of the gene III protein.

An irrelevant humanized IgG, 4D5-IgG, also known as Herceptin®, was coated onto Nunc Maxisorp immunosorbant plates at 2 microg/mL in phosphate buffered saline solution (PBS). Phagemid particles from overnight cultures of XL1 Blue *E. coli* (Stratagene) were diluted in PBS containing 0.5% bovine serum albumin and 0.05% Tween-20. The phagemid particles were mixed with serial dilutions of Herceptin® in solution, equilibrated for 20 min in a non-adsorbent plate (Nunc F96), then transferred to the Herceptin®-coated Maxisorp plate for detection of unbound phage. After 20 min, the plate was washed with PBS/Tween, and developed with an anti-phage monoclonal antibody-HRP conjugate (Pharmacia) and OPD substrate (Sigma). Displacement curves (FIG. 1) showed $IC_{50}$ values of about 100-300 nM for each of the constructs, pY0192-569, pY0192-570, pY0317-569, and pY0317-570.

EXAMPLE 4

BIAcore™ Analysis of IgG Binding to Anti-VEGF Fab Tagged with an IgG-Fc Peptide Ligand A surface plasmon resonance instrument (BIAcore, Inc., Piscataway, N.J.) was used to measure binding of an irrelevant IgG, 4D5-IgG, also known as Herceptin®, to Fab that previously had been bound to an immobilized VEGF biosensor chip.

Fab variants encoded by pY0317 and pY0317-570 (control anti-VEGF high affinity, humanized Fab, and anti-VEGF high affinity, humanized Fab tagged with an IgG-Fc peptide ligand domain, respectively; see Example 2, supra, and WO 98/45331) were expressed in *E. coli* and purified by protein-G (Pharmacia) affinity chromatography. Recombinant human VEGF was immobilized onto BIAcore™ CM-5 biosensor chips (BIAcore, Inc.) as described (Muller et al., 1998, supra). After VEGF immobilization, the chip was blocked with ethanolamine, and the peptide-ligand tagged Y0317-570 Fab, or Y0317 control, was injected in PBS buffer containing 0.05% Tween-20 and 0.01% sodium azide. Following Fab injection, Herceptin® was injected, and the dissociation off-rate ($k_{off}$) following injection was observed.

The results (FIG. 2) show that Herceptin® bound to the tagged but not to the control Y0317 Fab. Using a 1:1 Langmuir binding model (Karlsson et al. (1991), *J. Immunuol. Methods* 145:229-240 (1991)), a $k_{off}$ of $2.8 \times 10^{-3}$, $sec^{-1}$, and a corresponding dissociation half-life ($t_{1/2}$) of 8.5 min were calculated for Y0317-570. Limitations of material prevented reliable on-rate determinations. However, the observed $k_{off}$ suggests an equilibrium binding affinity, $K_d$, of 30 nM to 300 nM (assuming $k_{on}$ of $10^4$-$10^5$ $M^{-1}$ $sec^{-1}$), consistent with peptide binding and phage-ELISA results (above). Importantly, the BIAcore™ results (FIG. 2) also show that the tagged Fab can simultaneously binding both antigen (immobilized VEGF) and an irrelevant IgG.

EXAMPLE 5

IgG-Fc Peptide Ligand Tagged Anti-VEGF Fabs have Prolonged Elimination Half Times The blood clearance rates and tissue distribution of the IgG-Fc peptide ligand-tagged anti-VEGF Fab (Fab-Y0317-570) are compared to those of the untagged control anti-VEGF Fab Y0317. Determinations of the elimination half time and volume of distribution are made in New Zealand White Rabbits of 2.8 to 3 kg weight. The amount of test article present in the plasma samples is determined using any method known in the art, such as, e.g., ELISA, or RIA.

Pharmacokinetic analysis is performed using the test article plasma concentrations. Group mean plasma data for each test article conforms to a multi-exponential profile when plotted against the time post-dosing. The data are fit by a standard two-compartment model with bolus input and first-order rate constants for distribution and elimination phases. The general equation for the best fit of the data for i.v. administration is: $c(t) = Ae^{-\alpha t} + Be^{-\beta t}$, where c(t) is the plasma concentration at time t, A and B are intercepts on the Y-axis, and $\alpha$ and $\beta$ are the apparent first-order rate constants for the distribution and elimination phases, respectively. The $\alpha$-phase is the initial phase of the clearance and reflects distribution of the protein into all extracellular fluid of the animal, whereas the second or $\beta$-phase portion of the decay curve represents true plasma clearance. Methods for fitting such equations are well known in the art. For example, $A = D/V(\alpha - k21)/(\alpha - \beta)$, $B = D/V(\beta - k21)/(\alpha - \beta)$, and $\alpha$ and $\beta$ (for $\alpha > \beta$) are roots of the quadratic equation: $r^2 + (k12 + k21 + k10)r + k21k10 = 0$ using estimated parameters of V=volume of distribution, k10=elimination rate, k12=transfer rate from compartment 1 to compartment 2 and k21=transfer rate from compartment 2 to compartment 1, and D=the administered dose.

On the morning of the study six New Zealand White rabbits (body weight 2.8-3.0 kg) were placed in restrainers. Catheters were installed in an ear artery for blood sample collection and in a contralateral ear vein for dosing.

Rabbits were divided into two groups (n=3/group). Group 1 animals received and IV bolus of control anti-VEGF Fab-Y0317. Rabbits in Group 2 received Fab-Y0317-570. A summary of group assignment and dosing information is presented in the table below.

| Group | Weight (kg) | Dose Group | Nominal Dose (mg/kg) | Dose Conc. (mg/mL) | Dose Vol. (mL) |
|---|---|---|---|---|---|
| 1 | 2.9 | Control-Fab-Y0317 | 1 | 3 | 0.97 |
| 1 | 3.0 | Control-Fab-Y0317 | 1 | 3 | 1.00 |
| 1 | 2.9 | Control-Fab-Y0317 | 1 | 3 | 0.97 |
| 2 | 2.8 | Fab-Y0317-570 | 1 | 3 | 0.93 |
| 2 | 3.0 | Fab-Y0317-570 | 1 | 3 | 1.00 |
| 2 | 2.9 | Fab-Y0317-570 | 1 | 3 | 0.97 |

Serial blood samples (0.5 mL) were collected just prior to dosing and at 10, 20 40 min, 1, 2, 3, 4, 6, 8, 24 and 48 hr after dose administration. Blood was collected in serum separator tubes, allowed to clot (~30 min) at room temperature, and centrifuged. Serum was harvested and immediately stored at −70 C until analyzed.

ELISA plates were coated with 0.5 microg/ml VEGF in 50 mM carbonate buffer, pH 9.6, at 4° C. overnight and blocked with 0.5% bovine serum albumin, 10 ppm Proclin 300 (Supelco, Bellefonte, Pa.) in PBS (8 mM $Na_2HPO_4$, 1.5 mM $KH_2PO_4$, 2.7 mM KCl and 137 mM NaCl, pH 7.2) at room temperature for 1 hour. Standards (0.41-100 ng/ml) and two-fold serial dilutions of samples (minimum dilution 1:100) in PBS containing 0.5% bovine serum albumin, 0.05% polysorbate 20, 0.25% CHAPS, 0.2% bovine gamma globulins (Sigma, St. Louis, Mo.) and 5 mM EDTA were incubated on the plates for 2 hours. Bound antibody was detected using peroxidase labeled goat $F(ab')_2$ anti-human IgG $F(ab')_2$ (Jackson ImmunoResearch, West Grove, Pa.), followed by 3,3',5, 5'-tetramethyl benzidine (Kirkegaard & Perry Laboratories) as the substrate. Plates were washed between steps. Absorbance was read at 450 nm on a Titerek stacker reader (ICN, Costa Mesa, Calif.). The standard curve was fitted using a four-parameter regression curve-fitting program (Kaleidagraph, Synergy Software, Reading, Pa.). Data points which fell in the range of the standard curve were used for calculating the Fab concentrations in samples.

Data analysis: Graphs of concentration versus time profiles were made using KaleidaGraph (KaleidaGraph™ V. 3.09 Copyright 1986-1997. Synergy Software. Reading, Pa.). Values reported as less than reportable. (LTR) were not included in the PK analysis and are not represented graphically. Pharmacokinetic parameters were determined by compartmental analysis using WinNonlin software (WinNonlin® Professional V. 3.1 WinNonlin™ Copyright 1998-1999. Pharsight Corporation. Mountain View, Calif.). Pharmacokinetic parameters were computed as described elsewhere (Ritschel W A and Kearns G L. Handbook of basic pharmacokinetics including clinical applications, 5th edition. American Pharmaceutical Assoc., Washington, D.C. Copyright 1999).

Figure 3:
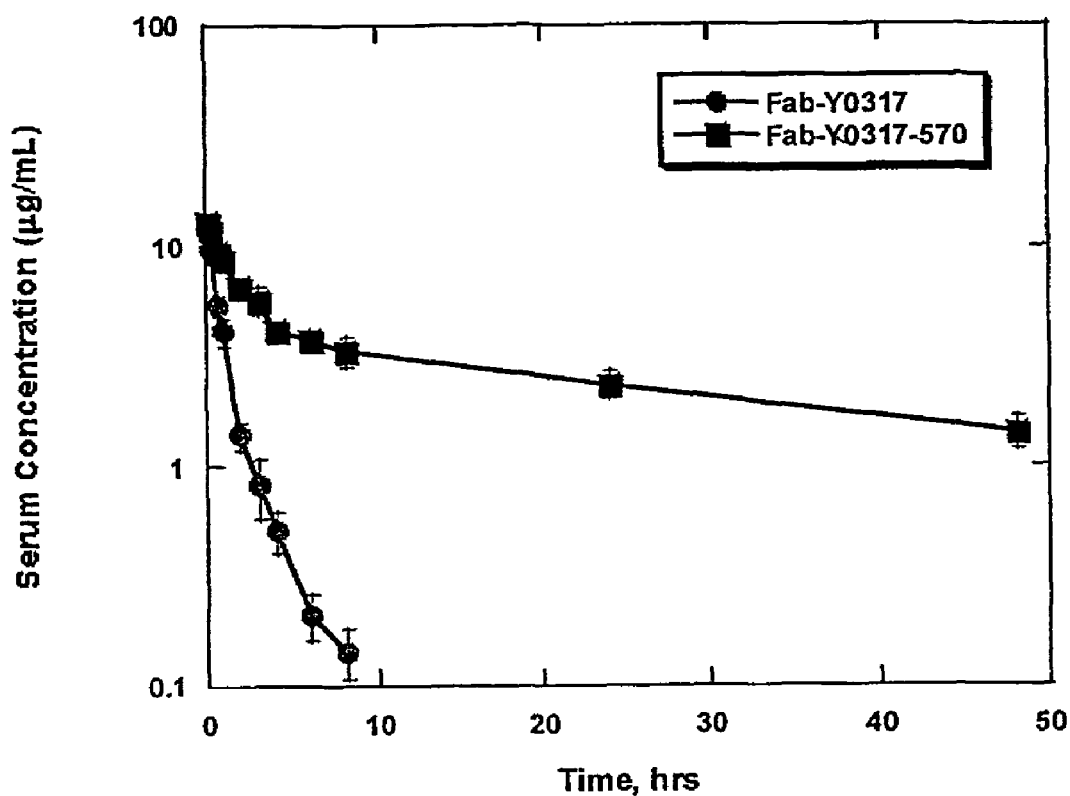
FIG. 3. Group average serum concentration vs. time data (±SD) are presented in the figure for Fab-Y0317-570 and Fab-Y0317.

The results are reported in FIG. 3. A two-compartment model with bolus input and first-order output (WinNonlin) was used to fit observed serum concentration vs. time data. Calculated pharmacokinetic parameters ware presented in the table below.

| Pharmacokinetic Parameter Summary (IV bolus; 1 mg/kg) | | |
|---|---|---|
| Parameter | Group 1 Control Fab-Y0317 | Group 2 Fab-Y0317-570 |
| AUC (h*µg/mL) | 13.6 ± 1.2 | 215 ± 56 |
| Cmax (µg/mL) | 15.6 ± 0.6 | 13 ± 0.7 |
| CL (mL/h/kg) | 74.2 ± 6.7 | 4.8 ± 1.1 |
| K10 half-life (hr) | 0.6 ± 0.02 | 11.3 ± 3.6 |
| alpha half-life (hr) | 0.39 ± 0.03 | 1.15 ± 0.31 |
| beta half-life (hr) | 1.93 ± 0.27 | 37.6 ± 19 |
| Vl (mL/kg) | 64.1 ± 2.37 | 75.2 ± 4.23 |
| Vss (mL/kg) | 112 ± 7.7 | 225 ± 54 |

The initial volume of distribution (V1) for both agents was approximately equal to serum volume. The estimated steady state volume of distribution (Vss) for Fab-Y0317-570 (225 mL/kg) was approximately 2 fold higher than estimated for the control Fab (112 mL/kg) suggesting a significant amount of binding to endogenous IgG. Control Fab-Y0317 was eliminated approximately 15-fold faster from the serum (clearance=74 mL/h/kg) compared to Fab-Y0317-570 (4.8 mL/h/d). The overall exposure (AUC) of Fab-Y0317-570 was 16 times higher than for Fab-Y0317. Fab-Y0317 was undetectable in the serum 24 h after dosing but serum concentrations of Fab-Y0317-570 were still above 1 µg/mL 48 h after dosing. Both the distribution (alpha) half-life (1.15 h) and the elimination (beta) half-life (37.6 h) were significantly longer than the control Fab.

These results suggest that addition of a 13 amino acid that binds to endogenous IgG to Fab-Y0317 can significantly slow Fab clearance, increase half-life and enhance overall exposure.

EXAMPLE 6

Serum Albumin Peptide Ligands

Phage Libraries and Selection Conditions-Phage-displayed peptide libraries were selected against rabbit, rat and human albumin. Phage libraries expressing random peptide sequences fused to gene 8 (Lowman et al., Biochem. 37, 8870 (1998)) were pooled into 5 groups: Pool A contained $CX_2GPX_4C$ (SEQ ID NO: 133), $X_4CX_2GPX_4CX_4$ (SEQ ID NO: 134) and $X_iCX_jCX_k$ where j=8-10; Pool B contained $X_{20}$ and $X_iCX_jCX_k$ where j=4-7; Pool C contained $X_8$ and $X_2CX_jCX_2$ where j=4-6; Pool D contained $X_2CX_jCX_2$ where j=7-10; Pool E contained $CX_6CX_6CCX_3CX_6C$ (SEQ ID NO: 135), $CCX_3CX_6C$ (SEQ ID NO: 136), $CCX_5CX_4CX_4CC$ (SEQ ID NO: 137), $CXCX_7CX_3CX_6$ (SEQ ID NO: 138) where X represents any of the 20 naturally occurring L-amino acids. In each case i+j+k=18 and |i−k|<2. Each of the 10 libraries has in excess of 108 clones.

The phage library pools were suspended in binding buffer (PBS, 1% ovalbumin, 0.005% Tween 20) and sorted against rabbit, rat or human albumin immobilized directly on maxisorp plates (10 µg/ml in PBS, overnight at 4° C.; plates were blocked with Blocker Casein (Pierce Chemical, Rockford, Ill.)). After 2 hours, unbound phage were removed by repetitive washing (PBS, 0.05% Tween 20) and bound phage were eluted with 500 mM KCl, 10 mM HCl, pH 2. Eluted phage were propagated in XL1-Blue cells with VCSM13 helper phage (Stratagene, La Jolla, Calif.). Enrichment was monitored by titering the number of phage that bound to an albumin coated well compared to a well coated with ovalbumin or casein.

Phage ELISA—Phage clones (~$10^{11}$ phage) were added to plates coated with rat, rabbit or human albumin. The microtiter plate was washed with wash buffer and bound phage were detected with HRP/Anti-M13 Conjugate. The amount of HRP bound was measured using ABTS/$H_2O_2$ substrate and monitoring the change at 405 nm.

The peptide sequences displayed by phage clones selected for binding to rabbit, human or rat albumin are shown in FIG. 4. Also indicated is the ability of individual phage clones to bind the 3 species of immobilized albumin. This was tested using a phage ELISA. Note that clone RB, selected for binding to rat albumin is also capable of binding human and rabbit albumin.

Sequence Maturation on Monovalent Phage—Partially randomized libraries were designed using oligonucleotides coding for each of the selected clones in FIG. 4, but synthesized with a 70-10-10-10 mixture of bases as described (Dennis et al., Nature 404, 465 (2000)). Although the potential diversity of these libraries is the same as the initial naïve libraries, each 'soft randomized' library maintains a bias towards the selected sequence in FIG. 4. Each library was again selected for binding to rat, rabbit or human albumin regardless of its origin. For example, the library resulting from soft randomization of clone RB was selected against rat, rabbit or human albumin even though it was originally identified for binding to rat albumin. Sequences identified following soft randomization are shown in FIG. 5 along with their species specificity as determined by phage ELISA. Most clones appear to be specific for the species of albumin for which they were selected, however, clones from the RB soft randomization library bind to all three species.

Figure 6:
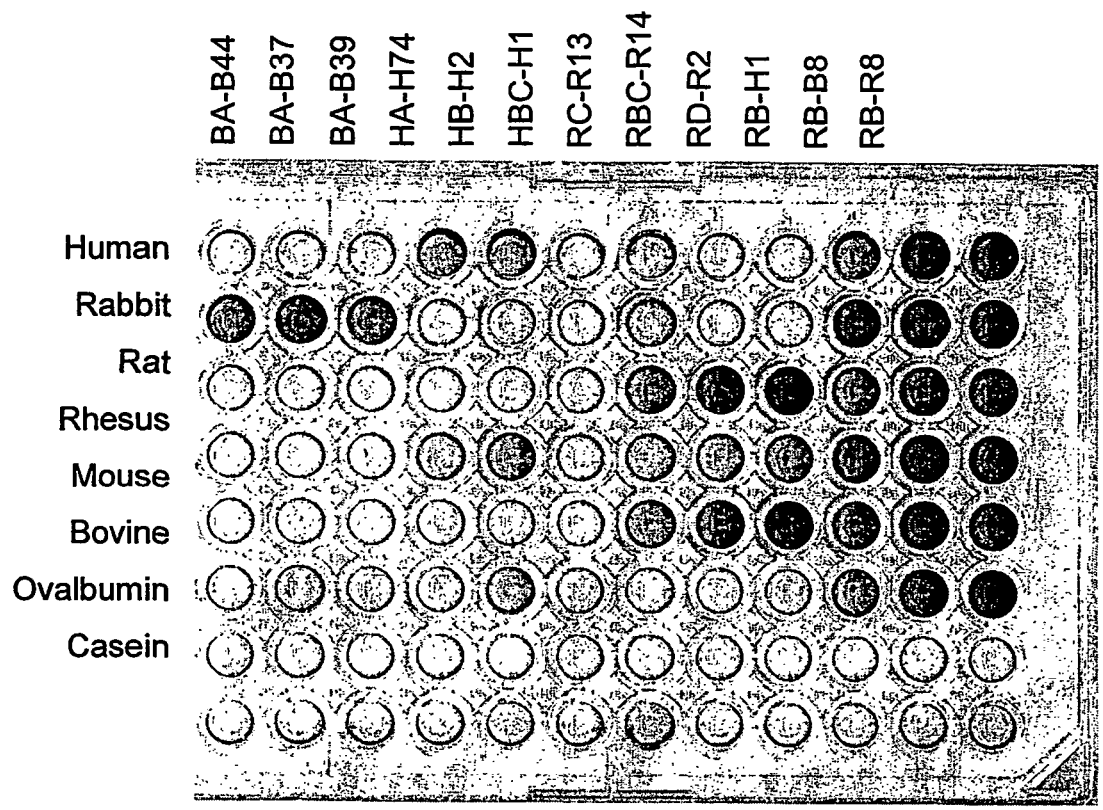
FIG. 6. Clones originating from the RB soft randomization library were found by ELISA to bind each of these species of albumin and were specific for albumin based upon their lack of binding to ovalbumin and casein.

Phage clones were also tested for binding to rhesus, mouse and bovine albumin. Clones originating from the RB soft randomization library were found to bind each of these species of albumin as well and were specific for albumin based upon their lack of binding to ovalbumin and casein (FIG. 6). Clones that bind to multiple species of albumin (multi-species binders) are listed in FIG. 7.

Figure 8B:
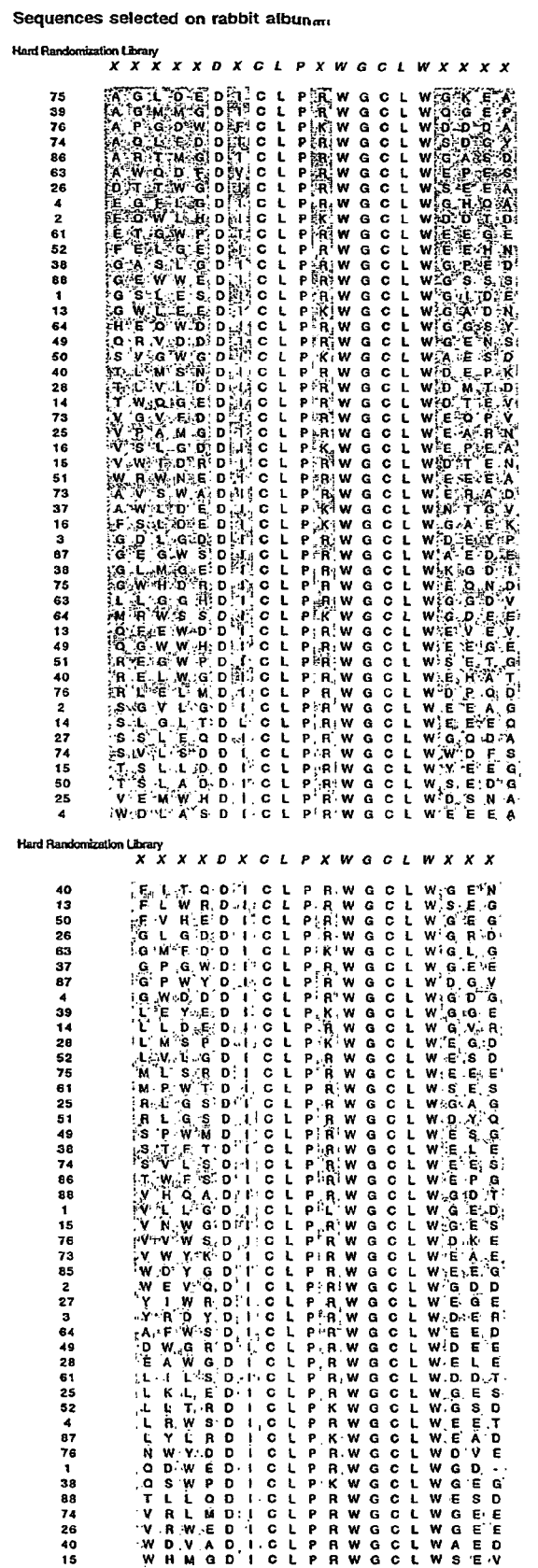

Hard randomization—Sequences from soft randomization of the RB sequence were further matured using a hard randomization strategy. A new library was designed that kept highly selected residues (underlined) constant $X_5$DXCLPXWGCLWX$_4$ (SEQ ID NO: 366), while fully randomizing the remaining positions. A second library, one residue shorter at both the N and C terminus was also constructed. Sequences from these libraries selected against rat, rabbit and human albumin are shown in FIGS. 8A, 8B, and 8C respectively.

Peptide Synthesis—Peptides were synthesized by either manual or automated (Milligen 9050) Fmoc-based solid (phase synthesis on a 0.25 mmol scale using a PEG-polystyrene resin (Bodanszky M., (1984) Principles of Peptide Synthesis, Springer, Berlin). Side chain protecting groups were removed and the peptides were cleaved from the resin with 95% trifluoroacetic acid (TFA) and 5% triisopropylsilane. A saturated iodine solution in acetic acid was added for oxidation of disulfide bonds. Peptides were purified by reversed phase HPLC using a water/acetonitrile gradient containing 0.1% TFA. Peptides were >95% pure by analytical HPLC and its identity verified by mass spectrometry.

The carboxy terminal lysine of peptide SA08 was derivatized with NHS-LC-biotin (Pierce Chemical, Rockford, Ill.) and purified by HPLC as above yielding SA08b (Ac-QGLIGDICLPRWGCLWGDSVK$_b$ (SEQ ID NO: 124)-n where K$_b$ refers to lysine-biotin).

SA08b Binding Assay—Rabbit, rat or mouse albumin was immobilized directly on maxisorp plates at 10 μg/ml in PBS, overnight at 4° C. Plates were blocked using Blocker Casein (Pierce Chemical, Rockford, Ill.) for 1 hr, at 25° C. Serially diluted samples were suspended in binding buffer (above) and added to the plate followed by the addition of 10 nM SA08b for 1 hr, at 25° C. The microtiter plate was washed with PBS, 0.05% Tween 20 and the SA08b bound to albumin was detected with Streptavidin/HRP. The amount of HRP bound was measured using ABTS/$H_2O_2$ substrate and monitoring the change at 405 nm.

Figure 10:
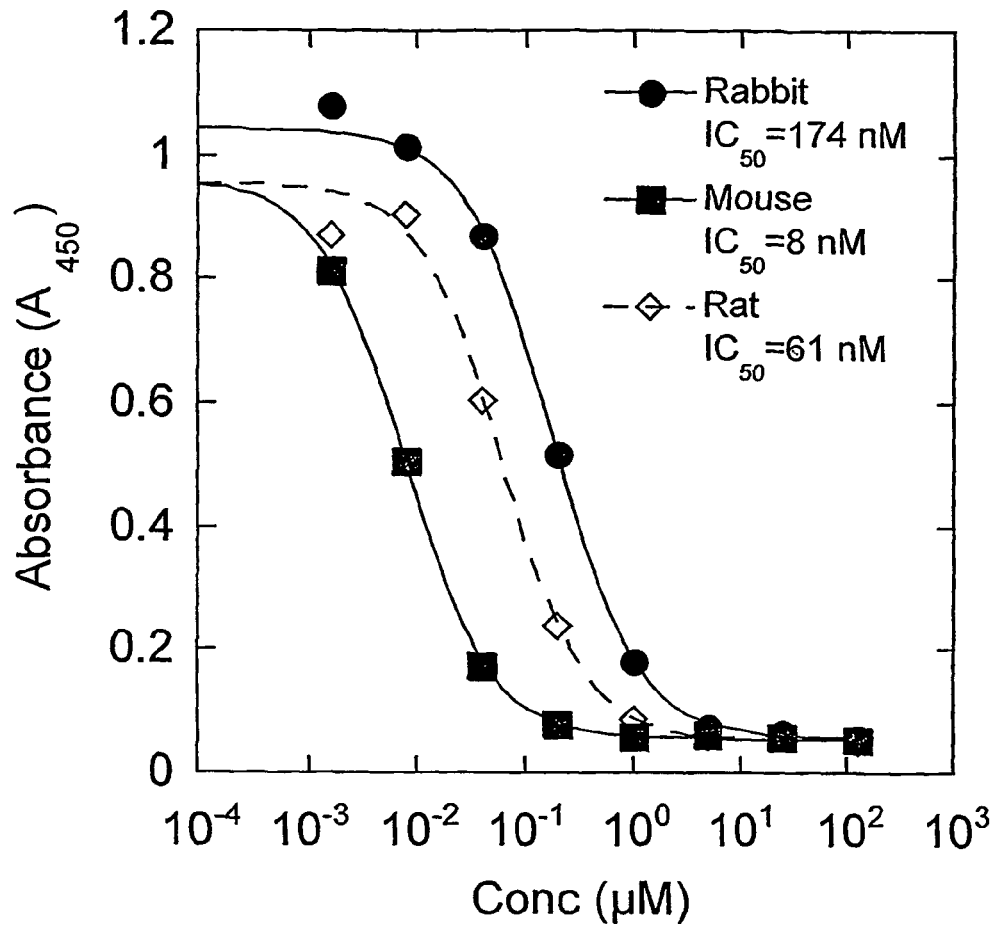
FIG. 10. Peptides corresponding to the SA06 identified phage sequence was synthesized and its affinity for rat, rabbit or mouse albumin measured using the SA08b binding assay.

Peptides corresponding to identified phage sequences were synthesized and their affinity for rat, rabbit or mouse albumin measured using the SA08b binding assay (FIGS. 9 and 10).

Construction, Expression and Purification of Albumin Binding Fab Fusions—In order to test whether association with albumin could increase the half-life of proteins and peptides in vivo, the sequence of SA06 was fused to a Fab fragment (D3H44) directed for binding tissue factor (TF). The SA06 sequence was added to the carboxy terminus of either the light chain (D3H44-L) or heavy chain (D3H44-Ls) of the Fab. In addition, as a precaution against folding problems, identical constructions were made but with the intrachain disulfide replaced by alanines (D3H44-Ls and D3H44Hs, respectively) as depicted in FIG. 11.

The fusions were expressed under control of the alkaline phosphatase promoter and secreted from *E. coli* using the stII secretion signal. Fab fusions were recovered from the periplasm by suspending cells in 1 mM EDTA, 10 mM Tris-HCl, pH8, for 1 hr at 4° C. Cell debris was removed by centrifugation and the anti-TF Fab was selectively purified using a Hi-Trap (Amersham Pharmacia Biotech, Piscataway, N.J.) TF affinity column. Properly folded D3H44L or D3H44-Ls was further purified using a rabbit albumin affinity column (rabbit albumin coupled to CNBr-activated Sepharose 4B, Amersham Pharmacia Biotech, Piscataway, N.J.). Both columns were washed with PBS and eluted with 50 mM HCl. Eluted fractions were neutralized with 1 M Tris pH 8. Endotoxin was further removed following extraction with triton X114 (Aida and Pabst, J. Immunol. Methods 132, 191 (1990)).

Figure 12:
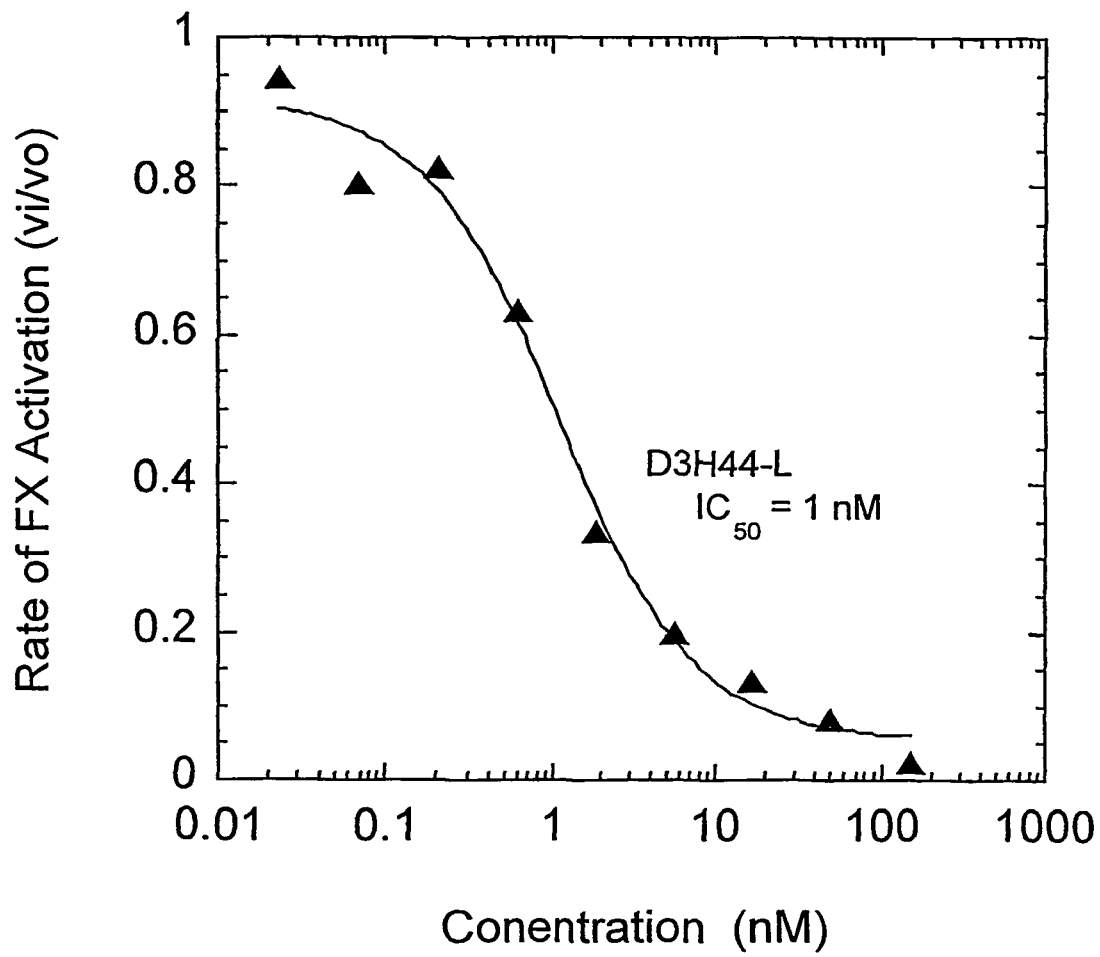
FIG. 12. Purified D3H44 fusions retained their ability to bind TF as measured using a FX activation assay.
Figure 13:
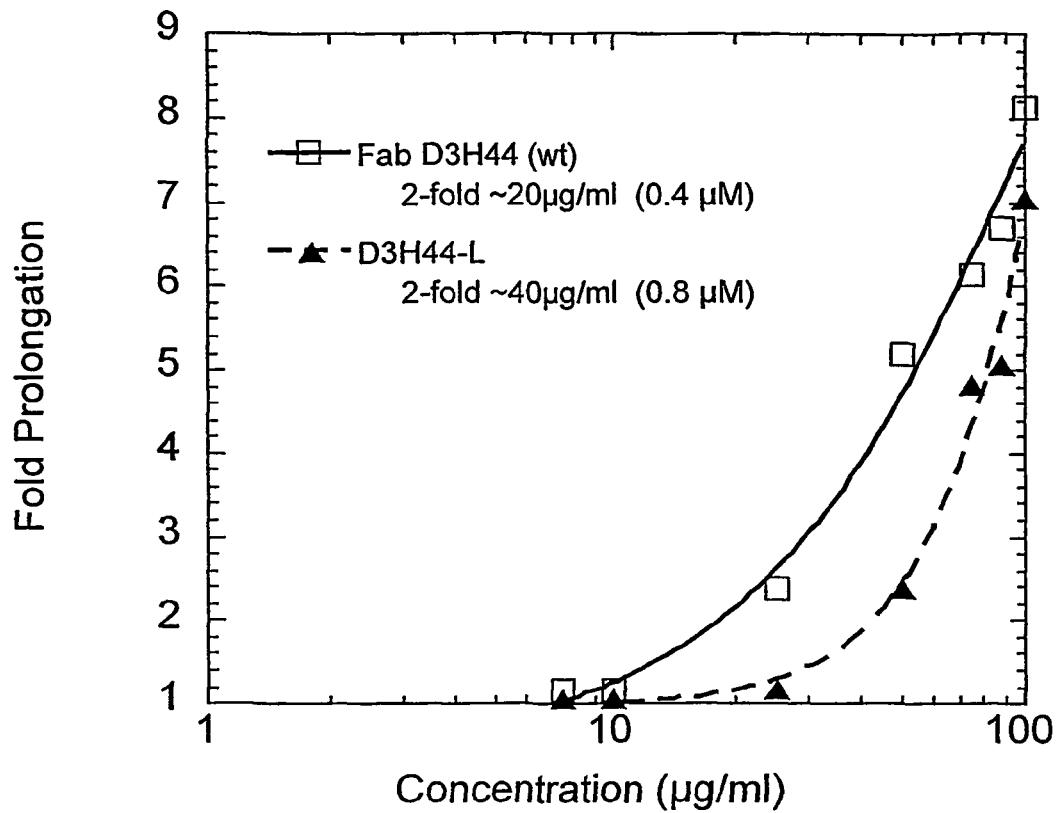
FIG. 13. Purified D3H44 fusions retained their ability to bind TF as measured using a prothrombin time assay that measures prolongation of tissue factor dependent clotting.
Figure 14:
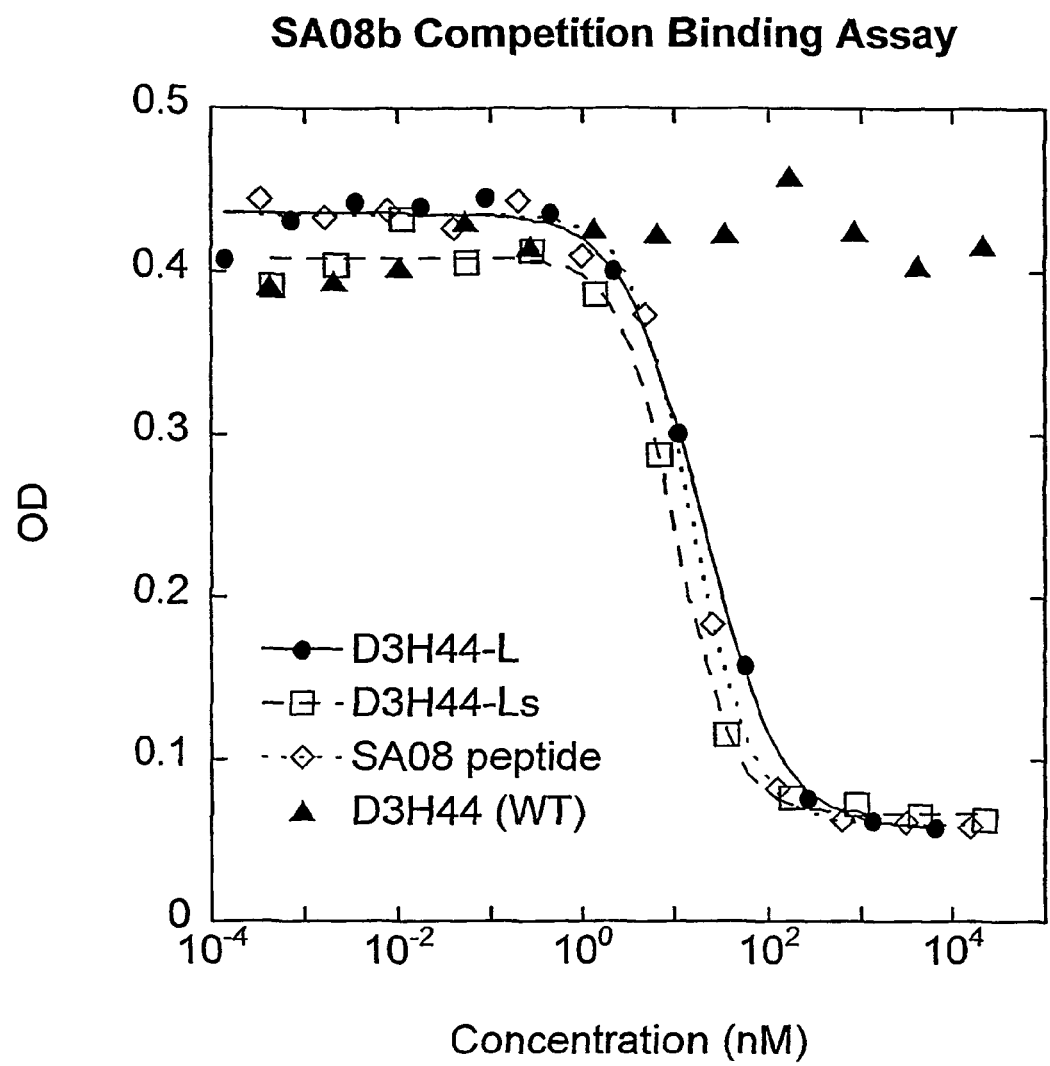
FIG. 14 Unlike D3H44 lacking the albumin binding sequence (WT), both D3H44-L and D3H44-Ls are able to bind to albumin as measured in the SA08b binding assay.
Figure 15:
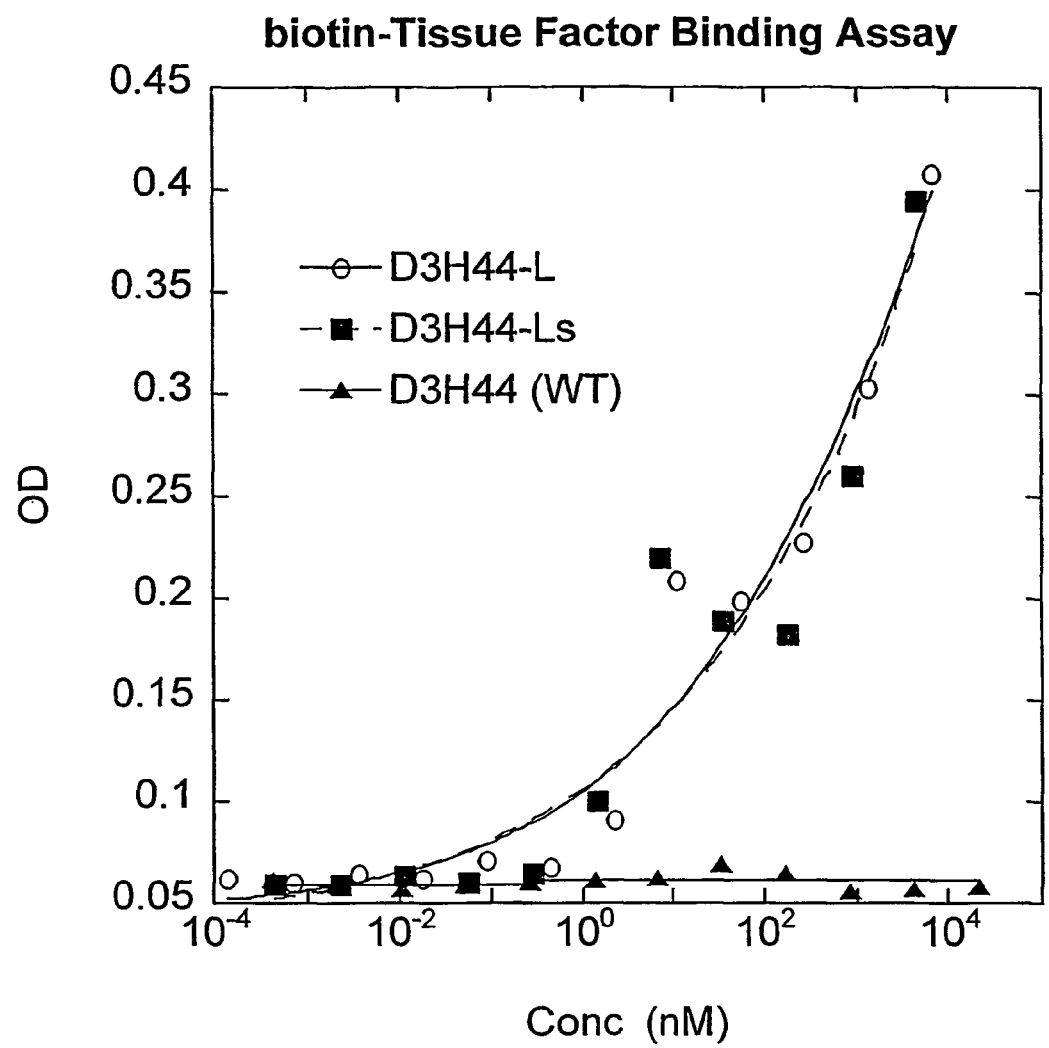
FIG. 15 Both D3H44 albumin-binding fusions are capable of binding TF and albumin simultaneously as judged by a biotin-TF binding assay.

Purified D3H44 fusions retained their ability to bind TF as measured using a FX activation assay (FIG. 12), and a prothrombin time assay that measures prolongation of tissue factor dependent clotting (FIG. 13)(for methods see Dennis et al., Nature 404, 465 (2000)). Unlike D3H44 lacking the albumin binding sequence (WT), both D3H44-L and D3H44-Ls are able to bind to albumin as measured in the SA08b binding assay (FIG. 14). Further, both D3H44 albumin-binding fusions are capable of binding TF and albumin simultaneously as judged by a biotin-TF binding assay (FIG. 15). In this assay, the binding of the D3H44 fusions to immobilized albumin is detected with biotinylated TF. Wild-type D3H44 (WT) is unable to bind albumin and thus does not generate a signal upon addition of biotinylated TF.

Pharmacokinetics of D3H44 albumin-binding fusions—D3H44 variants were given as a 0.5 mg/kg bolus in rabbit. Each group consisted of 3 rabbits (5 in the F(ab')$_2$ group). Serum samples taken at the indicated time points were serially diluted and the concentration of D3H44 determined using a TF binding ELISA.

Pharmacokinetic analysis is performed using the test article plasma concentrations. Group mean plasma data for each test article conforms to a multi-exponential profile when plotted against the time post-dosing. The data are fit by a standard two-compartment model with bolus input and first-order rate constants for distribution and elimination phases. The general equation for the best fit of the data for i.v. administration is: $c(t)=Ae^{-\alpha t}+Be^{-\beta t}$, where c(t) is the plasma concentration at time t, A and B are intercepts on the Y-axis, and α and β are the apparent first-order rate constants for the distribution and elimination phases, respectively. The α-phase is the initial phase of the clearance and reflects distribution of the protein into all extracellular fluid of the animal, whereas the second or β-phase portion of the decay curve represents true plasma clearance. Methods for fitting such equations are well known in the art. For example, $A=D/V(\alpha-k21)/(\alpha-\beta)$, $B=D/V(\beta-k21)/(\alpha-\beta)$, and α and β (for α>β) are roots of the quadratic equation: $r^2+(k12+k21+k10)r+k21k10=0$ using estimated parameters of V=volume of distribution, k10=elimination rate, k12=transfer rate from compartment 1 to compartment 2 and k21=transfer rate from compartment 2 to compartment 1, and D=the administered dose.

Data analysis: Graphs of concentration versus time, profiles were made using KaleidaGraph (KaleidaGraph™ V. 3.09 Copyright 1986-1997. Synergy Software. Reading, Pa.). Values reported as less than reportable (LTR) were not included in the PK analysis and are not represented graphically. Pharmacokinetic parameters were determined by compartmental analysis using WinNonlin software (WinNonlin® Professional V. 3.1 WinNonlin™ Copyright 1998-1999. Pharsight Corporation. Mountain View, Calif.). Pharmacokinetic parameters were computed as described elsewhere (Ritschel W A and Kearns GL. Handbook of basic pharmacokinetics including clinical applications, 5th edition. American Pharmaceutical Assoc., Washington, D.C. Copyright 1999).

Figure 16:
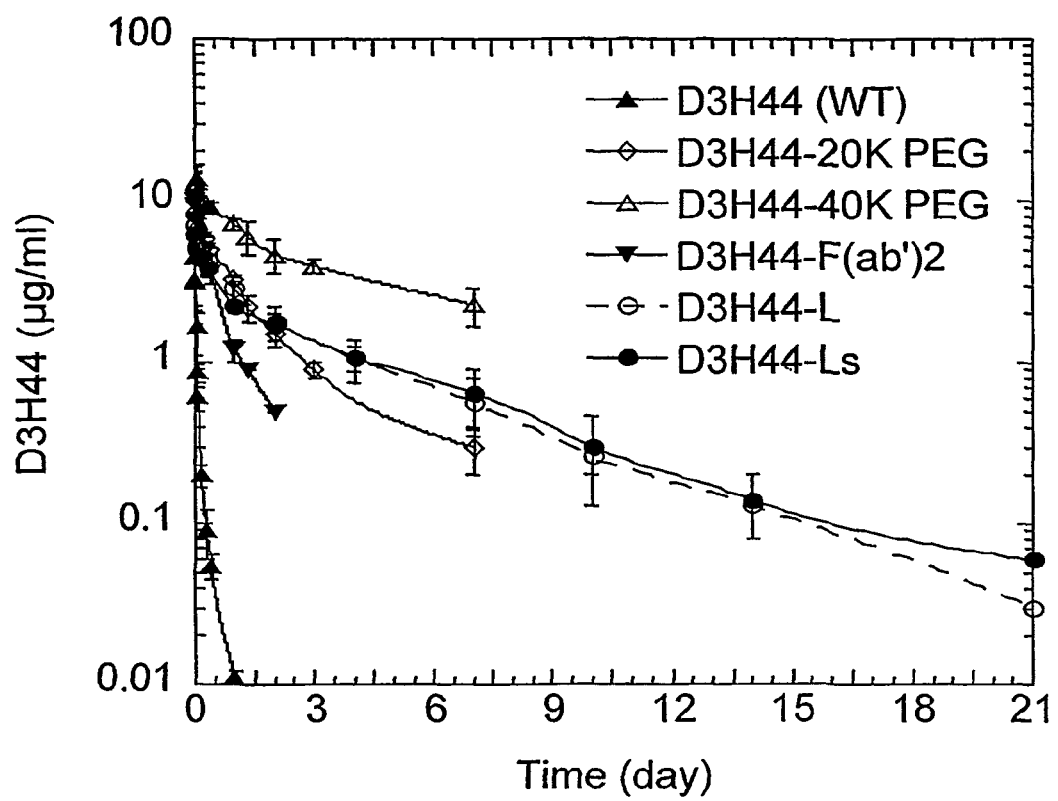
FIG. 16 Fusion of the albumin binding peptide to D3H44 results in a protein having improved pharmacokinetic parameters.

Fusion of the albumin binding peptide to D3H44 results in a protein having improved pharmacokinetic parameters (FIGS. 16 and 17). D3H44L has a 70-fold increase in half-life (K10-HL) relative to wild-type Fab and a comparable half-life to D3H44 Fabs derivatized with 20K or 40K polyethylene glycol (PEG).

All publications cited herein are expressly incorporated by reference in their entirety.

Table of Sequence Identification Numbers

| SEQ ID No: | Location in Specification/FIGS (Page Nos./FIG. Nos.) | SEQUENCE * |
|---|---|---|
| 1 | 30 | GGGSGGG |
| 2 | 30, 32 | ETQRCTWHMGELVWCEREHN |
| 3 | 30, 31, 32 | KEASCSYWLGELVWCVAGVE |
| 4 | 31 | GGGPGGG |
| 5 | 31 | DRG GWA GMA RRC TGC KCT TRS CAC MTG GGC GAG CTG GTC TGG TGC RVC RVM BKC GAS KDW |
| 6 | 31 | DRS VWG SVG RRC TGC KCC TRS YRS MTG GGC GAG CTG GTC TGG TGC RNC VVS NBS GWS KDM |
| 7 | 31 | DNS NNS NNS VNS TGC BVG TDS HRS MDS GGC GAG STC KKG WRG TGC RNM NNS NNS NNS NNM |
| 8 | 31, 32, 36 | DCAWHLGELVWCT |
| 9 | 3, 13 | XXXXXXLVW |
| 10 | 3, 13 | XXXXGELVW |
| 11 | 3, 13 | XXXXCXXXXXLVWCXXXXX |
| 12 | 3, 13 | XXXXCXXXXGELVWCXXXXX |
| 13 | 3, 13 | $X_1X_2X_3X_4CX_5X_6X_7X_8GELVWCX_9X_{10}X_{11}X_{12}X_{13}$ |
| 14 | 3, 13 | $X_1X_2X_3X_4CX_5X_6X_7X_8GELVWCX_9X_{10}X_{11}X_{12}X_{13}$ |
| 15 | 32 | DLADCSWHMGELVWCSRVEG |
| 16 | 32 | WEADCAWHLGELVWCTPMEF |
| 17 | 32 | KEASCSYWLGELVWCDTLTE |
| 18 | 32, 33 | KEASCSYWLGELVWCSPGVE |
| 19 | 32 | KEASCSYWLGELVWCSGVEG |
| 20 | 32 | KEASCSYWLGELVWCSAGVE |
| 21 | 33 | ESEDCSYWLGELVWCVAGVE |
| 22 | 33 | EKEDCSYWLGELVWCVAGVE |
| 23 | 33 | EDPDCSYWLGELVWCVAGVE |
| 24 | 33 | EEADCSYWLGELVWCVAGVE |
| 25 | 33 | NADDCSYWLGELVWCVAGVE |
| 26 | 33 | SETTCSYWLGELVWCVAGVE |
| 27 | 33 | AWKTCQWLGELVWCVAGVE |
| 28 | 33 | DLADCSYWLGELVWCSRVEG |
| 29 | 33 | KEADCAWHLGELVWCVAGVE |
| 30 | 33 | KEAECSYHLGELVWCVAGVE |
| 31 | 33 | KEARCWYWHGELVWCSDPEE |
| 32 | 33 | KEASCSYHLGELVWCVAGVE |
| 33 | 33 | KEASCSWHLGELVWCVAGVE |
| 34 | 33 | KEASCSYWLGELVWCTEGVE |
| 35 | 33 | KEASCSYWLGELVWCDDGVE |
| 36 | 33 | KEASCSYWLGELVWCSEGVE |
| 37 | 33 | KEASCSYWLGEVWKCKSGVE |
| 38 | 33 | KEASCSYWLGELVWCDNGVE |
| 39 | 33 | KEASCSYWLGELVWCDTFDE |
| 40 | 33 | KEASCSYWLGELVWCDGLDE |
| 41 | 33 | KEASCSYWLGELVWCVGLDE |
| 42 | 33 | KEASCSYWLGELVWCEDTLE |

-continued

Table of Sequence Identification Numbers

| SEQ ID No: | Location in Specification/FIGS (Page Nos./FIG. Nos.) | SEQUENCE * |
|---|---|---|
| 43 | 33 | KEASCSYWLGELVWCEDTME |
| 44 | 33 | KEASCSYWLGELVWCEDMME |
| 45 | 33 | WVEDCSWHMGELVWCDGGEF |
| 46 | 33 | KEASCSYWLGELVWCDWMNG |
| 47 | 33 | KEASCSYWLGELVWCDDTPV |
| 48 | 33 | KEASCSYWLGELVWCDDYGE |
| 49 | 33 | KEASCSYWLGELVWCSDLWE |
| 50 | 33 | WRGGCSWHMGELVWCEHDME |
| 51 | 33 | AVSKCSFHMGELVWCSDVMN |
| 52 | 33 | NQVSCSYSRGELVWCSKQSQ |
| 53 | 33 | GRMECAWHQGELVWCTPTLE |
| 54 | 33 | GTMECSWHQGELVWCTPTLA |
| 55 | 33 | EMRDCSWHLGELVWCAHMEG |
| 56 | 33 | GSWECAYHLGELVWCETGSG |
| 57 | 34 | VAEPCAYHLGELVWCEVLKG |
| 58 | 34 | KEAMCSYWLGELVWCESDMP |
| 59 | 34 | DLADCSWHLGELVWCSRVEG |
| 60 | 34 | DLADCSWHLGELVWCVGLDE |
| 61 | 34 | WVEDCSWHLGELVWCVGLDF |
| 62 | 34 | KVADCAWHMGELVWCTEVEG |
| 63 | 34 | GEEDCSYHLGELVMCTELDD |
| 64 | 34 | GVADCAWHLGELVWCTERED |
| 65 | 34 | GEEDCAWHLGELVWCSGGDF |
| 66 | 34 | WEADCAWHLGELVWCTKVBE |
| 67 | 34 | GEADCSYHLGELVWCNDFEE |
| 68 | 34 | WVDCAYHLGELVWCSTFEE |
| 69 | 34 | WVEDCAWHMGELVWCTKVDE |
| 70 | 34 | READCAWHLGELVWCSERDL |
| 71 | 34 | EEASCAYHLGELVWCDAFDV |
| 72 | 34 | RVASCAWHLGELVWCDGLDG |
| 73 | 34 | GEADCAWHLGELVWCTKVEE |
| 74 | 34 | GEASCAYHLGELVWCDEGEG |
| 75 | 34 | RVEDCAYHLGELVWCTEGDE |
| 76 | 34 | EEPDCSWHLGELVMCTPMEV |
| 77 | 34 | KEADCAWHMGELVWCSEMEG |
| 78 | 34 | EQADCAWHLGELVWCTPMVF |
| 79 | 34 | EEPDCSWHLGELVWCTPIEV |
| 80 | 34 | GEPDCAWHLGELVWCTPMVF |
| 81 | 34 | GEQDCSYHMGELVWCTTVDG |
| 82 | 34 | GVRNCAYHLGELVWCTPMEF |
| 83 | 34 | RVADCAWHMGELVWCSELEV |
| 84 | 34 | GEADCAWHLGELVWCTPMDL |
| 85 | 34 | GEQDCSWHLGELVWCTPMEV |
| 86 | 34 | GMRDCSYHLGELVWCSDMEL |
| 87 | 35 | EVADCSWHLGELVWCTEGEF |
| 88 | 35 | GEEDCAWHLGELVWCTDVED |
| 89 | 35 | EVEDCAYHLGELVWCSDLEG |
| 90 | 35 | WEEDCAWHLGELVWCAEFDE |
| 91 | 35 | KEASCAWHLGELVWCSEVEE |
| 92 | 35 | AEADCAWHLGELVWCTKVEE |
| 93 | 35 | WAADCAWHLGELVWCTKVEE |
| 94 | 35 | WEPDCAWHLGELVWCTKVEE |
| 95 | 35 | WEAACAWHLGELVWCTKVEE |
| 96 | 35 | WEAACSWHLGELVWCTKVEE |
| 97 | 35 | WEADCAAHLGELVWCTKVEE |
| 98 | 35 | WEADCAWALGELVWCTKVEE |
| 99 | 35 | WEADCAWHAGELVWCTKVEE |
| 100 | 35 | WEADCAWHLAELVWCTKVEE |
| 101 | 35 | WEADCAWHLGALVWCTKVEE |
| 102 | 35 | WEADCAWHLGEAVWCTKVEE |
| 103 | 35 | WEADCAWHLGELAWCTKVEE |
| 104 | 35 | WEADCAWHLGELVACTKVEE |
| 105 | 35 | WEADCAWHLGELVWCAKVEE |
| 106 | 35 | WEADCAWHLGELVWCTAVEE |
| 107 | 35 | WEADCAWHLGELVWCTKAEE |
| 108 | 35 | WEADCAWHLGELVWCTKVAE |
| 109 | 36 | DCAWHLGELVWCTGGG |
| 110 | 36 | GGGWEADCAWHLGELVWCT |
| 111 | 36 | ACA AAC GCG TAC GCT GAC TGC GCT TGG CAC CTG GGC GAG CTG GTC TGG TGC ACC GGA GGA GGA GAT ATC CAG TTG ACC |

-continued

Table of Sequence Identification Numbers

| SEQ ID No: | Location in Specification/FIGS (Page Nos./FIG. Nos.) | SEQUENCE * |
|---|---|---|
| 112 | 36 | AAC AGG GGA GAG TGT GGA GGA GGA TGG GAA GCA GAC TGC GCT TGG CAC CTG GGC GAG CTG GTC TGG TGC ACC TAA GCT GAT CCT CTA C |
| 113 | 4, 11, 14 | FCXDWPXXXSC |
| 114 | 4, 11, 14 | VCYXXXICF |
| 115 | 4, 12, 14 | CYX, PGXC |
| 116 | 4, 12, 13 | DXCLPXWGCLW |
| 117 | 12 | WCDXXLXAXDLC |
| 118 | 12 | DLVXLGLECW |
| 119 | 12, FIGS.4, 9 | DLCLRDWGCLW |
| 120 | 12, FIG. 5 | DTCLPRWGCLW |
| 121 | 12, FIG 9 | MEDICLPRWGCLWED |
| 122 | 12, FIG. 9 | QRLMEDICLPRWGCLWEDDF |
| 123 | 12, FIGS.7, 9 | QGLIGDICLPRWGCLWGDSV |
| 124 | 12, 42, FIG. 9 | QGLIGDICLPRWGCLWGDSVK |
| 125 | 12 | EDICLPRWGCLWEDD |
| 126 | 12, FIG. 9 | RLMEDICLPRWGCLWEDD |
| 127 | 12, FIG. 9 | MEDICLPRWGCLWEDD |
| 128 | 12, FIG. 9 | RLMEDICLARWGCLWEDD |
| 129 | 13 | EVRSFCTDWPAEKSCKPLRG |
| 130 | 13, FIGS.4, 5 | RAPESFVCYWETICFERSEQ |
| 131 | 13 | EMCYFPGICWM |
| 132 | 30 | GELVW |
| 133 | 40 | CXXGPXXXXC |
| 134 | 40 | XXXXCXXGPXXXXCXXXX |
| 135 | 41 | CXXXXXXCXXXXXXCCXXXCXXXXXXC |
| 136 | 41 | CCXXXCXXXXXC |
| 137 | 41 | CCXXXXXCXXXXCXXXXCC |
| 138 | 41 | CXCXXXXXXXXCXXXCXXXXXX |
| 139 | 3, 13 | $X_1X_2X_3X_4$GELVW |
| 140 | FIGS.4, 5 | EMCYFPGICWM |
| 141 | FIG. 4 | CEVALDACRGGESGCCRHICELIRQLC |
| 142 | FIG. 4 | CGCVDVSDWDCWSECLWSHGA |
| 143 | FIG. 4 | DLCDVDFCWF |
| 144 | FIG. 4 | DTCVDLVRLGLECWG |
| 145 | FIG. 4 | KSCSELHWLLVEECLF |
| 146 | FIG. 4 | MDELAFYCGTWECLMHQEQK |
| 147 | FIG. 4 | RNEDPCVVLLEMGLECWEGV |
| 148 | FIGS.4, 5 | EVRSFCTDWPAEKSCKPLRG |
| 149 | FIGS.4, 5 | GENWCDSTLMAYDLCGQVNM |
| 150 | FIGS.4, 5, 7 | QRQMVDFCLPQWGCLWGDGF |
| 151 | FIG. 5 | ALCYFPGICWM |
| 152 | FIG. 5 | ASETCYFPGICWMVE |
| 153 | FIG. 5 | DICYIPGICWM |
| 154 | FIG. 5 | DLCYFPGICWM |
| 155 | FIG. 5 | DMCYFPGICFN |
| 156 | FIG. 5 | DMCYFPGICWL |
| 157 | FIG. 5 | DSEVCYFPGICWSGT |
| 158 | FIG. 5 | DVCYFPGTCWM |
| 159 | FIG. 5 | EHDMCYFPGICWIAD |
| 160 | FIG. 5 | EICYFPGICWI |
| 161 | FIG. 5 | EICYFPGICWM |
| 162 | FIG. 5 | ELCYFPGTCWM |
| 163 | FIG. 5 | ELCYFPGTCWP |
| 164 | FIG. 5 | ELCYFPGICWT |
| 165 | FIG. 5 | EMCYFPGICWS |
| 166 | FIG. 5 | EMCYFPGICWT |
| 167 | FIG. 5 | ETCYFPGICWL |
| 168 | FIG. 5 | EVCYFPGICWE |
| 169 | FIG. 5 | EVCYFPGICWF |
| 170 | FIG. 5 | EVCYFPGICWM |
| 171 | FIG. 5 | EVRSFCTDWPAHYSCTSLQG |
| 172 | FIG. 5 | GEDWCDSTLLAFDLCGEGAR |
| 173 | FIG. 5 | GENWCDWVLLAYDLCGEDNT |
| 174 | FIG. 5 | GGEICYFPGICRVLP |
| 175 | FIG. 5 | GMCYFPGICWA |
| 176 | FIG. 5 | G-RSFCMDWPAHKSCTPLML |
| 177 | FIG. 5 | GTEVCYFPGICWGGG |
| 178 | FIG. 5 | GVRTFCQDWPAHNSCKLLRG |
| 179 | FIG. 5 | HAEICYFPGICWTER |
| 180 | FIG. 5 | TVEMCYYPGICWISP |
| 181 | FIG. 5 | KLCYFPGTCWS |

-continued

Table of Sequence Identification Numbers

| SEQ ID No: | Location in Specification/FIGS (Page Nos./FIG. Nos.) | SEQUENCE * |
|---|---|---|
| 182 | FIG. 5 | KTCYFPGICWM |
| 183 | FIG. 5 | KTETCYFPGICWMSG |
| 184 | FIG. 5 | KVCYFPGICWM |
| 185 | FIG. 5 | LAEMCYFPGTCWMSA |
| 186 | FIG. 5 | LVPERTVCYFESICYERSEL |
| 187 | FIG. 5 | MELWCDSTLMAYDLCGDFNM |
| 188 | FIG. 5 | MEPSRSVCYAEGICFDRGEQ |
| 189 | FIG. 5 | NDETCYFPGVCWKSG |
| 190 | FIG. 5 | QCFPGWVK |
| 191 | FIG. 5 | QTELCYFPGICWNES |
| 192 | FIG. 5 | QTRSFCADWPRHESCKPLRG |
| 193 | FIG. 5 | RAAESSVCYWPGICFDRTEQ |
| 194 | FIG. 5 | RAPERWVCYWEGICFDRYEQ |
| 195 | FIG. 5 | RDTVCYFPGTCWMAS |
| 196 | FIG. 5 | REPASLVCYFEDICFVRAEA |
| 197 | FIG. 5 | RGPDVCYWPSICFERSMP |
| 198 | FIG. 5 | RMPASLPCYWETICYESSEQ |
| 199 | FIG. 5 | RRTCDWPHNSCKLRG |
| 200 | FIG. 5 | RTAESLVCYWPGICFAQSER |
| 201 | FIG. 5 | SGATCYVPGICWTHA |
| 202 | FIG. 5 | SREVCYYPGICWNGA |
| 203 | FIG. 5 | SYAPCYFPGICWMGN |
| 204 | FIG. 5 | TTEMCYFPGICWKTE |
| 205 | FIG. 5 | VQEVCYFPGICWNQE |
| 206 | FIG. 5 | VRDMCYFPGICWKSE |
| 207 | FIGS.5, 7 | NRQMEDICLPQWGCLWGDDF |
| 208 | FIGS.5, 7 | QRHPEDICLPRWGCLWGDDD |
| 209 | FIG. 5 | DFDLCLPDWGCLWDD |
| 210 | FIG. 5 | DICLERWGCLW |
| 211 | FIG. 5 | DICLPAWGCLW |
| 212 | FIG. 5 | DICLPDWGCLW |
| 213 | FIG. 5 | DICLPEWGCLW |
| 214 | FIG. 5 | DICLPVWGCLW |
| 215 | FIG. 5 | DLCLPEWGCLW |
| 216 | FIG. 5 | DLCLPKWGCLW |
| 217 | FIG. 5 | DLCLPVWGCLW |
| 218 | FIG. 5 | DSCGDLLRLGLECWA |
| 219 | FIG. 5 | DTCADLVRLGLECWA |
| 220 | FIG. 5 | DTCDDLVQLGLECWA |
| 221 | FIG. 5 | DTCEDLVRLGLECWA |
| 222 | FIG. 5 | DTCSDLVGLGLECWA |
| 223 | FIG. 5 | EEDLCLPVWGCLWGA |
| 224 | FIG. 5 | EEDVCLPVWGCLWEG |
| 225 | FIG. 5 | EFDLCLPTWGCLWED |
| 226 | FIG. 5 | ERQMEDFCLPQWGCLWGDGV |
| 227 | FIG. 5 | ERQMVDFCLPKWGCLWGDGF |
| 228 | FIG. 5 | EWDVCFPAWGCLWDQ |
| 229 | FIG. 5 | EWDVCLPHWGCLWDG |
| 230 | FIG. 5 | FEDFCLPNWGCLWGS |
| 231 | FIG. 5 | FEDLCVVRWGCLWGD |
| 232 | FIG. 5 | GRQVVDFCLPKWGCLWEEGL |
| 233 | FIG. 5 | KMGRVDFCLPKWGCLWGDEL |
| 234 | FIG. 5 | KSRMGDFCLPEWGCLWGDEL |
| 235 | FIG. 5 | LRIFEDICLPKWGCLWGEGF |
| 236 | FIG. 5 | MDDTCLHHWGCLWDE |
| 237 | FIG. 5 | MDDLCLPNWGCLWGD |
| 238 | FIG. 5 | MFDLCLPKWGCLWGN |
| 239 | FIG. 5 | MWDVCFPDWGCLWDV |
| 240 | FIG. 5 | NTCADLVRLGLECWA |
| 241 | FIG. 5 | NWDLCFPDWGCLWDD |
| 242 | FIG. 5 | QGDFWDICLPRWGCLSGEGY |
| 243 | FIG. 5 | QGGMGDFCLPQWGCLWGEDL |
| 244 | FIG. 5 | QGYMVDFCLPRWGCLWGDAN |
| 245 | FIG. 5 | QMHMMDICLPKWGCLWGDTS |
| 246 | FIG. 5 | QMQMSDFCLPQWGCLWGDGY |
| 247 | FIG. 5 | QRHNNDFCLPKWGCLWGDGY |
| 248 | FIG. 5 | QRLMWEICLPLWGCLWGDGL |
| 249 | FIG. 5 | QRPIMDFCLPKWGCLWEDGF |
| 250 | FIG. 5 | QRQIMDFCLPHWGCLWGDGF |
| 251 | FIG. 5 | QRQVVDFCLPQWGCLWGDGS |
| 252 | FIG. 5 | QSQLEDFCLPKWGCLWGDGF |
| 253 | FIG. 5 | QSYMEDTCLPRWGCLSDDAS |
| 254 | FIG. 5 | RWQTEDVCLPKWGCLFGDGV |

-continued

Table of Sequence Identification Numbers

| SEQ ID No: | Location in Specification/FIGS (Page Nos./FIG. Nos.) | SEQUENCE * |
|---|---|---|
| 255 | FIG. 5 | SEDFCLPVWGCLWED |
| 256 | FIG. 5 | VWDLCLPQWGCLWDE |
| 257 | FIG. 5 | WDDICFRDWGCLWGS |
| 258 | FIG. 5 | WEDLCLPDWGCLWED |
| 259 | FIGS. 5, 7 | HRLVBDICLPRWGCLWGNDF |
| 260 | FIGS. 5, 7 | HSQMEDTCLPRWGCLWGDEL |
| 261 | FIGS. 5, 7 | LIFMEDVCLPQWGCLWEDGV |
| 262 | FIGS. 5, 7 | LRLMDNTCLPRWGCLWDDGF |
| 263 | FIGS. 5, 7 | LWANEDICLPKWGCLWEDDF |
| 264 | FIGS. 5, 7 | QRDMGDICLPRWGCLWEDGV |
| 265 | FIGS. 5, 7 | QRLMEDTCLPRWGCLWGDRF |
| 266 | FIGS. 5, 7 | QWHMEDTCLPQWGCLWGDVL |
| 267 | FIGS. 5, 7 | QWQMENVCLPKWGCLWEELD |
| 268 | FIGS. 5, 7 | QWQVMDTCLPRWGCLWADEY |
| 269 | FIGS. 5, 9 | DICLPRWGCLW |
| 270 | FIG. 8 | AAQVGDICLPRWGCLWSEYA |
| 271 | FIG. 8 | AGWAADVCLPRWGCLWEEDV |
| 272 | FIG. 8 | ALFEDVCLPVWGCLWGGE |
| 273 | FIG. 8 | AQANGDICLPRWGCLWEAEI |
| 274 | FIG. 8 | ASDPGDVCLPRWGCLWGESF |
| 275 | FIG. 8 | ASDRGDLCLPYWGCLWGPDG |
| 276 | FIG. 8 | ASEWDVCLPTWGCLWMEG |
| 277 | FIG. 8 | ASNWEDVCLPRWGCLWGERN |
| 278 | FIG. 8 | ASTPRDTCLPRWGCLWSEDA |
| 279 | FIG. 8 | ASVVDDTCLPVWGCLWGEDI |
| 280 | FIG. 8 | ATMEDDICLPRWGCLWGAEE |
| 281 | FIG. 8 | AYSADICLPRWGCLWMSE |
| 282 | FIG. 8 | DEDFEDYCLPPWGCLWGSSM |
| 283 | FIG. 8 | DGEEGDLCLPRWGCLWALEH |
| 284 | FIG. 8 | EDWEDTCLPQWGCLWEGM |
| 285 | FIG. 8 | EDWTDLCLPAWGCLWDTE |
| 286 | FIG. 8 | EEDSDICLPRWGCLWNTS |
| 287 | FIG. 8 | EGEEVDICLPQWGCLWGYPV |
| 288 | FIG. 8 | EGTWDDFCLPRWGCLWLGER |
| 289 | FIG. 8 | EGYWDLCLPRWGCLWELE |
| 290 | FIG. 8 | ELGEDLCLPRWGCLWGSE |
| 291 | FIG. 8 | ERWEGDVCLPRWGCLWGESG |
| 292 | FIG. 8 | ETWSDVCLPRWGCLWGAS |
| 293 | FIG. 8 | EVGDLDLCLPRWGCLWGNDK |
| 294 | FIG. 8 | FRDGEDFCLPQWGCLWADTS |
| 295 | FIG. 8 | GDMVNDFCLPRWGCLWGSEN |
| 296 | FIG. 8 | GDWMIDICLPKWGCLWDEKA |
| 297 | FIG. 8 | GDYVDLCLPGWGCLWEDG |
| 298 | FIG. 8 | GIEWGDTCLPKWGCLWRVEG |
| 299 | FIG. 8 | GQQGEDVCLPVWGCLWDTSS |
| 300 | FIG. 8 | GRMGTDLCLPRWGCLWGEVE |
| 301 | FIG. 8 | GRYPMDLCLPRWGCLWEDSA |
| 302 | FIG. 8 | GSAGDDLCLPRWGCLWERGA |
| 303 | FIG. 8 | GVLDDICLPRWGCLWGPK |
| 304 | FIG. 8 | HASDWDVCLPGWGCLWEEDD |
| 305 | FIG. 8 | HEWERDTCLPRWGCLWRDGD |
| 306 | FIG. 8 | HMEYIDDVCLPGWGCLWASE |
| 307 | FIG. 8 | IDYTDLCLPAWGCLWELE |
| 308 | FIG. 8 | IEHEDLCLPRWGCLWAVD |
| 309 | FIG. 8 | TSEWDLCLPRWGCLWDRS |
| 310 | FIG. 8 | ISWADVCLPKWGCLWGKD |
| 311 | FIG. 8 | TSWGDLCLPRWGCLWEGS |
| 312 | FIG. 8 | KKVSGDICLPIWGCLWDNDY |
| 313 | FIG. 8 | KLWDDICLPRWGCLWSPL |
| 314 | FIG. 8 | LAWPDVCLPRWGCLWGGM |
| 315 | FIG. 8 | LGVTHDTCLIPRWGCLWDEVG |
| 316 | FIG. 8 | LLESDDICLPRWGCLWHEDG |
| 317 | FIG. 8 | LNESDICLPTWGCLWGVD |
| 318 | FIG. 8 | LPEQDVCLPVWGCLWDAN |
| 319 | FIG. 8 | LVWEEDFCLPKWGCLWGAED |
| 320 | FIG. 8 | MAWGDVCLPRWGCLWAGG |
| 321 | FIG. 8 | MQAESDFCLPHWGCLWDEGT |
| 322 | FIG. 8 | MQGPLDTCLPRWGCLWGGVD |
| 323 | FIG. 8 | NEEWDVCLPRWGCLWGGV |
| 324 | FIG. 8 | NVGWNDICLPRWGCLWAQES |
| 325 | FIG. 8 | QELQDFCLPRWGCLWGVG |
| 326 | FIG. 8 | QGVEWDVCLPQWGCLWTREV |
| 327 | FIG. 8 | QMPLEDICLPRWGCLWEGRE |

-continued

Table of Sequence Identification Numbers

| SEQ ID No: | Location in Specification/FIGS (Page Nos./FIG. Nos.) | SEQUENCE * |
|---|---|---|
| 328 | FIG. 8 | QREWDVCLPRWGCLWSDV |
| 329 | FIG. 8 | QRFWDTCLPRWGCLWGGD |
| 330 | FIG. 8 | REEWGDLCLPTWGCLWETKK |
| 331 | FIG. 8 | RLDAWDICLPQWGCLWEEPS |
| 332 | FIG. 8 | RVFTDVCLPRWGCLWDLG |
| 333 | FIG. 8 | RVWTEDVCLPRWGCLWSEGN |
| 334 | FIG. 8 | SEAPGDYCLPRWGCLWAQEK |
| 335 | FIG. 8 | SGWDDVCLPVWGCLWGPS |
| 336 | FIG. 8 | SIREYDVCLPKWGCLWEPSA |
| 337 | FIG. 8 | SPTEWDMCLPKWGCLWGDAL |
| 338 | FIG. 8 | SSASDYCLPRWGCLWGDL |
| 339 | FIG. 8 | SSGLEDICLPNWGCLWADGS |
| 340 | FIG. 8 | SVGWGDTCLPVWGCLWGEGG |
| 341 | FIG. 8 | SWQGDICLPRWGCLWGVD |
| 342 | FIG. 8 | SYETDVCLPYWGCLWEDA |
| 343 | FIG. 8 | SYWGDVCLPRWGCLWSEA |
| 344 | FIG. 8 | TAMDEDVCLPRWGCLWGSGS |
| 345 | FIG. 8 | TEENWDLCLPRWGCLWGDDW |
| 346 | FIG. 8 | TEIGQDFCLPRWGCLWVPGT |
| 347 | FIG. 8 | TLEWDMCLPRWGCLWTEQ |
| 348 | FIG. 8 | TLGWPDFCLPKWGCLWRESD |
| 349 | FIG. 8 | TLSNQDTCLPGWGCLWGGIN |
| 350 | FIG. 8 | TSGSDDTCLPVWGCLWGEDS |
| 351 | FIG. 8 | TSTGGDLCLPRWGCLWDSSE |
| 352 | FIG. 8 | TWP-GDLCLPRWGCLWEAES |
| 353 | FIG. 8 | VGEFDICLPRWGCLWDAE |
| 354 | FIG. 8 | VSEMDDICLPLWGCLWADAP |
| 355 | FIG. 8 | VSEWEDICLPSWGCLWETQD |
| 356 | FIG. 8 | VTSWDVCLPRWGCLWEED |
| 357 | FIG. 8 | VVGDGDFCLPKWGCLWDQAR |
| 358 | FIG. 8 | VVWDDDVCLPRWGCLWEEYG |
| 359 | FIG. 8 | WDHELDFCLPVWGCLWAEDV |
| 360 | FIG. 8 | WLWEDLCLPKWGCLWEED |
| 361 | FIG. 8 | WSDSDDVCLPRWGCLWGNVA |
| 362 | FIG. 8 | WTESEDTCLPGWGCLWGPEV |
| 363 | FIG. 8 | WVEEGDICLPRWGCLWESVE |
| 364 | FIG. 8 | WVPFEDVCLPRWGCLWSSYQ |
| 365 | FIG. 8 | XXXXDXCLPXWGCLWXXX |
| 366 | 42, FIG. 8 | XXXXXDXCLPXWGCLWXXXX |
| 367 | FIG. 8 | AFWSDICLPRWGCLWEED |
| 368 | FIG. 8 | AGLDEDTCLPRWGCLWGKEA |
| 369 | FIG. 8 | AGMMGDICLPRWGCLWQGEP |
| 370 | FIG. 8 | APGDWDFCLPKWGCLWDDDA |
| 371 | FIG. 8 | AQLFDDTCLPRWGCLWSDGY |
| 372 | FIG. 8 | ARTMGDICLPRWGCLWGASD |
| 373 | FIG. 8 | AVSWADICLPRWGCLWERAD |
| 374 | FIG. 8 | AWLDEDICLPKWGCLWNTGV |
| 375 | FIG. 8 | AWQDFDVCLPRWGCLWEPES |
| 376 | FIG. 8 | DTTWGDICLPRWGCLWSEEA |
| 377 | FIG. 8 | DWGRDICLPRWGCLWDEE |
| 378 | FIG. 8 | EAWGDICLPRWGCLWELE |
| 379 | FIG. 8 | EGFLGDICLPRWGCLWGHQA |
| 380 | FIG. 8 | EQWLHDICLPKWGCLWDDTD |
| 381 | FIG. 8 | ETGWPDICLPRWGCLWEEGE |
| 382 | FIG. 8 | FELGEDICLPRWGCLWEEHN |
| 383 | FIG. 8 | FITQDTCLPRWGCLWGEN |
| 384 | FIG. 8 | FLWRDICLPRWGCLWSEG |
| 385 | FIG. 8 | FSLDEDICLPKWGCLWGAEK |
| 386 | FIG. 8 | FVHEDTCLPRWGCLWGEG |
| 387 | FIG. 8 | GASLGDICLPRWGCLWGPED |
| 388 | FIG. 8 | GDLGDDICLPRWGCLWDEYP |
| 389 | FIG. 8 | GEGWSDICLPRWGCLWAEDE |
| 390 | FIG. 8 | GEWWEDICLPRWGCLWGSSS |
| 391 | FIG. 8 | GLGDDICLPRWGCLWGRD |
| 392 | FIG. 8 | GLMGEDICLPRWGCLWKGDI |
| 393 | FIG. 8 | GMFDDICLPKWGCLWGLG |
| 394 | FIG. 8 | GPGWDICLPRWGCLWGEE |
| 395 | FIG. 8 | GPWYDICLPRWGCLWDGV |
| 396 | FIG. 8 | GSLESDICLPRWGCLWGIDE |
| 397 | FIG. 8 | GWDDDICLPRWGCLWGDG |
| 398 | FIG. 8 | GWHDRDTCLPRWGCLWEQND |
| 399 | FIG. 8 | GWLEEDICLPKWGCLWGADN |
| 400 | FIG. 8 | HEQWDDICLPRWGCLWGGSY |

-continued

Table of Sequence Identification Numbers

| SEQ ID No: | Location in Specification/FIGS (Page Nos./FIG. Nos.) | SEQUENCE * |
|---|---|---|
| 401 | FIG. 8 | LEYEDICLPKWGCLWGGE |
| 402 | FIG. 8 | LILSDICLPRWGCLWDDT |
| 403 | FIG. 8 | LKLEDICLPRWGCLWGES |
| 404 | FIG. 8 | LLDEDICLPRWGCLWGVR |
| 405 | FIG. 8 | LLGGHDICLPRWGCLWGGDV |
| 406 | FIG. 8 | LLTRDICLPKWGCLWGSD |
| 407 | FIG. 8 | LMSPDICLPKWGCLWEGD |
| 408 | FIG. 8 | LRWSDICLPRWGCLWEET |
| 409 | FIG. 8 | LVLGDICLPRWGCLWESD |
| 410 | FIG. 8 | LYLRDICLPKWGCLWEAD |
| 411 | FIG. 8 | MLSRDICLPRWGCLWEEE |
| 412 | FIG. 8 | MPWTDICLPRWGCLWSES |
| 413 | FIG. 8 | MRWSSDICLPKWGCLWGDEE |
| 414 | FIG. 8 | NWYDDICLPRWGCLWDVE |
| 415 | FIG. 8 | QDWEDICLPRWGCLWGD |
| 416 | FIG. 8 | QFEWDDICLPRWGCLWEVEV |
| 417 | FIG. 8 | QGWWHDICLPRWGCLWEEGE |
| 418 | FIG. 8 | QRVDDDICLPRWGCLWGENS |
| 419 | FIG. 8 | QSWPDICLPKWGCLWGEG |
| 420 | FIG. 8 | REGWPDICLPRWGCLWSETG |
| 421 | FIG. 8 | RELWGDICLPRWGCLWEHAT |
| 422 | FIG. 8 | RLELMDICLPRWGCLWDPQD |
| 423 | FIG. 8 | RLGSDICLPRWGCLWDYQ |
| 424 | FIG. 8 | RLGSDICLPRWGCLWGAG |
| 425 | FIG. 8 | SGVLGDICLPRWGCLWEEAG |
| 426 | FIG. 8 | SLGLTDLCLPRWGCLWEEEQ |
| 427 | FIG. 8 | SPWIVIDICLPRWGCLWESG |
| 428 | FIG. 8 | SSLEQDICLPRWGCLWGQDA |
| 429 | FIG. 8 | STFTDICLPRWGCLWELE |
| 430 | FIG. 8 | SVGWGDICLPKWGCLWAESD |
| 431 | FIG. 8 | SVLSDDICLPRWGCLWWDFS |
| 432 | FIG. 8 | SVLSDICLPRWGCLWEES |
| 433 | FIG. 8 | TLLQDICLPRWGCLWESD |
| 434 | FIG. 8 | TLMSNDICLPRWGCLWDEPK |
| 435 | FIG. 8 | TLVLDDICLPRWGCLWDMTD |
| 436 | FIG. 8 | TSLADDICLPRWGCLWSEDG |
| 437 | FIG. 8 | TSLLDDICLPRWGCLWYEEG |
| 438 | FIG. 8 | TWFSDICLPRWGCLWEPG |
| 439 | FIG. 8 | TWQGEDICLPRWGCLWDTEV |
| 440 | FIG. 8 | VEMWHDICLPRWGCLWDSNA |
| 441 | FIG. 8 | VGVFDDICLPRWGCLWEQPV |
| 442 | FIG. 8 | VHQADTCLPRWGCLWGDT |
| 443 | FIG. 8 | VLLGDTCLPLWGCLWGED |
| 444 | FIG. 8 | VNWGDTCLPRWGCLWGES |
| 445 | FIG. 8 | VPANGDICLPRWGCLWEARN |
| 446 | FIG. 8 | VRLMDICLPRWGCLWGEE |
| 447 | FIG. 8 | VRWEDICLPRWGCLWGEE |
| 448 | FIG. 8 | VSLGDDICLPKWGCLWEPEA |
| 449 | FIG. 8 | VVWSDICLPRWGCLWDKE |
| 450 | FIG. 8 | VWIDRDTCLPRWGCLWDTEN |
| 451 | FIG. 8 | VWYKDICLPRWGCLWEAE |
| 452 | FIG. 8 | WDLASDICLPRWGCLWEEEA |
| 453 | FIG. 8 | WDVADICLPRWGCLWAED |
| 454 | FIG. 8 | WDYGDTCLPRWGCLWEEG |
| 455 | FIG. 8 | WEVQDICLPRWGCLWGDD |
| 456 | FIG. 8 | WHMGDICLPRWGCLWSEV |
| 457 | FIG. 8 | WKDFDICLPRWGCLWDDH |
| 458 | FIG. 8 | WLSDDICLPRWGCLWDDL |
| 459 | FIG. 8 | WLSEDICLPQWGCLWEES |
| 460 | FIG. 8 | WLSEDICLPRWGCLWAAD |
| 461 | FIG. 8 | WRWNEDICLPRWGCLWEEEA |
| 462 | FIG. 8 | YIWRDICLPRWGCLWEGE |
| 463 | FIG. 8 | YRDYDICLPRWGCLWDER |
| 464 | FIG. 8 | AGEWDICLPRWGCLWDVE |
| 465 | FIG. 8 | EIRWDFCLPRWGCLWDED |
| 466 | FIG. 8 | ESLGDICLPRWGCLWGSG |
| 467 | FIG. 8 | EVREWDICLPRWGCLWENWR |
| 468 | FIG. 8 | EYWGDICLPRWGCLWDWQ |
| 469 | FIG. 8 | FGQEWDTCLPRWGCLWGNEQ |
| 470 | FIG. 8 | IWQLEDICLPRWGCLWEDGL |
| 471 | FIG. 8 | KMWSDTCLPRWGCLWEEE |
| 472 | FIG. 8 | MGTKDTCLPRWGCLWAEA |
| 473 | FIG. 8 | MHEWDTCLPRWGCLWESS |

-continued

Table of Sequence Identification Numbers

| SEQ ID No: | Location in Specification/FIGS (Page Nos./FIG. Nos.) | SEQUENCE * |
|---|---|---|
| 474 | FIG. 8 | NTPTYDICLPRWGCLWGDVP |
| 475 | FIG. 8 | NWAENDICLPRWGCLWGDEN |
| 476 | FIG. 8 | QPVWSDICLPRWGCLWGEDH |
| 477 | FIG. 8 | RGLHDACLPWWGCLWAGS |
| 478 | FIG. 8 | RLFGDICLPRWGCLWQGE |
| 479 | FIG. 8 | SAREWDICLPTWGCLWEKDI |
| 480 | FIG. 8 | SGEWDTCLPRWGCLWGEG |
| 481 | FIG. 8 | SMFFDHCLPMWGCLWAEQ |
| 483 | FIG. 8 | TLFQDTCLPRWGCLWEES |
| 484 | FIG. 8 | VGEWDTCLPNWGCLWERE |
| 485 | FIG. 8 | WFPKDRCLPVWGCLWERH |
| 486 | FIG. 8 | WGMARDWCLPMWGCLWRGGG |
| 487 | FIG. 8 | WHLTDDICLPRWGCLWGDEQ |
| 488 | FIG. 8 | WWMADRCLPLWGCLWRGD |
| 489 | FIG. 8 | WWVRDLCLPTWGCLWSGK |
| 490 | FIG. 8 | YFDGDICLPRWGCLWGSD |
| 491 | FIG. 9 | EDICLPRWGCLWEDD |
| 492 | FIG. 8 | SWYGGDICLP-WGCLWSEES |

* X is an amino acid
For SEQ ID NO: 10: $X_1$ is Ala, Ser, or Thr; $X_2$ is Trp or Tyr; $X_3$ is His or Trp; $X_4$ is Leu or Met.
For SEQ ID NO: 13: $X_5$ is Ala, Ser, or Thr; $X_6$ is Trp or Tyr; $X_7$ is His or Trp; $X_8$ is Leu or Met; and $X_{1-4 \text{ and } 9-13}$ are each an amino acid.
For SEQ ID NO: 14: $X_4$ is Ser, Arg, or Asp; $X_5$ is Ala, Ser, or Thr; $X_6$ is Trp or Tyr; $X_7$ is His or Trp; $X_8$ is Leu or Met; $X_9$ is Glu, Ser, Thr, or Val; and $X_{1-3 \text{ and } 9-13}$ are each an amino acid.
For SEQ ID NO: 188: $X_1$ is Ile, Phe, Tyr, or Val.

What is claimed is:

1. A peptide ligand comprising a non-naturally occurring amino acid sequence, wherein the amino acid sequence is Xaa$_i$-Cys-Xaa$_j$-Cys-Xaa$_k$ that binds IgG-Fc, wherein Xaa is any amino acid, Xaa$_i$ is 0-4 amino acids, Xaa$_j$ is Xaa-Xaa-Xaa-Xaa-Xaa-Xaa-Leu-Val-Trp (SEQ ID NO:9), and Xaa$_k$ is 0-5 amino acids.

2. The peptide ligand of claim 1 wherein Xaa$_j$ is Xaa-Xaa-Xaa-Xaa-Gly-Glu-Leu-Val-Trp (SEQ ID NO: 10).

3. The peptide ligand of claim 2 wherein Xaa$_j$ is Xaa$_1$-Xaa$_2$-Xaa$_3$-Xaa$_4$-Gly-Glu-Leu-Val-Trp-Cys (SEQ ID NO: 10) and Xaa$_1$ is Ala, Ser, or Thr, Xaa$_2$ is Trp or Tyr, Xaa$_3$ is His, or Trp, and Xaa$_4$ is Leu or Met.

4. The peptide ligand of claim 1 or claim 2 comprising the amino acid sequence Xaa-Xaa-Xaa-Xaa-Cys-Xaa-Xaa-Xaa-Xaa-Xaa-Xaa-Leu-Val-Trp-Cys -Xaa-Xaa-Xaa-Xaa-Xaa (SEQ ID NO:11) wherein Xaa is any amino acid.

5. The peptide ligand of claim 4 comprising the amino acid sequence Xaa-Xaa-Xaa-Xaa-Cys-Xaa-Xaa-Xaa-Xaa-Gly-Glu-Leu-Val-Trp-Cys-Xaa-Xaa-Xaa-Xaa-Xaa (SEQ ID NO: 12).

6. The peptide ligand of claim 5 comprising the amino acid sequence Xaa$_1$-Xaa$_2$-Xaa$_3$-Xaa$_4$-Cys-Xaa$_5$-Xaa$_6$-Xaa$_7$-Xaa$_8$-Gly-Glu-Leu-Val-Trp-Cys-Xaa$_9$-Xaa$_{10}$-Xaa$_{11}$-Xaa$_{12}$-Xaa$_{13}$ (SEQ ID NO:13), wherein Xaa$_5$ is Ala, Ser, or Thr, Xaa$_6$ is Trp or Tyr, Xaa$_7$ is His, or Trp, Xaa$_8$ is Leu or Met, and Xaa$_{1-4}$ and $_{9-13}$ are each an amino acid.

7. The peptide ligand of claim 6 wherein Xaa$_4$ is Ser, Arg, or Asp; Xaa$_5$ is Ala, Ser, or Thr; Xaa$_6$ is Trp or Tyr; Xaa$_7$ is His or Trp; Xaa$_8$ is Leu or Met; and Xaa$_9$ is Glu, Ser, Thr or Val (SEQ ID NO: 14).

8. The peptide of claim 1 wherein the peptide ligand comprises the amino acid sequence DCAWHLGELVWCT (SEQ ID NO:8).

9. The peptide ligand of claim 1, wherein the amino acid sequence is cyclized by the presence of disulfide-bonded Cys residues.

10. The peptide ligand of claim 1, wherein the peptide ligand is less than 50 amino acid residues.

11. The peptide ligand of claim 1, wherein the peptide ligand is less than 40 amino acid residues.

12. The peptide ligand of claim 1, wherein the peptide ligand is between 10 and 30 amino acid residues.

13. The peptide ligand of claim 1, wherein the peptide ligand has an IC$_{50}$ for IgG-Fc of less than about 1 µM.

14. The peptide ligand of claim 1, wherein the peptide ligand has an IC$_{50}$ for IgG-Fc of less than about 100 nM.

15. The peptide ligand of claim 1, wherein the peptide ligand is non-covalently adsorbed or covalently bound to a macromolecule.

16. The peptide ligand of claim 15, wherein the macromolecule is a solid support.

17. The peptide ligand of claim 1, wherein the peptide ligand is labeled with a detectable moiety.

* * * * *

UNITED STATES PATENT AND TRADEMARK OFFICE
CERTIFICATE OF CORRECTION

PATENT NO. : 7,608,681 B2 Page 1 of 1
APPLICATION NO. : 10/149835
DATED : October 27, 2009
INVENTOR(S) : Dennis et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2114 days.

Signed and Sealed this

Twelfth Day of October, 2010

David J. Kappos
*Director of the United States Patent and Trademark Office*